United States Patent
Ohata et al.

(10) Patent No.: US 9,006,246 B2
(45) Date of Patent: Apr. 14, 2015

(54) TETRAHYDROCARBOLINE DERIVATIVE

(75) Inventors: Akira Ohata, Osaka (JP); Shingo Nakatani, Osaka (JP); Tetsuya Sugiyama, Ibaraki (JP); Takashi Morimoto, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/807,947

(22) PCT Filed: Jul. 5, 2011

(86) PCT No.: PCT/JP2011/065312
§ 371 (c)(1),
(2), (4) Date: Jan. 2, 2013

(87) PCT Pub. No.: WO2012/005227
PCT Pub. Date: Jan. 12, 2012

(65) Prior Publication Data
US 2013/0109699 A1     May 2, 2013

(30) Foreign Application Priority Data

| Jul. 6, 2010 | (JP) | ................................ 2010-154280 |
| Mar. 18, 2011 | (JP) | ................................ 2011-060765 |

(51) Int. Cl.

| C07D 471/14 | (2006.01) |
| C07D 471/04 | (2006.01) |
| A61K 31/496 | (2006.01) |
| A61K 31/4375 | (2006.01) |
| A61K 45/00 | (2006.01) |
| A61K 31/437 | (2006.01) |
| A61K 45/06 | (2006.01) |

(52) U.S. Cl.
CPC .............. C07D 471/14 (2013.01); C07D 471/04 (2013.01); A61K 31/4375 (2013.01); A61K 31/496 (2013.01); A61K 45/00 (2013.01); A61K 31/437 (2013.01); A61K 45/06 (2013.01)

(58) Field of Classification Search
CPC .............. C07D 471/14; C07D 471/046; A61K 31/496; A61K 31/4375
See application file for complete search history.

(56) References Cited

U.S. PATENT DOCUMENTS

| 2002/0010189 A1 | 1/2002 | Sui et al. |
| 2004/0116458 A1 | 6/2004 | Sawyer et al. |
| 2005/0215580 A1 | 9/2005 | Wang et al. |
| 2005/0256160 A1 | 11/2005 | Habashita et al. |
| 2013/0109699 A1 | 5/2013 | Ohata et al. |

FOREIGN PATENT DOCUMENTS

| JP | 2008-297278 A | 12/2008 |
| WO | 03/099765 A1 | 12/2003 |
| WO | 2012/005227 A1 | 1/2012 |
| WO | 2012/127885 A1 | 9/2012 |

OTHER PUBLICATIONS

Stella et al. Prodrug strategies to overcome poor water solubility. Advanced Drug Delivery Reviews. 59 (2007): 677-694.*
Seefeld et al. Inhibitors of bacterial enoyl acyl carrier protein reductase (FabI): 2,9-disubstituted 1,2,3,4-tetrahydropyrido[3,4-b]indoles as potential antibacterial agents. Bioorganic & Medicial Chemistry, 11 (2001): 2241-2244.*
Search Report dated Mar. 27, 2012 issued by the International Searching Authority in related (not corresponding) International Application No. PCT/JP2012/050050 (PCT/ISA/210).
Xiaoming Zhang, et al., "Oxidative methods for promoting iminium cation cyclization reactions," Tetrahedron Letters, 1993, 34(33), pp. 5239 to 5242.
International Search Report for PCT/JP2011/065312 dated Sep. 13, 2011 [PCT/ISA/210].
Office Action, dated Aug. 26, 2013, issued by the Intellectual Property Office of New Zealand, in counterpart Application No. 603575.
U.S. Appl. No. 14/005,062, filed Sep. 13, 2013; inventor = Akira Ohata et al.
Bhonsle et al., "Novel Method for Mining QSPR-Relevant Conformations", Chem. Eng. Comm., 195:1396-1423 (2008).
Communication for EP 11803561.7 dated Apr. 9, 2014, with Supplementary European Search Report (dated Mar. 31, 2014).
Communication dated Jun. 4, 2014 issued by the European Patent Office in counterpart European Patent Application No. 12761051.7.
Office Action, Issued by the U.S. Patent and Trademark Office, Dated Aug. 28, 2014, in counterpart U.S. Appl. No. 14/005,062.
Dorwald, F. Z., "Side Reactions in Organic Synthesis," A Guide to Successful Synthesis Design, Wiley-VCH Veriag GmbH & Co. KGaA, 2005, p. IX of Preface, ISBN: 3-527-31021-5.

* cited by examiner

*Primary Examiner* — Anna Pagonakis
(74) *Attorney, Agent, or Firm* — Sughrue Mion, PLLC

(57) ABSTRACT

An object of the present invention is to provide a drug having the inhibitory activity on ENPP2 which is a different target from that of the existing drug, as a medicament useful in a urinary excretion disorder patient for whom the existing drug has the insufficient effect.
The present invention provides a compound represented by the general formula (I):

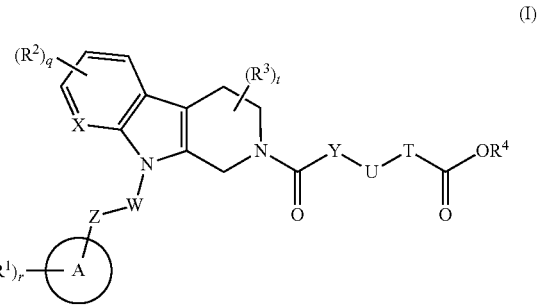

(I)

(wherein definition of each group is as defined in the description) having the ENPP2 inhibitory activity, a salt thereof or a solvate thereof or a prodrug thereof, and an agent for preventing or treating urinary excretion disorder and/or improving symptoms thereof, containing them as an active ingredient.

22 Claims, 1 Drawing Sheet

TETRAHYDROCARBOLINE DERIVATIVE

TECHNICAL FIELD

The present invention relates to a tetrahydrocarboline derivative having the ENPP2 inhibitory activity, a salt thereof or a solvate thereof or a prodrug thereof (hereinafter, referred to as present compound) as well as use thereof.

BACKGROUND ART

Urinary excretion disorder is a disorder in which urine becomes difficult to be excreted, and the cause thereof is reduction in bladder contraction due to neurogenic bladder, urethra oppression due to prostatomegaly or the like. In main advanced countries, it is said that even the number of patient with urinary excretion disorder accompanied with prostatomegaly exceeds at least 15 million. Currently, a mainstream drug for urinary excretion disorder is α1 antagonists, but there is reported that in about a half of them, the drug efficacy is insufficient, and the effect is attenuated due to long term use. However, under the current circumstances, development of a therapeutic effective in those patients is not sufficient.

Meanwhile, ENPP2 (Ectonucleotide Pyrophosphatase/Phosphodiesterase 2) is also called Autotaxin or LysoPLD, and is an enzyme producing lysophosphatidic acid (hereinafter, abbreviated as LPA) which is a lysophospholipid, in blood (see Non-Patent Document 1). Since ENPP2 is highly expressed in many cancerous tissues, and promotes mobility of a cancer cell, it was concerned as a molecule involved in metastasis or infiltration of cancer at the beginning (see Non-Patent Document 2), but was later confirmed to be a main enzyme producing LPA, and possibilities of involvement in a variety of physiological functions in which LPA is involved, have been reported (see Non-Patent Document 3, and see Patent Document 1). For example, since LPA is involved in contraction of prostate or urethra, there is a possibility that ENPP2 which is an producing enzyme thereof becomes a new target of treatment of urinary excretion disorder. However, use as a drug for urinary excretion disorder is not shown at all in the prior art documents concerning an ENPP2 inhibitor which have previously been reported, for example, Non-Patent Documents 4 to 6, Patent Document 2 concerning an imidazole derivative, Patent Document 3 concerning piperidine and piperazine derivatives, and Patent Document 4 concerning a thiazole derivative.

On the other hand, as the prior art concerning the present compound, there are the followings. That is, an antibacterial agent having the phosphopantetheineadenyltransferase (PPAT) inhibitory activity consisting of a compound represented by the general formula (A):

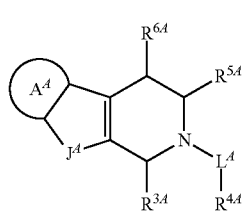

(A)

(wherein ring $A^A$ represents an aryl or hetroaryl group in which an arbitrary substitutable ring atom may be substituted, $J^A$ represents —$NR^{2A'}$— etc. (wherein $R^{2A'}$ represents optionally substituted aralkyl etc.), $R^{3A}$ represents a hydrogen atom etc., $L^A$ represents —(CO)— etc., $R^{4A}$ represents a C1-C8 aliphatic group etc., a group represented by $R^{4A}$ is substituted with —(CO)$OR^4$ etc. (wherein $R^4$ represents a hydrogen atom etc.) and $R^{5A}$ and $R^{6A}$ each represent independently a hydrogen atom etc. (extract of a part of definitions of groups)) (see Patent Document 5), a mitochondrial benzodiazepine (MBR) receptor antagonist consisting of a compound represented by the general formula (B):

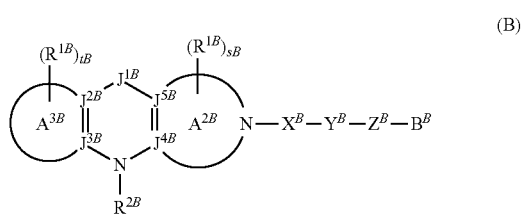

(B)

(wherein ring $A^{2B}$ represents a monocyclic nitrogen-containing hetrocycle, ring $A^{3B}$ represents a monocyclic carbon ring or a monocyclic heterocyclic ring, a plurality of $R^{1B}$s each represent independently a substituent, $R^{2B}$ represents a hydrogen atom or a substituent, tB and sB each represent independently an integer of 0 to 5, a sum of tB and sB is 5 or less, $J^{1B}$ represents a carbon atom optionally having a substituent etc., $J^{2B}$, $J^{3B}$, $J^{4B}$ and $J^{5B}$ each represent independently a carbon atom etc., $X^B$, $Y^B$ and $Z^B$ each represent independently a spacer in which the atom number of a main chain is 1 to 3 etc., and $B^B$ represents a hydrocarbon group optionally having a substituent etc. (extract of a part of definitions of groups)) (see Patent Document 6), an orphan intranuclear receptor agonist consisting of a compound represented by the general formula (D):

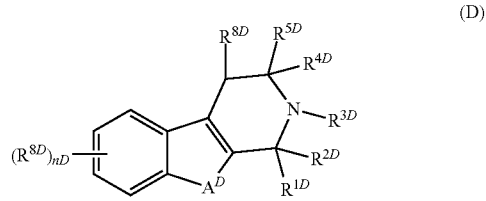

(D)

(wherein $A^D$ represents —$N(R^{9D})$— etc., $R^{1D}$ and $R^{2D}$ each represent independently a hydrogen atom etc., $R^{3D}$ represents —$C(O)R^{10D}$ (wherein $R^{10D}$ represents a hydrogen atom etc.) etc., $R^{4D}$, $R^{5D}$, $R^{6D}$ and $R^{7D}$ each represent independently a hydrogen atom etc., $R^{8D}$s each represent independently a halogen atom, —$C(O)OR^{23D}$ (wherein $R^{23D}$ represents a hydrogen atom etc.) or —$R^{27D}$ (wherein $R^{27D}$ represents optionally substituted alkyl etc.) and $R^{9D}$ represents optionally substituted alkyl etc. (extract of a part of definitions of groups)) (see Patent Document 7), an Xa factor inhibitor consisting of a compound represented by the general formula (E):

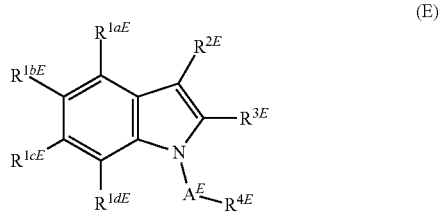

(E)

(wherein $R^{1aE}$, $R^{1bE}$, $R^{1cE}$ and $R^{1dE}$ each represent independently a hydrogen atom, a halogen or a C1-4 alkyl group etc., $R^{2E}$ and $R^{3E}$ are taken together to form —CH$_2$—CH$_2$—N(—CO—R$^{20E}$)—CH$_2$— (wherein $R^{20E}$ is phenyl, phenyl-C1-4 alkyl-, pyridyl or pyridyl-C1-4 alkyl-, phenyl is substituted with $R^{15aE}$, and pyridyl may be substituted with $R^{14E}$ at its nitrogen atom), $A^E$ represents —C1-4 alkyl- etc., and $R^{4E}$ represents phenyl having a substituent or pyridyl optionally having a substituent etc. (extract of a part of definitions of groups)) (see Patent Document 8) and a synthesis intermediate of a cholecystokinin or gastrin receptor binding agent consisting of a compound represented by the general formula (G):

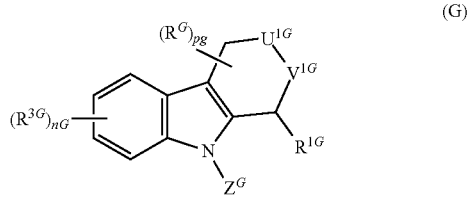

(wherein $U^{1G}$ represents —CH$_2$— etc., $V^{1G}$ represents —N(COR$^{4G}$)— etc. (wherein $R^{4G}$ represents an aryl group optionally having a substituent or an arylalkyl group optionally having a substituent etc.), $Z^G$ represents —C1-3 alkyl-R$^{8G}$ etc. (wherein $R^{8G}$ represents a phenyl group optionally having a substituent), $R^{3G}$ represents a halogen or an alkyl group etc., $R^G$ represents a C1-3 alkyl group, and nG and pG each represent an integer of 0 to 3 (extract of a part of definitions of groups)) (see Patent Document 9).

Further, as the prior art concerning the present compound, there are a PDE inhibitor (see Patent Documents 10 to 15), a histamine receptor antagonist (see Patent Document 16), a 5-HT2 antagonist (see Patent Document 17), a histamine H3 antagonist (see Patent Document 18), a 5-HT6 antagonist (see Patent Document 19), a PPAT inhibitor (see Patnet Document 20), a HDAC inhibitor (see Patent Document 21), a sPLA2 inhibitor (see Patent Document 22), a farnesyltransferase inhibitor (see Patent Document 23), an angiotensin II converting enzyme inhibitor (see Patent Document 24), an EDG-5 antagonist (see Patent Document 25), a PTPase inhibitor (see Patent Document 26), an ADAM-TS inhibitor (see Patent Document 27), an anti-cancer agent (see Patent Document 28), a kinesin-associated protein inhibitor (see Patent Document 29), a FabI inhibitor (see Patent Document 30), a melatonin derivative (see Patent Document 31), a VEGF expression inhibitor (see Patent Document 32) and an insulin receptor antagonist (see Patent Document 33) etc.

However, the present compound is not described in the any prior art, and it is not suggested that a compound described in each prior art has the ENPP2 inhibitory activity or is effective in urinary excretion disorder due to LPA.

PRIOR ART DOCUMENTS

Patent Documents

[Patent Document 1] International Publication No. 02/062389
[Patent Document 2] International Publication No. 09/046804
[Patent Document 3] International Publication No. 09/046841
[Patent Document 4] International Publication No. 09/046842
[Patent Document 5] International Publication No. 04/968802
[Patent Document 6] International Publication No. 04/113300
[Patent Document 7] International Publication No. 03/099821
[Patent Document 8] International Publication No. 99/033800
[Patent Document 9] International Publication No. 97/032860
[Patent Document 10] International Publication No. 02/064590
[Patent Document 11] International Publication No. 02/064591
[Patent Document 12] International Publication No. 00/012076
[Patent Document 13] International Publication No. 02/088123
[Patent Document 14] International Publication No. 01/087038
[Patent Document 15] International Publication No. 02/098875
[Patent Document 16] International Publication No. 09/055828
[Patent Document 17] U.S. Pat. No. 6,350,757
[Patent Document 18] International Publication No. 09/003003
[Patent Document 19] International Publication No. 07/028460
[Patent Document 20] International Publication No. 09/102377
[Patent Document 21] International Publication No. 04/113336
[Patent Document 22] International Publication No. 00/037022
[Patent Document 23] European Patent Application Publication No. 675112
[Patent Document 24] JP-A-60-246385
[Patent Document 25] International Publication No. 04/002531
[Patent Document 26] International Publication No. 03/033496
[Patent Document 27] International Publication No. 01/087883
[Patent Document 28] International Publication No. 08/103470
[Patent Document 29] International Publication No. 05/070930
[Patent Document 30] International Publication No. 00/072846
[Patent Document 31] International Publication No. 95/026723
[Patent Document 32] International Publication No. 06/058088
[Patent Document 33] International Publication No. 00/016798

Non-Patent Documents

[Non-Patent Document 1] Journal of Cell Biology, 2002, vol. 158. pp. 227-233
[Non-Patent Document 2] Journal of Biological Chemistry, 2004, vol. 279, 17th issue, pp. 17634-17639
[Non-Patent Document 3] Biochim Biophys Acta., 2008, 1781st issue, vol. 9, pp. 513-518

[Non-Patent Document 4] Bioorganic & Medicinal Chemistry Letters, 2007, vol. 17, 6th issue, pp. 1634-1640

[Non-Patent Document 5] Journal of Pharmacology And Experimental Therapeutics, 2008, vol. 327, 3rd issue, pp. 809-19

[Non-Patent Document 6] Biochimica et Biophysica Acta, 2008, vol. 1781, 9th issue, pp. 588-94

DISCLOSURE OF THE INVENTION

Problems to be Solved by the Invention

An object of the present invention is to develop a compound having the inhibitory activity on ENPP2 which is a different target from that of the existing drugs in order to provide a drug useful for a patient with urinary excretion disorder for whom the existing drugs have the insufficient effect.

Means to Solve the Problems

The present inventors paid an attention to ENPP2 as a new target for preventing or treating urinary excretion disorder or improving symptoms thereof, and intensively studied in order to find out an inhibitory compound thereof and, as a result, found out compounds shown by the general formula (I). Further, the present inventors found out that those compounds are effective in preventing or treating urinary excretion disorder or improving symptoms thereof, resulting in completion of the present invention.

That is, the present invention is as follows:

[1] A compound represented by the general formula (I):

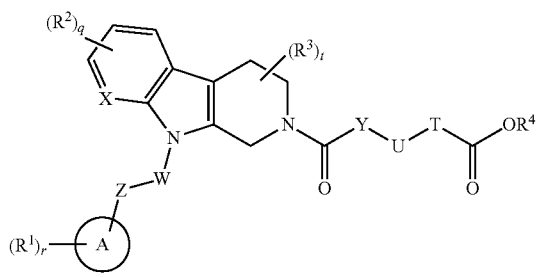

(I)

[wherein $R^1$ represents a halogen atom, a C1-4 alkyl group, a C1-4 alkoxy group, a C1-4 haloalkyl group, a C1-4 haloalkoxy group, a carboxyl group, a cyano group, a C1-3 alkylsulfonyl group, a carbamoyl group or

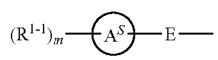

(wherein, the ring $A^S$ represents a 5- to 7-membered monocycle, E represents a bond, a methylene group or an oxygen atom, $R^{1-1}$ represents a halogen atom, a C1-4 alkyl group, a C1-4 alkoxy group, a C1-4 haloalkyl group or a C1-4 haloalkoxy group, and m represents an integer of 0 to 3, provided that groups represented by a plurality of $R^{1-1}$s may be the same or different, respectively), $R^2$ represents a hydrogen atom, a halogen atom, a C1-4 alkyl group, a C1-4 alkoxy group or a C1-4 haloalkyl group, $R^3$ represents a C1-4 alkyl group, $R^4$ represents a hydrogen atom or a C1-4 alkyl group, the ring A represents (i), a C3-7 monocyclic carbon ring, (ii) a C8-10 bicyclic carbon ring, (iii) a 4- to 7-membered monocyclic hetrocycle containing 1 to 4 heteroatoms selected from an oxygen atom, a nitrogen atom and a sulfur atom or (iv) a 8- to 10-membered bicyclic heterocyclic ring containing 1 to 4 heteroatoms selected from an oxygen atom, a nitrogen atom and a sulfur atom, X represents a nitrogen atom or a carbon atom, T represents a bond or a straight C1-4 alkylene group, a C2-4 alkenylene group or a C2-4 alkynylene group, optionally substituted with one or two $R^5$ (in the groups, $R^5$ represents a C1-4 alkyl group, a hydroxy group or an amino group), U represents (i) a methylene group, (ii) an oxygen atom, (iii) —$NR^6$— (in the group, $R^6$ represents a hydrogen atom, or a C1-4 alkyl group) or (iv) a 3- to 7-membered monocycle, a C5-10 bridged carbon ring or a 5- to 10-membered bridged heterocyclic ring, optionally substituted with one to five of $R^7$ (in the groups, $R^7$ represents a halogen atom, a C1-4 alkyl group, a hydroxy group, an oxo group, a C1-4 alkoxy group, a C1-4 haloalkoxy group, a cyano group or a benzyloxy group), Y represents (i) a bond, (ii) a straight C1-3 alkylene group or a C2-3 alkenylene group, optionally substituted with one or two $R^8$ (in the groups, $R^8$ represents a methyl group), W represents a bond or a straight C1-3 alkylene group, Z represents a methylene group, an oxygen atom or an optionally oxidized sulfur atom, q represents an integer of 1 to 4, r represents an integer of 0 to 5, and t represents an integer of 0 to 2, provided that groups represented by a plurality of $R^1$s, $R^2$s, $R^3$s, $R^5$s, $R^7$s and $R^8$s may be the same or different, respectively, and two $R^3$s and two $R^5$s bound to the same carbon atom may be taken together with a carbon atom to which they are bound, to form a C3-5 cycloalkyl], a salt thereof or a solvate thereof or a prodrug thereof.

[2] The compound according to the above mentioned [1], which is represented by the general formula (II):

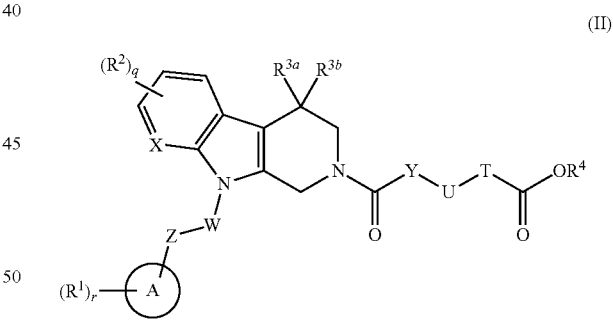

(II)

[wherein $R^{3a}$ and $R^{3b}$ each represent independently a hydrogen atom or a methyl group, and other symbols are as defined in the above mentioned [1], provided that $R^{3a}$ and $R^{3b}$ may be taken together with a carbon atom to which they are bound, to form cyclopropyl].

[3] The compound according to the above mentioned [1] or [2], wherein Y is a straight C1-3 alkylene group optionally substituted with one or two $R^8$s (in the group, $R^8$ is as defined in the above mentioned [1]).

[4] The compound according to any one of the above mentioned [1] to [3], wherein X is a nitrogen atom.

[5] The compound according to any one of the above mentioned [1] to [3], wherein X is a carbon atom.

[6] The compound according to any one of the above mentioned [1] to [5], wherein $R^4$ is a hydrogen atom.

[7] The compound according the above mentioned [6], which is represented by the general formula (IV-2):

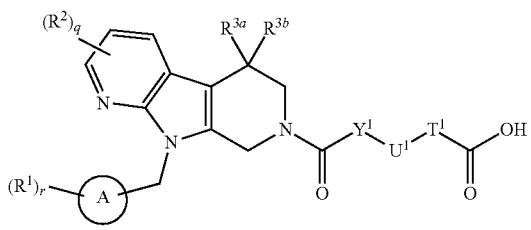

(IV-2)

(wherein $U^1$ represents a 5- to 7-membered monocycle or a C5-10 bridged carbon ring, optionally substituted with one to five $R^7$s (in the groups, $R^7$ is as defined in the above mentioned [1]), $Y^1$ represents a methylene group or an ethylene group, optionally substituted with one or two $R^8$s, $T^1$ represents a bond or a methylene group or an ethylene group, optionally substituted with one or two $R^5$s, and other symbols are as defined in the above mentioned [1] and [2]).

[8] The compound according to the above mentioned [7], wherein $Y^1$ is an unsubstituted methylene group, and $T^1$ is a bond or an unsubstituted methylene group.

[9] The compound according to any one of the above mentioned [1] to [8], wherein the C5-10 bridged carbon ring in the C5-10 bridged carbon ring optionally substituted with one to five $R^7$s is bicyclo[2.2.1]heptane or bicyclo[2.2.2]octane.

[10] The compound according to the above mentioned [7] or [8], wherein the 5- to 7-membered monocycle in the 5- to 7-membered monocycle optionally substituted with one to five $R^7$s is (i) a C5-7 monocyclic carbon ring or (ii) a 5- to 7-membered monocyclic heterocyclic ring containing one to four heteroatoms selected from an oxygen atom, a nitrogen atom and a sulfur atom.

[11] The compound according to the above mentioned [10], wherein the C5-7 monocyclic carbon ring is (i) a C5-7 monocyclic aromatic carbocycle or (ii) a C5-7 monocyclic non-aromatic carbocycle.

[12] The compound according to the above mentioned [11], wherein the C5-7 monocyclic aromatic carbocycle is benzene, and the C5-7 monocyclic non-aromatic carbocycle is cyclopentane or cyclohexane.

[13] The compound according to the above mentioned [10], wherein the 5- to 7-membered monocycle in the 5- to 7-membered monocycle optionally substituted with one to five $R^7$s is (i) a 5- to 7-membered monocyclic aromatic heterocyclic ring containing one to four heteroatoms selected from an oxygen atom, a nitrogen atom and a sulfur atom, or (ii) a 5- to 7-membered monocyclic non-aromatic heterocyclic ring containing one to four heteroatoms selected from an oxygen atom, a nitrogen atom and a sulfur atom.

[14] The compound according to the above mentioned [6], which is represented by the general formula (IV-3):

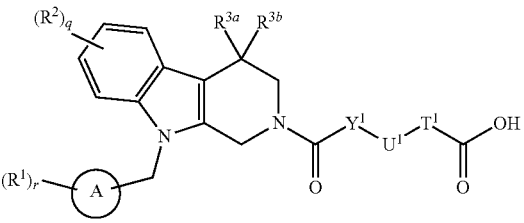

(IV-3)

(wherein all symbols are as defined in the above mentioned [1] to [7]).

[15] The compound according to the above mentioned [6], which is represented by the general formula (V):

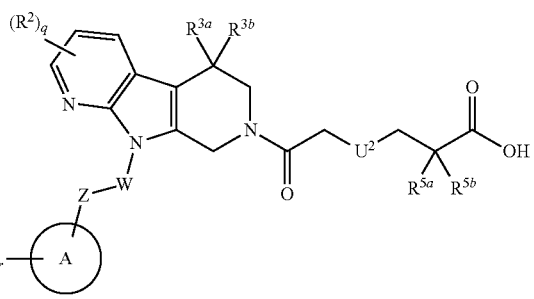

(V)

(wherein $U^2$ represents a methylene group, an oxygen atom or —$NR^6$—, $R^{5a}$ and $R^{5b}$ each represent independently a hydrogen atom or a methyl group, and other symbols are as defined in the above mentioned [1], provided that $R^{5a}$ and $R^{5b}$ may be taken together with a carbon atom to which they are bound, to form cyclopropyl).

[16] The compound according to any one of the above mentioned [1] to [15], wherein the ring A is (i) a 5- to 6-membered monocyclic heterocyclic ring containing one to four heteroatoms selected from an oxygen atom, a nitrogen atom and a sulfur atom or (ii) a 9- to 10-membered bicyclic heterocyclic ring containing one to four heteroatoms selected from an oxygen atom, a nitrogen atom and a sulfur atom.

[17] The compound according to any one of the above mentioned [1] to[15], wherein the ring A is a C5-6 monocyclic carbon ring or a C9-10 bicyclic carbon ring.

[18] The compound according to the above mentioned [16], wherein the 5- to 6-membered monocyclic heterocyclic ring containing one to four heteroatoms selected from an oxygen atom, a nitrogen atom and a sulfur atom is thiophene, furan, pyrazole, isoxazole, thiazole or pyridine, and the 9- to 10-membered bicyclic heterocyclic ring containing one to four heteroatoms selected from an oxygen atom, a nitrogen atom and a sulfur atom is benzothiophene, indole or imidazopyridine.

[19] The compound according to the above mentioned [17], wherein the C5-6 monocyclic carbon ring is cyclopentane, cyclohexane, cyclohexene or benzene, and the C9-10 bicyclic carbocyle is naphthalene.

[20] The compound according to the above mentioned [14], wherein the compound represented by the general formula (IV-3) is (1) cis-4-(2-{9-[(2,5-dimethyl-1,3-thiazol-4-yl)methyl]-1,3,4,9-tetrahydro-2H-beta-carbolin-2-yl}-2-oxoethyl)cyclohexanecarboxylic acid, or
(2) rel-[(2R,6S)-4-(2-{9-[(5-chloro-2-thienyl)methyl]-1,3,4,9-tetrahydro-2H-beta-carbolin-2-yl}-2-oxoethyl)-2,6-dimethyl-1-piperazinyl]acetic acid.

[21] The compound according to the above mentioned [18], wherein the compound represented by the general formula (IV-2) is 4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methylbenzoic acid.

[22] The compound according to the above mentioned [19], wherein the compound represented by the general formula (IV-2) is:
(1) cis-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(2) trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(3) trans-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(4) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,
(5) 4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,
(6) 4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}bicyclo[2.2.2]octane-1-carboxylic acid,
(7) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,
(8) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,
(9) (1R,3R)-3-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,
(10) (1R,3R)-3-{2-[9-(4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,
(11) (1R,3R)-3-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,
(12) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,
(13) 4-{2-[9-(2,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,
(14) trans-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid,
(15) trans-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid,
(16) 2-methoxy-4-{2-oxo-2[9-(2,4,5-trifluorobenzyl)-5,6,8,9-tetrahydro-7H-pyrido[4',3':4,5]pyrrolo[2,3-b]pyridin-7-yl]ethyl}benzoic acid,
(17) 4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,
(18) 4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,
(19) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, or
(20) 4-{2[9-(3,5-difluorobenzyl)-5,6,8,9-tetrahydro-7H-pyrido[4',3':4,5]pyrrolo[2,3-b]pyridin-7-yl]-2-oxoethyl}-2-methoxybenzoic acid.

[23] The compound according to the above mentioned [19], wherein the compound represented by the general formula (V) is 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoic acid.

[24] A pharmaceutical composition containing the compound represented by the general formula (I) as defined in the above mentioned [1], a salt thereof or a solvate thereof or a prodrug thereof as an active ingredient.

[25] An agent for preventing or treating urinary excretion disorder and/or improving symptoms thereof, containing the compound represented by the general formula (I) as defined in the above mentioned [1], a salt thereof or a solvate thereof or a prodrug thereof as an active ingredient.

[26] An agent for preventing and/or treating cancer, interstitial pneumonia or pulmonary fibrosis, sclerodermia, pain, fibromyalgia or rheumatoid arthritis, containing the compound represented by the general formula (I) as defined in the above mentioned [1], a salt thereof or a solvate thereof or a prodrug thereof as an active ingredient.

[27] The agent according to the above mentioned [25], wherein the urinary excretion disorder is a urinary excretion disorder accompanied with prostatomegaly.

[28] The agent according to the above mentioned [25], wherein a urethra internal pressure is reduced.

[29] The agent according to the above mentioned [26], wherein the symptom accompanied with urinary excretion disorder is slowing of urinary stream, division of urinary stream, interruption of urinary stream, delayed urination, straining at urination and/or terminal dribbling.

[30] An ENPP2 inhibitor, containing the compound represented by the general formula (I) as defined in the above mentioned [1], a salt thereof or a solvate thereof or a prodrug thereof as an active ingredient.

[31] A urethra internal pressure lowering agent, containing the compound represented by the general formula (I) as defined in the above mentioned [1], a salt thereof or a solvate thereof or a prodrug thereof as an active ingredient.

[32] A medicament, comprising a combination of the compound represented by the general formula (I) as defined in the above mentioned [1], a salt thereof or a solvate thereof or a prodrug thereof, with an a1 blocker, a 5α-reductase inhibitor, an anti-androgen agent and/or an acetylcholinesterase inhibitor.

[33] A method of preventing or treating urinary excretion disorder and/or improving symptoms thereof, comprising administering an effective amount of the compound represented by the general formula (I) as defined in the above mentioned [1], a salt thereof or a solvate thereof or a prodrug thereof to a patient in need of prevention or treatment of urinary excretion disorder and/or improvement in symptoms thereof.

[34] The compound represented by the general formula (I) as defined in the above mentioned [1], a salt thereof or a solvate thereof or a prodrug thereof, for preventing or treating urinary excretion disorder and/or improving symptoms thereof.

Effect of the Invention

The present compound is an effective agent for preventing or treating urinary excretion disorder, particularly, a urinary excretion disorder accompanied with prostatomegaly and/or improving symptoms thereof.

DETAILED DESCRIPTION OF THE INVENTION

Figure 1:
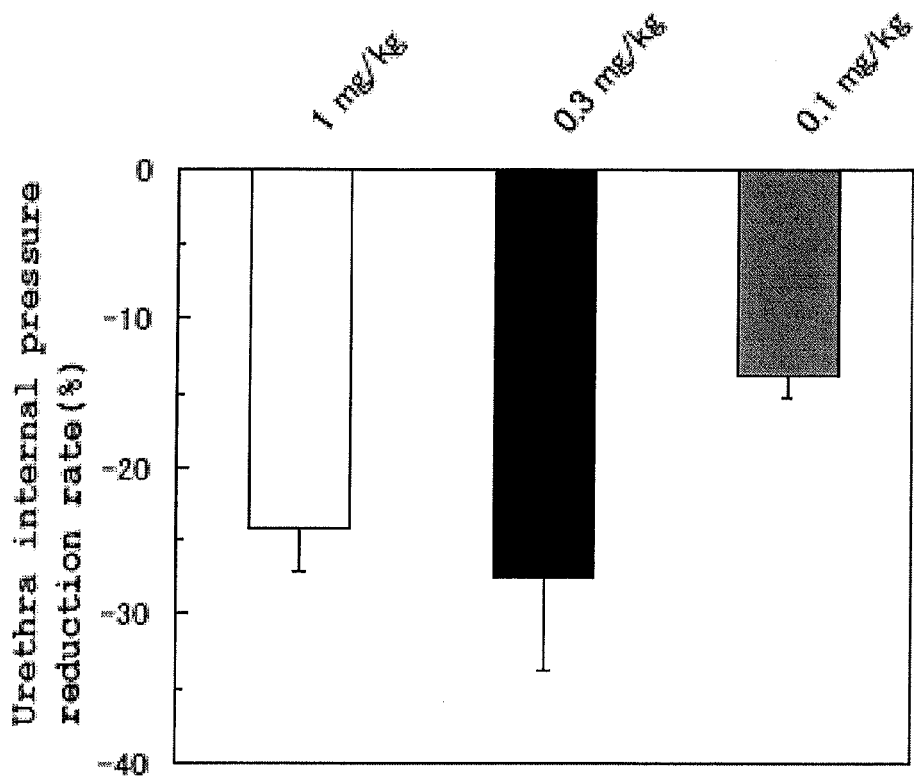
FIG. 1 shows the action (average±standard deviation (n=3 to 6)) of the present compound (compound described in Example 3) on a urethra internal pressure of a rat under urethane anesthesia.

The present invention will be explained in detail below.

In the present specification, examples of the halogen atom include a fluorine atom, a chlorine atom, a bromine atom and an iodine atom.

In the present specification, examples of the C1-3 alkyl group include a methyl group, an ethyl group, an n-propyl group and an isopropyl group.

In the present specification, examples of the C1-4 alkyl group include a methyl group, an ethyl group, an n-propyl group, an isopropyl group, an n-butyl group, an isobutyl group, a sec-butyl group and a tert-butyl group.

In the present specification, the C2-3 alkenylene group refers to an ethenylene group and a propenylene group.

In the present specification, the C2-4 alkenylene group refers to an ethenylene group, a propenylene group and a butenylene group.

In the present specification, the C2-3 alkynylene group refers to an ethynylene group and a propynylene group.

In the present specification, the C2-4 alkynylene group refers to an ethynylene group, a propynylene group and a butynylene group.

In the present specification, examples of the C1-3 alkoxy group include a methoxy group, an ethoxy group, an n-propoxy group, an isopropoxy group and the like.

In the present specification, examples of the C1-4 alkoxy group include a methoxy group, an ethoxy group, an n-propoxy group, an isopropoxy group, an n-butoxy group, an isobutoxy group, a sec-butoxy group, a tert-butoxy group and the like.

In the present specification, examples of the linear C1-3 alkylene group include a methylene group, an ethylene group and an n-propylene group.

In the present specification, examples of the linear C1-4 alkylene group include a methylene group, an ethylene group, an n-propylene group and an n-butylene group.

In the present specification, examples of the C1-3 haloalkyl group include a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group and the like.

In the present specification, examples of the C1-4 haloalkyl group include a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, a 4-bromobutyl and the like.

In the present specification, examples of the C1-3 haloalkoxy group include a trifluoromethoxy group, a trichloromethoxy group, a chloromethoxy group, a bromomethoxy group, a fluoromethoxy group, an iodomethoxy group, a difluoromethoxy group, a dibromomethoxy group, a 2-chloroethoxy group, a 2,2,2-trifluoroethoxy group, a 2,2,2-trichloroethoxy group, a 3-bromopropoxy group, a 3-chloropropoxy group, a 2,3-dichloropropoxy group and the like.

In the present specification, examples of the C1-4 haloalkoxy group include a trifluoromethoxy group, a trichloromethoxy group, a chloromethoxy group, a bromomethoxy group, a fluoromethoxy group, an iodomethoxy group, a difluoromethoxy group, a dibromomethoxy group, a 2-chloroethoxy group, a 2,2,2-trifluoroethoxy group, a 2,2,2-trichloroethoxy group, a 3-bromopropoxy group, a 3-chloropropoxy group, a 2,3-dichloropropoxy group, a 1-fluorobutoxy group, a 4-fluorobutoxy group, a 1-chlorobutoxy group and the like.

In the present specification, examples of the C1-3 alkylsulfonyl group include a methylsulfonyl group, an ethylsulfonyl group, a propylsulfonyl group and the like.

In the present specification, examples of the C3-5 cycloalkyl group include a cyclopropyl group, a cyclobutyl group and a cyclopentyl group.

In the present specification, examples of the "C3-7 monocyclic carbon ring" represented by the ring A include cyclopropane, cyclobutane, cyclopentane, cyclohexane, cyclobutene, cyclopentene, cyclohexene, cyclopentadiene, cyclohexadiene, benzene, cycloheptane, cycloheptene, cycloheptadiene and the like, examples of the "C5-6 monocyclic carbon ring" include cyclopentane, cyclohexane, cyclopentene, cyclohexene, cyclopentadiene, cyclohexadiene, benzene and the like, examples of the "C8-10 bicyclic carbon ring" include pentalene, perhydropentalene, indene, perhydroindene, indane, azulene, perhydroazulene, naphthalene, dihydronaphthalene, tetrahydronaphthalene, perhydronaphthalene and the like, and examples of the "C9-10 bicyclic carbon ring" include indene, perhydroindene, indane, azulene, perhydroazulene, naphthalene, dihydronaphthalene, tetrahydronaphthalene, perhydronaphthalene and the like.

Meanwhile, in the present specification, examples of the "4- to 7-membered monocyclic heterocyclic ring containing one to four heteroatoms selected from an oxygen atom, a nitrogen atom and a sulfur atom" represented by the ring A include azetidine, oxetane, thietane, pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolan, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like, and examples of the "5- to 6-membered monocyclic heterocyclic ring containing one to four heteroatoms selected from an oxygen atom, a nitrogen atom and a sulfur atom" include pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolan, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane and the like.

In the present specification, examples of the "8- to 10-membered bicyclic heterocyclic ring containing one to four heteroatoms selected from an oxygen atom, a nitrogen atom and a sulfur atom" represented by the ring A include thienopyrazole, thienoimidazole, pyrazolothiazole, indole, isoindole, indolizine, benzofuran, isobenzofuran, benzothiophene, isobenzothiophene, indazole, purine, benzoxazole, benzothiazole, benzoimidazole, imidazopyridine, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzoimidazole, perhydrobenzoimidazole, dioxaindane, benzodithiolane, dithianaphthalene, quinoline, isoquinoline, quinolizine, phthalazine, pteridine, naphthyridine, quinoxaline, quinazoline, cinnoline, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, benzodioxane, chromane, benzodithiane and the like, and examples of the "9- to 10-membered bicyclic heterocyclic ring containing one to four heteroatoms selected from an oxygen atom, a nitrogen atom and a sulfur atom" represented by the ring A include indole, isoindole, indolizine, benzofuran, isobenzofuran, benzothiophene, isobenzothiophene, indazole, purine, benzoxazole, benzothiazole, benzoimidazole, imidazopyridine, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzoimidazole, perhydrobenzoimidazole, dioxaindane, benzodithiolane, dithianaphthalene, quinoline, isoquinoline, quinolizine, phthalazine, pteridine, naphthyridine, quinoxaline, quinazoline, cinnoline, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, benzodioxane, chromane, benzodithiane and the like.

In the present specification, examples of the "3- to 7-membered monocycle" of the "3- to 7-membered monocycle optionally substituted with one to five $R^7$s" represented by U include cyclopropane, cyclobutane, cyclobutene, cyclobutadiene, oxirane, aziridine, thiirane, azetidine, oxetane, thietane, cyclopentane, cyclohexane, cyclopentene, cyclohexene, cyclopentadiene, cyclohexadiene, benzene, cycloheptane, cycloheptene, cycloheptadiene, pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolan, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the present specification, examples of the "5- to 7-membered monocycle" of the "5- to 7-membered monocycle optionally substituted with one to five $R^7$s" represented by $U^1$ include cyclopentane, cyclohexane, cyclopentene, cyclohexene, cyclopentadiene, cyclohexadiene, benzene, cycloheptane, cycloheptene, cycloheptadiene, pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolane, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the present specification, when the "3- to 7-membered monocycle" in the "3- to 7-membered monocycle optionally substituted with one to five $R^7$s" represented by U is a "C3-7 monocyclic carbon ring", examples of the "C3-7 monocyclic carbon ring" include cyclopropane, cyclobutane, cyclobutene, cyclobutadiene, cyclopentane, cyclohexane, cyclopentene, cyclohexene, cyclopentadiene, cyclohexadiene, benzene, cycloheptane, cycloheptene and cycloheptadiene, among which, examples of the C3-7 monocyclic aromatic carbon ring include benzene and examples of the "C3-7 monocyclic non-aromatic carbon ring" include cyclopropane, cyclobutane, cyclobutene, cyclobutadiene, cyclopentane, cyclohexane, cyclopentene, cyclohexene, cyclopentadiene, cyclohexadiene, cycloheptane, cycloheptene and cycloheptadiene.

In the present specification, when the "5- to 7-membered monocycle" in the "5- to 7-membered monocycle optionally substituted with one to five $R^7$s" represented by U or $U^1$ is a "C5-7 monocyclic carbon ring", examples of the "C5-7 monocyclic carbon ring" include cyclopentane, cyclohexane, cyclopentene, cyclohexene, cyclopentadiene, cyclohexadiene, benzene, cycloheptane, cycloheptene and cycloheptadiene, among which, example of the C5-7 monocyclic aromatic carbon ring include benzene and examples of the "C5-7 monocyclic non-aromatic carbon ring" include cyclopentane, cyclohexane, cyclopentene, cyclohexene, cyclopentadiene, cyclohexadiene, cycloheptane, cycloheptene and cycloheptadiene.

In the present specification, when the "3- to 7-membered monocycle" in the "3- to 7-membered monocycle optionally substituted with one to five $R^7$s" represented by U is a "3- to 7-membered monocyclic heterocyclic ring containing one to four heteroatoms selected from an oxygen atom, a nitrogen atom and a sulfur atom", examples of the "3- to 7-membered monocyclic heterocyclic ring containing one to four heteroatoms selected from an oxygen atom, a nitrogen atom and a sulfur atom" include oxirane, aziridine, thiirane, azetidine, oxetane, thietane, pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolan, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like, among which, examples of the "3- to 7-membered monocyclic aromatic heterocyclic ring containing one to four heteroatoms selected from an oxygen atom, a nitrogen atom and a sulfur atom" include pyrrole, imidazole, triazole, tetrazole, pyrazole, furan, thiophene, oxazole, isoxazole, thiazole, isothiazole, furazan, oxadiazole, thiadiazole, pyridine, pyrazine, pyrimidine and pyridazine, and examples of the "3- to 7-membered monocyclic non-aromatic heterocyclic ring" include oxirane, aziridine, thiirane, azetidine, oxetane, thietane, pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrothiadiazole, tetrahydrothiadiazole, dioxolane, dithiolane, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the present specification, when the "5- to 7-membered monocycle" in the "5- to 7-membered monocycle optionally substituted with one to five $R^7$s" represented by $U^1$ is a "5- to 7-membered monocyclic heterocyclic ring containing one to four heteroatoms selected from an oxygen atom, a nitrogen atom and a sulfur atom", examples of the "5- to 7-membered monocyclic heterocyclic ring containing one to four heteroatoms selected from an oxygen atom, a nitrogen atom and a sulfur atom" include pyrrole, oxazole, isoxazole, thiazole, isothiazole, pyrroline, pyrrolidine, dihydrooxazole, tetrahydrooxazole, dihydroisoxazole, tetrahydroisoxazole, dihydrothiazole, tetrahydrothiazole, dihydroisothiazole, tetrahydroisothiazole, imidazole, pyrazole, furazan, oxadiazole, thiadiazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, furan, dihydrofuran, tetrahydrofuran, dioxolan, thiophene, dihydrothiophene, tetrahydrothiophene, dithiolane, pyridine, oxazine, thiazine, dihydropyridine, tetrahydropyridine, piperidine, dihydrooxazine, tetrahydrooxazine, dihydrothiazine, tetrahydrothiazine, morpholine, thiomorpholine, pyrazine, pyrimidine, pyridazine, oxadiazine, thiadiazine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, pyran, dihydropyran, tetrahydropyran, oxathiane, dioxane, thiopyran, dihydrothiopyran, tetrahydrothiopyran, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like, among which, examples of the "5- to 7-membered monocyclic aromatic heterocyclic ring containing one to four heteroatoms selected from an oxygen atom, a nitrogen atom and a sulfur atom" include pyrrole, imidazole, triazole, tetrazole, pyrazole, furan, thiophene, oxazole, isoxazole, thiazole, isothiazole, furazan, oxadiazole, thiadiazole, pyridine, pyrazine, pyrimidine and pyridazine, and examples of the "5- to 7-membered monocyclic non-aromatic heterocyclic ring" include pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrothiadiazole, tetrahydrothiadiazole, dioxolane, dithiolane, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine and the like.

In the present specification, examples of the "C5-10 bridged carbon ring" in the "C5-10 bridged carbon ring optionally substituted with one to five $R^7$s" represented by U or $U^1$ include bicyclo[1.1.1]pentane, bicyclo[2.1.1]hexane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[3.2.1]octane, bicyclo[2.2.2]oct-2-ene, bicyclo[3.3.1]nonane, bicyclo[3.2.2]nonane, adamantane, noradamantane and the like.

In the present specification, examples of the "5- to 10-membered bridged heterocyclic ring" in the "5- to 10-membered bridged heterocyclic ring optionally substituted with one to five $R^7$s" represented by U or $U^1$ include azabicyclo[2.1.1]hexane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

In the present specification, the "5- to 7-membered monocycle" represented by the ring $A^S$ is as defined in the "5- to 7-membered monocycle" represented by $U^1$.

In the present specification, examples of the "optionally oxidized sulfur atom" represented by Z include a sulfur atom, —SO— or —SO$_2$—.

In the present invention, the ring A is preferably (i) a C3-6 monocyclic carbon ring or (ii) a 4- to 6-membered monocyclic heterocyclic ring containing one to four heteroatoms selected from an oxygen atom, a nitrogen atom and a sulfur atom, more preferably (i) a C5-6 monocyclic carbon ring or (ii) a 5- to 6-membered monocyclic heterocyclic ring containing one to four heteroatoms selected from an oxygen atom, a nitrogen atom and a sulfur atom, further preferably cycloheptane, cyclohexane, cyclohexene or benzene, or thiophene, furan, pyrazole, isooxazole, thiazole or pyridine, and most preferably cyclohexane, benzene, thiophene, pyridine, thiazole or pyrazole.

In the present invention, $R^1$ is preferably a halogen atom, a C1-3 haloalkyl group or a C1-3 haloalkoxy group, and more preferably a halogen atom or a C1-3 haloalkyl group.

In the present invention, Z is preferably a methylene group.

In the present invention, W is preferably a bond when Z is a methylene group, and W is a methylene group or an ethylene group when Z is an oxygen atom or an optionally oxidized sulfur atom.

In the present invention, the "5- to 7-membered monocycle" in the "5- to 7-membered monocycle optionally substituted with one to five $R^7$s (in the group, $R^7$ is as defined above)" represented by $U^1$ is preferably a C5-7 monocyclic carbon ring and a 5- to 7-membered monocyclic non-aromatic heterocyclic ring, more preferably benzene, cyclohexane, cyclopentane, pyrrolidine, piperazine and piperidine, and further preferably benzene, cyclopentane or cyclohexane. The "C5-10 bridged carbon ring" in the "C5-10 bridged carbon ring optionally substituted with one to five $R^7$s" represented by U or $U^1$ is preferably bicyclo[2.2.1]heptane or bicyclo[2.2.2]octane.

In the present invention, Y is preferably a straight C1-3 alkylene group optionally substituted with one or two $R^8$s (in the group, $R^8$ is as defined above), more preferably a methylene group or an ethylene group, optionally substituted with one or two $R^8$s (in the groups, $R^8$ is as defined above), and further preferably an unsubstituted methylene group.

In the present invention, when U is a 3- to 7-membered monocycle, a C5-10 bridged carbon ring or a 5- to 10-membered bridged heterocyclic ring, optionally substituted with one to five $R^7$s (in the groups, $R^7$ is as defined above), a compound in which Y is a methylene group or an ethylene group, optionally substituted with one or two $R^8$s (in the groups, $R^8$ is as defined above) and T is a bond, or a methylene group or an ethylene group, optionally substituted with one or two $R^5$s (in the groups, $R^5$ is as defined above) is preferable, a compound in which Y is an unsubstituted methylene group and T is a bond or an unsubstituted methylene group is more preferable, and a compound in which Y is an unsubstituted methylene group, and T is a bond is further preferable.

In the present invention, when U is a methylene group, an oxygen atom or —$NR^6$— (in the group, $R^6$ is as defined above), a compound in which Y is an unsubstituted methylene group and T is an ethylene group optionally substituted with one or two $R^5$s (in the group, $R^5$ is as defined above) is preferable.

In the present invention, the compound represented by the general formula (I) is preferably a compound represented by the general formula (II):

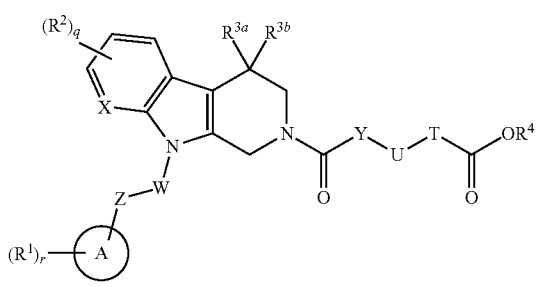

(II)

(wherein all symbols are as defined above), more preferably a compound represented by the general formula (III):

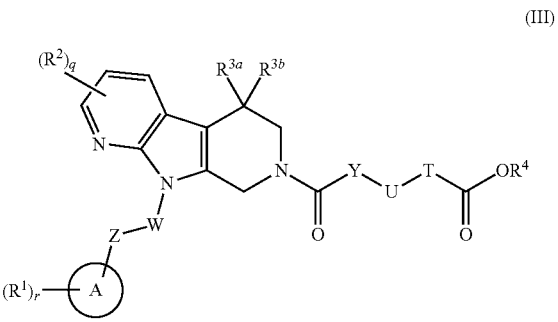

(III)

(wherein all symbols are as defined above) or a compound represented by the general formula (III-1):

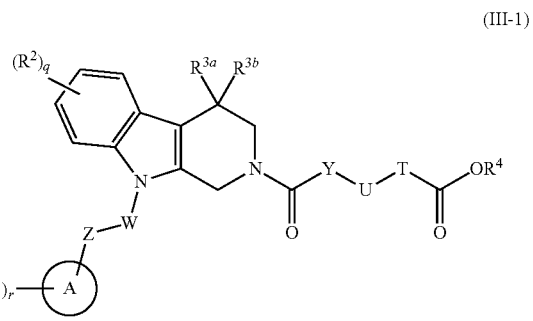

(III-1)

(wherein all symbols are as defined above), and further preferably a compound represented by the general formula (IV):

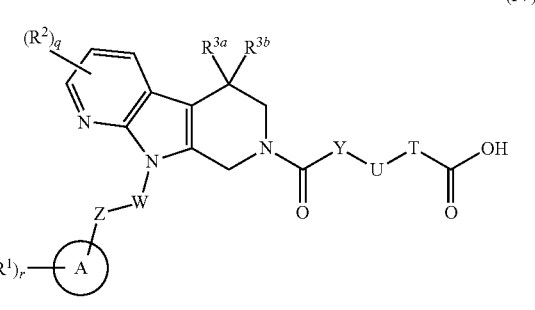

(IV)

(wherein all symbols are as defined above) or a compound represented by the general formula (IV-1):

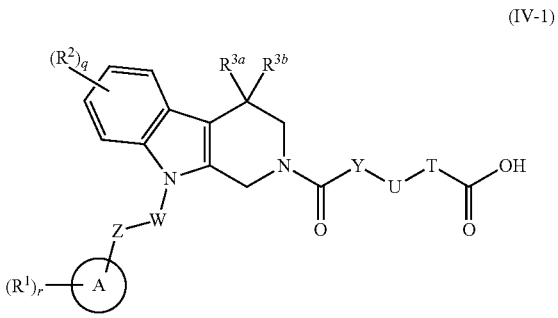

(IV-1)

(wherein all symbols are as defined above).

Herein, of the compound represented by the general formula (IV), when U is a 5- to 7-membered monocycle or a C5-10 bridged carbon ring, optionally substituted with one to five R⁷s (in the groups, R⁷ is as defined above), a compound represented by the general formula (IV-2):

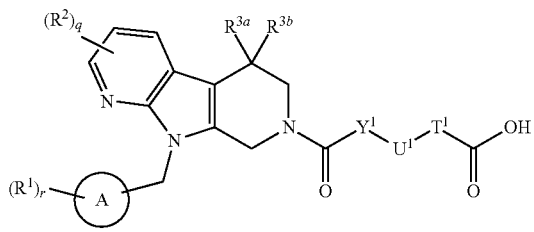

(IV-2)

(wherein U¹ represents a 5- to 7-membered monocycle or a C5-10 bridged carbon ring, optionally substituted with one to five R⁷s (in the groups, R⁷ is as defined above), Y¹ represents a methylene group or an ethylene group, optionally substituted with one or two R⁸s, T¹ represents a bond, or a methylene group or an ethylene group, optionally substituted with one or two R⁵s, and other symbols are as defined above) is preferable, a compound in which Y¹ is an unsubstituted methylene group and T¹ is a bond or an unsubstituted methylene group in the general formula (IV-2) is more preferable, and a compound in which Y¹ is an unsubstituted methylene group and T¹ is a bond is further preferable.

Similarly, of the compound represented by the general formula (IV-1), when U is a 5- to 7-membered monocycle or a C5-10 bridged carbon ring, optionally substituted with one to five R⁷s (in the groups, R⁷ is as defined above), a compound represented by the general formula (IV-3):

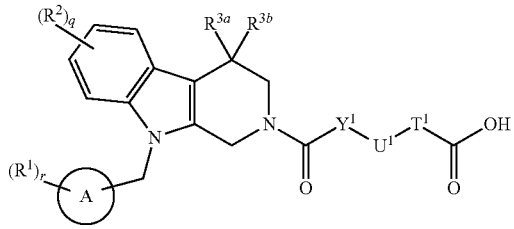

(IV-3)

(wherein all symbols are as defined above) is preferable, a compound in which Y¹ represents an unsubstituted methylene group and T¹ is a bond or an unsubstituted methylene group in the general formula (IV-3) is more preferable, and a compound in which Y¹ represents an unsubstituted methylene group and T¹ is a bond is further preferable.

Of the compound represented by the general formula (IV), a compound in which U is a methylene group, an oxygen atom or —NR⁶— (in the group, R⁶ is as defined above) is preferably a compound represented by the general formula (V):

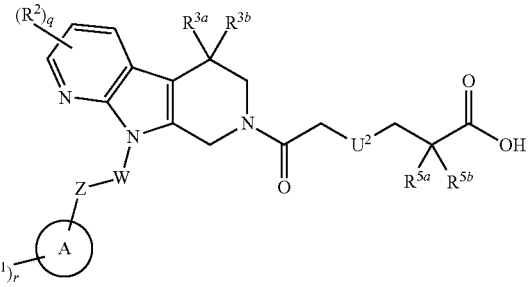

(V)

(wherein U² represents a methylene group, an oxygen atom or —NR⁶—, R⁵ᵃ and R⁵ᵇ each represent independently a hydrogen atom or a methyl group, and other symbols are as defined above), and more preferably a compound represented by the general formula (VI):

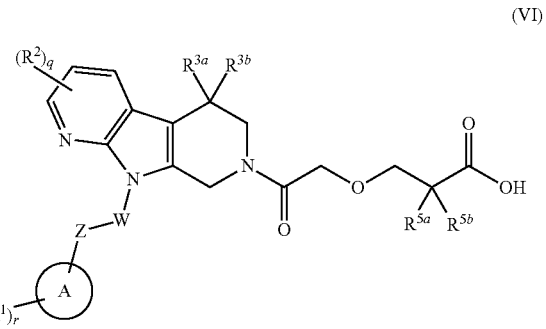

(VI)

(wherein all symbols are as defined above).

Of the present compound, a compound in which U is a C3-7 monocyclic carbon ring or a C5-10 bridged carbon ring, optionally substituted with one to five R⁷s (in the groups, R⁷ is as defined above), the ring A is a C3-6 monocyclic carbon ring or a C8-10 bicyclic carbon ring, and X is a nitrogen atom is preferably:

(1) cis-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid, (2) trans-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid, (3) (cis-4-{[9-(3-fluorobenzyl)-5,6,8,9-tetrahydro-7H-pyrido[4',3':4,5]pyrrolo[2,3-b]pyridin-7-yl]carbonyl}cyclohexyl)acetic acid, (4) (trans-4-{[9-(3-fluorobenzyl)-5,6,8,9-tetrahydro-7H-pyrido[4',3':4,5]pyrrolo[2,3-b]pyridin-7-yl]carbonyl}cyclohexyl)acetic acid, (5) 3-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid, (6) 4-{[9-(3-fluorobenzyl)-5,6,8,9-tetrahydro-7H-pyrido[4',3':4,5]pyrrolo[2,3-b]pyridin-7-yl]carbonyl}benzoic acid, (7) 4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid, (8) cis-4-{2-[9-(4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid, (9) cis-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(10) cis-4-{2-oxo-2-[9-(3,4,5-trifluorobenzyl)-5,6,8,9-tetrahydro-7H-pyrido[4',3':4,5]pyrrolo[2,3-b]pyridin-7-yl]ethyl}cyclohexanecarboxylic acid,
(11) cis-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(12) cis-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid,
(13) cis-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(15) cis-4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(16) cis-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(19) cis-4-{2-[9-(3,5-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(22) trans-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid,
(23) trans-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(25) trans-4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(26) trans-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(29) trans-4-{2-[9-(3,5-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(30) trans-4-{2-[9-(4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(31) trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(32) trans-4-{2-oxo-2-[9-(3,4,5-trifluorobenzyl)-5,6,8,9-tetrahydro-7H-pyrido[4',3':4,5]pyrrolo[2,3-b]pyridin-7-yl]ethyl}cyclohexanecarboxylic acid,
(33) trans-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(36) cis-4-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethyl}cyclohexanecarboxylic acid,
(37) trans-4-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethyl}cyclohexanecarboxylic acid,
(38) trans-4-{2-[9-(4-cyanobenzyl)-5,5-dimethyl-5,6,8,9-tetrahydro-7H-pyrido[4',3':4,5]pyrrolo[2,3-b]pyridin-7-yl]-2-oxoethyl}cyclohexanecarboxylic acid,
(39) trans-4-{2-[9-(3,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(40) trans-4-{2-oxo-2-[9-(2,3,4-trifluorobenzyl)-5,6,8,9-tetrahydro-7H-pyrido[4',3':4,5]pyrrolo[2,3-b]pyridin-7-yl]ethyl}cyclohexanecarboxylic acid,
(41) trans-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(43) 4-{2-[9-(4-cyanobenzyl)-5,6,8,9-tetrahydro-7H-pyrido[4',3':4,5]pyrrolo[2,3-b]pyridin-7-yl]-2-oxoethyl}benzoic acid,
(44) cis-4-{2-[9-(3,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(45) cis-4-{2-oxo-2-[9-(2,3,4-trifluorobenzyl)-5,6,8,9-tetrahydro-7H-pyrido[4',3':4,5]pyrrolo[2,3-b]pyridin-7-yl]ethyl}cyclohexanecarboxylic acid,
(46) cis-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(47) cis-4-{2-[9-(3,4-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid,
(48) trans-4-{2-[9-(3,5-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(49) trans-4-{2-[9-(3-chloro-5-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(50) cis-4-{2-[9-(3,5-difluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(51) cis-4-{2-[9-(3-chloro-5-fluorobenzyl)-5,6,8,9-tetrahydro-7H-pyrido[4',3':4,5]pyrrolo[2,3-b]pyridin-7-yl]-2-oxoethyl}cyclohexanecarboxylic acid,
(57) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-ethoxybenzoic acid,
(58) 2-ethoxy-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid,
(59) (3-{2-[9-(3-fluorobenzyl)-5,6,8,9-tetrahydro-7H-pyrido[4',3':4,5]pyrrolo[2,3-b]pyridin-7-yl]-2-oxoethyl}phenyl)acetic acid,
(60) (3-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)acetic acid,
(61) 4-{3-[9-(3-fluorobenzyl)-5,6,8,9-tetrahydro-7H-pyrido[4',3':4,5]pyrrolo[2,3-b]pyridin-7-yl]-3-oxopropyl}benzoic acid,
(62) 4-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid,
(63) 3-{3-[9-(3-fluorobenzyl)-5,6,8,9-tetrahydro-7H-pyrido[4',3':4,5]pyrrolo[2,3-b]pyridin-7-yl]-3-oxopropyl}benzoic acid,
(64) 3-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid,
(65) 2-chloro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid,
(66) 3-fluoro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid,
(67) 3-chloro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid,
(68) 2-{3-[9-(3-fluorobenzyl)-5,6,8,9-tetrahydro-7H-pyrido[4',3':4,5]pyrrolo[2,3-b]pyridin-7-yl]-3-oxopropyl}benzoic acid,

(69) 2-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid,
(70) 2-chloro-4-{2-[9-(2,4-difluorobenzyl)-5,6,8,9-tetrahydro-7H-pyrido[4',3':4,5]pyrrolo[2,3-b]pyridin-7-yl]-2-oxoethyl}carboxylic acid,
(71) 2-fluoro-4-{2-[9-(3-fluorobenzyl)-5,6,8,9-tetrahydro-7H-pyrido[4',3':4,5]pyrrolo[2,3-b]pyridin-7-yl]-2-oxoethyl}carboxylic acid,
(72) 4-{2-[9-(3-fluorobenzyl)-5,6,8,9-tetrahydro-7H-pyrido[4',3':4,5]pyrrolo[2,3-b]pyridin-7-yl]-2-oxoethyl}-3-methylcarboxylic acid,
(73) 4-{2-[9-(2-cyclohexylethyl)-5,6,8,9-tetrahydro-7H-pyrido[4',3':4,5]pyrrolo[2,3-b]pyridin-7-yl]-2-oxoethyl}benzoic acid,
(74) 4-{2-[9-(3-fluorobenzyl)-5,6,8,9-tetrahydro-7H-pyrido[4',3':4,5]pyrrolo[2,3-b]pyridin-7-yl]-2-oxoethyl}-2-methoxybenzoic acid,
(75) 4-{2-[9-(3-fluorobenzyl)-5,6,8,9-tetrahydro-7H-pyrido[4',3':4,5]pyrrolo[2,3-b]pyridin-7-yl]-2-oxoethyl}-3-methoxybenzoic acid,
(76) (4-{2-[9-(3-fluorobenzyl)-5,6,8,9-tetrahydro-7H-pyrido[4',3':4,5]pyrrolo[2,3-b]pyridin-7-yl]-2-oxoethyl}phenyl)acetic acid,
(77) (4-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)acetic acid,
(78) 4-{2-[9-(3-fluorobenzyl)-5,6,8,9-tetrahydro-7H-pyrido[4',3':4,5]pyrrolo[2,3-b]pyridin-7-yl]-2-oxoethyl}-2-methylbenzoic acid,
(79) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-fluorobenzoic acid,
(80) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-methoxybenzoic acid,
(81) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-3-methoxybenzoic acid,
(82) (2-{2-[9-(3-fluorobenzyl)-5,6,8,9-tetrahydro-7H-pyrido[4',3':4,5]pyrrolo[2,3-b]pyridin-7-yl]-2-oxoethyl}phenyl)acetic acid,
(83) (2-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)acetic acid,
(84) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-3-methoxybenzoic acid,
(85) 2-(4-{2-[9-(3-fluorobenzyl)-5,6,8,9-tetrahydro-7H-pyrido[4',3':4,5]pyrrolo[2,3-b]pyridin-7-yl]-2-oxoethyl}phenyl)-2-methylpropanoic acid,
(86) 2-(4-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)-2-methylpropanoic acid,
(87) 4-{2-[9-(3-fluorobenzyl)-5,6,8,9-tetrahydro-7H-pyrido[4',3':4,5]pyrrolo[2,3-b]pyridin-7-yl]-2-oxoethyl}-2-hydroxybenzoic acid,
(88) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-hydroxybenzoic acid,
(89) 2-(benzyloxy)-4-{2-[9-(2,4-difluorobenzyl)-5,6,8,9-tetrahydro-7H-pyrido[4',3':4,5]pyrrolo[2,3-b]pyridin-7-yl]-2-oxoethyl}benzoic acid,
(90) 4-{2-[9-(3,5-difluorobenzyl)-5,6,8,9-tetrahydro-7H-pyrido[4',3':4,5]pyrrolo[2,3-b]pyridin-7-yl]-2-oxoethyl}-2-methoxybenzoic acid,
(91) 2-methoxy-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid,
(92) 4-{2-[9-(4-fluorobenzyl)-5,6,8,9-tetrahydro-7H-pyrido[4',3':4,5]pyrrolo[2,3-b]pyridin-7-yl]-2-oxoethyl}-2-methoxybenzoic acid,
(93) 4-{2-[9-(4-chlorobenzyl)-5,6,8,9-tetrahydro-7H-pyrido[4',3':4,5]pyrrolo[2,3-b]pyridin-7-yl]-2-oxoethyl}-2-methoxybenzoic acid,
(94) 4-{2-[9-(3-chlorobenzyl)-5,6,8,9-tetrahydro-7H-pyrido[4',3':4,5]pyrrolo[2,3-b]pyridin-7-yl]-2-oxoethyl}-2-methoxybenzoic acid,
(95) 4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2-methoxybenzoic acid,
(97) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2-methoxybenzoic acid,
(98) 4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2-methoxybenzoic acid,
(101) 4-{2-[9-(4-chlorobenzyl)-5,6,8,9-tetrahydro-7H-pyrido[4',3':4,5]pyrrolo[2,3-b]pyridin-7-yl]-2-oxoethyl}-2-methylbenzoic acid,
(102) 4-{2-[9-(3-chlorobenzyl)-5,6,8,9-tetrahydro-7H-pyrido[4',3':4,5]pyrrolo[2,3-b]pyridin-7-yl]-2-oxoethyl}-2-methylbenzoic acid,
(103) 4-{2-[9-(3,5-difluorobenzyl)-5,6,8,9-tetrahydro-7H-pyrido[4',3':4,5]pyrrolo[2,3-b]pyridin-7-yl]-2-oxoethyl}-2-methylbenzoic acid,
(104) 2-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid,
(105) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2-methylbenzoic acid,
(106) 4-{2-[9-(3,4-difluorobenzyl)-5,6,8,9-tetrahydro-7H-pyrido[4',3':4,5]pyrrolo[2,3-b]pyridin-7-yl]-2-oxoethyl}-2-methoxybenzoic acid,
(111) 4-{2-[9-(4-fluorobenzyl)-5,6,8,9-tetrahydro-7H-pyrido[4',3':4,5]pyrrolo[2,3-b]pyridin-7-yl]-2-oxoethyl}-2-methylbenzoic acid,
(112) 4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2-methylbenzoic acid,
(113) 4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2-methylbenzoic acid,
(114) 4-{2-[9-(3,4-difluorobenzyl)-5,6,8,9-tetrahydro-7H-pyrido[4',3':4,5]pyrrolo[2,3-b]pyridin-7-yl]-2-oxoethyl}-2-methylbenzoic acid,
(118) 4-{2-[9-(4-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid,
(119) 4-{2-[9-(4-chlorobenzyl)-5,6,8,9-tetrahydro-7H-pyrido[4',3':4,5]pyrrolo[2,3-b]pyridin-7-yl]-2-oxoethyl}-2,6-dimethoxybenzoic acid,
(120) 4-{2-[9-(2,4-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid,
(125) 4-{2-[9-(3-chlorobenzyl)-5,6,8,9-tetrahydro-7H-pyrido[4',3':4,5]pyrrolo[2,3-b]pyridin-7-yl]-2-oxoethyl}-2,6-dimethoxybenzoic acid,
(126) 4-{2-[9-(3,5-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (127) 2,6-dimethoxy-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid, (128) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (129) 4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (130) 4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (132) 4-{2-[9-(3,4-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (133) 4-{2-[9-(3-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid, (134) cis-3-{2-[9-(3-fluorobenzyl)-5,6,8,9-tetrahydro-7H-pyrido[4',3':4,5]pyrrolo[2,3-b]pyridin-7-yl]-2-oxoethyl}cyclobutanecarboxylic acid, (135) cis-3-{2-[9-(2,4-difluorobenzyl)-5,6,8,9-tetrahydro-7H-pyrido[4',3':4,5]pyrrolo[2,3-b]pyridin-7-yl]-2-oxoethyl}cyclobutanecarboxylic acid, (136) trans-3-{2-[9-(3-fluorobenzyl)-5,6,8,9-tetrahydro-7H-pyrido[4',3':4,5]pyrrolo[2,3-b]pyridin-7-yl]-2-oxoethyl}cyclobutanecarboxylic acid, (137) trans-3-{2-[9-(2,4-difluorobenzyl)-5,6,8,9-tetrahydro-7H-pyrido[4',3':4,5]pyrrolo[2,3-b]pyridin-7-yl]-2-oxoethyl}cyclobutanecarboxylic acid, (138) 4-{(1E)-3-[9-(3-fluorobenzyl)-5,6,8,9-tetrahydro-7H-pyrido[4',3':4,5]pyrrolo[2,3-b]pyridin-7-yl]-3-oxo-1-propen-1-yl}benzoic acid, (139) cis-4-{2-[9-(3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (140) cis-4-{2-[9-(2,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (141) trans-4-{2-[9-(3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (142) trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (143) trans-1-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid, (144) trans-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (145) trans-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (146) trans-4-{2-[9-(3-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (148) trans-4-{2-[9-(3,5-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (149) trans-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (150) trans-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (151) trans-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (153) cis-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (154) cis-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (155) cis-4-{2-[9-(3-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (156) cis-4-{2-[9-(3,5-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (157) cis-1-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid, (158) cis-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (159) cis-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (160) cis-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (163) cis-4-{2-[9-(3,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (169) trans-4-{2-[9-(3,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid, (171) (1R,3R)-3-{2-[9-(3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (172) (1R,3R)-3-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (173) (1S ,3S)-3-{2-[9-(3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (174) (1R,3R)-3-{2-[9-(3,5-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (176) (1R,3R)-3-{2-[9-(4-chlorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (177) (1R,3R)-3-{2-[9-(3-chlorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (178) (1R,3R)-3-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (179) (1R,3R)-3-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (180) (1R,3R)-3-{2-[9-(4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (181) (1R,3R)-3-{2-[9-(3,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (184) (1R,3R)-1,2,2-trimethyl-3-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclopentanecarboxylic acid, (187) (1R,3R)-3-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (188) (1S,3S)-3-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid, (189) 4-{2-[9-(2,4-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (190) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (191) 4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (192) 4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}bicyclo[2.2.2]octane-1-carboxylic acid, (193) 4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (194) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (195) 4-{2-[9-(3-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (196) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (197) 4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (201) 4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (202) 4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (205) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, (206) 4-{2-[9-(2,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, (207) 4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, or (208) 4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid, a salt thereof or a solvate thereof or a prodrug thereof.

Of the present compound, a compound in which U is a 3- to 7-membered monocyclic heterocyclic ring containing one to four heteroatoms selected from an oxygen atom, a nitrogen atom and a sulfur atom, and optionally substituted with one to five $R^7$s (in the group, $R^7$ is as defined above), the ring A is a C3-6 monocyclic carbon ring or a C8-10 bicyclic carbon ring, and X is a nitrogen atom is preferably:

(1) 1-{2-[9-(3-fluorobenzyl)-5,6,8,9-tetrahydro-7H-pyrido[4',3':4,5]pyrrolo[2,3-b]pyridin-7-yl]-2-oxoethyl}-1H-pyrazole-4-carboxylic acid, (2) 1-{2-[9-(3-fluorobenzyl)-5,6,8,9-tetrahydro-7H-pyrido[4',3':4,5]pyrrolo[2,3-b]pyridin-7-yl]-2-oxoethyl}-5-methyl-1H-imidazole-4-carboxylic acid, (3) 1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazole-4-carboxylic acid, (4) 3-(1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazol-4-yl)propanoic acid, (5) (1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazol-4-yl)acetic acid, (6) 1-{2-[9-(3-fluorobenzyl)-5,6,8,9-tetrahydro-7H-pyrido[4',3':4,5]pyrrolo[2,3-b]pyridin-7-yl]-2-oxoethyl}-2-piperidinecarboxylic acid, (7) 1-{2-[9-(3-fluorobenzyl)-5,6,8,9-tetrahydro-7H-pyrido[4',3':4,5]pyrrolo[2,3-b]pyridin-7-yl]-2-oxoethyl}-3-piperidinecarboxylic acid, (8) (3-{2-[9-(3-fluorobenzyl)-5,6,8,9-tetrahydro-7H-pyrido[4',3':4,5]pyrrolo[2,3-b]pyridin-7-yl]-2-oxoethyl}-2-oxo-1-imidazolidinyl)acetic acid, (9) 1-{3-[9-(3-fluorobenzyl)-5,6,8,9-tetrahydro-7H-pyrido[4',3':4,5]pyrrolo[2,3-b]pyridin-7-yl]-3-oxopropyl}-3-piperidinecarboxylic acid,

(10) (4-{3-[9-(3-fluorobenzyl)-5,6,8,9-tetrahydro-7H-pyrido[4',3':4,5]pyrrolo[2,3-b]pyridin-7-yl]-3-oxopropyl}-1H-1,2,3-triazol-1-yl)acetic acid,

(11) (1-{3-[9-(3-fluorobenzyl)-5,6,8,9-tetrahydro-7H-pyrido[4',3':4,5]pyrrolo[2,3-b]pyridin-7-yl]-3-oxopropyl}-3-pyrrolidinyl)acetic acid,

(12) (4-{3-[9-(3-fluorobenzyl)-5,6,8,9-tetrahydro-7H-pyrido[4',3':4,5]pyrrolo[2,3-b]pyridin-7-yl]-3-oxopropyl}-1-piperazinyl)acetic acid,

(13) 1-{3-[9-(3-fluorobenzyl)-5,6,8,9-tetrahydro-7H-pyrido[4',3':4,5]pyrrolo[2,3-b]pyridin-7-yl]-3-oxopropyl}-1,2,3,6-tetrahydro-4-pyridinecarboxylic acid,

(14) (1-{2-[9-(3-fluorobenzyl)-5,6,8,9-tetrahydro-7H-pyrido[4',3':4,5]pyrrolo[2,3-b]pyridin-7-yl]-2-oxoethyl}-3-pyrrolidinyl)acetic acid,

(15) (1-{2-[9-(3-fluorobenzyl)-5,6,8,9-tetrahydro-7H-pyrido[4',3':4,5]pyrrolo[2,3-b]pyridin-7-yl]-2-oxoethyl}-4-piperidinyl)acetic acid,

(16) (4-{2-[9-(3-fluorobenzyl)-5,6,8,9-tetrahydro-7H-pyrido[4',3':4,5]pyrrolo[2,3-b]pyridin-7-yl]-2-oxoethyl}-1-piperazinyl)acetic acid,

(17) 1-{2-[9-(3-fluorobenzyl)-5,6,8,9-tetrahydro-7H-pyrido[4',3':4,5]pyrrolo[2,3-b]pyridin-7-yl]-2-oxoethyl}-3-pyrrolidinecarboxylic acid,

(18) (1-{2-[9-(3-fluorobenzyl)-5,6,8,9-tetrahydro-7H-pyrido[4',3':4,5]pyrrolo[2,3-b]pyridin-7-yl]-2-oxoethyl}-2-pyrrolidinyl)acetic acid,

(19) (2S)-1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinecarboxylic acid,

(20) 1-{3-[9-(3-fluorobenzyl)-5,6,8,9-tetrahydro-7H-pyrido[4',3':4,5]pyrrolo[2,3-b]pyridin-7-yl]-3-oxopropyl}-4-piperidinecarboxylic acid,

(21) 1-{2-[9-(4-chloro-2-fluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid,

(23) (2R)-1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinecarboxylic acid,

(24) (1-{3-[9-(3-fluorobenzyl)-5,6,8,9-tetrahydro-7H-pyrido[4',3':4,5]pyrrolo[2,3-b]pyridin-7-yl]-3-oxopropyl}-4-piperidinyl)acetic acid,

(25) (1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinyl)acetic acid,
(26) 1-{3-[9-(3-fluorobenzyl)-5,6,8,9-tetrahydro-7H-pyrido[4',3':4,5]pyrrolo[2,3-b]pyridin-7-yl]-3-oxopropyl}-3-pyrrolidinecarboxylic acid,
(27) 1-{3-[9-(3-fluorobenzyl)-5,6,8,9-tetrahydro-7H-pyrido[4',3':4,5]pyrrolo[2,3-b]pyridin-7-yl]-3-oxopropyl}-2-piperidinecarboxylic acid,
(28) (1-{2-[9-(4-chloro-2-fluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinyl)acetic acid,
(30) (4-{2-[9-(4-chloro-2-fluorobenzyl)-5,5-dimethyl-5,6,8,9-tetrahydro-7H-pyrido[4',3':4,5]pyrrolo[2,3-b]pyridin-7-yl]-2-oxoethyl}-1-piperidinyl)acetic acid,
(32) (4-{[9-(3-fluorobenzyl)-5,6,8,9-tetrahydro-7H-pyrido[4',3':4,5]pyrrolo[2,3-b]pyridin-7-yl]carbonyl}-1-piperidinyl)acetic acid,
(33) (4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-1-piperazinyl)acetic acid,
(35) (4-{2-[9-(3,5-dichlorobenzyl)-5,6,8,9-tetrahydro-7H-pyrido[4',3':4,5]pyrrolo[2,3-b]pyridin-7-yl]-2-oxoethyl}-1-piperazinyl)acetic acid,
(38) 1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-4-piperidinecarboxylic acid,
(40) 1-{2-[9-(3,5-dichlorobenzyl)-5,6,8,9-tetrahydro-7H-pyrido[4',3':4,5]pyrrolo[2,3-b]pyridin-7-yl]-2-oxoethyl}-4-piperidinecarboxylic acid,
(43) 1-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid,
(44) 1-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid,
(46) (1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-4-piperidinyl)acetic acid,
(48) (1-{2-[9-(3,5-dichlorobenzyl)-5,6,8,9-tetrahydro-7H-pyrido[4',3':4,5]pyrrolo[2,3-b]pyridin-7-yl]-2-oxoethyl}-4-piperidinyl)acetic acid,
(52) (4-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethyl}-1-piperazinyl)acetic acid,
(54) (4-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-1-piperazinyl)acetic acid,
(57) (1-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinyl)acetic acid,
(58) (1-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-4-piperidinyl)acetic acid,
(61) 1-{2-[9-(3-fluorobenzyl)-5,6,8,9-tetrahydro-7H-pyrido[4',3':4,5]pyrrolo[2,3-b]pyridin-7-yl]-2-oxoethyl}-4-methyl-4-piperidinecarboxylic acid,
(62) 1-{2-[9-(2,4-difluorobenzyl)-5,6,8,9-tetrahydro-7H-pyrido[4',3':4,5]pyrrolo[2,3-b]pyridin-7-yl]-2-oxoethyl}-4-methyl-4-piperidinecarboxylic acid,
(63) 1-{2-[9-(3-fluorobenzyl)-5,6,8,9-tetrahydro-7H-pyrido[4',3':4,5]pyrrolo[2,3-b]pyridin-7-yl]-2-oxoethyl}-4-hydroxy-4-piperidinecarboxylic acid,
(64) 1-{2-[9-(2,4-difluorobenzyl)-5,6,8,9-tetrahydro-7H-pyrido[4',3':4,5]pyrrolo[2,3-b]pyridin-7-yl]-2-oxoethyl}-4-hydroxy-4-piperidinecarboxylic acid,
(65) 1-{2-[9-(3-fluorobenzyl)-5,6,8,9-tetrahydro-7H-pyrido[4',3':4,5]pyrrolo[2,3-b]pyridin-7-yl]-2-oxoethyl}-4-methoxy-4-piperidinecarboxylic acid,
(66) 1-{2-[9-(2,4-difluorobenzyl)-5,6,8,9-tetrahydro-7H-pyrido[4',3':4,5]pyrrolo[2,3-b]pyridin-7-yl]-2-oxoethyl}-4-methoxy-4-piperidinecarboxylic acid,
(67) rel-[(2R,6S)-4-{2-[9-(3-fluorobenzyl)-5,6,8,9-tetrahydro-7H-pyrido[4',3':4,5]pyrrolo[2,3-b]pyridin-7-yl]-2-oxoethyl}-2,6-dimethyl-1-piperazinyl]acetic acid,
(68) rel-[(2R,6S)-4-{2-[9-(2,4-difluorobenzyl)-5,6,8,9-tetrahydro-7H-pyrido[4',3':4,5]pyrrolo[2,3-b]pyridin-7-yl]-2-oxoethyl}-2,6-dimethyl-1-piperazinyl]acetic acid,
(69) rel-[(3R,5S)-4-{2-[9-(3-fluorobenzyl)-5,6,8,9-tetrahydro-7H-pyrido[4',3':4,5]pyrrolo[2,3-b]pyridin-7-yl]-2-oxoethyl}-3,5-dimethyl-1-piperazinyl]acetic acid,
(70) rel-[(3R,5S)-4-{2-[9-(2,4-difluorobenzyl)-5,6,8,9-tetrahydro-7H-pyrido[4',3':4,5]pyrrolo[2,3-b]pyridin-7-yl]-2-oxoethyl}-3,5-dimethyl-1-piperazinyl]acetic acid,
(71) 1-{2-[9-(3-fluorobenzyl)-5,6,8,9-tetrahydro-7H-pyrido[4',3':4,5]pyrrolo[2,3-b]pyridin-7-yl]-2-oxoethyl}-1,2,3,6-tetrahydro-4-pyridinecarboxylic acid,
(72) 1-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,3,6-tetrahydro-4-pyridinecarboxylic acid,
(73) 5-{3-[9-(3-fluorobenzyl)-5,6,8,9-tetrahydro-7H-pyrido[4',3':4,5]pyrrolo[2,3-b]pyridin-7-yl]-3-oxopropyl}-2-thiophenecarboxylic acid,
(74) 5-{3-[9-(2,4-difluorobenzyl)-5,6,8,9-tetrahydro-7H-pyrido[4',3':4,5]pyrrolo[2,3-b]pyridin-7-yl]-3-oxopropyl}-2-thiophenecarboxylic acid, or
(75) 5-{2-[9-(3-fluorobenzyl)-5,6,8,9-tetrahydro-7H-pyrido[4',3':4,5]pyrrolo[2,3-b]pyridin-7-yl]-2-oxoethyl}-2-thiophenecarboxylic acid, a salt thereof or a solvate thereof or a prodrug thereof.

Of the present compound, a compound in which U is a C3-7 monocycle or a C5-10 bridged carbon ring, optionally substituted with one to five $R^7$s (in the groups, $R^7$ is as defined above), the ring A is (i) a 5- to 6-membered monocyclic heterocyclic ring containing one to four heteroatoms selected from an oxygen atom, a nitrogen atom and a sulfur atom or (ii) a C8-10 bicyclic heterocyclic ring containing one to four heteroatoms selected from an oxygen atom, a nitrogen atom and a sulfur atom, and X is a nitrogen atom is preferably:
(1) cis-4-(2-{9-[(4-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(2) cis-4-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(3) trans-4-(2-{9-[(4-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(4) trans-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(5) trans-4-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(6) cis-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,
(8) cis-4-(2-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid, (9) cis-4-(2-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid,

(10) trans-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(12) cis-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(14) trans-4-(2-{9-[(6-chloro-3-pyridinyl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid,

(15) trans-4-(2-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid,

(16) trans-4-(2-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid,

(18) 4-(2-{9-[(6-chloro-3-pyridinyl)methyl]-5,6,8,9-tetrahydro-7H-pyrido[4',3':4,5]pyrrolo[2,3-b]pyridin-7-yl}-2-oxoethyl)benzoic acid,

(20) 4-(2-{9-[(1,3-dimethyl-1H-pyrazol-5-yl)methyl]-5,6,8,9-tetrahydro-7H-pyrido[4',3':4,5]pyrrolo[2,3-b]pyridin-7-yl}-2-oxoethyl)benzoic acid,

(21) 4-(2-{9-[(2,5-dimethyl-1,3-thiazol-4-yl)methyl]-5,6,8,9-tetrahydro-7H-pyrido[4',3':4,5]pyrrolo[2,3-b]pyridin-7-yl}-2-oxoethyl)benzoic acid,

(22) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)benzoic acid,

(27) [1-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-4-piperidinyl]acetic acid,

(28) [[1-(2-{9-[(5-chloro-2-thienyl)methyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid,

(29) trans-4-(2-{9-[(5-fluoro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(30) cis-4-(2-{9-[(5-fluoro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(31) trans-4-(2-{9-[(5-fluoro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(32) cis-4-(2-{9-[(5-fluoro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid,

(42) 2-methoxy-4-[2-oxo-2-(9-{[5-(trifluoromethyl)-2-thienyl]methyl}-5,6,8,9-tetrahydro-7H-pyrido[

(46) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2-methoxybenzoic acid,

(47) 4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methoxybenzoic acid,

(50) 4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methylbenzoic acid,

(51) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2-methylbenzoic acid,

(58) 4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2,6-dimethoxybenzoic acid,

(59) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2,6-dimethoxybenzoic acid,

(66) trans-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(67) trans-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(69) cis-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(70) cis-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(80) (1R,3R)-3-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid,

(81) (1R,3R)-3-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid,

(84) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid,

(85) 4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid,

(92) 4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(93) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(94) 4-{2-[9-(3-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(95) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(96) 4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(97) 4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, or

(99) 4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, a salt thereof or a solvate thereof or a prodrug thereof.

Of the present compound, a compound in which U is a C3-7 monocycle or a C5-10 bridged carbon ring, optionally substituted with one to five $R^7$s (in the groups, $R^7$ is as defined above), and X is a carbon atom is preferably:

(2) 1-{2-[9-(4-chloro-2-fluorobenzyl)-1,3,4,9-tetrahydro-2H-beta-carbolin-2-yl]-2-oxoethyl}-4-piperidinecarboxylic acid, (3) (4-{2-[9-(3-chloro-2,4-difluorobenzyl)-1,3,4,9-tetrahydro-2H-beta-carbolin-2-yl]-2-oxoethyl}-1-piperazinyl)acetic acid, (5) (4-{2-[9-(3,5-dichlorobenzyl)-1,3,4,9-tetrahydro-2H-beta-carbolin-2-yl]-2-oxoethyl}-1-piperazinyl)acetic acid, (8) 1-{2-[9-(3-chloro-2,4-difluorobenzyl)-1,3,4,9-tetrahydro-2H-beta-carbolin-2-yl]-2-oxoethyl}-4-piperidinecarboxylic acid,
(9) 1-{2-[9-(3,5-dichlorobenzyl)-1,3,4,9-tetrahydro-2H-beta-carbolin-2-yl]-2-oxoethyl}-4-piperidinecarboxylic acid,
(12) cis-4-{2-[9-(4-cyanobenzyl)-1,3,4,9-tetrahydro-2H-beta-carbolin-2-yl]-2-oxoethyl}cyclohexanecarboxylic acid,
(13) cis-4-(2-{9-[(6-chloro-3-pyridinyl)methyl]-1,3,4,9-tetrahydro-2H-beta-carbolin-2-yl}-2-oxoethyl)cyclohexanecarboxylic acid,
(15) cis-4-(2-{9-[(1,3-dimethyl-1H-pyrazol-5-yl)methyl]-1,3,4,9-tetrahydro-2H-beta-carbolin-2-yl}-2-oxoethyl)cyclohexanecarboxylic acid,
(16) cis-4-(2-{9-[(2,5-dimethyl-1,3-thiazol-4-yl)methyl]-1,3,4,9-tetrahydro-2H-beta-carbolin-2-yl}-2-oxoethyl)cyclohexanecarboxylic acid,
(17) (1-{2-[9-(3-chloro-2,4-difluorobenzyl)-1,3,4,9-tetrahydro-2H-beta-carbolin-2-yl]-2-oxoethyl}-4-piperidinyl) acetic acid, or
(19) (1-{2-[9-(3,5-dichlorobenzyl)-1,3,4,9-tetrahydro-2H-beta-carbolin-2-yl]-2-oxoethyl}-4-piperidinyl)acetic acid, a salt thereof or a solvate thereof or a prodrug thereof.

Of the present compound, a compound in which U is a 3- to 7-membered monocyclic heterocyclic ring containing one to four heteroatoms selected from an oxygen atom, a nitrogen atom and a sulfur atom, and optionally substituted with one to five $R^7$s (in the group, $R^7$ is as defined above), and X is a carbon atom is preferably:
(1) [1-(2-{9-[(5-chloro-2-thienyl)methyl]-1,3,4,9-tetrahydro-2H-beta-carbolin-2-yl}-2-oxoethyl)-4-piperidinyl]acetic acid,
(3) 1-(2-{9-[(5-chloro-2-thienyl)methyl]-1,3,4,9-tetrahydro-2H-beta-carbolin-2-yl}-2-oxoethyl)-4-piperidinecarboxylic acid,
(6) [4-(2-{9-[(5-chloro-2-thienyl)methyl]-1,3,4,9-tetrahydro-2H-beta-carbolin-2-yl}-2-oxoethyl)-1-piperazinyl]acetic acid,
(8) 1-(2-{9-[(5-chloro-2-thienyl)methyl]-1,3,4,9-tetrahydro-2H-beta-carbolin-2-yl}-2-oxoethyl)-4-methyl-4-piperidinecarboxylic acid, or
(13) rel-[(2R,6S)-4-(2-{9-[(5-chloro-2-thienyl)methyl]-1,3,4,9-tetrahydro-2H-beta-carbolin-2-yl}-2-oxoethyl)-2,6-dimethyl-1-piperazinyl]acetic acid, a salt thereof or a solvate thereof or a prodrug thereof.

And, of the present compound, a compound in which U is a methylene group, an oxygen atom or —$NR^6$— (in the group, $R^6$ is as defined above), X is a nitrogen atom, and the ring A is a C3-6 monocyclic carbon ring or a C8-10 bicyclic carbon ring is preferably:
(1) 6-[9-(cyclohexylmethyl)-5,6,8,9-tetrahydro-7H-pyrido[4',3':4,5]pyrrolo[2,3-b]pyridin-7-yl]-6-oxohexanoic acid,
(2) 6-[9-(2-cyclohexylethyl)-5,6,8,9-tetrahydro-7H-pyrido[4',3':4,5]pyrrolo[2,3-b]pyridin-7-yl]-6-oxohexanoic acid,
(3) 6-[9-(3-cyclohexylpropyl)-5,6,8,9-tetrahydro-7H-pyrido[4',3':4,5]pyrrolo[2,3-b]pyridin-7-yl]-6-oxohexanoic acid,
(4) 6-[9-(4-cyclohexylbutyl)-5,6,8,9-tetrahydro-7H-pyrido[4',3':4,5]pyrrolo[2,3-b]pyridin-7-yl]-6-oxohexanoic acid,
(5) 6-[9-(3,4-dichlorobenzyl)-5,6,8,9-tetrahydro-7H-pyrido[4',3':4,5]pyrrolo[2,3-b]pyridin-7-yl]-6-oxohexanoic acid,
(6) 6-[9-(3,5-dichlorobenzyl)-5,6,8,9-tetrahydro-7H-pyrido[4',3':4,5]pyrrolo[2,3-b]pyridin-7-yl]-6-oxohexanoic acid,
(7) 6-[9-(3,4-dimethylbenzyl)-5,6,8,9-tetrahydro-7H-pyrido[4',3':4,5]pyrrolo[2,3-b]pyridin-7-yl]-6-oxohexanoic acid,
(8) 6-[9-(3,5-dimethylbenzyl)-5,6,8,9-tetrahydro-7H-pyrido[4',3':4,5]pyrrolo[2,3-b]pyridin-7-yl]-6-oxohexanoic acid,
(9) 6-[9-(3,5-difluorobenzyl)-5,6,8,9-tetrahydro-7H-pyrido[4',3':4,5]pyrrolo[2,3-b]pyridin-7-yl]-6-oxohexanoic acid,
(10) 6-[9-(3,4-difluorobenzyl)-5,6,8,9-tetrahydro-7H-pyrido[4',3':4,5]pyrrolo[2,3-b]pyridin-7-yl]-6-oxohexanoic acid,
(11) 6-oxo-6-[9-(3,4,5-trifluorobenzyl)-5,6,8,9-tetrahydro-7H-pyrido[4',3':4,5]pyrrolo[2,3-b]pyridin-7-yl]hexanoic acid,
(12) 6-[9-(cyclohexylmethyl)-5,6,8,9-tetrahydro-7H-pyrido[4',3':4,5]pyrrolo[2,3-b]pyridin-7-yl]-2,2-dimethyl-6-oxohexanoic acid,
(13) 6-[9-(2-cyclohexylethyl)-5,6,8,9-tetrahydro-7H-pyrido[4',3':4,5]pyrrolo[2,3-b]pyridin-7-yl]-2,2-dimethyl-6-oxohexanoic acid,
(14) 6-[9-(3-cyclohexylpropyl)-5,6,8,9-tetrahydro-7H-pyrido[4',3':4,5]pyrrolo[2,3-b]pyridin-7-yl]-2,2-dimethyl-6-oxohexanoic acid,
(15) 6-[9-(4-cyclohexylbutyl)-5,6,8,9-tetrahydro-7H-pyrido[4',3':4,5]pyrrolo[2,3-b]pyridin-7-yl]-2,2-dimethyl-6-oxohexanoic acid,
(16) 6-[9-(3,4-dichlorobenzyl)-5,6,8,9-tetrahydro-7H-pyrido[4',3':4,5]pyrrolo[2,3-b]pyridin-7-yl]-2,2-dimethyl-6-oxohexanoic acid,
(17) 6-[9-(3,5-dichlorobenzyl)-5,6,8,9-tetrahydro-7H-pyrido[4',3':4,5]pyrrolo[2,3-b]pyridin-7-yl]-2,2-dimethyl-6-oxohexanoic acid,
(18) 6-[9-(3,4-dimethylbenzyl)-5,6,8,9-tetrahydro-7H-pyrido[4',3':4,5]pyrrolo[2,3-b]pyridin-7-yl]-2,2-dimethyl-6-oxohexanoic acid,
(19) 6-[9-(3,5-dimethylbenzyl)-5,6,8,9-tetrahydro-7H-pyrido[4',3':4,5]pyrrolo[2,3-b]pyridin-7-yl]-2,2-dimethyl-6-oxohexanoic acid,
(20) 6-[9-(3,5-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(21) 6-[9-(3,4-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(22) 2,2-dimethyl-6-oxo-6-[9-(3,4,5-trifluorobenzyl)-5,6,8,9-tetrahydro-7H-pyrido[4',3':4,5]pyrrolo[2,3-b]pyridin-7-yl]hexanoic acid,
(23) ethyl 7-(9-benzyl-5,6,8,9-tetrahydro-7H-pyrido[4',3':4,5]pyrrolo[2,3-b]pyridin-7-yl)-7-oxoheptanoate,
(24) methyl 6-[9-(4-fluorobenzyl)-5,6,8,9-tetrahydro-7H-pyrido[4',3':4,5]pyrrolo[2,3-b]pyridin-7-yl]-6-oxohexanoate,
(25) methyl 6-[9-(3-chloro-4-fluorobenzyl)-5,6,8,9-tetrahydro-7H-pyrido[4',3':4,5]pyrrolo[2,3-b]pyridin-7-yl]-6-oxohexanoate,
(26) ethyl 7-[9-(4-fluorobenzyl)-5,6,8,9-tetrahydro-7H-pyrido[4',3':4,5]pyrrolo[2,3-b]pyridin-7-yl]-7-oxoheptanoate,
(27) ethyl 7-[9-(3-chloro-4-fluorobenzyl)-5,6,8,9-tetrahydro-7H-pyrido[4',3':4,5]pyrrolo[2,3-b]pyridin-7-yl]-7-oxoheptanoate,
(28) ethyl 6-(9-benzyl-5,6,8,9-tetrahydro-7H-pyrido[4',3':4,5]pyrrolo[2,3-b]pyridin-7-yl)-2,2-dimethyl-6-oxohexanoate,
(29) methyl 6-[9-(3-chloro-4-fluorobenzyl)-5,6,8,9-tetrahydro-7H-pyrido[4',3':4,5]pyrrolo[2,3-b]pyridin-7-yl]-2,2-dimethyl-6-oxohexanoate,
(31) methyl 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoate,
(32) ethyl 6-[9-(3-fluorobenzyl)-5,6,8,9-tetrahydro-7H-pyrido[4',3':4,5]pyrrolo[2,3-b]pyridin-7-yl]-3,3-dimethyl-6-oxohexanoate,

(33) 5-(9-benzyl-5,6,8,9-tetrahydro-7H-pyrido[4',3':4,5]pyrrolo[2,3-b]pyridin-7-yl)-5-oxopentanoic acid,
(34) 6-(9-benzyl-5,6,8,9-tetrahydro-7H-pyrido[4',3':4,5]pyrrolo[2,3-b]pyridin-7-yl)-6-oxohexanoic acid,
(35) 7-(9-benzyl-5,6,8,9-tetrahydro-7H-pyrido[4',3':4,5]pyrrolo[2,3-b]pyridin-7-yl)-7-oxoheptanoic acid,
(36) 6-[9-(3-chlorobenzyl)-5,6,8,9-tetrahydro-7H-pyrido[4',3':4,5]pyrrolo[2,3-b]pyridin-7-yl]-6-oxohexanoic acid,
(37) 6-[9-(3-chloro-4-fluorobenzyl)-5,6,8,9-tetrahydro-7H-pyrido[4',3':4,5]pyrrolo[2,3-b]pyridin-7-yl]-6-oxohexanoic acid,
(38) 7-[9-(4-fluorobenzyl)-5,6,8,9-tetrahydro-7H-pyrido[4',3':4,5]pyrrolo[2,3-b]pyridin-7-yl]-7-oxoheptanoic acid,
(39) 7-[9-(3-chloro-4-fluorobenzyl)-5,6,8,9-tetrahydro-7H-pyrido[4',3':4,5]pyrrolo[2,3-b]pyridin-7-yl]-7-oxoheptanoic acid,
(40) 6-oxo-6-[9-(3-phenylpropyl)-5,6,8,9-tetrahydro-7H-pyrido[4',3':4,5]pyrrolo[2,3-b]pyridin-7-yl]hexanoic acid,
(41) 6-(9-benzyl-5,6,8,9-tetrahydro-7H-pyrido[4',3':4,5]pyrrolo[2,3-b]pyridin-7-yl)-2,2-dimethyl-6-oxohexanoic acid,
(42) 7-[9-(3-chlorobenzyl)-5,6,8,9-tetrahydro-7H-pyrido[4',3':4,5]pyrrolo[2,3-b]pyridin-7-yl]-7-oxoheptanoic acid,
(43) 6-[9-(3-chlorobenzyl)-5,6,8,9-tetrahydro-7H-pyrido[4',3':4,5]pyrrolo[2,3-b]pyridin-7-yl]-2,2-dimethyl-6-oxohexanoic acid,
(44) 6-[9-(3-fluorobenzyl)-5,6,8,9-tetrahydro-7H-pyrido[4',3':4,5]pyrrolo[2,3-b]pyridin-7-yl]-6-oxohexanoic acid,
(45) 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(46) 6-[9-(3-chloro-4-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(49) 5-oxo-5-[9-(3-phenylpropyl)-5,6,8,9-tetrahydro-7H-pyrido[4',3':4,5]pyrrolo[2,3-b]pyridin-7-yl]pentanoic acid,
(50) 7-oxo-7-[9-(3-phenylpropyl)-5,6,8,9-tetrahydro-7H-pyrido[4',3':4,5]pyrrolo[2,3-b]pyridin-7-yl]heptanoic acid,
(51) 6-oxo-6-[9-(2-phenoxyethyl)-5,6,8,9-tetrahydro-7H-pyrido[4',3':4,5]pyrrolo[2,3-b]pyridin-7-yl]hexanoic acid,
(52) 3-{2-[9-(3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid,
(53) 2-{2-[9-(3-fluorobenzyl)-5,6,8,9-tetrahydro-7H-pyrido[4',3':4,5]pyrrolo[2,3-b]pyridin-7-yl]-2-oxoethoxy}-2-methylpropanoic acid,
(54) 3-({2-[9-(3-fluorobenzyl)-5,6,8,9-tetrahydro-7H-pyrido[4',3':4,5]pyrrolo[2,3-b]pyridin-7-yl]-2-oxoethyl}amino)-2,2-dimethylpropanoic acid,
(55) 6-(9'-benzyl-8',9'-dihydrospiro[cyclopropane-1,5'-pyrido[4',3':4,5]pyrrolo[2,3-b]pyridin]-7'(6'H)-yl)-6-oxohexanoic acid,
(56) 3-[{2-[9-(3-fluorobenzyl)-5,6,8,9-tetrahydro-7H-pyrido[4',3':4,5]pyrrolo[2,3-b]pyridin-7-yl]-2-oxoethyl}(methyl)amino]-2,2-dimethylpropanoic acid,
(57) 6-[9-(3-fluorobenzyl)-5,6,8,9-tetrahydro-7H-pyrido[4',3':4,5]pyrrolo[2,3-b]pyridin-7-yl]-3,3-dimethyl-6-oxohexanoic acid,
(58) 6-[9-(3-fluorobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoic acid,
(59) 6-[9-(3-fluorobenzyl)-5,5-dimethyl-5,6,8,9-tetrahydro-7H-pyrido[4',3':4,5]pyrrolo[2,3-b]pyridin-7-yl]-2,2-dimethyl-6-oxohexanoic acid,
(60) 6-[9-(3-fluorobenzyl)-5-methyl-5,6,8,9-tetrahydro-7H-pyrido[4',3':4,5]pyrrolo[2,3-b]pyridin-7-yl]-2,2-dimethyl-6-oxohexanoic acid,
(61) 6-[9-(cyclopentylmethyl)-5,6,8,9-tetrahydro-7H-pyrido[4',3':4,5]pyrrolo[2,3-b]pyridin-7-yl]-6-oxohexanoic acid,
(62) 6-[9-(3-cyclohexen-1-ylmethyl)-5,6,8,9-tetrahydro-7H-pyrido[4',3':4,5]pyrrolo[2,3-b]pyridin-7-yl]-6-oxohexanoic acid,
(63) 6-oxo-6-{9-[2-(phenylthio)ethyl]-5,6,8,9-tetrahydro-7H-pyrido[4',3':4,5]pyrrolo[2,3-b]pyridin-7-yl}hexanoic acid,
(66) 6-[9-(cyclopropylmethyl)-5,6,8,9-tetrahydro-7H-pyrido[4',3':4,5]pyrrolo[2,3-b]pyridin-7-yl]-2,2-dimethyl-6-oxohexanoic acid,
(67) 6-[9-(cyclobutylmethyl)-5,6,8,9-tetrahydro-7H-pyrido[4',3':4,5]pyrrolo[2,3-b]pyridin-7-yl]-2,2-dimethyl-6-oxohexanoic acid,
(68) 6-[9-(cyclopentylmethyl)-5,6,8,9-tetrahydro-7H-pyrido[4',3':4,5]pyrrolo[2,3-b]pyridin-7-yl]-2,2-dimethyl-6-oxohexanoic acid,
(69) 6-[9-(3-cyclohexen-1-ylmethyl)-5,6,8,9-tetrahydro-7H-pyrido[4',3':4,5]pyrrolo[2,3-b]pyridin-7-yl]-2,2-dimethyl-6-oxohexanoic acid,
(70) 2,2-dimethyl-6-oxo-6-{9-[2-(phenylthio)ethyl]-5,6,8,9-tetrahydro-7H-pyrido[4',3':4,5]pyrrolo[2,3-b]pyridin-7-yl}hexanoic acid,
(73) methyl 5-(9-benzyl-5,6,8,9-tetrahydro-7H-pyrido[4',3':4,5]pyrrolo[2,3-b]pyridin-7-yl)-5-oxopentanoate,
(74) methyl 6-[9-(3-chlorobenzyl)-5,6,8,9-tetrahydro-7H-pyrido[4',3':4,5]pyrrolo[2,3-b]pyridin-7-yl]-6-oxohexanoate,
(75) methyl 6-oxo-6-[9-(3-phenylpropyl)-5,6,8,9-tetrahydro-7H-pyrido[4',3':4,5]pyrrolo[2,3-b]pyridin-7-yl]hexanoate,
(77) ethyl 7-[9-(3-chlorobenzyl)-5,6,8,9-tetrahydro-7H-pyrido[4',3':4,5]pyrrolo[2,3-b]pyridin-7-yl]-7-oxoheptanoate,
(78) methyl 6-[9-(3-fluorobenzyl)-5,6,8,9-tetrahydro-7H-pyrido[4',3':4,5]pyrrolo[2,3-b]pyridin-7-yl]-6-oxohexanoate,
(79) methyl 5-oxo-5-[9-(3-phenylpropyl)-5,6,8,9-tetrahydro-7H-pyrido[4',3':4,5]pyrrolo[2,3-b]pyridin-7-yl]pentanoate,
(80) methyl 6-(9'-benzyl-8',9'-dihydrospiro[cyclopropane-1,5'-pyrido[4',3':4,5]pyrrolo[2,3-b]pyridin]-7'(6'H)-yl)-6-oxohexanoate,
(81) 6-[9-(4-fluorobenzyl)-5,6,8,9-tetrahydro-7H-pyrido[4',3':4,5]pyrrolo[2,3-b]pyridin-7-yl]-6-oxohexanoic acid,
(82) 6-oxo-6-[9-(4-phenylbutyl)-5,6,8,9-tetrahydro-7H-pyrido[4',3':4,5]pyrrolo[2,3-b]pyridin-7-yl]hexanoic acid,
(83) 7-oxo-7-[9-(4-phenylbutyl)-5,6,8,9-tetrahydro-7H-pyrido[4',3':4,5]pyrrolo[2,3-b]pyridin-7-yl]heptanoic acid,
(84) 6-oxo-6-[9-(3-phenoxypropyl)-5,6,8,9-tetrahydro-7H-pyrido[4',3':4,5]pyrrolo[2,3-b]pyridin-7-yl]hexanoic acid,
(85) 6-[9-(cyclobutylmethyl)-5,6,8,9-tetrahydro-7H-pyrido[4',3':4,5]pyrrolo[2,3-b]pyridin-7-yl]-6-oxohexanoic acid,
(86) ethyl 7-oxo-7-[9-(3-phenylpropyl)-5,6,8,9-tetrahydro-7H-pyrido[4',3':4,5]pyrrolo[2,3-b]pyridin-7-yl]heptanoate,
(87) 6-oxo-6-[9-(2-phenylethyl)-5,6,8,9-tetrahydro-7H-pyrido[4',3':4,5]pyrrolo[2,3-b]pyridin-7-yl]hexanoic acid,
(88) 7-oxo-7-[9-(2-phenylethyl)-5,6,8,9-tetrahydro-7H-pyrido[4',3':4,5]pyrrolo[2,3-b]pyridin-7-yl]heptanoic acid,
(89) 6-[9-(cyclopropylmethyl)-5,6,8,9-tetrahydro-7H-pyrido[4',3':4,5]pyrrolo[2,3-b]pyridin-7-yl]-6-oxohexanoic acid,

(90) methyl 5-oxo-5-[9-(4-phenylbutyl)-5,6,8,9-tetrahydro-7H-pyrido[4',3':4,5]pyrrolo[2,3-b]pyridin-7-yl]pentanoate,
(91) methyl 6-oxo-6-[9-(4-phenylbutyl)-5,6,8,9-tetrahydro-7H-pyrido[4',3':4,5]pyrrolo[2,3-b]pyridin-7-yl]hexanoate,
(92) methyl 6-oxo-6-[9-(2-phenoxyethyl)-5,6,8,9-tetrahydro-7H-pyrido[4',3':4,5]pyrrolo[2,3-b]pyridin-7-yl]hexanoate,
(93) 5-oxo-5-[9-(4-phenylbutyl)-5,6,8,9-tetrahydro-7H-pyrido[4',3':4,5]pyrrolo[2,3-b]pyridin-7-yl]pentanoic acid,
(94) ethyl 6-[9-(3-fluorobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoate,
(95) 2-({2-[9-(3-fluorobenzyl)-5,6,8,9-tetrahydro-7H-pyrido[4',3':4,5]pyrrolo[2,3-b]pyridin-7-yl]-2-oxoethyl}amino)-2-methylpropanoic acid,
(96) ethyl 7-oxo-7-[9-(4-phenylbutyl)-5,6,8,9-tetrahydro-7H-pyrido[4',3':4,5]pyrrolo[2,3-b]pyridin-7-yl]heptanoate,
(97) methyl 5-oxo-5-[9-(2-phenylethyl)-5,6,8,9-tetrahydro-7H-pyrido[4',3':4,5]pyrrolo[2,3-b]pyridin-7-yl]pentanoate,
(98) methyl 6-oxo-6-[9-(2-phenylethyl)-5,6,8,9-tetrahydro-7H-pyrido[4',3':4,5]pyrrolo[2,3-b]pyridin-7-yl]hexanoate,
(99) ethyl 7-oxo-7-[9-(2-phenylethyl)-5,6,8,9-tetrahydro-7H-pyrido[4',3':4,5]pyrrolo[2,3-b]pyridin-7-yl]heptanoate,
(100) methyl 6-(9-benzyl-6,6-dimethyl-5,6,8,9-tetrahydro-7H-pyrido[4',3':4,5]pyrrolo[2,3-b]pyridin-7-yl)-6-oxohexanoate,
(101) 5-oxo-5-[9-(2-phenylethyl)-5,6,8,9-tetrahydro-7H-pyrido[4',3':4,5]pyrrolo[2,3-b]pyridin-7-yl]pentanoic acid or
(102) methyl 6-(9-benzyl-6-methyl-5,6,8,9-tetrahydro-7H-pyrido[4',3':4,5]pyrrolo[2,3-b]pyridin-7-yl)-6-oxohexanoate,
(103) 6-[9-(3-cyanobenzyl)-5,6,8,9-tetrahydro-7H-pyrido[4',3':4,5]pyrrolo[2,3-b]pyridin-7-yl]-2,2-dimethyl-6-oxohexanoic acid,
(104) 6-[9-(4-cyanobenzyl)-5,6,8,9-tetrahydro-7H-pyrido[4',3':4,5]pyrrolo[2,3-b]pyridin-7-yl]-2,2-dimethyl-6-oxohexanoic acid,
(105) 3-({1-[9-(3-fluorobenzyl)-5,6,8,9-tetrahydro-7H-pyrido[4',3':4,5]pyrrolo[2,3-b]pyridin-7-yl]-1-oxo-2-propanyl}amino)-2,2-dimethylpropanoic acid,
(106) {3-[9-(3-fluorobenzyl)-5,6,8,9-tetrahydro-7H-pyrido[4',3':4,5]pyrrolo[2,3-b]pyridin-7-yl]-3-oxopropoxy}acetic acid,
(107) 6-[9-(4-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(108) 6-[9-(4-chlorobenzyl)-5,6,8,9-tetrahydro-7H-pyrido[4',3':4,5]pyrrolo[2,3-b]pyridin-7-yl]-2,2-dimethyl-6-oxohexanoic acid,
(111) {4-[9-(3-fluorobenzyl)-5,6,8,9-tetrahydro-7H-pyrido[4',3':4,5]pyrrolo[2,3-b]pyridin-7-yl]-4-oxobutoxy}acetic acid,
(114) 5-({[9-(3-fluorobenzyl)-5,6,8,9-tetrahydro-7H-pyrido[4',3':4,5]pyrrolo[2,3-b]pyridin-7-yl]carbonyl}oxy)pentanoic acid,
(115) 2,2-dimethyl-6-oxo-6-[9-(2,4,6-trifluorobenzyl)-5,6,8,9-tetrahydro-7H-pyrido[4',3':4,5]pyrrolo[2,3-b]pyridin-7-yl]hexanoic acid,
(116) 6-[9-(4-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(117) 6-[9-(2,3-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(118) 2,2-dimethyl-6-oxo-6-[9-(2,3,6-trifluorobenzyl)-5,6,8,9-tetrahydro-7H-pyrido[4',3':4,5]pyrrolo[2,3-b]pyridin-7-yl]hexanoic acid,
(119) 6-[9-(3-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(120) 6-[9-(2,4-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(121) 6-[9-(3-chloro-2,4-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(122) 6-[9-(4-chloro-3-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(123) 6-[9-(3-chloro-5-fluorobenzyl)-5,6,8,9-tetrahydro-7H-pyrido[4',3':4,5]pyrrolo[2,3-b]pyridin-7-yl]-2,2-dimethyl-6-oxohexanoic acid,
(124) 2,2-dimethyl-6-oxo-6-[9-(2,3,4-trifluorobenzyl)-5,6,8,9-tetrahydro-7H-pyrido[4',3':4,5]pyrrolo[2,3-b]pyridin-7-yl]hexanoic acid,
(125) 2,2-dimethyl-6-oxo-6-[9-(2,3,4,6-tetrafluorobenzyl)-5,6,8,9-tetrahydro-7H-pyrido[4',3':4,5]pyrrolo[2,3-b]pyridin-7-yl]hexanoic acid,
(126) 2,2-dimethyl-6-oxo-6-[9-(pentafluorobenzyl)-5,6,8,9-tetrahydro-7H-pyrido[4',3':4,5]pyrrolo[2,3-b]pyridin-7-yl]hexanoic acid,
(129) 6-[9-(2,5-difluorobenzyl)-5,6,8,9-tetrahydro-7H-pyrido[4',3':4,5]pyrrolo[2,3-b]pyridin-7-yl]-2,2-dimethyl-6-oxohexanoic acid,
(130) 2,2-dimethyl-6-oxo-6-[9-(2,4,5-trifluorobenzyl)-5,6,8,9-tetrahydro-7H-pyrido[4',3':4,5]pyrrolo[2,3-b]pyridin-7-yl]hexanoic acid,
(131) 6-[9-(2-fluoro-3-methylbenzyl)-5,6,8,9-tetrahydro-7H-pyrido[4',3':4,5]pyrrolo[2,3-b]pyridin-7-yl]-2,2-dimethyl-6-oxohexanoic acid,
(133) 2,2-dimethyl-6-oxo-6-[9-(2,3,4,5-tetrafluorobenzyl)-5,6,8,9-tetrahydro-7H-pyrido[4',3':4,5]pyrrolo[2,3-b]pyridin-7-yl]hexanoic acid,
(135) 2,2-dimethyl-6-oxo-6-[9-(2,3,5,6-tetrafluorobenzyl)-5,6,8,9-tetrahydro-7H-pyrido[4',3':4,5]pyrrolo[2,3-b]pyridin-7-yl]hexanoic acid,
(136) 6-[9-(2-fluoro-4-methylbenzyl)-5,6,8,9-tetrahydro-7H-pyrido[4',3':4,5]pyrrolo[2,3-b]pyridin-7-yl]-2,2-dimethyl-6-oxohexanoic acid,
(139) 6-[9-(4-fluoro-3-methylbenzyl)-5,6,8,9-tetrahydro-7H-pyrido[4',3':4,5]pyrrolo[2,3-b]pyridin-7-yl]-2,2-dimethyl-6-oxohexanoic acid,
(142) 5-({[9-(3-fluorobenzyl)-5,6,8,9-tetrahydro-7H-pyrido[4',3':4,5]pyrrolo[2,3-b]pyridin-7-yl]carbonyl}oxy)-2,2-dimethylpentanoic acid,
(143) 4-({[9-(3-fluorobenzyl)-5,6,8,9-tetrahydro-7H-pyrido[4',3':4,5]pyrrolo[2,3-b]pyridin-7-yl]carbonyl}oxy)-2,2-dimethylbutanoic acid,
(144) 6-[9-(3-fluoro-5-methylbenzyl)-5,6,8,9-tetrahydro-7H-pyrido[4',3':4,5]pyrrolo[2,3-b]pyridin-7-yl]-2,2-dimethyl-6-oxohexanoic acid,
(151) 6-[9-(3-fluoro-4-methylbenzyl)-5,6,8,9-tetrahydro-7H-pyrido[4',3':4,5]pyrrolo[2,3-b]pyridin-7-yl]-2,2-dimethyl-6-oxohexanoic acid,
(154) 6-[9-(4-chloro-3-methylbenzyl)-5,6,8,9-tetrahydro-7H-pyrido[4',3':4,5]pyrrolo[2,3-b]pyridin-7-yl]-2,2-dimethyl-6-oxohexanoic acid, (157) 6-[9-(2-fluoro-5-methylbenzyl)-5,6,8,9-tetrahydro-7H-pyrido[4',3':4,5]pyrrolo[2,3-b]pyridin-7-yl]-2,2-dimethyl-6-oxohexanoic acid, (158) 6-[9-(2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid, (162) 6-[9-(4-chloro-2-fluorobenzyl)-5,6,8,9-tetrahydro-7H-pyrido[4',3':4,5]pyrrolo[2,3-b]pyridin-7-yl]-3,3-dimethyl-6-oxohexanoic acid, (163) 6-[9-(2,4-difluorobenzyl)-5,6,8,9-tetrahydro-7H-pyrido[4',3':4,5]pyrrolo[2,3-b]pyridin-7-yl]-3,3-dimethyl-6-oxohexanoic acid, (164) 6-[9-(3-chloro-2,4-difluorobenzyl)-5,6,8,9-tetrahydro-7H-pyrido[4',3':4,5]pyrrolo[2,3-b]pyridin-7-yl]-3,3-dimethyl-6-oxohexanoic acid, (166) 6-[9-(5-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid, (167) 2,2-dimethyl-6-oxo-6-[9-(2,3,5-trifluorobenzyl)-5,6,8,9-tetrahydro-7H-pyrido[4',3':4,5]pyrrolo[2,3-b]pyridin-7-yl]hexanoic acid, (169) 5-({[9-(3-fluorobenzyl)-5,6,8,9-tetrahydro-7H-pyrido[4',3':4,5]pyrrolo[2,3-b]pyridin-7-yl]carbonyl}amino)-2,2-dimethylpentanoic acid, (170) 4-({[9-(3-fluorobenzyl)-5,6,8,9-tetrahydro-7H-pyrido[4',3':4,5]pyrrolo[2,3-b]pyridin-7-yl]carbonyl}amino)-2,2-dimethylbutanoic acid, (171) 6-[9-(4-carbamoylbenzyl)-1,3,4,9-tetrahydro-2H-beta-carbolin-2-yl]-2,2-dimethyl-6-oxohexanoic acid, (172) 6-[9-(4-cyanobenzyl)-5,5-dimethyl-5,6,8,9-tetrahydro-7H-pyrido[4',3':4,5]pyrrolo[2,3-b]pyridin-7-yl]-2,2-dimethyl-6-oxohexanoic acid, (174) 6-[9-(4-chloro-2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid, (176) 6-[9-(3-chloro-2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid, (177) 2-{3-[9-(3-fluorobenzyl)-5,6,8,9-tetrahydro-7H-pyrido[4',3':4,5]pyrrolo[2,3-b]pyridin-7-yl]-3-oxopropoxy}-2-methylpropanoic acid, (178) 6-[9-(4-fluorobenzyl)-5,6,8,9-tetrahydro-7H-pyrido[4',3':4,5]pyrrolo[2,3-b]pyridin-7-yl]-3,3-dimethyl-6-oxohexanoic acid, (179) 3,3-dimethyl-6-oxo-6-[9-(3,4,5-trifluorobenzyl)-5,6,8,9-tetrahydro-7H-pyrido[4',3':4,5]pyrrolo[2,3-b]pyridin-7-yl]hexanoic acid, (180) 6-[9-(4-chlorobenzyl)-5,6,8,9-tetrahydro-7H-pyrido[4',3':4,5]pyrrolo[2,3-b]pyridin-7-yl]-3,3-dimethyl-6-oxohexanoic acid, (181) 3,3-dimethyl-6-oxo-6-[9-(2,4,5-trifluorobenzyl)-5,6,8,9-tetrahydro-7H-pyrido[4',3':4,5]pyrrolo[2,3-b]pyridin-7-yl]hexanoic acid, (183) 6-[9-(3,5-dichlorobenzyl)-5,6,8,9-tetrahydro-7H-pyrido[4',3':4,5]pyrrolo[2,3-b]pyridin-7-yl]-3,3-dimethyl-6-oxohexanoic acid, (186) 6-[9-(4-chloro-3-fluorobenzyl)-5,6,8,9-tetrahydro-7H-pyrido[4',3':4,5]pyrrolo[2,3-b]pyridin-7-yl]-3,3-dimethyl-6-oxohexanoic acid, (188) 3,3-dimethyl-6-oxo-6-[9-(2,3,4,6-tetrafluorobenzyl)-5,6,8,9-tetrahydro-7H-pyrido[4',3':4,5]pyrrolo[2,3-b]pyridin-7-yl]hexanoic acid, (189) 3-{2-[9-(4-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (190) 6-[9-(4-chloro-3,5-difluorobenzyl)-5,6,8,9-tetrahydro-7H-pyrido[4',3':4,5]pyrrolo[2,3-b]pyridin-7-yl]-2,2-dimethyl-6-oxohexanoic acid, (191) 6-[9-(4-chloro-2,5-difluorobenzyl)-5,6,8,9-tetrahydro-7H-pyrido[4',3':4,5]pyrrolo[2,3-b]pyridin-7-yl]-2,2-dimethyl-6-oxohexanoic acid, (192) 6-[9-(4-cyanobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoic acid, (193) 3-{2-[9-(2,4-difluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (194) 2,2-dimethyl-3-{2-oxo-2-[9-(3,4,5-trifluorobenzyl)-5,6,8,9-tetrahydro-7H-pyrido[4',3':4,5]pyrrolo[2,3-b]pyridin-7-yl]ethoxy}propanoic acid, (195) 2,2-dimethyl-3-{2-oxo-2-[9-(2,4,5-trifluorobenzyl)-5,6,8,9-tetrahydro-7H-pyrido[4',3':4,5]pyrrolo[2,3-b]pyridin-7-yl]ethoxy}propanoic acid, (196) 3-{2-[9-(4-chlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (197) 3-{2-[9-(4-chloro-2-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (198) 3-{2-[9-(4-chloro-3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (199) 3-{2-[9-(3-chloro-4-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (201) 2,2-dimethyl-3-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethoxy}propanoic acid, (203) 3-{2-[9-(3-chloro-2,4-difluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (206) 3-{2-[9-(3,4-dichlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (207) 3-{2-[9-(3,5-dichlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid, (210) 2-{3-[9-(4-fluorobenzyl)-5,6,8,9-tetrahydro-7H-pyrido[4',3':4,5]pyrrolo[2,3-b]pyridin-7-yl]-3-oxopropoxy}-2-methylpropanoic acid, (211) 2-{3-[9-(2,4-difluorobenzyl)-5,6,8,9-tetrahydro-7H-pyrido[4',3':4,5]pyrrolo[2,3-b]pyridin-7-yl]-3-oxopropoxy}-2-methylpropanoic acid, (212) 2-methyl-2-{3-oxo-3-[9-(3,4,5-trifluorobenzyl)-5,6,8,9-tetrahydro-7H-pyrido[4',3':4,5]pyrrolo[2,3-b]pyridin-7-yl]propoxy}propanoic acid, (213) 2-methyl-2-{3-oxo-3-[9-(2,4,5-trifluorobenzyl)-5,6,8,9-tetrahydro-7H-pyrido[4',3':4,5]pyrrolo[2,3-b]pyridin-7-yl]propoxy}propanoic acid, (214) 2-methyl-2-{3-oxo-3-[9-(2,3,4,6-tetrafluorobenzyl)-5,6,8,9-tetrahydro-7H-pyrido[4',3':4,5]pyrrolo[2,3-b]pyridin-7-yl]propoxy}propanoic acid, (215) 2-{3-[9-(4-chlorobenzyl)-5,6,8,9-tetrahydro-7H-pyrido[4',3':4,5]pyrrolo[2,3-b]pyridin-7-yl]-3-oxopropoxy}-2-methylpropanoic acid, (216) 2-{3-[9-(4-chloro-2-fluorobenzyl)-5,6,8,9-tetrahydro-7H-pyrido[4',3':4,5]pyrrolo[2,3-b]pyridin-7-yl]-3-oxopropoxy}-2-methylpropanoic acid, (217) 2-{3-[9-(4-chloro-3-fluorobenzyl)-5,6,8,9-tetrahydro-7H-pyrido[4',3':4,5]pyrrolo[2,3-b]pyridin-7-yl]-3-oxopropoxy}-2-methylpropanoic acid, (226) 6-[9-(3-chloro-4-methoxybenzyl)-5,6,8,9-tetrahydro-7H-pyrido[4',3':4,5]pyrrolo[2,3-b]pyridin-7-yl]-2,2-dimethyl-6-oxohexanoic acid, (229) 6-[9-(3-chloro-4-methylbenzyl)-5,6,8,9-tetrahydro-7H-pyrido[4',3':4,5]pyrrolo[2,3-b]pyridin-7-yl]-2,2-dimethyl-6-oxohexanoic acid, (230) 6-[9-(3-fluoro-4-methoxybenzyl)-5,6,8,9-tetrahydro-7H-pyrido[4',3':4,5]pyrrolo[2,3-b]pyridin-7-yl]-2,2-dimethyl-6-oxohexanoic acid, (234) 6-[9-(3-fluoro-5-methoxybenzyl)-5,6,8,9-tetrahydro-7H-pyrido[4',3':4,5]pyrrolo[2,3-b]pyridin-7-yl]-2,2-dimethyl-6-oxohexanoic acid, (235) 6-[9-(2-fluoro-3-methoxybenzyl)-5,6,8,9-tetrahydro-7H-pyrido[4',3':4,5]pyrrolo[2,3-b]pyridin-7-yl]-2,2-dimethyl-6-oxohexanoic acid, (238) 6-[9-(4-fluoro-3-methoxybenzyl)-5,6,8,9-tetrahydro-7H-pyrido[4',3':4,5]pyrrolo[2,3-b]pyridin-7-yl]-2,2-dimethyl-6-oxohexanoic acid, (241) 6-[9-(3-fluorobenzyl)-5,6,8,9-tetrahydro-7H-pyrido[4',3':4,5]pyrrolo[2,3-b]pyridin-7-yl]-3-hydroxy-2,2-dimethyl-6-oxahexanoic acid, (242) 1-{4-[9-(3-fluorobenzyl)-5,6,8,9-tetrahydro-7H-pyrido[4',3':4,5]pyrrolo[2,3-b]pyridin-7-yl]-4-oxobutyl}cyclopropanecarboxylic acid, (243) 1-{4-[9-(2,4-difluorobenzyl)-5,6,8,9-tetrahydro-7H-pyrido[4',3':4,5]pyrrolo[2,3-b]pyridin-7-yl]-4-oxobutyl}cyclopropanecarboxylic acid, (244) (2E)-6-[9-(3-fluorobenzyl)-5,6,8,9-tetrahydro-7H-pyrido[4',3':4,5]pyrrolo[2,3-b]pyridin-7-yl]-6-oxo-2-hexenoic acid, (245) (2E)-6-[9-(2,4-difluorobenzyl)-5,6,8,9-tetrahydro-7H-pyrido[4',3':4,5]pyrrolo[2,3-b]pyridin-7-yl]-6-oxo-2-hexenoic acid, (246) (2S)-2-amino-6-[9-(3-fluorobenzyl)-5,6,8,9-tetrahydro-7H-pyrido[4',3':4,5]pyrrolo[2,3-b]pyridin-7-yl]-6-oxohexanoic acid, or (247) (2S)-2-amino-6-[9-(2,4-difluorobenzyl)-5,6,8,9-tetrahydro-7H-pyrido[4',3':4,5]pyrrolo[2,3-b]pyridin-7-yl]-6-oxohexanoic acid, a salt thereof or a solvate thereof or a prodrug thereof.

And, of the present compound, a compound in which U is a methylene group, an oxygen atom or —NR$^6$— (in the group, R$^6$ is as defined above), X is a carbon atom, and the ring A is a C3-6 monocyclic carbon ring or a C8-10 bicyclic carbon ring is preferably (1) methyl 5-(9-benzyl-1,3,4,9-tetrahydro-2H-beta-carbolin-2-yl)-5-oxopentanoate, (2) ethyl 6-(9-benzyl-1,3,4,9-tetrahydro-2H-beta-carbolin-2-yl)-2,2-dimethyl-6-oxohexanoate, (3) 6-(9-benzyl-1,3,4,9-tetrahydro-2H-beta-carbolin-2-yl)-6-oxohexanoic acid, (4) 7-(9-benzyl-1,3,4,9-tetrahydro-2H-beta-carbolin-2-yl)-7-oxoheptanoic acid, (5) 6-[9-(3-methoxybenzyl)-1,3,4,9-tetrahydro-2H-beta-carbolin-2-yl]-6-oxohexanoic acid, (6) 6-[9-(4-chlorobenzyl)-1,3,4,9-tetrahydro-2H-beta-carbolin-2-yl]-6-oxohexanoic acid, (7) 6-[9-(4-fluorobenzyl)-1,3,4,9-tetrahydro-2H-beta-carbolin-2-yl]-6-oxohexanoic acid, (8) 6-[9-(3-chlorobenzyl)-1,3,4,9-tetrahydro-2H-beta-carbolin-2-yl]-6-oxohexanoic acid, (9) 6-[9-(3-fluorobenzyl)-1,3,4,9-tetrahydro-2H-beta-carbolin-2-yl]-6-oxohexanoic acid,

(10) 6-[9-(2-fluorobenzyl)-1,3,4,9-tetrahydro-2H-beta-carbolin-2-yl]-6-oxohexanoic acid,

(11) 6-[9-(4-methylbenzyl)-1,3,4,9-tetrahydro-2H-beta-carbolin-2-yl]-6-oxohexanoic acid,

(12) 6-oxo-6-[9-(3-phenylpropyl)-1,3,4,9-tetrahydro-2H-beta-carbolin-2-yl]hexanoic acid,

(13) 6-[9-(3-chloro-4-fluorobenzyl)-1,3,4,9-tetrahydro-2H-beta-carbolin-2-yl]-6-oxohexanoic acid,

(16) 6-(9-benzyl-1,3,4,9-tetrahydro-2H-beta-carbolin-2-yl)-2,2-dimethyl-6-oxohexanoic acid,

(17) 7-[9-(4-fluorobenzyl)-1,3,4,9-tetrahydro-2H-beta-carbolin-2-yl]-7-oxoheptanoic acid,

(18) 7-[9-(3-chlorobenzyl)-1,3,4,9-tetrahydro-2H-beta-carbolin-2-yl]-7-oxoheptanoic acid,

(19) 7-[9-(3-chloro-4-fluorobenzyl)-1,3,4,9-tetrahydro-2H-beta-carbolin-2-yl]-7-oxoheptanoic acid,

(20) 7-oxo-7-[9-(3-phenylpropyl)-1,3,4,9-tetrahydro-2H-beta-carbolin-2-yl]heptanoic acid,

(21) 2,2-dimethyl-6-oxo-6-[9-(3-phenylpropyl)-1,3,4,9-tetrahydro-2H-beta-carbolin-2-yl]hexanoic acid,

(22) 6-{9-[3-(4-fluorophenyl)propyl]-1,3,4,9-tetrahydro-2H-beta-carbolin-2-yl}-6-oxohexanoic acid,

(23) 7-{9-[3-(4-fluorophenyl)propyl]-1,3,4,9-tetrahydro-2H-beta-carbolin-2-yl}-7-oxoheptanoic acid,

(24) 6-{9-[3-(3-chlorophenyl)propyl]-1,3,4,9-tetrahydro-2H-beta-carbolin-2-yl}-6-oxohexanoic acid,

(25) 7-{9-[3-(3-chlorophenyl)propyl]-1,3,4,9-tetrahydro-2H-beta-carbolin-2-yl}-7-oxoheptanoic acid,

(26) 6-(9-benzyl-1,3,4,9-tetrahydro-2H-beta-carbolin-2-yl)-3,3-dimethyl-6-oxohexanoic acid,

(27) methyl 6-[9-(3-chlorobenzyl)-1,3,4,9-tetrahydro-2H-beta-carbolin-2-yl]-6-oxohexanoate,

(28) methyl 6-[9-(4-chlorobenzyl)-1,3,4,9-tetrahydro-2H-beta-carbolin-2-yl]-6-oxohexanoate,

(29) methyl 6-[9-(4-fluorobenzyl)-1,3,4,9-tetrahydro-2H-beta-carbolin-2-yl]-6-oxohexanoate,

(30) methyl 6-[9-(3-methylbenzyl)-1,3,4,9-tetrahydro-2H-beta-carbolin-2-yl]-6-oxohexanoate,

(31) methyl 6-[9-(2-fluorobenzyl)-1,3,4,9-tetrahydro-2H-beta-carbolin-2-yl]-6-oxohexanoate,

(32) methyl 6-[9-(4-methylbenzyl)-1,3,4,9-tetrahydro-2H-beta-carbolin-2-yl]-6-oxohexanoate,

(33) methyl 6-oxo-6-[9-(3-phenylpropyl)-1,3,4,9-tetrahydro-2H-beta-carbolin-2-yl]hexanoate,

(34) methyl 6-[9-(3-chloro-4-fluorobenzyl)-1,3,4,9-tetrahydro-2H-beta-carbolin-2-yl]-6-oxohexanoate,

(36) ethyl 7-[9-(3-chloro-4-fluorobenzyl)-1,3,4,9-tetrahydro-2H-beta-carbolin-2-yl]-7-oxoheptanoate,

(37) ethyl 2,2-dimethyl-6-oxo-6-[9-(3-phenylpropyl)-1,3,4,9-tetrahydro-2H-beta-carbolin-2-yl]hexanoate,

(38) 6-[9-(3-methylbenzyl)-1,3,4,9-tetrahydro-2H-beta-carbolin-2-yl]-6-oxohexanoic acid,

(39) 6-[9-(2-methoxybenzyl)-1,3,4,9-tetrahydro-2H-beta-carbolin-2-yl]-6-oxohexanoic acid,

(40) methyl 6-(9-benzyl-1,3,4,9-tetrahydro-2H-beta-carbolin-2-yl)-6-oxohexanoate,

(41) ethyl 7-(9-benzyl-1,3,4,9-tetrahydro-2H-beta-carbolin-2-yl)-7-oxoheptanoate,

(42) methyl 6-[9-(3-fluorobenzyl)-1,3,4,9-tetrahydro-2H-beta-carbolin-2-yl]-6-oxohexanoate,

(43) methyl 6-[9-(3-methoxybenzyl)-1,3,4,9-tetrahydro-2H-beta-carbolin-2-yl]-6-oxohexanoate,

(44) methyl 4-{[2-(6-methoxy-6-oxohexanoyl)-1,2,3,4-tetrahydro-9H-beta-carbolin-9-yl]methyl}benzoate,

(45) methyl 6-[9-(4-methoxybenzyl)-1,3,4,9-tetrahydro-2H-beta-carbolin-2-yl]-6-oxohexanoate,

(47) ethyl 7-oxo-7-[9-(3-phenylpropyl)-1,3,4,9-tetrahydro-2H-beta-carbolin-2-yl]heptanoate,

(48) ethyl 7-[9-(4-fluorobenzyl)-1,3,4,9-tetrahydro-2H-beta-carbolin-2-yl]-7-oxoheptanoate,

(49) ethyl 7-[9-(3-chlorobenzyl)-1,3,4,9-tetrahydro-2H-beta-carbolin-2-yl]-7-oxoheptanoate,
(50) methyl 6-{9-[3-(4-fluorophenyl)propyl]-1,3,4,9-tetrahydro-2H-beta-carbolin-2-yl}-6-oxohexanoate,
(51) ethyl 7-{9-[3-(4-fluorophenyl)propyl]-1,3,4,9-tetrahydro-2H-beta-carbolin-2-yl}-7-oxoheptanoate,
(52) ethyl 6-(9-benzyl-1,3,4,9-tetrahydro-2H-beta-carbolin-2-yl)-3,3-dimethyl-6-oxohexanoate,
(53) 5-(9-benzyl-1,3,4,9-tetrahydro-2H-beta-carbolin-2-yl)-5-oxopentanoic acid,
(54) 6-[9-(2-chlorobenzyl)-1,3,4,9-tetrahydro-2H-beta-carbolin-2-yl]-6-oxohexanoic acid,
(55) 6-[9-(2-methylbenzyl)-1,3,4,9-tetrahydro-2H-beta-carbolin-2-yl]-6-oxohexanoic acid,
(56) 6-[9-(4-methoxybenzyl)-1,3,4,9-tetrahydro-2H-beta-carbolin-2-yl]-6-oxohexanoic acid,
(57) methyl 6-[9-(2-chlorobenzyl)-1,3,4,9-tetrahydro-2H-beta-carbolin-2-yl]-6-oxohexanoate,
(58) methyl 6-[9-(2-methylbenzyl)-1,3,4,9-tetrahydro-2H-beta-carbolin-2-yl]-6-oxohexanoate,
(59) methyl 6-{9-[3-(3-chlorophenyl)propyl]-1,3,4,9-tetrahydro-2H-beta-carbolin-2-yl}-6-oxohexanoate,
(60) ethyl 7-{9-[3-(3-chlorophenyl)propyl]-1,3,4,9-tetrahydro-2H-beta-carbolin-2-yl}-7-oxoheptanoate,
(62) methyl 6-[9-(2-methoxybenzyl)-1,3,4,9-tetrahydro-2H-beta-carbolin-2-yl]-6-oxohexanoate,
(63) methyl 2-{[2-(6-methoxy-6-oxohexanoyl)-1,2,3,4-tetrahydro-9H-beta-carbolin-9-yl]methyl}benzoate,
(64) methyl 6-oxo-6-{9-[2-(trifluoromethyl)benzyl]-1,3,4,9-tetrahydro-2H-beta-carbolin-2-yl}hexanoate,
(68) 6-[9-(3-chlorobenzyl)-1,3,4,9-tetrahydro-2H-beta-carbolin-2-yl]-2,2-dimethyl-6-oxohexanoic acid,
(69) 6-[9-(3-chloro-4-fluorobenzyl)-1,3,4,9-tetrahydro-2H-beta-carbolin-2-yl]-2,2-dimethyl-6-oxohexanoic acid,
(70) 6-[9-(3-fluorobenzyl)-1,3,4,9-tetrahydro-2H-beta-carbolin-2-yl]-2,2-dimethyl-6-oxohexanoic acid,
(71) 6-[9-(4-cyanobenzyl)-1,3,4,9-tetrahydro-2H-beta-carbolin-2-yl]-2,2-dimethyl-6-oxohexanoic acid, or
(75) 6-[9-(4-cyanobenzyl)-1,3,4,9-tetrahydro-2H-beta-carbolin-2-yl]-3,3-dimethyl-6-oxohexanoic acid, a salt thereof or a solvate thereof or a prodrug thereof.

And, of the present compound, a compound in which U is a methylene group, an oxygen atom or —NR$^6$— (in the group, R$^6$ is as defined above), X is a nitrogen atom, and the ring A is (i) a 5- to 6-membered monocyclic heterocyclic ring containing one to four heteroatoms selected from an oxygen atom, a nitrogen atom and a sulfur atom or (ii) a C8-10 bicyclic heterocyclic ring containing one to four heteroatoms selected from an oxygen atom, a nitrogen atom and a sulfur atom is preferably:

(1) 6-oxo-6-[9-(2-thienylmethyl)-5,6,8,9-tetrahydro-7H-pyrido[4',3':4,5]pyrrolo[2,3-b]pyridin-7-yl]hexanoic acid,
(2) 6-oxo-6-[9-(3-thienylmethyl)-5,6,8,9-tetrahydro-7H-pyrido[4',3':4,5]pyrrolo[2,3-b]pyridin-7-yl]hexanoic acid,
(3) 6-{9-[(5,6-dichloro-3-pyridinyl)methyl]-5,6,8,9-tetrahydro-7H-pyrido[4',3':4,5]pyrrolo[2,3-b]pyridin-7-yl}-6-oxohexanoic acid,
(4) 6-{9-[(6-chloro-3-pyridinyl)methyl]-5,6,8,9-tetrahydro-7H-pyrido[4',3':4,5]pyrrolo[2,3-b]pyridin-7-yl}-6-oxohexanoic acid,
(9) 2,2-dimethyl-6-oxo-6-[9-(2-thienylmethyl)-5,6,8,9-tetrahydro-7H-pyrido[4',3':4,5]pyrrolo[2,3-b]pyridin-7-yl]hexanoic acid,
(10) 2,2-dimethyl-6-oxo-6-[9-(3-thienylmethyl)-5,6,8,9-tetrahydro-7H-pyrido[4',3':4,5]pyrrolo[2,3-b]pyridin-7-yl]hexanoic acid,
(11) 6-{9-[(5,6-dichloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,
(12) 6-{9-[(6-chloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,
(17) methyl 6-(9-benzyl-5,6,8,9-tetrahydro-7H-pyrido[4',3':4,5]pyrrolo[2,3-b]pyridin-7-yl)-6-oxohexanoate,
(20) 6-{9-[(1,3-dimethyl-1H-pyrazol-5-yl)methyl]-5,6,8,9-tetrahydro-7H-pyrido[4',3':4,5]pyrrolo[2,3-b]pyridin-7-yl}-2,2-dimethyl-6-oxohexanoic acid,
(22) 6-{9-[(5-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,
(23) 6-{9-[(1-methyl-1H-indol-4-yl)methyl]-5,6,8,9-tetrahydro-7H-pyrido[4',3':4,5]pyrrolo[2,3-b]pyridin-7-yl}-6-oxohexanoic acid,
(24) 6-[9-(2-furylmethyl)-5,6,8,9-tetrahydro-7H-pyrido[4',3':4,5]pyrrolo[2,3-b]pyridin-7-yl]-2,2-dimethyl-6-oxohexanoic acid,
(25) 6-[9-(3-furylmethyl)-5,6,8,9-tetrahydro-7H-pyrido[4',3':4,5]pyrrolo[2,3-b]pyridin-7-yl]-2,2-dimethyl-6-oxohexanoic acid,
(28) methyl 6-{9-[(1,3-dimethyl-1H-pyrazol-5-yl)methyl]-5,6,8,9-tetrahydro-7H-pyrido[4',3':4,5]pyrrolo[2,3-b]pyridin-7-yl}-2,2-dimethyl-6-oxohexanoate,
(30) 6-oxo-6-[9-(3-pyridinylmethyl)-5,6,8,9-tetrahydro-7H-pyrido[4',3':4,5]pyrrolo[2,3-b]pyridin-7-yl]hexanoic acid,
(31) 6-[9-(2-furylmethyl)-5,6,8,9-tetrahydro-7H-pyrido[4',3':4,5]pyrrolo[2,3-b]pyridin-7-yl]-6-oxohexanoic acid,
(32) 6-[9-(3-furylmethyl)-5,6,8,9-tetrahydro-7H-pyrido[4',3':4,5]pyrrolo[2,3-b]pyridin-7-yl]-6-oxohexanoic acid,
(34) 2,2-dimethyl-6-{9-[(5-methyl-3-isoxazolyl)methyl]-5,6,8,9-tetrahydro-7H-pyrido[4',3':4,5]pyrrolo[2,3-b]pyridin-7-yl}-6-oxohexanoic acid,
(36) methyl 2,2-dimethyl-6-{9-[(1-methyl-1H-pyrazol-5-yl)methyl]-5,6,8,9-tetrahydro-7H-pyrido[4',3':4,5]pyrrolo[2,3-b]pyridin-7-yl}-6-oxohexanoate,
(37) 6-oxo-6-[9-(4-pyridinylmethyl)-5,6,8,9-tetrahydro-7H-pyrido[4',3':4,5]pyrrolo[2,3-b]pyridin-7-yl]hexanoic acid,
(38) 2,2-dimethyl-6-{9-[(1-methyl-1H-imidazol-5-yl)methyl]-5,6,8,9-tetrahydro-7H-pyrido[4',3':4,5]pyrrolo[2,3-b]pyridin-7-yl}-6-oxohexanoic acid,
(40) 6-{9-[(5-methyl-3-isoxazolyl)methyl]-5,6,8,9-tetrahydro-7H-pyrido[4',3':4,5]pyrrolo[2,3-b]pyridin-7-yl}-6-oxohexanoic acid,
(43) 6-oxo-6-[9-(2-pyridinylmethyl)-5,6,8,9-tetrahydro-7H-pyrido[4',3':4,5]pyrrolo[2,3-b]pyridin-7-yl]hexanoic acid,
(44) 2,2-dimethyl-6-{9-[(1-methyl-1H-pyrazol-5-yl)methyl]-5,6,8,9-tetrahydro-7H-pyrido[4',3':4,5]pyrrolo[2,3-b]pyridin-7-yl}-6-oxohexanoic acid,
(46) 6-{9-[(1-methyl-1H-imidazol-5-yl)methyl]-5,6,8,9-tetrahydro-7H-pyrido[4',3':4,5]pyrrolo[2,3-b]pyridin-7-yl}-6-oxohexanoic acid,
(47) 6-{9-[(1-methyl-1H-imidazol-2-yl)methyl]-5,6,8,9-tetrahydro-7H-pyrido[4',3':4,5]pyrrolo[2,3-b]pyridin-7-yl}-6-oxohexanoic acid,
(50) 2,2-dimethyl-6-{9-[(1-methyl-1H-imidazol-2-yl)methyl]-5,6,8,9-tetrahydro-7H-pyrido[4',3':4,5]pyrrolo[2,3-b]pyridin-7-yl}-6-oxohexanoic acid,
(52) 6-(9-benzyl-6-methyl-5,6,8,9-tetrahydro-7H-pyrido[4',3':4,5]pyrrolo[2,3-b]pyridin-7-yl)-6-oxohexanoic acid,
(55) 6-{9-[(6-chloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(56) 6-{9-[(5-fluoro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(57) 2,2-dimethyl-6-{9-[(1-methyl-1H-pyrazol-4-yl)methyl]-5,6,8,9-tetrahydro-7H-pyrido[4',3':4,5]pyrrolo[2,3-b]pyridin-7-yl}-6-oxohexanoic acid,

(58) 6-{9-[(1,3-dimethyl-1H-pyrazol-4-yl)methyl]-5,6,8,9-tetrahydro-7H-pyrido[4',3':4,5]pyrrolo[2,3-b]pyridin-7-yl}-2,2-dimethyl-6-oxohexanoic acid,

(59) 6-{9-[(3-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(60) 6-{9-[(6-chloro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(61) 6-{9-[(2,5-dimethyl-1,3-thiazol-4-yl)methyl]-5,6,8,9-tetrahydro-7H-pyrido[4',3':4,5]pyrrolo[2,3-b]pyridin-7-yl}-2,2-dimethyl-6-oxohexanoic acid,

(62) 6-{9-[(3-fluoro-4-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(63) 6-{9-[(5-chloro-2-thienyl)methyl]-5,6,8,9-tetrahydro-7H-pyrido[4',3':4,5]pyrrolo[2,3-b]pyridin-7-yl}-6-oxohexanoic acid,

(64) 6-{9-[(5-fluoro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(65) 6-{9-[(3-fluoro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(66) 6-{9-[(4-chloro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(67) 6-{9-[(2,4-dimethyl-1,3-thiazol-5-yl)methyl]-5,6,8,9-tetrahydro-7H-pyrido[4',3':4,5]pyrrolo[2,3-b]pyridin-7-yl}-2,2-dimethyl-6-oxohexanoic acid,

(68) 6-{9-[(2-chloro-4-pyridinyl)methyl]-5,6,8,9-tetrahydro-7H-pyrido[4',3':4,5]pyrrolo[2,3-b]pyridin-7-yl}-2,2-dimethyl-6-oxohexanoic acid,

(69) 6-{9-[(5-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(70) 6-{9-[(2,5-dimethyl-3-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(74) 6-{9-[(4-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(76) 6-{9-[(5-carbamoyl-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(77) 6-{9-[(5-cyano-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(79) 6-{9-[(2-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(82) 6-{9-[(5-chloro-3-thienyl)methyl]-5,6,8,9-tetrahydro-7H-pyrido[4',3':4,5]pyrrolo[2,3-b]pyridin-7-yl}-3,3-dimethyl-6-oxohexanoic acid,

(84) 6-{9-[(4-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(85) 6-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2,2-dimethyl-6-oxohexanoic acid,

(89) 6-{9-[(5-chloro-2-thienyl)methyl]-5,6,8,9-tetrahydro-7H-pyrido[4',3':4,5]pyrrolo[2,3-b]pyridin-7-yl}-3,3-dimethyl-6-oxohexanoic acid,

(90) 6-{9-[(2,5-dimethyl-3-thienyl)methyl]-5,6,8,9-tetrahydro-7H-pyrido[4',3':4,5]pyrrolo[2,3-b]pyridin-7-yl}-3,3-dimethyl-6-oxohexanoic acid,

(91) 6-{9-[(4-chloro-2-thienyl)methyl]-5,6,8,9-tetrahydro-7H-pyrido[4',3':4,5]pyrrolo[2,3-b]pyridin-7-yl}-3,3-dimethyl-6-oxohexanoic acid,

(95) 6-{9-[(6-chloro-3-pyridinyl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid,

(96) 6-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid,

(97) 6-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid,

(98) 6-{9-[(5-fluoro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid,

(99) 3-(2-{9-[(4-chloro-2-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid, (100) 3-(2-{9-[(5-chloro-3-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid, (101) 3-(2-{9-[(5-chloro-2-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid, (102) 3-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid, (106) 2-(3-{9-[(4-chloro-2-thienyl)methyl]-5,6,8,9-tetrahydro-7H-pyrido[4',3':4,5]pyrrolo[2,3-b]pyridin-7-yl}-3-oxopropoxy)-2-methylpropanoic acid, (107) 2-(3-{9-[(5-chloro-3-thienyl)methyl]-5,6,8,9-tetrahydro-7H-pyrido[4',3':4,5]pyrrolo[2,3-b]pyridin-7-yl}-3-oxopropoxy)-2-methylpropanoic acid, (108) 2-(3-{9-[(5-chloro-2-thienyl)methyl]-5,6,8,9-tetrahydro-7H-pyrido[4',3':4,5]pyrrolo[2,3-b]pyridin-7-yl}-3-oxopropoxy)-2-methylpropanoic acid, (111) 6-{9-[(4,5-dichloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid, (112) 6-{9-[(5-fluoro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid, (118) 2,2-dimethyl-6-{9-[(2-methyl-1,3-thiazol-5-yl)methyl]-5,6,8,9-tetrahydro-7H-pyrido[4',3':4,5]pyrrolo[2,3-b]pyridin-7-yl}-6-oxohexanoic acid, (127) (2Z)-6-[9-(3-fluorobenzyl)-5,6,8,9-tetrahydro-7H-pyrido[4',3':4,5]pyrrolo[2,3-b]pyridin-7-yl]-6-oxo-2-hexenoic acid, or (128) 6-[9-(3-fluorobenzyl)-5,6,8,9-tetrahydro-7H-pyrido[4',3':4,5]pyrrolo[2,3-b]pyridin-7-yl]-6-oxo-2-hexynoic acid, a salt thereof or a solvate thereof or a prodrug thereof.

And, of the present compound, a compound in which U is a methylene group, an oxygen atom or —NR$^6$—(in the group, R$^6$ is as defined above), X is a carbon atom, and the ring A is (i) a 5- to 6-membered monocyclic heterocyclic ring containing one to four heteroatoms selected from an oxygen atom, a nitrogen atom and a sulfur atom or (ii) a C8-10 bicyclic heterocyclic ring containing one to four heteroatoms selected from an oxygen atom, a nitrogen atom and a sulfur atom is preferably:

(1) 6-{9-[(2,5-dimethyl-1,3-thiazol-4-yl)methyl]-1,3,4,9-tetrahydro-2H-beta-carbolin-2-yl}-2,2-dimethyl-6-oxohexanoic acid,
(2) 6-{9-[(6-chloro-3-pyridinyl)methyl]-1,3,4,9-tetrahydro-2H-beta-carbolin-2-yl}-2,2-dimethyl-6-oxohexanoic acid,
(3) 6-{9-[(1,3-dimethyl-1H-pyrazol-5-yl)methyl]-1,3,4,9-tetrahydro-2H-beta-carbolin-2-yl}-2,2-dimethyl-6-oxohexanoic acid,
(5) 6-{9-[(6-chloro-3-pyridinyl)methyl]-1,3,4,9-tetrahydro-2H-beta-carbolin-2-yl}-3,3-dimethyl-6-oxohexanoic acid,
(7) 6-{9-[(1,3-dimethyl-1H-pyrazol-5-yl)methyl]-1,3,4,9-tetrahydro-2H-beta-carbolin-2-yl}-3,3-dimethyl-6-oxohexanoic acid, or
(8) 6-{9-[(2,5-dimethyl-1,3-thiazol-4-yl)methyl]-1,3,4,9-tetrahydro-2H-beta-carbolin-2-yl}-3,3-dimethyl-6-oxohexanoic acid, a salt thereof or a solvate thereof or a prodrug thereof.

In the present invention, unless it is explicitly stated otherwise, as apparent to a person skilled in the art, a symbol:

represents that a substituent is bound to a far side of a paper plane (i.e. α-configuration),

represents that a substituent is bound to a near side of a paper plane (i.e. β-configuration), and

represents α-configuration, β-configuration or an arbitrary mixture thereof.

In the present invention, unless particularly indicated, all isomers are included. For example, an alkyl group includes a straight group and a branched group. Further, an isomer due to the presence of an asymmetric carbon etc. (R, S body, α, β configuration, enantiomer, diastereomer), an optically active body having optical rotation (D, L, d, and l forms), a polar form by chromatographic separation (high polar form, low polar form), an equilibrium compound (e.g. tautomer generated in an amide bond etc.), a rotational isomer, a mixture of them at an arbitrary ratio, and a racemic mixture are all included in the present invention.

The compound represented by the general formula (I) is converted into a corresponding salt by the known method. As a salt, a water-soluble salt is preferable. Examples of a suitable salt include acid addition salts (e.g. inorganic acid salts such as hydrochloride, hydrobromide, hydroiodide, sulfate, phosphate and nitrate, organic acid salts such as acetate, lactate, tartrate, benzoate, citrate, methanesulfonate, ethanesulfonate, benzenesulfonate, toluenesulfonate, isethionate, glucuronate, gluconate, etc.), salts of an alkali metal (potassium, sodium etc.), salts of an alkaline earth metal (calcium, magnesium etc.), ammonium salts or salts of a pharmaceutically acceptable organic amine (e.g. tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.) etc.

The compound represented by the general formula (I) and a salt thereof can be also converted into a solvate. It is preferable that the solvate is low-toxic and water-soluble. Examples of a suitable solvate include solvates with water, or an alcoholic solvent (e.g. ethanol etc.).

And, the prodrug of the compound represented by the general formula (I) refers to a compound which is converted into the compound represented by the general formula (I) by a reaction with an enzyme or gastric acid etc. in a living body. Specifically, examples include, when the compound represented by the general formula (I) has an amino group, compounds in which the amino group is eicosanoylated, alanylated, pentylaminocarbonized, (5-methyl-2-oxo-1,3-dioxolene-4-yl)methoxycarbonylated, tetrahydrofuranylated, pyrrolidylmethylated, pivaloyloxymethylated, acetoxymethylated, or tert-butylated, when the compound represented by the general formula (I) has a hydroxy group, compounds in which the hydroxy group is acetylated, palmitoylated, propanoylated, pivaloylated, succinylated, fumarylated, alanylated, or dimethylaminomethylcarbonylated and, when the compound represented by the general formula (I) has a carboxy group, compounds in which the carboxy group is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolene-4-yl)methylesterified, cyclohexyloxycarbonylethylesterified, or methylamidated, and these compounds can be produced by the known method. And, the prodrug of the compound represented by the general formula (I) may be any of a hydrate and a non-hydrate. Alternatively, the prodrug of the compound represented by the general formula (I) may be a compound which is changed into the compound represented by the general formula (I) under the physiological condition, as described in "Development of Medicaments", vol. 7 "Molecular Design", p. 163-198, published by HirokawaShoten in 1990.

Further, each atom constituting the compound represented by the general formula (I) may be substituted with an isotope thereof (e.g. $^2$H, $^3$H, $^{13}$C, $^{14}$C, $^{35}$S, $^{125}$I etc.) etc.

[Process for Producing the Present Compound]

The present compound represented by the general formula (I) can be produced, for example, by the following method, the method shown in Examples or a method in accordance with them.

Of the compound represented by the general formula (I), a compound represented by the general formula (I-A):

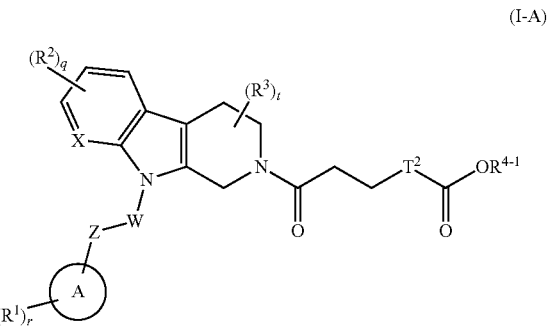

(I-A)

(wherein $T^2$ represents a straight C1-3 alkylene group optionally substituted with one or two $R^5$s, $R^{4-1}$ represents a C1-4 alkyl group, and other symbols are as defined above) can be produced by the method shown in the following reaction step formula 1 and, of the compound represented by the general formula (I), a compound in which U is a methylene group, T is a straight C1-3 alkylene group optionally substituted with one or two $R^5$s (in the group, $R^5$ is as defined above), and $R^4$ is a hydrogen atom can be produced by further subjecting the compound represented by the general formula (I-A) to a deprotection reaction.

Herein, the deprotection reaction, for example, in the case of a deprotection reaction by alkali hydrolysis, is performed, for example, at 0 to 40° C. using hydroxide of an alkali metal (e.g. sodium hydroxide, potassium hydroxide, lithium hydroxide etc.), hydroxide of an alkaline earth metal (e.g. barium hydroxide, calcium hydroxide etc.) or carbonate (e.g. sodium carbonate, potassium carbonate etc.) or an aqueous solution thereof or a mixture thereof in an organic solvent (e.g. methanol, tetrahydrofuran, dioxane etc.).

an unsubstituted straight C1-3 alkylene group, $T^b$ represents a straight C1-3 alkylene group substituted with one or two $R^5$s, and other symbols are as defined above.)

In the reaction step formula 1, the reaction 1-1 is known, and can be performed, for example, by reacting a compound represented by the general formula (I-A-3) and a compound represented by the general formula (I-A-4) at 0° C. to a refluxing temperature in an organic solvent (e.g. tetrahydrofuran, dichloromethane, chloroform, benzene, toluene, xylene, hexane, heptane, cyclohexane, diethyl ether, dioxane, acetone, ethyl methyl ketone, acetonitrile, dimethyl sulfoxide, N,N-dimethylformamide, dimethylacetamide, ethyl acetate etc.) and in the presence or absence of a catalyst (e.g. potassium iodide, sodium iodide, tetrabutylammonium iodide etc.) in the presence of a base (e.g. potassium carbonate, sodium carbonate, cesium carbonate, sodium hydride etc.).

In the reaction step formula 1, the reaction 1-2 is known, and can be performed, for example, by reacting a compound represented by the general formula (I-A-1) and a compound Reaction step formula 1

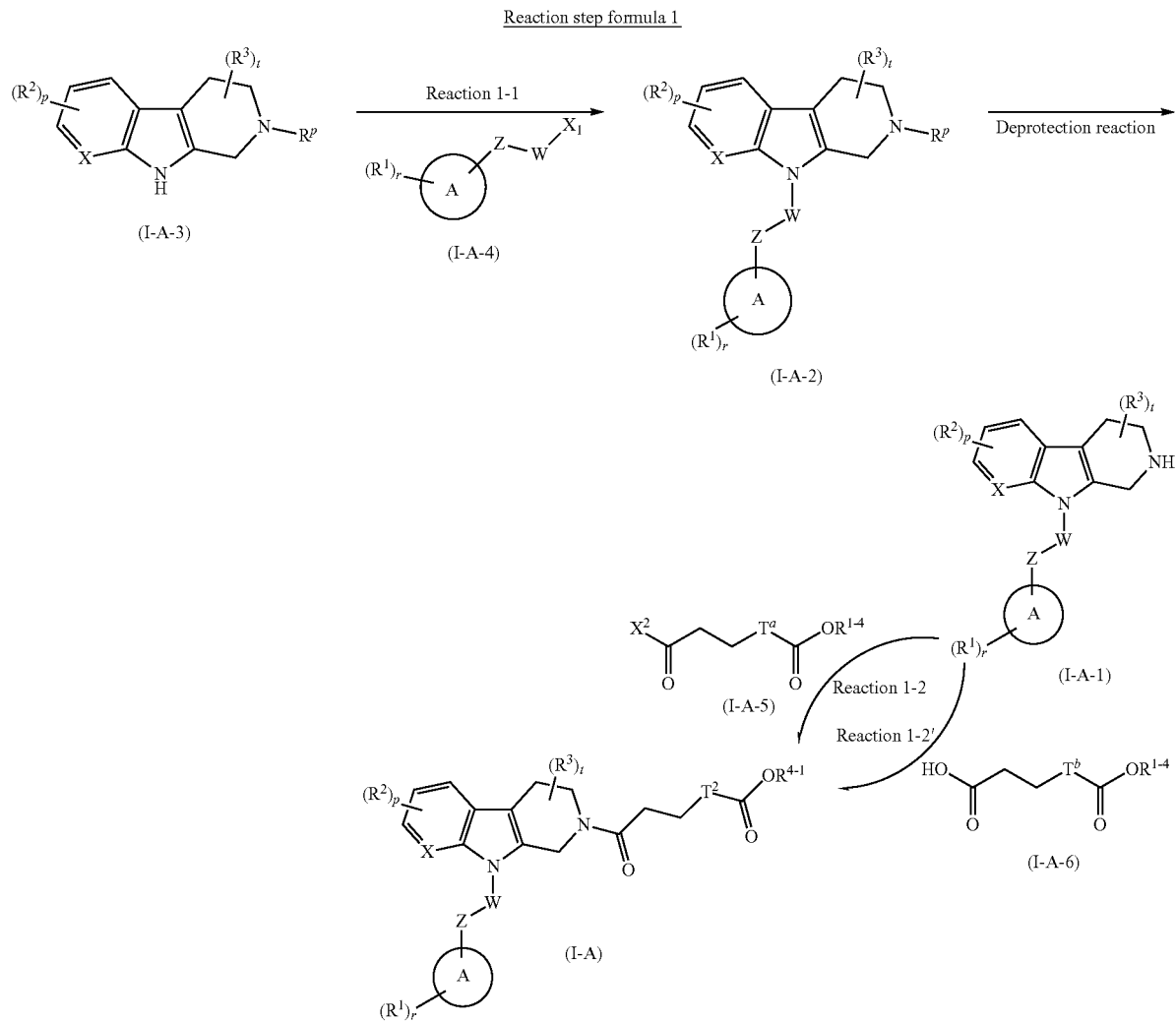

(wherein $R^p$ represents a protective group for an amino group (e.g. tert-butoxycarbonyl group, benzyloxycarbonyl group, fluorenylcarbonyl group, trityl group, o-nitrobenzenesulfenyl group etc.), $X^1$ and $X^2$ represent a halogen atom, $T^a$ represents represented by the general formula (I-A-5) at −20° C. to a refluxing temperature in an organic solvent (e.g. chloroform, dichloromethane, diethyl ether, tetrahydrofuran etc.) in the presence of a base (e.g. pyridine, triethylamine, dimethylaniline, dimethylaminopyridine, diisopropylethylamine etc.). Alternatively, the reaction 1-2 can be also performed by reacting a compound represented by the general formula (I-A-1) and a compound represented by the general formula (I-A-5) at 0° C. to a refluxing temperature using an aqueous alkali solution (e.g. aqueous sodium bicarbonate solution or sodium hydroxide solution etc.) in an organic solvent (e.g. dioxane, tetrahydrofuran, diethyl ether etc.).

In the reaction step formula 1, the reaction 1-2' is known, and can be performed, for example, by a method using a condensing agent, a method using acid halide, a method using a mixed acid anhydride etc.

The method using a condensing agent is performed, for example, by reacting a compound represented by the general formula (I-A-1) and a compound represented by the general formula (I-A-6) at 0° C. to a refluxing temperature using a condensing agent (e.g. 1,3-dicyclohexylcarbodiimide (DCC), ethylene dichloride (EDC), 1,1'-carbonyldiimidazole (CDI), 2-chloro-1-methylpyridinium iodine, 1-propylphosphonic acid cyclic anhydride (PPA) etc.) and using or not using 1-hydroxybenzotriazole (HOBt), in an organic solvent (e.g. chloroform, dichloromethane, N,N-dimethylformamide, diethyl ether, tetrahydrofuran etc.) or without a solvent and in the presence or absence of a base (e.g. pyridine, triethylamine, dimethylaniline, dimethylaminopyridine etc.).

The method using acid halide is performed, for example, by reacting a compound represented by the general formula (I-A-6) with an acid halidizing agent (e.g. oxalyl chloride, thionyl chloride etc.) at –20° C. to a refluxing temperature in an organic solvent (e.g. chloroform, dichloromethane, diethyl ether, tetrahydrofuran, dimethoxyethane etc.) or without a solvent, and reacting the resulting acid halide with a compound represented by the general formula (I-A-1) at 0° C. to a refluxing temperature in an organic solvent (e.g. chloroform, dichloromethane, diethyl ether, tetrahydrofuran, acetonitrile, ethyl acetate etc.) in the presence of a base (e.g. pyridine, triethylamine, dimethylaniline, dimethylaminopyridine, diisopropylethylamine etc.). Alternatively, the method using acid halide can be also performed by reacting the resulting acid halide with a compound represented by the general formula (I-A-1) at 0° C. to a refluxing temperature using an aqueous alkali solution (e.g. aqueous sodium bicarbonate solution or sodium hydroxide solution etc.) in an organic solvent (e.g. dioxane, tetrahydrofuran, dichloromethane etc.) in the presence or absence of a phase transfer catalyst (e.g. quaternary ammonium salt such as tetrabutylammonium chloride, triethylbenzylammonium chloride, trioctylmethylammonium chloride, trimethyldecylammonium chloride, tetramethylammonium bromide etc., and others).

On the other hand, the method using a mixed acid anhydride can be also performed, for example, by reacting a compound represented by the general formula (I-A-6) with acid halide (e.g. pivaloyl chloride, tosyl chloride, mesyl chloride etc.), or an acid derivative (e.g. ethyl chloroformate, isobutyl chloroformate etc.) at 0° C. to a refluxing temperature in an organic solvent (e.g. chloroform, dichloromethane, diethyl ether, tetrahydrofuran etc.) or without a solvent in the presence of a base (e.g. pyridine, triethylamine, dimethylaniline, dimethylaminopyridine, diisopropylethylamine etc.), and reacting the resulting mixed acid anhydride with a compound represented by the general formula (I-A-1) at 0° C. to a refluxing temperature in an organic solvent (e.g. chloroform, dichloromethane, diethyl ether, tetrahydrofuran etc.).

It is desirable that these reactions are all performed in the inert gas (argon, nitrogen etc.) atmosphere under the anhydrous condition.

Of the compound represented by the general formula (I), a compound represented by the general formula (I-B):

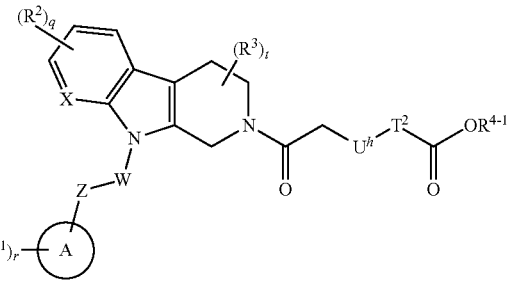

(I-B)

(wherein $U^h$ represents an oxygen atom or $-NR^6-$, and other symbols are as defined above) can be produced by the method shown in the following reaction step formula 2 and, of the compound represented by the general formula (I), a compound in which U is $-N(CH_3)-$ can be produced by further subjecting a compound in which $U^h$ is $-NH-$, of the compound represented by the general formula (I-B), to a reductive amination reaction. On the other hand, of the compound represented by the general formula (I), a compound in which U is an oxygen atom or $-NR^6-$ (in the group, $R^6$ is as defined above), T is a straight C1-3 alkylene group optionally substituted with one or two $R^5$s (in the group, $R^5$ is as defined above), and $R^4$ is a hydrogen atom can be produced by further subjecting the compound represented by the general formula (I-B) to a deprotection reaction.

Herein, the reductive amination reaction is well-known, and can be performed, for example, by a reaction at 0 to 100° C. in a mixed solvent of an inert organic solvent (dimethylformamide, dimethyl sulfoxide, chloroform, methylene chloride, dichloroethane, diethyl ether, tetrahydrofuran, acetonitrile etc.) and acetic acid in the presence of a reducing agent (sodium triacetoxyborohydride, sodium cyanoborohydride etc.).

On the other hand, the deprotection reaction, for example, in the case of a deprotection reaction by alkali hydrolysis, can be performed, for example, at 0 to 40° C. in an organic solvent (e.g. methanol, tetrahydrofuran, dioxane etc.) using hydroxide of an alkali metal (e.g. sodium hydroxide, potassium hydroxide, lithium hydroxide etc.), hydroxide of an alkaline earth metal (e.g. barium hydroxide, calcium hydroxide etc.) or carbonate (e.g. sodium carbonate, potassium carbonate etc.) or an aqueous solution thereof or a mixture thereof.

Reaction step formula 2

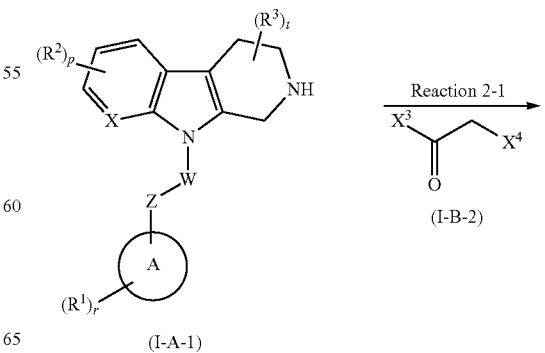

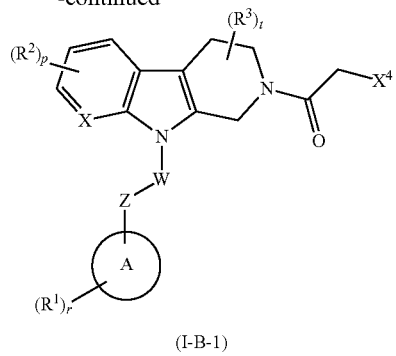

(I-B-1)

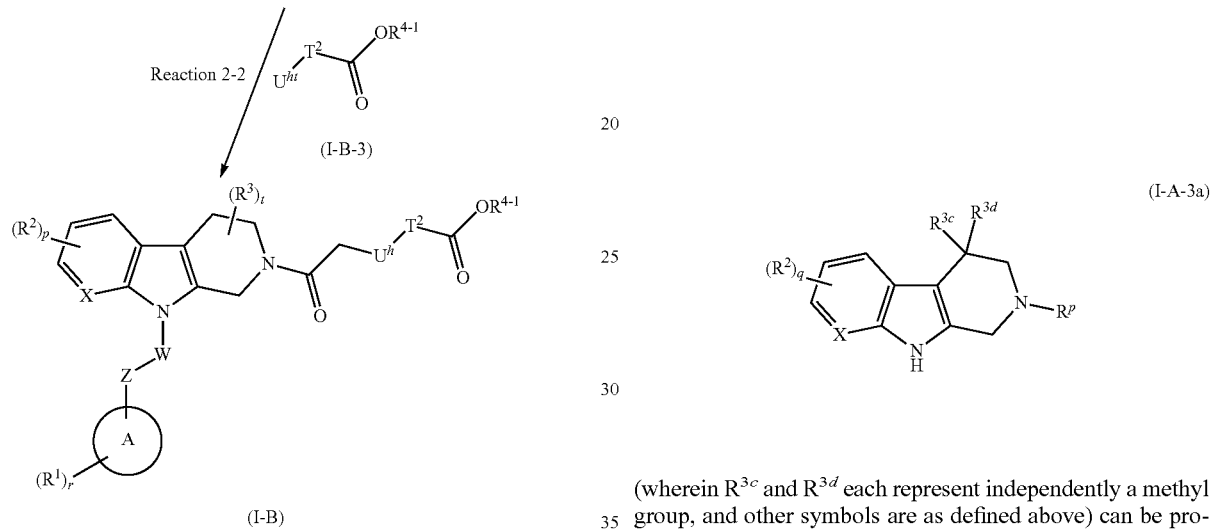

(wherein $X^3$ and $X^4$ each represent independently a halogen atom, $U^{ht}$ represents a hydroxy group or an amino group, and other symbols are as defined above.)

In the reaction step formula 2, the reaction 2-1 can be performed by the same method as that of the reaction 1-2, and the reaction 2-2 can be performed by the same method as that of the reaction 1-1.

Of the compound represented by the general formula (I-A-3) in the reaction step formula 1, a compound represented by the general formula (I-A-3a):

(I-A-3a)

(wherein $R^{3c}$ and $R^{3d}$ each represent independently a methyl group, and other symbols are as defined above) can be produced by the method shown in the following reaction step formula 3.

Reaction step formula 3

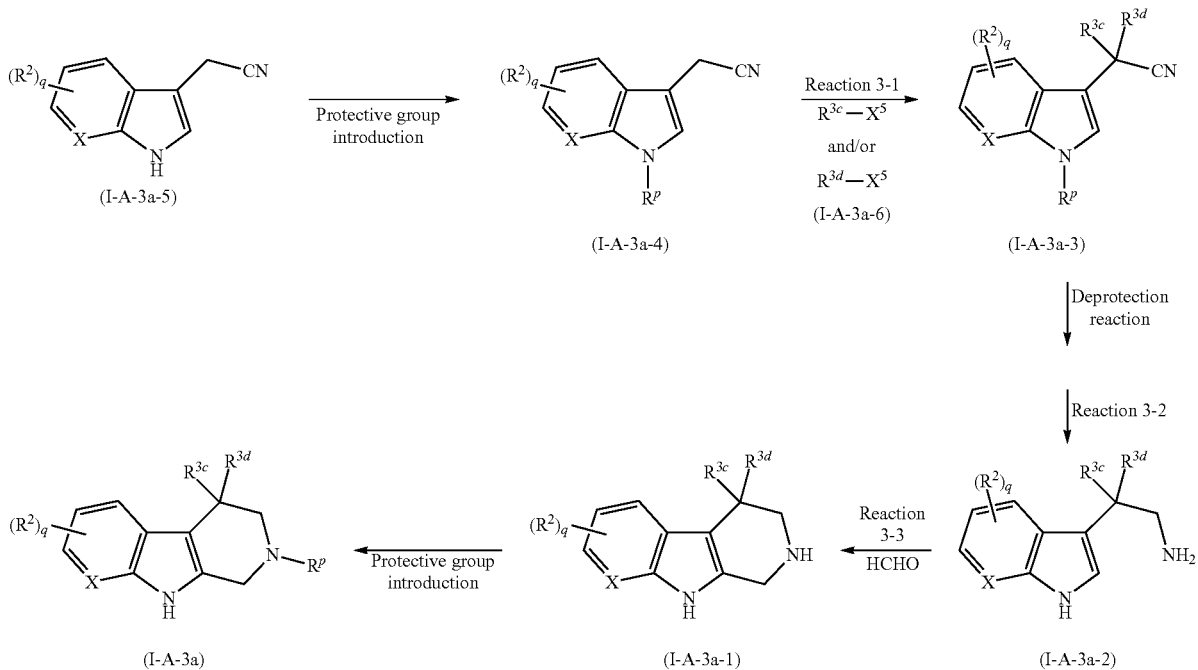

(wherein X⁵ represents a halogen atom, and other symbols are as defined above.)

In the reaction step formula 3, the reaction 3-1 can be performed by the same method as that of the reaction 1-1. The reaction 3-2 is known, and is performed, for example, by a reaction at about −10° C. to a refluxing temperature in an organic solvent (methanol, ethanol, tetrahydrofuran, diethyl ether etc.) in the presence of a reducing agent (lithium aluminum hydride, lithium borohydride, sodium borohydride, borane-pyridine complex, borane-tetrahydrofuran complex etc.). Alternatively, the reaction is performed at a temperature of 0 to 200° C. in an inert solvent [ether solvent (e.g. tetrahydrofuran, dioxane, dimethoxyethane, diethyl ether etc.), alcohol solvent (e.g. methanol, ethanol etc.), benzene solvent (e.g. benzene, toluene etc.), ketone solvent (e.g. acetone, methyl ethyl ketone etc.), nitrile solvent (e.g. acetonitrile etc.), amide solvent (e.g. dimethylformamide etc.), water, ethyl acetate, acetic acid or a mixed solvent of two or more of them etc.] in the presence of a hydrogenation catalyst (e.g. palladium carbon, palladium black, palladium, palladium hydroxide, platinum dioxide, nickel, Raney nickel, ruthenium chloride etc.), in the presence or absence of an inorganic acid (e.g. hydrochloric acid, sulfuric acid, hypochlorous acid, boric acid, tetrafluoroboric acid etc.) or an organic acid (e.g. acetic acid, p-toluenesulfonic acid, oxalic acid, trifluoroacetic acid, formic acid etc.), in the hydrogen atmosphere under an ordinary pressure or under increased pressure, or in the presence of ammonium formate. When the inorganic acid or the organic acid is used, a salt thereof may be used.

And, the reaction 3-3 is known, and can be performed by reacting a compound represented by the general formula (I-A-3a-2) and formaldehyde at 0° C. to a refluxing temperature in an organic solvent (e.g. tetrahydrofuran, dichloromethane, chloroform, benzene, toluene, xylene, hexane, heptane, cyclohexane, diethyl ether, dioxane, acetone, ethyl methyl ketone, acetonitrile, dimethyl sulfoxide, N,N-dimethylformamide, dimethylacetamide, ethyl acetate etc.) in the presence of an acid (e.g. hydrogen chloride, sulfuric acid, acetic acid, trifluoroacetic acid etc.).

Of the compound represented by the general formula (I-A-6) in the reaction step formula 1, a compound represented by the general formula (I-A-6a):

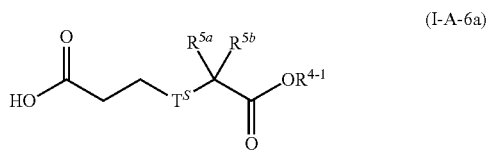

(I-A-6a)

(wherein, $T^S$ represents a methylene group or an ethylene group, and other symbols are as defined above) can be produced by the method shown in the following reaction step formula 4.

Reaction step formula 4

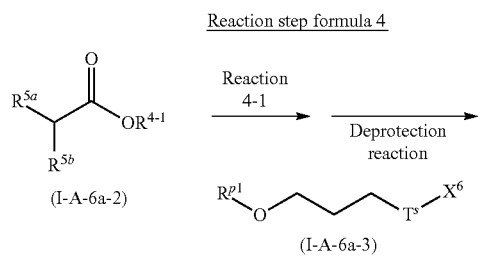

(I-A-6a-2)

(I-A-6a-3)

-continued

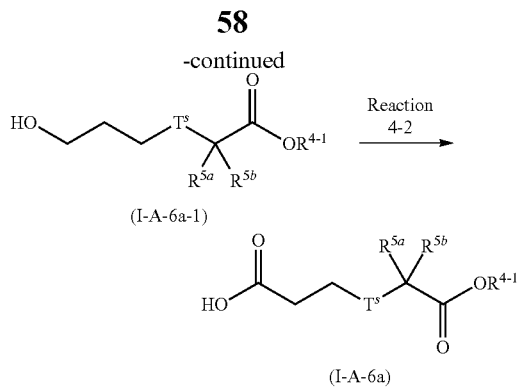

(I-A-6a-1)

(I-A-6a)

(wherein, $X^6$ represents a leaving group (e.g. halogen atom etc.), $R^{p1}$ represents a protective group for a hydroxy group (e.g. methoxymethyl group, benzyl group or tetrahydropyranyl group etc.), and other symbols are as defined above.)

In the reaction step formula 4, the reaction 4-1 is known, and can be performed, for example, by reacting a compound represented by the general formula (I-A-6a-2) and a compound represented by the general formula (I-A-6a-3) at −78° C. to a refluxing temperature in an organic solvent (e.g. tetrahydrofuran, benzene, toluene, xylene, hexane, heptane, cyclohexane, diethyl ether, dioxane, dimethyl sulfoxide, N,N-dimethylformamide, dimethylacetamide etc.) in the presence of a base (e.g. lithium hexamethyldisilazide, lithium diisopropylamide and sodium hexamethyldisilazide etc.).

On the other hand, of the compound represented by the general formula (I-A-6), a compound represented by the general formula (I-A-6b):

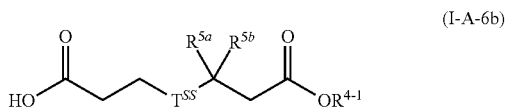

(I-A-6b)

(wherein $T^{SS}$ represents a bond or a methylene group, and other symbols are as defined above) can be produced by the method shown in the following reaction step formula 5.

Reaction step formula 5

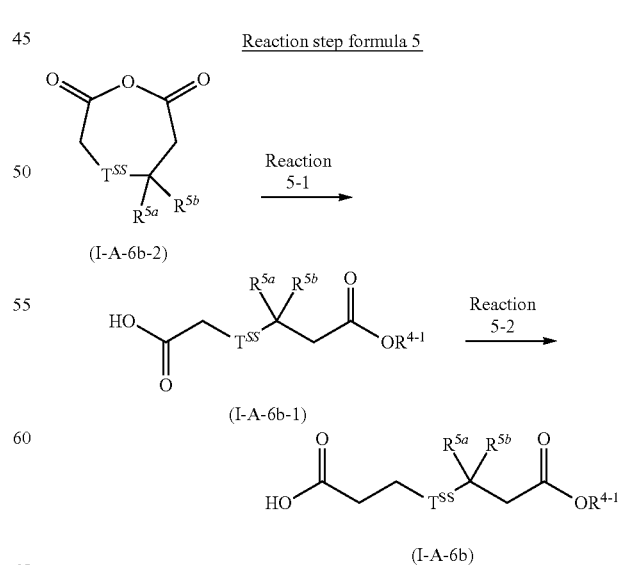

(I-A-6b-2)

(I-A-6b-1)

(I-A-6b)

(wherein all symbols are as defined above)

In the reaction step formula 5, the reaction 5-1 is known, and can be performed, for example, at 0° C. to a refluxing temperature in an organic solvent (e.g. methanol, ethanol etc.) in the presence or absence of a base (e.g. sodium methoxide, sodium ethoxide etc.). And, the reaction 5-2 is known, and can be performed, for example, by reacting a compound represented by the general formula (I-A-6b-1) with an acid halidizing agent (e.g. oxalyl chloride, thionyl chloride etc.) at −20° C. to a refluxing temperature in an organic solvent (e.g. chloroform, dichloromethane, diethyl ether, tetrahydrofuran, dimethoxyethane etc.) or without a solvent, reacting the resulting acid halide at −20° C. to a refluxing temperature in an organic solvent (e.g. chloroform, dichloromethane, diethyl ether, tetrahydrofuran, acetonitrile, ethyl acetate etc.) in the presence of a diazomethylating agent (e.g. diazomethane, trimethylsilyldiazomethane etc.), and subjecting the resulting diazomethyl ketone to a reaction at −20° C. to a refluxing temperature in an organic solvent (e.g. dioxane, tetrahydrofuran, dichloromethane etc.) or without a solvent in the presence of an alcohol (e.g. methanol, ethanol, propanol, butanol, benzyl alcohol etc.) in the presence of a base (e.g. pyridine, triethylamine, dimethylaniline, dimethylaminopyridine, diisopropylethylamine etc.).

Of a compound represented by the general formula (I-C):

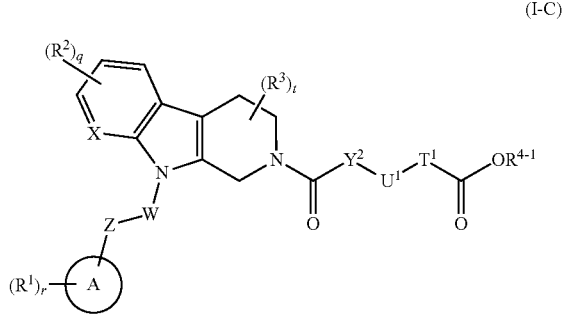

(I-C)

(wherein $Y^2$ represents a bond, or a methylene group or an ethylene group, optionally substituted with one or two $R^8$s, and other symbols are as defined above), when the "5- to 7-membered monocycle" in the "5- to 7-membered monocycle optionally substituted with one to five $R^7$s (in the group, $R^7$ is as defined above)" represented by $U^1$ is a C5-7 monocyclic carbon ring or a 5- to 7-membered monocyclic heterocyclic ring having a carbon atom binding to $Y^2$, or $U^1$ is a C5-10 bridged carbon ring optionally substituted with one to five $R^7$s, an objective compound can be produced by subjecting a compound represented by the general formula (I-A-1) and a compound represented by the general formula (I-C-1):

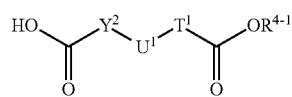

(I-C-1)

(wherein all symbols are as defined above) to the same reaction as the reaction 1-2' in the reaction step formula 1, or can be also produced by subjecting a compound represented by the general formula (I-C-2):

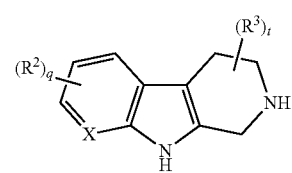

(I-C-2)

(wherein all symbols are as defined above) and a compound represented by the general formula (I-C-1) to the same reaction as the reaction 1-2' in the reaction step formula 1, and further subjecting to the same reaction as the reaction 1-1 in the reaction step formula 1 using a compound represented by the general formula (I-A-4).

On the other hand, of the compound represented by the general formula (I-C), a compound in which the "5- to 7-membered monocycle" in the "5- to 7-membered monocycle optionally substituted with one to five $R^7$s (in the formula, $R^7$ is as defined above)" represented by $U^1$ is a 5- to 7-membered monocyclic nitrogen-containing heterocyclic ring having a nitrogen atom binding to $Y^2$ can be produced by subjecting a compound represented by the general formula (I-C-3):

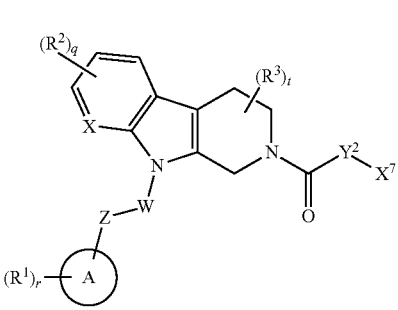

(I-C-3)

(wherein $X^7$ represents a halogen atom, and other symbols are as defined above) and a compound represented by the general formula (I-C-4):

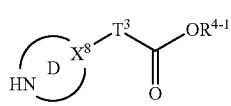

(I-C-4)

(wherein the ring D represents a 5- to 7-membered monocyclic nitrogen-containing heterocyclic ring optionally substituted with one to five $R^7$s (in the group, $R^7$ is as defined above), $X^8$ represents a carbon atom or a nitrogen atom, and other symbols are as defined above) to the same reaction as the reaction 1-1 in the reaction step formula 1. Further, of the compound represented by the general formula (I), a compound in which U is a 5- to 7-membered monocycle or a C5-10 bridged carbon ring, optionally substituted with one to five $R^7$s (in the groups, $R^7$ is as defined above), Y is a bond or a methylene group or an ethylene group, optionally substituted with one or two $R^8$s (in the groups, $R^8$ is as defined above), T is a bond, or a methylene group or an ethylene group, optionally substituted with one or two $R^5$s (in the groups, $R^5$ is as defined above), and $R^4$ is a hydrogen atom can be produced by further subjecting the compound represented by the general formula (I-C) to a deprotection reaction.

Herein, examples of the "5- to 7-membered monocyclic nitrogen-containing heterocyclic ring" in the "5- to 7-membered monocyclic nitrogen-containing heterocyclic ring optionally substituted with one to five $R^7$s" represented by the ring D include pyrrole, pyrroline, pyrrolidine, tetrahydrooxazole, tetrahydroisooxazole, tetrahydrothiazole, tetrahydroisothiazole, imidazole, pyrazole, imidazoline, imidazolidine, pyrazoline, pyrazolidine, dihydrofurazan, tetrahydrofurazan, dihydrooxadiazole, tetrahydrooxadiazole, dihydrothiadiazole, tetrahydrothiadiazole, triazole, triazoline, triazolidine, tetrazole, tetrazoline, tetrazolidine, dihydropyridine, tetrahydropyridine, piperidine, tetrahydrooxazine, tetrahydrothiazine, morpholine, thiomorpholine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxadiazine, tetrahydrooxadiazine, dihydrothiadiazine, tetrahydrothiadiazine, azepine, dihydroazepine, tetrahydroazepine, perhydroazepine, perhydrooxazepine, perhydrothiazepine, diazepine, dihydrodiazepine, tetrahydrodiazepine, perhydrodiazepine, tetrahydrooxadiazepine, perhydrooxadiazepine, tetrahydrothiadiazepine and perhydrothiadiazepine.

In addition, the compound represented by the general formula (I-C-3) can be produced by the same method as the method of producing the compound represented by the general formula (I-B-1) in the reaction step formula 2.

In the above reaction step formula, a method of introducing a protective group into an amino group can be performed by the method described in T. W. Greene, Protective Groups in Organic Synthesis, Wiley, New York, 1999, for example, in introduction of a protective group such as a tert-butoxycarbonyl group, a benzyloxycarbonyl group, a fluorenylcarbonyl group, a trityl group, an o-nitrobenzenesulfenyl group etc. of $R^p$, the introduction can be performed by a reaction at −50 to 100° C. in a solvent such as dichloromethane, chloroform, 1,2-dichloroethane, tetrahydrofuran, dioxane, toluene, ethyl acetate or water using di-tert-butyl dicarbonate, benzyloxycarbonyl chloride, fluorenylcarbonyl chloride, trityl chloride, o-nitrobenzenesulfenyl chloride or the like, respectively. Thereupon, if necessary, introduction can be performed using a base such as amines such as triethylamine, diisopropylethylamine and the like, organic acid salts such as sodium 2-ethylhexanoate and potassium 2-ethylhexanoate, or inorganic bases such as sodium hydroxide and potassium carbonate.

In the above reaction step formula, a reaction of deprotecting a protective group for a carboxyl group, a hydroxy group or an amino group is well-known, and examples include a deprotection reaction by alkali hydrolysis, a deprotection reaction under the acidic condition, a deprotection reaction by hydrogenolysis, a deprotection reaction of a silyl group, a deprotection reaction using a metal, a deprotection reaction using an organometal and the like.

For example, the deprotection reaction by alkali hydrolysis is performed at a temperature of 0 to 40° C. in an organic solvent (methanol, tetrahydrofuran or 1,4-dioxane alone, or a mixed solvent consisting of a plurality of solvents among them at an arbitrary ratio) using hydroxide of an alkali metal (sodium hydroxide, potassium hydroxide, lithium hydroxide etc.), hydroxide of an alkaline earth metal (barium hydroxide, calcium hydroxide etc.) or carbonate (sodium carbonate, potassium carbonate etc.) or an aqueous solution thereof or a mixture thereof.

On the other hand, the deprotection reaction under the acidic condition is performed, for example, at a temperature of 0 to 100° C. in an organic solvent (dichloromethane, chloroform, 1,4-dioxane, ethyl acetate or anisole alone, or a mixed solvent consisting of a plurality of solvents among them at an arbitrary ratio) in an organic acid (acetic acid, trifluoroacetic acid, methanesulfonic acid, p-toluenesulfonic acid etc.), or an inorganic acid (hydrochloric acid, sulfuric acid etc.) or a mixture thereof (hydrogen bromide/acetic acid etc.).

The deprotection reaction by hydrogenolysis is performed, for example, at a temperature of 0 to 200° C. in a solvent (ether solvent (tetrahydrofuran, 1,4-dioxane, dimethoxyethane, diethyl ether etc.), alcohol solvent (methanol, ethanol etc.), benzene solvent (benzene, toluene etc.), ketone solvent (acetone, methyl etheyl ketone etc.), nitrile solvent (acetonitrile etc.), amide solvent (N,N-dimethylformamide etc.), water, ethyl acetate, acetic acid, or a mixed solvent of two or more of them), in the presence of a catalyst (palladium-carbon, palladium black, palladium hydroxide, platinum oxide, Raney nickel etc.), under the hydrogen atmosphere under ordinary pressure or increased pressure, or in the presence of ammonium formate. The deprotection reaction of a silyl group is performed, for example, at a temperature of 0 to 40°C. in an organic solvent which is miscible with water (tetrahydrofuran or acetonitrile alone, or a mixed solvent consisting of a plurality of solvents among them at an arbitrary ratio) using tetrabutylammonium fluoride.

The deprotection reaction using a metal is performed, for example, at a temperature of 0 to 40° C. in an acidic solvent (acetic acid, buffer having a pH of 4.2 to 7.2, or a mixed solvent of those solutions and an organic solvent such as tetrahydrofuran) in the presence of a zinc powder by applying ultrasound or applying no ultrasound.

The deprotection reaction using a metal complex is performed, for example, at a temperature of 0 to 40° C. in an organic solvent (dichloromethane, N,N-dimethylformamide, tetrahydrofuran, ethyl acetate, acetonitrile, 1,4-dioxane, ethanol etc.), water or a mixed solvent of them in the presence of a trap reagent (tributyltin hydroride, triethylsilane, dimedone, morpholine, diethylamine, pyrrolidine etc.), an organic acid (acetic acid, formic acid, 2-ethylhexanoic acid etc.) and/or an ortanic acid salt (sodium 2-ethylhexanoate, potassium 2-ethylhexanoate etc.) in the presence or absence of a phosphine reagent (triphenylphosphine etc.), using a metal complex (tetrakistriphenylphosphinepalladium (0), bis(triphenylphosphine)palladium (II) dichloride, palladium (II) acetate, tris (triphenylphosphine)rhodium (I) chloride etc.).

Alternatively, in addition to the foregoing, the deprotection reaction can be performed, for example, by the method described in T. W. Greene, Protective Groups in Organic Synthesis, Wiley, New York, 1999.

Examples of a protective group for a carboxyl group include methyl, ethyl, tert-butyl, trichloroethyl, benzyl (Bn), phenacyl, p-methoxybenzyl, trityl, 2-chlorotrityl etc.

Example of a protective group for an amino group include a benzyloxycarbonyl group, a tert-butoxycarbonyl group, an allyloxycarbonyl (Alloc) group, a 1-methyl-1-(4-biphenyl) ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl(SEM) group and the like.

Examples of a protective group for a hydroxy group include methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc) and the like.

Of the present compound, compounds other than those shown above can be produced by the known method, for example, the method described in Comprehensive Organic Transformations: A Guide to Functional Group Preparations, 2nd Edition (Richard C. Larock, John Wiley & Sons Inc, 1999) and the like, or by using a combination of a method in which a part of the known method is modified and the like.

In each reaction in the present specification, compounds represented by the general formula (I-A-3), the general formula (I-A-4), the general formula (I-A-5), the general formula (I-A-6), the general formula (I-B-2), the general formula (I-B-3), the general formula (I-A-3a-5), the general formula (I-A-3a-6), the general formula (I-A-6a-2), the general formula (I-A-6a-3), the general formula (I-A-6b-2), the general formula (I-C-1), the general formula (I-C-2) and the general formula (I-C-4), respectively, are known, or can be easily produced by the known method such as Tetrahedron Letters, 2002, Vol. 43, No. 22, p. 4059-4061 and WO 2000/52032 and the like.

In each reaction in the present specification, a reaction accompanying heating can be performed using a water bath, an oil bath, a sand bath or a microwave as apparent to a person skilled in the art.

In each reaction in the present specification, conveniently, a solid phase-supporting reagent supported by a high-molecular polymer (e.g. polystyrene, polyacrylamide, polypropylene, polyethylene glycol etc.) may be used.

In each reaction in the present specification, the reaction product can be purified by the ordinary purification means, for example, a method such as distillation under ordinary pressure or under reduced pressure, high performance liquid chromatography using silica gel or magnesium silicate, thin layer chromatography, ion exchange resin, scavenger resin, column chromatography, washing, or recrystallization. Purification may be performed for every reaction, or may be performed after completion of several reactions.

[Toxicity]

Since toxicity of the present compound is low, it can be used safely as a medicament.

[Application to Medicaments]

The present compound is useful as an agent for preventing or treating urinary excretion disorder, particularly, a urinary excretion disorder accompanied with prostatomegaly and/or improving symptoms thereof accompanied with urinary excretion disorder (slowing of urinary stream, division of urinary stream, interruption of urinary stream, delayed urination, straining at urination, terminal dribbling etc.). In addition, the present compound is useful as an agent for treating cancer, interstitial pneumonia or pulmonary fibrosis, sclerodermia, pain, fibromyalgia or rheumatoid arthritis.

The present compound may be administered by combining with, for example, an α1 blocker (e.g. tamsulosin, silodosin, prazosin, terazosin, bunazosin, alfuzosin, indoramin, naftopidil, doxazosin mesilate, urapidil, AIO-8507L etc.) and the like, an acetylcholinesterase inhibitor (e.g. distigmine, neostigmine etc.), a 5α-reductase inhibitor (e.g. finasteride, GI-998745 etc.) or an anti-androgen agent (e.g. oxendolone, osaterone acetate, bicalutamide etc.) for, for example, (1) complementing and/or enhancing the preventing, treating and/or symptom improving effect thereof, (2) improving dynamics or absorption thereof, reducing a dose thereof, and/or (3) reducing the side effect thereof.

A concomitant agent of the present compound and other drug may be administered in a form of a compounding agent in which both ingredients are incorporated in one preparation, or may take a form in which both ingredients are administered by formulating into separate preparations. When administered by formulating into separate preparations, simultaneous administration and administration at different times are included. And, administration at different times may be such that the present compound is administered first, and other drug is administered later, or other drug is administered first, and the present compound is administered later, and respective administration methods may be the same or different.

A dose of the aforementioned other drug can be appropriately selected based on a dose which is clinically used. And, a compounding ratio of the present compound and other drug can be appropriately selected depending on an age and a weight of a subject to be administered, an administration method, an administration time, a target disease, symptom, a combination and the like. For example, other drug may be used at 0.01 to 100 parts by mass based on 1 part by mass of the present compound. Other drug may be administered by combining arbitrary two or more kinds at an appropriate proportion. And, the aforementioned drug includes not only drugs which have been found out up to now, but also drugs which will be found out from now on.

In order to use the present compound or a concomitant agent of the present compound and other drug for the aforementioned purpose, usually, it is systemically or locally administered in an oral or parenteral form.

A dose of the present compound is different depending on an age, a weight, symptom, therapeutic effect, an administration method, a treatment time and the like, but usually, the present compound is orally administered in a range of 1 µg to 1 g per once per adult, once to several times a day, or parenterally administered in a range of 0.1 µg to 300 mg per once per adult, once to several times a day, or intravenously continuously administered in a range of 1 hour to 24 hours a day.

Of course, as described above, since a dose varies depending on a variety of conditions, the dose is sufficient at a dose smaller than the aforementioned dose in some cases, or administration beyond the range is required in some cases.

When the present compound or a concomitant agent of the present compound and other drug is administered, it is used as a solid agent for internal use or a solution for oral administration (internal use), a sustained-release preparation in oral administration, or injectables, external preparations, inhalants or suppositories for parenteral administration.

The solid preparation for oral administration (internal use) includes, for example, tablets, pills, capsules, powders and granulars. The capsules include hard capsules and soft capsules.

In such the solid agent for internal use, one or more active substances are formulated into preparations as they are, or after mixing with excipients (e.g. lactose, mannitol, glucose, microcrystalline cellulose, starch etc.), binders (e.g. hydroxypropylcellulose, polyvinyl pyrrolidone, magnesium aluminate metasilicate etc.), disintegrating agents (e.g. calcium carboxymethylcellulose etc.), lubricants (e.g. magnesium stearate etc.), stabilizers, solubilization aids (e.g. glutamic acid, aspartic acid etc.) or the like, according to the conventional method, and are used. Alternatively, if necessary, active substances may be covered with coating agents (e.g. white sugar, gelatin, hydroxylpropylcellulose, hydroxypropylmethylcellulose phthalate etc.), or may be covered with two or more layers. Further, capsules of substances which can be absorbed, such as gelatin, are also included.

The liquid for oral administration (internal use) includes pharmaceutically acceptable solutions, suspensions, emulsions, syrups and elixirs. In such the liquid formulations, one or more active substances are dissolved, suspended or emulsified in diluents (e.g. purified water, ethanol, or mixed liquids of them etc.) which are generally used. Further, this liquid formulation may contain wetting agents, suspending agents, emulsifiers, sweeteners, flavors, fragrances, preservatives or buffers.

And, sustained-release preparations in oral administration are also effective. A gel forming substance used in these sustained-release preparations is a substance which is swollen while containing a solvent, thereby, mutually linking colloidal particles thereof to have a three dimensional network structure, and can form a jelly-like body which has no flowability. The substance is mainly used as binders, thickeners and sustained-release bases from a view point of preparations. For example, gum arabic, agar, polyvinyl pyrrolidone, sodium alginate, alginic acid propylene glycol ester, carboxyvinyl polymer, carboxymethylcellulose, carboxymethylcellulose sodium, guar gum, gelatin, hydroxypropylmethylcellulose, hydroxypropylcellulose, polyvinyl alcohol, methylcellulose or hydroxyethylmethylcellulose can be used.

Injectables for parenteral administration include solutions, suspensions, emulsions and solid injectables which are used by dissolving or suspending in a solvent upon use. Injectables are used by dissolving, suspending or emulsifying one or more active substances in a solvent. As the solvent, for example, distilled water for injection, physiological saline, vegetable oil, alcohols such as propylene glycol, polyethylene glycol, and ethanol and the like, and a combination of them are used. Further, the injectables may contain stabilizers, solubilization aids (e.g. glutamic acid, aspartic acid, Polysorbate 80 (registered trademark) etc.), suspending agents, emulsifiers, soothing agents, buffers or preservatives. These are produced by sterilization or a sterile operation method at a final step. Alternatively, injectables can be also used as aseptic solid agents (e.g. lyophilized products are produced, and dissolved in distilled water for injection or other solvent which has been sterilized or are aseptic, before use thereof).

A dosage form of the external preparations for parenteral administration includes, for example, sprays, inhalants, spraying agents, aerosols, ointments, gels, creams, fomentations, patches, liniments and nose drops. These contain one or more active substances, and prepared by the known method or formulation which is ordinarily used.

Sprays, inhalants and spraying agents may contain stabilizers such as sodium hydrogen sulfite and buffers imparting isotonicity, for example, isotonics such as sodium chloride, sodium citrate or citric acid, in addition to diluents which are generally used. A method of producing spraying agents is described in detail, for example, in U.S. Pat. Nos. 2,868,691 and 3,095,355.

The inhalants for parenteral administration include aerosols, powders for inhalation or solutions for inhalation, and the solutions for inhalation may be a form which is used by dissolving or suspending in water or other suitable medium upon use.

These inhalants are produced in accordance with the known method.

For example, in the case of solutions for inhalation, they are prepared by appropriately selecting antiseptics (e.g benzalkonium chloride, paraben etc.), colorants, buffering agents (e.g. sodium phosphate, sodium acetate etc.), isotonizing agents (e.g. sodium chloride, concentrated glycerin etc.), thickeners (e.g. carboxyvinyl polymer etc.), absorption enhancers and the like, if necessary.

In the case of powders for inhalation, they are prepared by appropriately selecting lubricants (e.g. stearic acid and a salt thereof etc.), binders (e.g. starch, dextrin etc.), excipients (e.g. lactose, cellulose etc.), colorants, antiseptics (e.g benzalkonium chloride, paraben etc.) or absorption enhancers, if necessary.

When solutions for inhalation are administered, usually, a sprayer (e.g. atomizer, nebulizer etc.) is used and, when powders for inhalation are administered, usually, an inhalation administration equipment for powdery drugs is used.

Ointments are produced by formulation which is known or ordinarily used. For example, ointments are prepared by kneading or melting one or more active substances in a base. An ointment base is selected from ointment bases which are known or orginarily used. For example, ointment bases selected from higher fatty acid or higher fatty acid ester (e.g. adipic acid, myristic acid, palmitic acid, stearic acid, oleic acid, adipic acid ester, myristic acid ester, palmitic acid ester, stearic acid ester, oleic acid ester etc.), waxes (e.g. beeswax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc.), glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption enhancers or rash preventing agents are used alone, or by mixing two or more kinds. Further, ointment bases may contain humectants, preservatives, stabilizers, antioxidants or flavoring agents.

Gel agents are produced by formulation which is known or ordinarily used. For example, gel agents are prepared by melting one or more active substances in a base. A gel base is selected from gel bases which are known or ordinarily used. For example, gel bases selected from lower alcohols (e.g. ethanol, isopropyl alcohol etc.), gelling agents (e.g. carboxymethylcellulose, hydroxyethylcellulose, hydroxypropylcellulose, ethylcellulose etc.), neutralizing agents (e.g. triethanolamine, diisopropanolamine etc.), surfactants (e.g. monostearic acid polyethylene glycol etc.), gums, water, absorption enhancers and rash preventing agents are used alone, or by mixing two or more kinds. Further, gel bases may contain preservatives, antioxidants or flavoring agents.

Creams are prepared by formulation which is known or ordinarily used. For example, creams are prepared by melting or emulsifying one or more active substances in a base. A cream base is selected from cream bases which are known or ordinarily used. For example, cream bases selected from higher fatty acid esters, lower alcohols, hydrocarbons, polyhydric alcohols (e.g. propylene glycol, 1,3-butylene glycol etc.), higher alcohols (e.g. 2-hexyldecanol, cetanol etc.), emulsifiers (e.g. polyoxyethylene alkyl ethers, fatty acid esters etc.), water, absorption enhancers and rash preventing agents are used alone, or by mixing two or more kinds. Further, cream bases may contain preservatives, antioxidants or flavoring agents.

Fomentations are produced by formulation which is known or ordinarily used. For example, fomentations are produced by melting one or more active substances in a base, and spreading and coating a melt as a kneaded product on a support. A fomentation is selected from fomentations which are known or ordinarily used. For example, fomentations selected from thickeners (e.g. polyacrylic acid, polyvinyl pyrrolidone, gum arabic, starch, gelatin, methylcellulose etc.), wetting agents (e.g. urea, glycerin, propylene glycol etc.), fillers (e.g. kaolin, zinc oxide, talc, calcium, magnesium etc.), water, solubilization aids, tackiness imparting agents and rash preventing agents are used alone, or by mixing two or more kinds. Further, fomentations may contain preservatives, antioxidants or flavoring agents.

Patches are produced by formulation which is known or ordinarily used. For example, patches are produced by melting one or more active substances in a base, and spreading and coating a melt on a support. A base for patches is selected from bases for patches which are known or ordinarily used. For example, bases for patches selected from polymer bases, fats and oils, higher fatty acids, tackiness imparting agents and rash preventing agents are used alone, or by mixing two or more kinds. Further, bases for patches may contain preservatives, antioxidants or flavoring agents.

Liniments are produced by formulation which is known or ordinarily used. For example, liniments are prepared by dissolving, suspending or emulsifying one or more active substances in a base selected from water, alcohols (e.g. ethanol, polyethylene glycol etc.), higher fatty acid, glycerin, soaps, emulsifiers and suspending agents alone, or two or more kinds of them. Further, liniments may contain preservatives, antioxidants or flavoring agents.

Other composition for parenteral administration includes suppositories for rectal administration or pessaries for intravaginal administration, which contain one or more active substances, and are formulated by the conventional method.

An entire content of all patent documents and non-patent documents or reference documents which are explicitly cited in the present specification is cited herein as a part of the present specification.

EXAMPLES

The present invention will be described in detail below by way of Examples and Biological Example, but the present invention is not limited to them. A name of the compound of the present invention and a name of compounds shown in Examples were named by ACD/Name (version 6.00, manufactured by Advanced Chemistry Development Inc.).

A solvent in parenthesis shown at places of separation by chromatography and in TLC indicates an elution solvent or a development solvent used, and a proportion indicates a volumetric ratio. The numerical value shown at places of NMR is a measurement value of $^1$H-NMR when a described measurement solvent is used.

The reverse phase high performance liquid chromatography analysis conditions for measuring a HPLC retention time are as follows:

Instrument used: Waters LC/MS

Mass spectrometer: ZMD 4000 manufactured by Waters

ELSD detector: 75 ELS detector manufactured by Sedex

Column: UNIZON US-C18, 5 µm, 50×4.6 mm

Column temperature: 50° C.

Flow rate: 3 mL/min

Mobile phase A: 0.1% (trifluoroacetic acid-5% methanol)/aqueous solution

Mobile phase B: 0.1% trifluoroacetic acid-methanol solution

LC-MS/ELS Gradient:

TABLE 1

| Time (min) | % A | % B |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

Example 9-(3-phenylpropyl)-2,3,4,9-tetrahydro-1H-beta-carboline hydrochloride

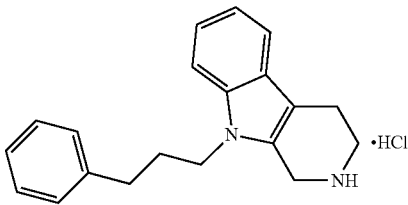 [SMILES: c1ccc(CCCn2c3c(c4ccccc42)CCNC3)cc1 ; Cl]

Tert-butyl 1,3,4,9-tetrahydro-2H-β-carboline-2-carboxylate (CAS No. 168824-94-0) (545 mg) was dissolved in N,N-dimethylformamide (5 mL), (3-bromopropyl)benzene (478 mg), tetrabutylammonium bromide (32 mg) and cesium carbonate (782 mg) were sequentially added and, the mixture was stirred at 60° C. for 4 hours. The reaction mixture was cooled to room temperature, and poured into water, followed by extraction with ethyl acetate. The organic layer was washed sequentially with water and an aqueous saturated sodium chloride solution, dried with anhydrous magnesium sulfate, and concentrated. The residue was purified by silica gel column chromatography (hexane:ethyl acetate=9:1). Further, to the resulting compound (162 mg) was added a 4N hydrogen chloride dioxane solution (3 mL) at room temperature, and the mixture was stirred for 1 hour. The reaction mixture was concentrated to obtain the title compound (121 mg) having the following physical property values.

TLC: Rf 0.47 (chloroform:methanol=9:1);

$^1$H-NMR (DMSO-$d_6$): δ 1.84-2.04 (m, 2 H), 2.55-2.66 (m, 2 H), 2.94 (t, J=5.5 Hz, 2 H), 3.41 (t, J=5.5 Hz, 2 H), 4.12 (t, J=7.3 Hz, 2 H), 4.40 (s, 2 H), 7.00-7.10 (m, 1 H), 7.10-7.22 (m, 4 H), 7.22-7.34 (m, 2 H), 7.41 (d, J=8.2 Hz, 1 H), 7.47 (d, J=7.7 Hz, 1 H), 9.67 (s, 2 H).

Example 2 methyl 6-oxo-6-[9-(3-phenylpropyl)-1,3,4,9-tetrahydro-2H-beta-carbolin-2-yl]hexanoate

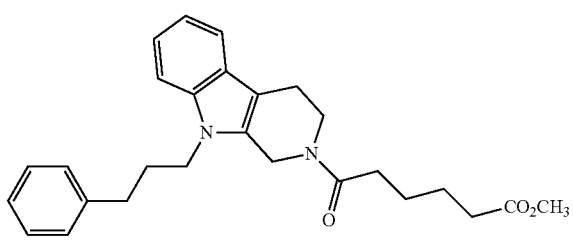 [SMILES: COC(=O)CCCCC(=O)N1CCc2c(n(CCCc3ccccc3)c3ccccc23)C1]

To a pyridine (1 ml) solution of the compound (100 mg) produced in Example 1 was added methyl 6-chloro-6-oxo-hexanoate (0.052 mL) at room temperature, and the mixture was stirred for 2 hours. To the reaction mixture was added water, followed by extraction with ethyl acetate. The extract was sequentially washed with water and an aqueous saturated sodium chloride solution, dried with anhydrous magnesium sulfate, and concentrated. The residue was purified by silica gel column chromatography (hexane:ethyl acetate=6:4) to obtain the title compound (90 mg) having the following physical property values.

TLC: Rf 0.45 (hexane:ethyl acetate=1:1);
$^1$H-NMR (CDCl$_3$): δ 1.57-1.86 (m, 4 H) 2.00-2.25 (m, 2 H) 2.33-2.42 (m, 2 H) 2.45-2.57 (m, 2 H) 2.59-2.96 (m, 4 H) 3.62-3.71 (m, 3 H) 3.71-3.97 (m, 2 H) 3.97-4.12 (m, 2 H) 4.41-4.87 (m, 2 H) 7.05-7.36 (m, 8 H) 7.43-7.54 (m, 1 H).

Example 3

6-oxo-6-[9-(3-phenylpropyl)-1,3,4,9-tetrahydro-2H-beta-carbolin-2-yl]hexanoic acid

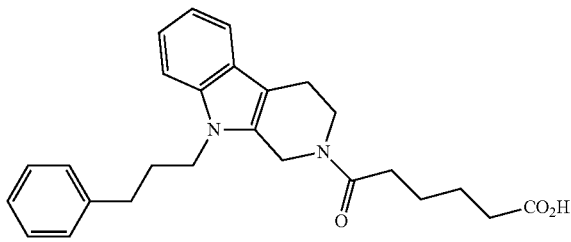 [SMILES: O=C(O)CCCCC(=O)N1CCc2c(n(CCCc3ccccc3)c3ccccc23)C1]

To a mixed solution of the compound (83 mg) produced in Example 2 in ethylene glycol dimethyl ether (1 mL) and methanol (1 mL) was added a 1 N aqueous sodium hydroxide solution (1 mL) at room temperature, and the mixture was stirred for 2 hours. To the reaction mixture was added 1 N hydrochloric acid (1 mL) and water, followed by extraction with ethyl acetate. The extract was washed with an aqueous saturated sodium chloride solution, dried with anhydrous sodium sulfate, and concentrated. The residue was purified by silica gel column chromatography (chloroform:methanol:water=50:10:1) to obtain the title compound (66 mg) having the following physical property values.

TLC: Rf 0.50 (chloroform:methanol:water=50:10:1);
$^1$H-NMR (CDCl$_3$): δ 1.61-1.89 (m, 4 H) 1.99-2.21 (m, 2 H) 2.30-2.59 (m, 4 H) 2.60-2.76 (m, 2 H) 2.75-2.94 (m, 2 H) 3.69-3.97 (m, 2 H) 3.87-4.11 (m, 2 H) 4.42-4.84 (m, 2 H) 5.52-6.86 (m, 1 H) 7.03-7.38 (m, 8 H) 7.42-7.54 (m, 1 H).

Example 3(1)-Example 3(56)

A β-carboline derivative produced by operation in accordance with Example 1, and a corresponding carboxylic acid halide in place of methyl 6-chloro-6-oxohexanoate were used, which were subjected to operation in accordance with Example 2 and, if necessary, subjected to operation in accordance with Example 3, to obtain the following compounds.

Example 3(1)

methyl 5-(9-benzyl-1,3,4,9-tetrahydro-2H-beta-carbolin-2-yl)-5-oxopentanoate

TLC: Rf 0.33 (chloroform:methanol:aqueous ammonia=50:10:1);
$^1$H-NMR (CDCl$_3$): δ 1.81-2.09 (m, 2 H) 2.21-2.61 (m, 4 H) 2.78-2.97 (m, 2 H) 3.60-3.71 (m, 3 H) 3.73-3.98 (m, 2 H) 4.47-4.75 (m, 2 H) 5.23-5.32 (m, 2 H) 6.96-7.36 (m, 8 H) 7.46-7.60 (m, 1 H).

Example 3(2)

6-(9-benzyl-1,3,4,9-tetrahydro-2H-beta-carbolin-2-yl)-6-oxohexanoic acid

TLC: Rf 0.44 (chloroform:methanol:water=50:10:1);
$^1$H-NMR (DMSO-d$_6$): δ 1.33-1.65 (m, 4 H) 2.09-2.50 (m, 4 H) 2.61-2.87 (m, 2 H) 3.67-185 (m, 2 H) 4.63 (s, 2 H) 5.31-5.45 (m, 2 H) 6.95-7.12 (m, 4 H) 7.17-7.32 (m, 3 H) 7.37-7.47 (m, 2 H) 11.97 (s, 1 H).

Example 3(3)

7-(9-benzyl-1,3,4,9-tetrahydro-2H-beta-carbolin-2-yl)-7-oxoheptanoic acid

TLC: Rf 0.33 (chloroform:methanol:water=90:10:1);
$^1$H-NMR (DMSO-d$_6$): δ 1.11-1.59 (m, 6 H) 2.09-2.47 (m, 4 H) 2.62-2.84 (m, 2 H) 3.66-3.84 (m, 2 H) 4.63 (s, 2 H) 5.32-5.44 (m, 2 H) 6.95-7.13 (m, 4 H) 7.16-7.34 (m, 3 H) 7.37-7.49 (m, 2 H) 11.80-12.15 (m, 1 H).

Example 3(4)

6-[9-(3-methoxybenzyl)-1,3,4,9-tetrahydro-2H-beta-carbolin-2-yl]-6-oxohexanoic acid TLC: Rf 0.57 (chloroform:methanol:water=50:10:1);
$^1$H-NMR (CDCl$_3$): δ 1.45-1.88 (m, 4 H), 2.08-2.62 (m, 4 H), 2.71-3.04 (m, 2 H), 3.68-3.99 (m, 5 H), 4.36-4.80 (m, 2 H), 5.08-5.31 (s, 2 H), 6.49-6.67 (m, 2 H), 6.68-6.88 (m, 1 H), 6.99-7.35 (m, 4 H), 7.40-7.59 (m, 1 H).

Example 3(5)

6-[9-(4-chlorobenzyl)-1,3,4,9-tetrahydro-2H-beta-carbolin-2-yl]-6-oxohexanoic acid TLC: Rf 0.57 (chloroform:methanol:water=50:10:1);
$^1$H-NMR (CDCl$_3$): δ 1.51-1.88 (m, 4 H), 2.16-2.65 (m, 4 H), 2.68-3.03 (m, 2 H), 3.60-4.03 (m, 2 H), 4.35-4.79 (m, 2 H), 5.08-5.38 (s, 2 H), 6.85-7.04 (m, 2 H), 7.05-7.35 (m, 5 H), 7.44-7.64 (m, 1 H).

Example 3(6)

6-[9-(4-fluorobenzyl)-1,3,4,9-tetrahydro-2H-beta-carbolin-2-yl]-6-oxohexanoic acid TLC: Rf 0.52 (chloroform:methanol:water=50:10:1);
$^1$H-NMR (CDCl$_3$): δ 1.46-1.92 (m, 4 H), 2.09-2.66 (m, 4 H), 2.71-3.07 (m, 2 H), 3.69-4.03 (m, 2 H), 4.32-4.86 (m, 2 H), 5.08-5.37 (s, 2 H), 6.80-7.35 (m, 7 H), 7.42-7.65 (m, 1 H).

Example 3(7)

6-[9-(3-chlorobenzyl)-1,3,4,9-tetrahydro-2H-beta-carbolin-2-yl]-6-oxohexanoic acid TLC: Rf 0.30 (chloroform:methanol=15:1);
$^1$H-NMR (CDCl$_3$): δ 1.47-1.88 (m, 4 H), 2.19-2.60 (m, 4 H), 2.72-3.02 (m, 2 H), 3.63-4.08 (m, 2 H), 4.37-4.79 (m, 2 H), 5.10-5.35 (s, 2 H), 6.75-6.98 (m, 1 H), 6.96-7.35 (m, 6 H), 7.43-7.63 (m, 1 H).

Example 3(8)

6-[9-(3-fluorobenzyl)-1,3,4,9-tetrahydro-2H-beta-carbolin-2-yl]-6-oxohexanoic acid TLC: Rf 0.30 (chloroform:methanol=15:1);
$^1$H-NMR (CDCl$_3$): δ 1.44-1.87 (m, 4 H), 2.16-2.61 (m, 4 H), 2.71-3.07 (m, 2 H), 3.67-4.03 (m, 2 H), 4.29-4.86 (m, 2 H), 5.11-5.37 (s, 2 H), 6.57-7.04 (m, 3 H), 7.03-7.39 (m, 4 H), 7.44-7.62 (m, 1 H).

Example 3(9)

6-[9-(2-fluorobenzyl)-1,3,4,9-tetrahydro-2H-beta-carbolin-2-yl]-6-oxohexanoic acid TLC: Rf 0.31 (methylene chloride:methanol=15:1);
$^1$H-NMR (CDCl$_3$): δ 1.48-1.90 (m, 4 H), 2.20-2.59 (m, 4 H), 2.71-3.02 (m, 2 H), 3.68-4.02 (m, 2 H), 4.42-4.88 (m, 2 H), 5.29 (s, 2 H), 6.52-6.76 (m, 1 H), 6.81-7.40 (m, 6 H), 7.42-7.63 (m, 1 H).

Example 3(10)

6-[9-(4-methylbenzyl)-1,3,4,9-tetrahydro-2H-beta-carbolin-2-yl]-6-oxohexanoic acid TLC: Rf 0.31 (methylene chloride:methanol=15:1);
$^1$H-NMR (CDCl$_3$): δ 1.48-1.86 (m, 4 H), 2.12-2.58 (m, 7 H), 2.76-2.98 (m, 2 H), 3.66-4.01 (m, 2 H), 4.36-4.79 (m, 2 H), 5.20 (s, 2 H), 6.83-6.98 (m, 2 H), 6.99-7.39 (m, 5 H), 7.42-7.60 (m, 1 H).

Example 3(11)

6-[9-(3-chloro-4-fluorobenzyl)-1,3,4,9-tetrahydro-2H-beta-carbolin-2-yl]-6-oxohexanoic acid TLC: Rf 0.21 (methylene chloride:methanol=15:1);
$^1$H-NMR (CDCl$_3$): δ 1.54-1.87 (m, 4 H), 2.18-2.59 (m, 4 H), 2.76-3.00 (m, 2 H), 3.67-4.04 (m, 2 H), 4.39-4.78 (m, 2 H), 5.11-5.27 (m, 2 H), 6.73-6.93 (m, 1 H), 6.94-7.34 (m, 5 H), 7.43-7.60 (m, 1 H).

Example 3(14)

7-[9-(4-fluorobenzyl)-1,3,4,9-tetrahydro-2H-beta-carbolin-2-yl]-7-oxoheptanoic acid TLC: Rf 0.33 (methylene chloride:methanol=15:1);
$^1$H-NMR (CDCl$_3$): δ 1.17-1.84 (m, 6 H), 2.11-2.57 (m, 4 H), 2.73-3.03 (m, 2 H), 3.62-4.07 (m, 2 H), 4.36-4.82 (m, 2 H), 5.22 (s, 2 H), 6.83-7.34 (m, 7 H), 7.40-7.62 (m, 1 H).

Example 3(15)

7-[9-(3-chlorobenzyl)-1,3,4,9-tetrahydro-2H-beta-carbolin-2-yl]-7-oxoheptanoic acid TLC: Rf 0.33 (methylene chloride:methanol=15:1);
$^1$H-NMR (CDCl$_3$): δ 1.17-1.84 (m, 6 H), 2.14-2.58 (m, 4 H), 2.76-3.00 (m, 2 H), 3.65-4.05 (m, 2 H), 4.39-4.79 (m, 2 H), 5.22 (s, 2 H), 6.75-6.96 (m, 1 H), 6.96-7.35 (m, 6 H), 7.41-7.64 (m, 1 H).

Example 3(16)

7-[9-(3-chloro-4-fluorobenzyl)-1,3,4,9-tetrahydro-2H-beta-carbolin-2-yl]-7-oxoheptanoic acid TLC: Rf 0.33 (methylene chloride:methanol=15:1);
$^1$H-NMR (CDCl$_3$): δ 1.23-1.85 (m, 6 H), 2.13-2.59 (m, 4 H), 2.70-3.03 (m, 2 H), 3.68-4.06 (m, 2 H), 4.37-4.80 (m, 2 H), 5.20 (s, 2 H), 6.75-6.94 (m, 1 H), 6.95-7.32 (m, 5 H), 7.40-7.65 (m, 1 H).

Example 3(17)

7-oxo-7-[9-(3-phenylpropyl)-1,3,4,9-tetrahydro-2H-beta-carbolin-2-yl]heptanoic acid TLC: Rf 0.33 (chloroform:methanol:water=50:10:1);
$^1$H-NMR (DMSO-d$_6$): δ 1.20-1.38 (m, 2 H) 1.41-1.62 (m, 4 H) 1.85-2.06 (m, 2 H) 2.10-2.24 (m, 2 H) 2.35-2.81 (m, 6 H) 3.68-3.83 (m, 2 H) 4.02-4.17 (m, 2 H) 4.58-4.76 (m, 2 H) 6.98 (t, J=7.5 Hz, 1 H) 7.07 (t, J=7.5 Hz, 1 H) 7.12-7.31 (m, 5 H) 7.34 (d, J=7.5 Hz, 1 H) 7.40 (d, J=7.5 Hz, 1 H) 11.96 (s, 1 H).

Example 3(18)

6-{9-[3-(4-fluorophenyl)propyl]-1,3,4,9-tetrahydro-2H-beta-carbolin-2-yl}-6-oxohexanoic acid TLC: Rf 0.54 (chloroform:methanol:water=90:10:1);
$^1$H-NMR (DMSO-d$_6$): δ 1.39-1.67 (m, 4 H) 1.81-2.06 (m, 2 H) 2.12-2.81 (m, 8 H) 3.67-3.83 (m, 2 H) 3.99-4.17 (m, 2 H) 4.60-4.76 (m, 2 H) 6.98 (t, J=7.5 Hz, 1 H) 7.02-7.13 (m, 3 H) 7.13-7.27 (m, 2 H) 7.34 (d, J=8.0 Hz, 1 H) 7.40 (d, J=7.5 Hz, 1 H) 11.61-12.32 (m, 1 H).

Example 3(19)

7-{9-[3-(4-fluorophenyl)propyl]-1,3,4,9-tetrahydro-2H-beta-carbolin-2-yl}-7-oxoheptanoic acid

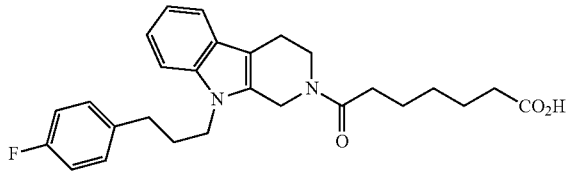 [SMILES: O=C(O)CCCCCC(=O)N1CCc2c(n(CCCc3ccc(F)cc3)c3ccccc23)C1]

TLC: Rf 0.54 (chloroform:methanol:water=90:10:1);
$^1$H-NMR (DMSO-d$_6$): δ 1.20-1.39 (m, 2 H) 1.38-1.66 (m, 4 H) 1.82-2.03 (m, 2 H) 2.11-2.82 (m, 8 H) 3.66-3.83 (m, 2 H) 3.99-4.17 (m, 2 H) 4.60-4.75 (m, 2 H) 6.98 (t, J=7.5 Hz, 1 H) 7.02-7.12 (m, 3 H) 7.12-7.28 (m, 2 H) 7.34 (d, J=8.0 Hz, 1 H) 7.40 (d, J=7.5 Hz, 1 H) 11.74-12.16 (m, 1 H).

Example 3(20)

6-{9-[3-(3-chlorophenyl)propyl]-1,3,4,9-tetrahydro-2H-beta-carbolin-2-yl}-6-oxohexanoic acid TLC: Rf 0.22 (chloroform:methanol:water=90:10:1);
$^1$H-NMR (DMSO-d$_6$): δ 1.40-1.66 (m, 4 H) 1.86-2.06 (m, 2 H) 2.13-2.81 (m, 8 H) 3.68-3.84 (m, 2 H) 4.02-4.16 (m, 2 H) 4.61-4.78 (m, 2 H) 6.94-7.02 (m, 1 H) 7.03-7.11 (m, 1 H) 7.11-7.43 (m, 6 H) 11.95 (s, 1 H).

Example 3(21)

7-{9-[3-(3-chlorophenyl)propyl]-1,3,4,9-tetrahydro-2H-beta-carbolin-2-yl}-7-oxoheptanoic acid TLC: Rf 0.31 (chloroform:methanol:water=90:10:1);
$^1$H-NMR (DMSO-$d_6$): δ 1.23-1.38 (m, 2 H) 1.42-1.64 (m, 4 H) 1.87-2.06 (m, 2 H) 2.11-2.81 (m, 8H) 3.68-3.83 (m, 2 H) 4.02-4.17 (m, 2 H) 4.59-4.78 (m, 2 H) 6.94-7.02 (m, 1 H) 7.03-7.12 (m, 1H) 7.12-7.44 (m, 6 H) 11.93 (s, 1 H).

Example 3(22)

methyl 6-[9-(3-chlorobenzyl)-1,3,4,9-tetrahydro-2H-beta-carbolin-2-yl]-6-oxohexanoate TLC: Rf 0.33 (hexane:ethyl acetate=1:1);
$^1$H-NMR (CDCl$_3$): δ 1.50-1.87 (m, 4 H), 2.16-2.59 (m, 4 H), 2.73-3.00 (m, 2 H), 3.57-3.69 (m, 3 H), 3.70-4.00 (m, 2 H), 4.41-4.77 (m, 2 H), 5.14-5.29 (m, 2 H), 6.77-6.91 (m, 1 H), 6.96-7.36 (m, 6 H), 7.41-7.63 (m, 1 H).

Example 3(23)

methyl 6-[9-(4-chlorobenzyl)-1,3,4,9-tetrahydro-2H-beta-carbolin-2-yl]-6-oxohexanoate TLC: Rf 0.43 (hexane:ethyl acetate=1:1);
$^1$H-NMR (CDCl$_3$): δ 1.54-1.84 (m, 4 H), 2.15-2.58 (m, 4 H), 2.71-3.01 (m, 2 H), 3.62-3.69 (m, 3 H), 3.69-4.01 (m, 2 H), 4.38-4.76 (m, 2 H), 5.12-5.31 (m, 2 H), 6.84-7.39 (m, 7 H), 7.41-7.63 (m, 1 H).

Example 3(24)

methyl 6-[9-(4-fluorobenzyl)-1,3,4,9-tetrahydro-2H-beta-carbolin-2-yl]-6-oxohexanoate TLC: Rf 0.36 (hexane:ethyl acetate=1:1);
$^1$H-NMR (CDCl$_3$): δ 1.46-1.75 (m, 4 H), 2.08-2.49 (m, 4 H), 2.69-2.89 (m, 2 H), 3.55-3.61 (m, 3 H), 3.62-3.91 (m, 2 H), 4.32-4.72 (m, 2 H), 5.06-5.23 (m, 2 H), 6.72-7.32 (m, 7 H), 7.32-7.55 (m, 1 H).

Example 3(25)

methyl 6-[9-(3-methylbenzyl)-1,3,4,9-tetrahydro-2H-beta-carbolin-2-yl]-6-oxohexanoate TLC: Rf 0.59 (hexane:ethyl acetate=1:1);
$^1$H-NMR (CDCl$_3$): δ 1.42-1.87 (m, 4 H), 2.11-2.58 (m, 7 H), 2.73-3.01 (m, 2 H), 3.59-3.71 (m, 3 H), 3.70-4.01 (m, 2 H), 4.36-4.81 (m, 2 H), 5.15-5.27 (m, 2 H), 6.64-7.40 (m, 7 H), 7.43-7.64 (m, 1 H).

Example 3(26)

methyl 6-[9-(2-fluorobenzyl)-1,3,4,9-tetrahydro-2H-beta-carbolin-2-yl]-6-oxohexanoate TLC: Rf 0.45 (hexane:ethyl acetate=1:1);
$^1$H-NMR (CDCl$_3$): δ 1.51-1.84 (m, 4 H), 2.19-2.58 (m, 4 H), 2.75-2.99 (m, 2 H), 3.60-3.70 (m, 3 H), 3.70-4.02 (m, 2 H), 4.46-4.82 (m, 2 H), 5.23-5.36 (s, 2 H), 6.53-6.70 (m, 1 H), 6.85-7.36 (m, 6 H), 7.42-7.60 (m, 1 H).

Example 3(27)

methyl 6-[9-(4-methylbenzyl)-1,3,4,9-tetrahydro-2H-beta-carbolin-2-yl]-6-oxohexanoate TLC: Rf 0.45 (hexane:ethyl acetate=1:1);
$^1$H-NMR (CDCl$_3$): δ 1.51-1.84 (m, 4 H), 2.09-2.56 (m, 7 H), 2.75-3.00 (m, 2 H), 3.57-3.69 (m, 3 H), 3.69-3.97 (m, 2 H), 4.38-4.78 (m, 2 H), 5.12-5.28 (m, 2 H), 6.82-7.37 (m, 7 H), 7.39-7.62 (m, 1 H).

Example 3(28)

methyl 6-[9-(3-chloro-4-fluorobenzyl)-1,3,4,9-tetrahydro-2H-beta-carbolin-2-yl]-6-oxohexanoate TLC: Rf 0.42 (hexane:ethyl acetate=1:1);
$^1$H-NMR (CDCl$_3$): δ 1.50-1.85 (m, 4 H), 2.22-2.59 (m, 4 H), 2.76-3.00 (m, 2 H), 3.60-3.72 (m, 3 H), 3.72-4.00 (m, 2 H), 4.43-4.75 (m, 2 H), 5.13-5.27 (m, 2 H), 6.73-6.94 (m, 1 H), 6.93-7.31 (m, 5 H), 7.43-7.61 (m, 1 H).

Example 3(30)

ethyl 7-[9-(3-chloro-4-fluorobenzyl)-1,3,4,9-tetrahydro-2H-beta-carbolin-2-yl]-7-oxoheptanoate TLC: Rf 0.32 (hexane:ethyl acetate=2:1);
$^1$H-NMR (CDCl$_3$): δ 1.11-1.85 (m, 9 H), 2.16-2.58 (m, 4 H), 2.71-3.03 (m, 2 H), 3.66-4.01 (m, 2 H), 4.11 (q, J=7.0 Hz, 2 H), 4.39-4.77 (m, 2 H), 5.07-5.32 (m, 2 H), 6.77-6.94 (m, 1 H), 6.93-7.35 (m, 5 H), 7.39-7.66 (m, 1 H).

Example 3(31)

6-[9-(3-methylbenzyl)-1,3,4,9-tetrahydro-2H-beta-carbolin-2-yl]-6-oxohexanoic acid TLC: Rf 0.31 (methylene chloride:methanol=15:1);
$^1$H-NMR (CDCl$_3$): δ 1.46-1.89 (m, 4 H), 2.11-2.58 (m, 7 H), 2.73-3.00 (m, 2 H), 3.68-4.01 (m, 2 H), 4.38-4.80 (m, 2 H), 5.20 (s, 2 H), 6.71-6.83 (m, 1 H), 6.82-6.94 (m, 1 H), 6.95-7.39 (m, 5 H), 7.41-7.61 (m, 1 H).

Example 3(32)

6-[9-(2-methoxybenzyl)-1,3,4,9-tetrahydro-2H-beta-carbolin-2-yl]-6-oxohexanoic acid TLC: Rf 0.46 (chloroform:methanol:water=50:10:1);
$^1$H-NMR (CDCl$_3$): δ 1.41-1.88 (m, 4 H), 2.15-2.62 (m, 4 H), 2.71-3.06 (m, 2 H), 3.66-4.04 (m, 5 H), 4.40-4.81 (m, 2 H), 5.15-5.35 (m, 2 H), 6.30-6.57 (m, 1 H), 6.66-6.84 (m, 1 H), 6.82-7.00 (m, 1 H), 7.01-7.38 (m, 4 H), 7.40-7.68 (m, 1 H).

Example 3(33)

methyl 6-(9-benzyl-1,3,4,9-tetrahydro-2H-beta-carbolin-2-yl)-6-oxohexanoate

TLC: Rf 0.44 (hexane:ethyl acetate=1:2);
$^1$H-NMR (CDCl$_3$): δ 1.47-1.85 (m, 4 H) 2.13-2.59 (m, 4 H) 2.78-2.97 (m, 2 H) 3.60-3.70 (m, 3 H) 3.71-3.99 (m, 2 H) 4.40-4.83 (m, 2 H) 5.21-5.33 (m, 2 H) 6.95-7.35 (m, 8 H) 7.45-7.58 (m, 1 H).

Example 3(34)

ethyl 7-(9-benzyl-1,3,4,9-tetrahydro-2H-beta-carbolin-2-yl)-7-oxoheptanoate

TLC: Rf 0.55 (hexane:ethyl acetate=1:2);
¹H-NMR (CDCl₃): δ 1.17-1.81 (m, 9 H) 2.13-2.54 (m, 4 H) 2.79-2.96 (m, 2 H) 3.70-3.99 (m, 2 H) 4.05-4.19 (m, 2 H) 4.40-4.79 (m, 2 H) 5.17-5.35 (m, 2 H) 6.90-7.40 (m, 8 H) 7.43-7.61 (m, 1 H).

Example 3(35)

methyl 6-[9-(3-fluorobenzyl)-1,3,4,9-tetrahydro-2H-beta-carbolin-2-yl]-6-oxohexanoate TLC: Rf 0.33 (hexane:ethyl acetate=1:1);
¹H-NMR (CDCl₃): δ 1.51-1.83 (m, 4 H), 2.15-2.58 (m, 4 H), 2.75-2.99 (m, 2 H), 3.60-3.71 (m, 3 H), 3.70-4.02 (m, 2 H), 4.40-4.77 (m, 2 H), 5.17-5.31 (m, 2 H), 6.59-7.02 (m, 3 H), 7.03-7.36 (m, 4 H), 7.40-7.65 (m, 1 H).

Example 3(36)

methyl 6-[9-(3-methoxybenzyl)-1,3,4,9-tetrahydro-2H-beta-carbolin-2-yl]-6-oxohexanoate TLC: Rf 0.33 (hexane:ethyl acetate=1:1);
¹H-NMR (CDCl₃): δ 1.54-1.79 (m, 4 H), 2.11-2.56 (m, 4 H), 2.77-2.95 (m, 2 H), 3.62-3.68 (m, 3 H), 3.68-3.97 (m, 5 H), 4.40-4.76 (m, 2 H), 5.14-5.27 (m, 2 H), 6.47-6.91 (m, 3 H), 7.01-7.38 (m, 4 H), 7.41-7.63 (m, 1 H).

Example 3(37)

methyl 4-{[2-(6-methoxy-6-oxohexanoyl)-1,2,3,4-tetrahydro-9H-beta-carbolin-9-yl]methyl}benzoate TLC: Rf 0.27 (hexane:ethyl acetate=1:1);
¹H-NMR (CDCl₃): δ 1.51-1.82 (m, 4 H), 2.15-2.57 (m, 4 H), 2.78-2.99 (m, 2 H), 3.56-3.71 (m, 3 H), 3.71-4.00 (m, 5 H), 4.41-4.74 (m, 2 H), 5.25-5.36 (m, 2 H), 7.02-7.26 (m, 5 H), 7.42-7.65 (m, 1 H), 7.86-8.04 (m, 2 H).

Example 3(38)

methyl 6-[9-(4-methoxybenzyl)-1,3,4,9-tetrahydro-2H-beta-carbolin-2-yl]-6-oxohexanoate TLC: Rf 0.26 (hexane:ethyl acetate=3:2);
¹H-NMR (CDCl₃): δ 1.46-1.87 (m, 4 H), 2.10-2.58 (m, 4 H), 2.75-2.97 (m, 2 H), 3.59-3.69 (m, 3 H), 3.68-3.98 (m, 5 H), 4.40-4.74 (m, 2 H), 5.12-5.25 (m, 2 H), 6.72-6.84 (m, 2 H), 6.88-7.02 (m, 2 H), 7.05-7.22 (m, 2 H), 7.24-7.33 (m, 1 H), 7.38-7.59 (m, 1 H).

Example 3(40)

ethyl 7-oxo-7-[9-(3-phenylpropyl)-1,3,4,9-tetrahydro-2H-beta-carbolin-2-yl]heptanoate TLC: Rf 0.29 (hexane:ethyl acetate=2:1);
¹H-NMR (CDCl₃): δ 1.16-1.33 (m, 3 H) 1.31-1.84 (m, 8 H) 1.98-2.96 (m, 8 H) 3.68-4.20 (m, 6 H) 4.43-4.83 (m, 2 H) 7.04-7.36 (m, 8 H) 7.41-7.57 (m, 1 H).

Example 3(41)

ethyl 7-[9-(4-fluorobenzyl)-1,3,4,9-tetrahydro-2H-beta-carbolin-2-yl]-7-oxoheptanoate TLC: Rf 0.30 (hexane:ethyl acetate=2:1);
¹H-NMR (CDCl₃): δ 1.12-1.84 (m, 9 H), 2.09-2.59 (m, 4 H), 2.72-3.01 (m, 2 H), 3.65-4.01 (m, 2 H), 4.11 (q, J=7.0 Hz, 2 H), 4.35-4.79 (m, 2 H), 5.06-5.37 (m, 2 H), 6.80-7.34 (m, 7 H), 7.39-7.64 (m, 1 H).

Example 3(42)

ethyl 7-[9-(3-chlorobenzyl)-1,3,4,9-tetrahydro-2H-beta-carbolin-2-yl]-7-oxoheptanoate TLC: Rf 0.34 (hexane:ethyl acetate=2:1);
¹H-NMR (CDCl₃): δ 1.11-1.86 (m, 9 H), 2.14-2.56 (m, 4 H), 2.74-3.03 (m, 2 H), 3.63-4.01 (m, 2 H), 4.11 (q, J=7.1 Hz, 2 H), 4.39-4.79 (m, 2 H), 5.10-5.34 (m, 2 H), 6.74-6.95 (m, 1 H), 6.96-7.34 (m, 6 H), 7.41-7.66 (m, 1 H).

Example 3(43)

methyl 6-{9-[3-(4-fluorophenyl)propyl]-1,3,4,9-tetrahydro-2H-beta-carbolin-2-yl}-6-oxohexanoate TLC: Rf 0.15 (hexane:ethyl acetate=2:1);
¹H-NMR (CDCl₃): δ 1.62-1.85 (m, 4 H) 2.00-2.16 (m, 2 H) 2.29-2.58 (m, 4 H) 2.58-2.74 (m, 2 H) 2.76-2.95 (m, 2 H) 3.63-3.70 (m, 3 H) 3.72-3.97 (m, 2 H) 3.99-4.10 (m, 2 H) 4.48-4.84 (m, 2 H) 6.90-7.04 (m, 2 H) 7.05-7.24 (m, 5 H) 7.44-7.53 (m, 1 H).

Example 3(44)

ethyl 7-{9-[3-(4-fluorophenyl)propyl]-1,3,4,9-tetrahydro-2H-beta-carbolin-2-yl}-7-oxoheptanoate TLC: Rf 0.22 (hexane:ethyl acetate=2:1);
¹H-NMR (CDCl₃): δ 1.26 (t, J=7.0 Hz, 3 H) 1.36-1.51 (m, 2 H) 1.58-1.83 (m, 4 H) 1.98-2.18 (m, 2 H) 2.24-2.56 (m, 4 H) 2.56-2.74 (m, 2 H) 2.76-2.94 (m, 2 H) 3.73-3.97 (m, 2 H) 3.98-4.20 (m, 4 H) 4.50-4.82 (m, 2 H) 6.89-7.04 (m, 2 H) 7.04-7.24 (m, 5 H) 7.41-7.55 (m, 1 H).

Example 3(45)

5-(9-benzyl-1,3,4,9-tetrahydro-2H-beta-carbolin-2-yl)-5-oxopentanoic acid

TLC: Rf 0.52 (chloroform:methanol:aqueous ammonia=50:10:1);
¹H-NMR (DMSO-d₆): δ 1.59-1.81 (m, 2 H) 2.15-2.48 (m, 4 H) 2.64-2.84 (m, 2 H) 3.70-3.84 (m, 2 H) 4.65 (s, 2 H) 5.33-5.42 (m, 2 H) 6.96-7.34 (m, 7 H) 7.38-7.48 (m, 2 H) 12.02 (s, 1 H).

Example 3(46)

6-[9-(2-chlorobenzyl)-1,3,4,9-tetrahydro-2H-beta-carbolin-2-yl]-6-oxohexanoic acid TLC: Rf 0.52 (chloroform:methanol:water=50:10:1);
¹H-NMR (CDCl₃): δ 1.46-1.87 (m, 4 H), 2.15-2.60 (m, 4 H), 2.73-3.03 (m, 2 H), 3.68-4.04 (m, 2 H), 4.35-4.79 (m, 2

H), 5.20-5.41 (m, 2 H), 6.19-6.46 (m, 1 H), 6.92-7.31 (m, 5 H), 7.32-7.47 (m, 1 H), 7.45-7.63 (m, 1 H).

Example 3(47)

6-[9-(2-methylbenzyl)-1,3,4,9-tetrahydro-2H-beta-carbolin-2-yl]-6-oxohexanoic acid TLC: Rf 0.30 (chloroform:methanol=15:1);
$^1$H-NMR (CDCl$_3$): δ 1.43-1.85 (m, 4 H), 2.09-2.67 (m, 7 H), 2.76-3.04 (m, 2 H), 3.67-4.01 (m, 2 H), 4.23-4.79 (m, 2 H), 5.11-5.27 (s, 2 H), 6.19-6.52 (m, 1 H), 6.81-7.34 (m, 6 H), 7.40-7.66 (m, 1 H).

Example 3(48)

6-[9-(4-methoxybenzyl)-1,3,4,9-tetrahydro-2H-beta-carbolin-2-yl]-6-oxohexanoic acid TLC: Rf 0.23 (chloroform:methanol=10:1);
$^1$H-NMR (CDCl$_3$): δ 1.46-1.87 (m, 4 H), 2.09-2.59 (m, 4 H), 2.71-3.01 (m, 2 H), 3.67-4.01 (m, 5 H), 4.37-4.80 (m, 2 H), 5.04-5.34 (m, 2 H), 6.70-6.86 (m, 2 H), 6.86-7.05 (m, 2 H), 7.03-7.38 (m, 3 H), 7.41-7.57 (m, 1 H).

Example 3(49)

methyl 6-[9-(2-chlorobenzyl)-1,3,4,9-tetrahydro-2H-beta-carbolin-2-yl]-6-oxohexanoate TLC: Rf 0.48 (hexane:ethyl acetate=1:1);
$^1$H-NMR (DMSO-d$_6$): δ 1.33-1.68 (m, 4 H), 2.19-2.47 (m, 4 H), 2.61-2.93 (m, 2 H), 3.48-3.61 (m, 3 H), 3.66-3.88 (m, 2 H), 4.47-4.69 (m, 2 H), 5.34-5.54 (m, 2 H), 6.18-6.40 (m, 1 H), 6.96-7.21 (m, 3 H), 7.20-7.39 (m, 2 H), 7.42-7.59 (m, 2 H).

Example 3(50)

methyl 6-[9-(2-methylbenzyl)-1,3,4,9-tetrahydro-2H-beta-carbolin-2-yl]-6-oxohexanoate TLC: Rf 0.38 (hexane:ethyl acetate=1:1);
$^1$H-NMR (CDCl$_3$): δ 1.50-1.87 (m, 4 H), 2.09-2.56 (m, 7 H), 2.77-2.99 (m, 2 H), 3.58-3.70 (m, 3 H), 3.70-4.05 (m, 2 H), 4.31-4.71 (m, 2 H), 5.10-5.30 (m, 2 H), 6.22-6.43 (m, 1 H), 6.79-7.32 (m, 6 H), 7.40-7.65 (m, 1 H).

Example 3(51)

methyl 6-{9-[3-(3-chlorophenyl)propyl]-1,3,4,9-tetrahydro-2H-beta-carbolin-2-yl}-6-oxohexanoate TLC: Rf 0.29 (hexane:ethyl acetate=3:2);
$^1$H-NMR (CDCl$_3$): δ 1.55-1.89 (m, 4 H), 1.99-2.97 (m, 10 H), 3.59-3.72 (m, 3 H), 3.71-3.99 (m, 2 H), 3.99-4.11 (m, 2 H), 4.45-4.88 (m, 2 H), 6.98-7.28 (m, 7 H), 7.43-7.54 (m, 1 H).

Example 3(52)

ethyl 7-{9-[3-(3-chlorophenyl)propyl]-1,3,4,9-tetrahydro-2H-beta-carbolin-2-yl}-7-oxoheptanoate TLC: Rf 0.34 (hexane:ethyl acetate=3:2);
$^1$H-NMR (CDCl$_3$): δ 1.25 (t, J=7.0 Hz, 3 H), 1.35-1.52 (m, 2 H), 1.57-1.84 (m, 4 H), 2.00-2.19 (m, 2 H), 2.24-2.94 (m, 8 H), 3.71-3.98 (m, 2 H), 3.99-4.19 (m, 4 H), 4.47-4.84 (m, 2 H), 6.99-7.28 (m, 7 H), 7.43-7.54 (m, 1 H).

Example 3(54)

methyl 6-[9-(2-methoxybenzyl)-1,3,4,9-tetrahydro-2H-beta-carbolin-2-yl]-6-oxohexanoate TLC: Rf 0.35 (hexane:ethyl acetate=1:1);
$^1$H-NMR (CDCl$_3$): δ 1.51-1.81 (m, 4 H), 2.18-2.57 (m, 4 H), 2.78-3.00 (m, 2 H), 3.60-3.71 (m, 3 H), 3.73-4.01 (m, 5 H), 4.44-4.80 (m, 2 H), 5.22 (s, 2 H), 6.35-6.51 (m, 1 H), 6.66-6.81 (m, 1 H), 6.83-6.99 (m, 1 H), 7.03-7.36 (m, 4 H), 7.44-7.60 (m, 1 H).

Example 3(55)

methyl 2-{[2-(6-methoxy-6-oxohexanoyl)-1,2,3,4-tetrahydro-9H-beta-carbolin-9-yl]methyl}benzoate TLC: Rf 0.38 (hexane:ethyl acetate=1:1);
$^1$H-NMR (CDCl$_3$): δ 1.41-1.86 (m, 4 H), 2.10-2.58 (m, 4 H), 2.76-3.08 (m, 2 H), 3.57-3.71 (m, 3 H), 3.71-4.11 (m, 5 H), 4.37-4.75 (m, 2 H), 5.62-5.79 (s, 2 H), 6.19-6.37 (m, 1 H), 6.98-7.41 (m, 5 H), 7.42-7.66 (m, 1 H), 7.91-8.20 (m, 1 H).

Example 3(56)

methyl 6-oxo-6-{9-[2-(trifluoromethyl)benzyl]-1,3,4,9-tetrahydro-2H-beta-carbolin-2-yl}hexanoate TLC: Rf 0.59 (hexane:ethyl acetate=1:1);
$^1$H-NMR (CDCl$_3$): δ 1.50-1.82 (m, 4 H) 2.14-2.57 (m, 4 H) 2.80-3.01 (m, 2 H) 3.57-3.72 (m, 3 H) 3.73-4.01 (m, 2 H) 4.38-4.76 (m, 2 H) 5.45 (s, 2 H) 6.36-6.49 (m, 1 H) 7.04-7.43 (m, 5 H) 7.49-7.63 (m, 1 H) 7.65-7.79 (m, 1 H).

Example 4

N,N-dimethyl-1-(1H-pyrrolo[2,3-b]pyridin-3-yl)methanamine

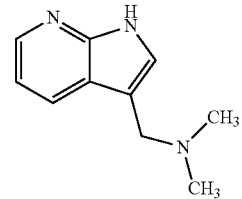

To a mixture of 7-azaindole (150 g), dimethylamine hydrochloride (114 g) and 1-butanol (1.275 L) was added a 37% aqueous formaldehyde solution (103 g), and the mixture was stirred on a 120° C. oil bath for 2.5 hours. The reaction solution was cooled to around 40° C., and placed into water (1.35 L), concentrated hydrochloric acid (54 mL) and methyl tert-butyl ether (MTBE) (630 mL) were added, the mixture was stirred, the layers were separated, and the aqueous layer was taken. This aqueous layer was further washed with MTBE, and a 48% aqueous sodium hydroxide solution was added. This was extracted with chloroform, and a small amount of methanol was added to the extraction solution, followed by drying with anhydrous sodium sulfate. A desiccant was distilled off, followed by concentration under

Example 5

3-(2-nitroethyl)-1H-pyrrolo[2,3-b]pyridine

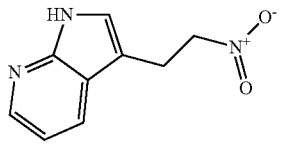 [SMILES: O=[N+]([O-])CCc1c[nH]c2ncccc12]

The compound (70.8 g) produced in Example 4 was dissolved in a mixed solution of methanol (600 mL) and nitromethane (600 mL), the solution was cooled to 6° C., dimethyl sulfate (42 mL) was added for about 30 seconds and, thereafter, the mixture was stirred on an ice bath for about 4 minutes. After stirred at room temperature for 15 minutes, the mixture was cooled again with an ice, and a 28% sodium methoxide/methanol solution (90.6 mL) was added dropwise for 14 minutes. The ice bath was removed, the mixture was stirred for 1.5 hours, and the precipitated pale yellowish white powder was filtered off. To the filtrate was added toluene (600 mL), this was concentrated on a 30° C. water bath under reduced pressure to obtain a yellowish white paste. To this were added ethyl acetate (600 mL) and an aqueous saturated sodium bicarbonate solution (1200 mL), this was shaken well to mix, insolubles (pale yellowish white powder) were filtered off using Celite, and layers were separated. The aqueous layer was extracted with ethyl acetate (600 mL), and the organic layers were combined, washed with an aqueous saturated sodium chloride solution (300 mL), and dried with anhydrous sodium sulfate. The solvent was distilled off under reduced pressure to obtain the title compound (51.25 g) having the following physical property values.

TLC: Rf 0.68 (chloroform:methanol:water=50:10:1);
$^1$H-NMR (CDCl$_3$): δ 3.49 (t, J=7.0 Hz, 2 H) 4.67 (t, J=7.0 Hz, 2 H) 7.12 (dd, J=8.00, 5.00 Hz, 1 H) 7.91 (dd, J=8.00, 1.50 Hz, 1 H) 8.34 (dd, J=5.00, 1.50 Hz, 1 H) 9.60 (s, 1 H).

Example 6

2-(1H-pyrrolo[2,3-b]pyridine-3-yl)ethanamine

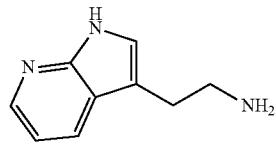 [SMILES: NCCc1c[nH]c2ncccc12]

The compound (114.9 g) produced in Example 5 was suspended in ethanol (1.15 L), and 20% palladium hydroxide/carbon (50% hydrous product, 57.7 g) was added. The mixture was stirred on a water bath at 70° C. for about 8 hours under the hydrogen atmosphere. After a temperature was returned to room temperature, the reaction was allowed to stand overnight under the nitrogen atmosphere, hydrogen replacement operation was performed again, and the reaction was stirred on a water bath at 70° C. for about 8 hours under the hydrogen atmosphere. After a temperature was returned to room temperature, a catalyst was filtered off using Celite. The filtrate was concentrated under reduced pressure to obtain the title compound (99.6 g) having the following physical property values.

TLC: Rf 0.14 (chloroform:methanol:water=90:10:1);
$^1$H-NMR (CDCl$_3$): δ 2.89 (t, J=6.5 Hz, 2 H) 3.01 (t, J=7.0 Hz, 2 H) 7.07 (dd, J=8.00, 5.00 Hz, 1 H) 7.15 (s, 1 H) 7.92 (dd, J=8.00, 1.50 Hz, 1 H) 8.29 (dd, J=5.00, 1.50 Hz, 1 H) 10.12 (s, 1 H).

Example 7

6,7,8,9-tetrahydro-5H-pyrido[4',3':4,5]pyrrolo[2,3-b]pyridine hydrochloride

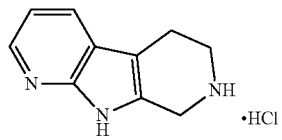 [SMILES: c1cnc2[nH]c3c(c2c1)CCNC3 ; Cl]

The compound (99.6 g) produced in Example 6 was dissolved in ethanol (2.89 L), a 4M hydrogen chloride/1,4-dioxane solution (150.5 mL) and a 37% aqueous formaldehyde solution (53.65 g) were added, and the mixture was heated to reflux for 3 hours. After allowed to cool to below 40° C., the reaction was diluted with diisopropyl ether (IPE) (3.4 L) and MTBE (2.38 L), and a crystal was filtered off. This crystal was washed with about 500 mL of MTBE, and dried under reduced pressure to obtain the title compound (85.72 g) having the following physical property values.

TLC: Rf 0.27 (chloroform:methanol:28% aqueous ammonia=90:10:1);
$^1$H-NMR (CDCl$_3$): δ 2.94 (t, J=6.0 Hz, 2 H) 3.40-3.44 (m, 2 H) 4.33 (s, 2 H), 7.14 (dd, J=8.00, 5.00 Hz, 1 H) 8.01 (dd, J=8.00, 1.50 Hz, 1 H) 8.23 (dd, J=5.00, 1.50 Hz, 1 H) 9.75 (s, 2 H), 11.87 (s, 1 H).

Example 8 tert-butyl 5,6,8,9-tetrahydro-7H-pyrido[4',3':4,5]pyrrolo[2,3-b]pyridine-7-carboxylate

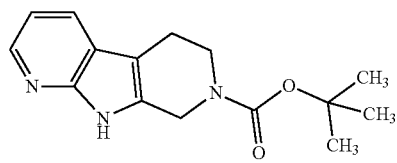 [SMILES: CC(C)(C)OC(=O)N1CCc2c([nH]c3ncccc23)C1]

The compound (95.9 g) produced in Example 7 was suspended in 1,4-dioxane (1.94 L), and a 1M aqueous sodium hydroxide solution (480 mL, 0.48 mol) was added. This solution was cooled with ice, di-tert-butyl dicarbonate (104.8 g) was added, and the mixture was stirred at room temperature for 12.5 hours. The reaction solution was placed into an aqueous saturated sodium dicarbonate solution (6 L), followed by extraction with ethyl acetate (2 L) three times. The extract solution was washed with an aqueous saturated sodium chloride solution (2 L), dried using anhydrous sodium sulfate, and concentrated under reduced pressure. The resulting pale brown solid was treated with a silica gel column (ethyl acetate) to collect target fractions. The solvent was distilled off under reduced pressure, hexane (880 mL) was added, and this was mixed, and allowed to stand overnight at room temperature. A crystal was filtered off, washed using a mixed solution (150 mL) of hexane:ethyl acetate (10:1) and dried at room temperature under reduced pressure to obtain the title compound (72.1 g) having the following physical property values.

TLC: Rf 0.60 (chloroform:methanol:28% aqueous ammonia=90:10:1);

$^1$H-NMR (CDCl$_3$): δ 1.51 (s, 9 H), 2.79 (t, J=6.0 Hz, 2 H) 3.79 (t, J=6.0 Hz, 2 H) 4.71 (s, 2 H), 7.05 (dd, J=8.00, 5.00 Hz, 1 H) 7.79 (m, 1 H) 8.23 (m, 1 H) 10.10-10.75 (m, 1 H).

Example 9

6-[9-(3-fluorobenzyl)-5,6,8,9-tetrahydro-7H-pyrido[4',3':4,5]pyrrolo[2,3-b]pyridin-7-yl]-6-oxohexanoic acid

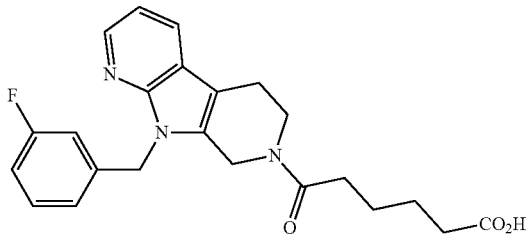 [SMILES: O=C(O)CCCCC(=O)N1CCc2c(n(Cc3cccc(F)c3)c3ncccc23)C1]

The compound produced in Example 8 in place of tert-butyl 1,3,4,9-tetrahydro-2H-β-carboline-2-carboxylate, and 1-(bromomethyl)-3-fluorobenzene in place of (3-bromopropyl)benzene were used, which were subjected to operation in accordance with Example 1→Example 2→Example 3 to obtain the title compound (81.5 mg) having the following physical property values.

TLC: Rf 0.43 (chloroform:methanol:water=50:10:1);

$^1$H-NMR (DMSO-d$_6$): δ 1.31-1.66 (m, 4 H) 2.09-2.48 (m, 4 H) 2.57-2.89 (m, 2 H) 3.63-3.89 (m, 2 H) 4.55-4.69 (m, 2 H) 5.42-5.54 (m, 2 H) 6.85-7.15 (m, 4 H) 7.26-7.40 (m, 1 H) 7.84-7.94 (m, 1H) 8.16-8.25 (m, 1 H) 11.93 (s, 1 H).

Example 9(1)-Example 9(83)

Corresponding alkyl halide in place of 1-(bromomethyl)-3-fluorobenzene, and the compound produced in Example 8 in place of tert-butyl-1,3,4,9-tetrahydro-2H-β-carboline-2-carboxylate were used, which were subjected to operation in accordance with Example 1 and, further, a corresponding carboxylic acid ester derivative in place of methyl 6-chloro-6-oxohexanoate was used, which was subjected to operation in accordance with Example 2 and, if necessary, subjected to operation in accordance with Example 3 to obtain the following compounds.

Example 9(1)

6-[9-(cyclohexylmethyl)-5,6,8,9-tetrahydro-7H-pyrido[4',3':4,5]pyrrolo[2,3-b]pyridin-7-yl]-6-oxohexanoic acid HPLC retention time (min): 4.06;
MS (ESI, Pos. 20 V): m/z=398 (M+H)$^+$.

Example 9(2)

6-[9-(2-cyclohexylethyl)-5,6,8,9-tetrahydro-7H-pyrido[4',3':4,5]pyrrolo[2,3-b]pyridin-7-yl]-6-oxohexanoic acid

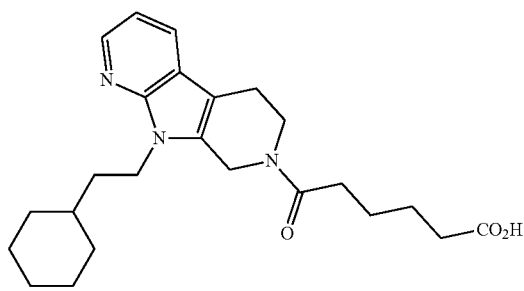 [SMILES: O=C(O)CCCCC(=O)N1CCc2c(n(CCC3CCCCC3)c3ncccc23)C1]

HPLC retention time (min): 4.30;
MS (ESI, Pos. 20 V): m/z=412 (M+H)$^+$.

Example 9(3)

6-[9-(3-cyclohexylpropyl)-5,6,8,9-tetrahydro-7H-pyrido[4',3':4,5]pyrrolo[2,3-b]pyridin-7-yl]-6-oxohexanoic acid HPLC retention time (min): 4.39;
MS (ESI, Pos. 20 V): m/z=426 (M+H)$^+$.

Example 9(4)

6-[9-(4-cyclohexylbutyl)-5,6,8,9-tetrahydro-7H-pyrido[4',3':4,5]pyrrolo[2,3-b]pyridin-7-yl]-6-oxohexanoic acid HPLC retention time (min): 4.51;
MS (ESI, Pos. 20 V): m/z=440 (M+H)$^+$.

Example 9(5)

6-[9-(3,4-dichlorobenzyl)-5,6,8,9-tetrahydro-7H-pyrido[4',3':4,5]pyrrolo[2,3-b]pyridin-7-yl]-6-oxohexanoic acid HPLC retention time (min): 4.41;
MS (ESI, Pos. 20 V): m/z=460 (M+H)$^+$.

Example 9(6)

6-[9-(3,5-dichlorobenzyl)-5,6,8,9-tetrahydro-7H-pyrido[4',3':4,5]pyrrolo[2,3-b]pyridin-7-yl]-6-oxohexanoic acid HPLC retention time (min): 4.44;
MS (ESI, Pos. 20 V): m/z=460 (M+H)$^+$.

Example 9(7)

6-[9-(3,4-dimethylbenzyl)-5,6,8,9-tetrahydro-7H-pyrido[4',3':4,5]pyrrolo[2,3-b]pyridin-7-yl]-6-oxohexanoic acid HPLC retention time (min): 4.21;
MS (ESI, Pos. 20 V): m/z=420 (M+H)$^+$.

Example 9(8)

6-[9-(3,5-dimethylbenzyl)-5,6,8,9-tetrahydro-7H-pyrido[4',3':4,5]pyrrolo[2,3-b]pyridin-7-yl]-6-oxohexanoic acid HPLC retention time (min): 4.21;
MS (ESI, Pos. 20 V): m/z=420 (M+H)$^+$.

Example 9(9)

6-[9-(3,4-difluorobenzyl)-5,6,8,9-tetrahydro-7H-pyrido[4',3':4,5]pyrrolo[2,3-b]pyridin-7-yl]-6-oxohexanoic acid HPLC retention time (min): 4.17;
MS (ESI, Pos. 20 V): m/z=428 (M+H)$^+$.

Example 9(10)

6-oxo-6-[9-(3,4,5-trifluorobenzyl)-5,6,8,9-tetrahydro-7H-pyrido[4',3':4,5]pyrrolo[2,3-b]pyridin-7-yl] hexanoic acid HPLC retention time (min): 4.31;
MS (ESI, Pos. 20 V): m/z=446 (M+H)$^+$.

Example 9(11)

ethyl 7-(9-benzyl-5,6,8,9-tetrahydro-7H-pyrido[4',3':4,5]pyrrolo[2,3-b]pyridin-7-yl)-7-oxoheptanoate TLC: Rf 0.34 (hexane:ethyl acetate=1:1);
$^1$H-NMR (CDCl$_3$): δ 1.18-1.78 (m, 9 H) 2.04-2.53 (m, 4 H) 2.73-2.92 (m, 2 H) 3.66-3.97 (m, 2 H) 4.11 (q, J=7.00 Hz, 2 H) 4.36-4.72 (m, 2 H) 5.40-5.55 (m, 2 H) 7.00-7.36 (m, 6 H) 7.73-7.86 (m, 1 H) 8.26-8.34 (m, 1 H).

Example 9(12)

methyl 6-[9-(4-fluorobenzyl)-5,6,8,9-tetrahydro-7H-pyrido[4',3':4,5]pyrrolo[2,3-b]pyridin-7-yl]-6-oxohexanoate TLC: Rf 0.24 (hexane:ethyl acetate=1:1);
$^1$H-NMR (CDCl$_3$): δ 1.64-1.78 (m, 4 H) 2.13-2.54 (m, 4 H) 2.74-2.91 (m, 2 H) 3.67 (s, 3 H) 3.69-3.95 (m, 2 H) 4.41-4.70 (m, 2 H) 5.38-5.50 (m, 2 H) 6.88-7.19 (m, 5 H) 7.74-7.85 (m, 1 H) 8.26-8.35 (m, 1 H).

Example 9(13)

methyl 6-[9-(3-chloro-4-fluorobenzyl)-5,6,8,9-tetrahydro-7H-pyrido[4',3':4,5]pyrrolo[2,3-b]pyridin-7-yl]-6-oxohexanoate TLC: Rf 0.20 (hexane:ethyl acetate=1:1);
$^1$H-NMR (CDCl$_3$): δ 1.65-1.77 (m, 4 H) 2.19-2.57 (m, 4 H) 2.74-2.94 (m, 2 H) 3.66 (s, 3 H) 3.71-3.99 (m, 2 H) 4.43-4.72 (m, 2 H) 5.35-5.49 (m, 2 H) 6.99-7.15 (m, 3 H) 7.16-7.24 (m, 1 H) 7.75-7.87 (m, 1 H) 8.27-8.34 (m, 1 H).

Example 9(14)

ethyl 7-[9-(4-fluorobenzyl)-5,6,8,9-tetrahydro-7H-pyrido[4',3':4,5]pyrrolo[2,3-b]pyridin-7-yl]-7-oxoheptanoate TLC: Rf 0.42 (hexane:ethyl acetate=1:1);
$^1$H-NMR (CDCl$_3$): δ 1.25 (t, J=7.50 Hz, 3 H) 1.32-1.79 (m, 4 H) 2.10-2.50 (m, 4 H) 2.73-2.92 (m, 2 H) 3.68-3.96 (m, 2 H) 4.11 (q, J=7.50 Hz, 2 H) 4.41-4.71 (m, 2 H) 5.39-5.49 (m, 2 H) 6.88-7.19 (m, 5 H) 7.73-7.86 (m, 1 H) 8.26-8.34 (m, 1 H).

Example 9(15)

ethyl 7-[9-(3-chloro-4-fluorobenzyl)-5,6,8,9-tetrahydro-7H-pyrido[4',3':4,5]pyrrolo[2,3-b]pyridin-7-yl]-7-oxoheptanoate TLC: Rf 0.42 (hexane:ethyl acetate=1:1);
$^1$H-NMR (CDCl$_3$): δ 1.25 (t, J=7.50 Hz, 3 H) 1.33-1.77 (m, 6 H) 2.16-2.52 (m, 4 H) 2.86 (m, J=5.50, 5.50 Hz, 2 H) 3.70-3.97 (m, 2 H) 4.11 (q, J=7.50 Hz, 2 H) 4.43-4.73 (m, 2 H) 5.35-5.47 (m, 2 H) 6.99-7.14 (m, 3 H) 7.16-7.24 (m, 1 H) 7.74-7.88 (m, 1 H) 8.26-8.34 (m, 1 H).

Example 9(16)

5-(9-benzyl-5,6,8,9-tetrahydro-7H-pyrido[4',3':4,5]pyrrolo[2,3-b]pyridin-7-yl)-5-oxopentanoic acid TLC: Rf 0.47 (chloroform:methanol:aqueous ammonia=50:10:1);
$^1$H-NMR (DMSO-d$_6$): δ 1.54-1.80 (m, 2 H) 2.12-2.56 (m, 4 H) 2.62-2.85 (m, 2 H) 3.66-3.83 (m, 2 H) 4.50-4.74 (m, 2 H) 5.39-5.55 (m, 2 H) 7.04-7.33 (m, 6 H) 7.84-7.92 (m, 1 H) 8.16-8.24 (m, 1 H).

Example 9(17)

6-(9-benzyl-5,6,8,9-tetrahydro-7H-pyrido[4',3':4,5]pyrrolo[2,3-b]pyridin-7-yl)-6-oxohexanoic acid TLC: Rf 0.48 (chloroform:methanol:aqueous ammonia=50:10:1);
$^1$H-NMR (DMSO-d$_6$): δ 1.33-1.60 (m, 4 H) 2.10-2.48 (m, 4 H) 2.62-2.85 (m, 2 H) 3.65-3.85 (m, 2 H) 4.61 (s, 2 H) 5.41-5.53 (m, 2 H) 7.03-7.36 (m, 6 H) 7.83-7.93 (m, 1 H) 8.16-8.24 (m, 1 H) 11.97 (s, 1 H).

Example 9(18)

7-(9-benzyl-5,6,8,9-tetrahydro-7H-pyrido[4',3':4,5]pyrrolo[2,3-b]pyridin-7-yl)-7-oxoheptanoic acid TLC: Rf 0.51 (chloroform:methanol:aqueous ammonia=50:10:1);
$^1$H-NMR (DMSO-d$_6$): δ 1.12-1.60 (m, 6 H) 2.09-2.47 (m, 4 H) 2.61-2.83 (m, 2 H) 3.65-3.83 (m, 2 H) 4.61 (s, 2 H) 5.39-5.54 (m, 2 H) 7.03-7.34 (m, 6 H) 7.85-7.92 (m, 1 H) 8.17-8.24 (m, 1 H) 11.95 (s, 1 H).

Example 9(19)

6-[9-(3-chlorobenzyl)-5,6,8,9-tetrahydro-7H-pyrido[4',3':4,5]pyrrolo[2,3-b]pyridin-7-yl]-6-oxohexanoic acid TLC: Rf 0.34 (methylene chloride:methanol=9:1);
$^1$H-NMR (DMSO-$d_6$): δ 1.40-1.59 (m, 4 H) 2.13-2.53 (m, 4 H) 2.64-2.86 (m, 2 H) 3.70-3.84 (m, 2 H) 4.59-4.67 (m, 2 H) 5.44-5.53 (m, 2 H) 6.98-7.14 (m, 2 H) 7.17-7.36 (m, 3 H) 7.90 (d, J=7.69 Hz, 1 H) 8.21 (d, J=4.76 Hz, 1 H) 11.95 (s, 1 H).

Example 9(20)

6-[9-(3-chloro-4-fluorobenzyl)-5,6,8,9-tetrahydro-7H-pyrido[4',3':4,5]pyrrolo[2,3-b]pyridin-7-yl]-6-oxohexanoic acid TLC: Rf 0.40 (methylene chloride:methanol=9:1);
$^1$H-NMR (DMSO-$d_6$): δ 1.42-1.58 (m, 4 H) 2.14-2.52 (m, 4 H) 2.63-2.83 (m, 2 H) 3.71-3.82 (m, 2 H) 4.62-4.69 (m, 2 H) 5.43-5.49 (m, 2 H) 7.02-7.15 (m, 2 H) 7.29-7.48 (m, 2 H) 7.90 (dd, J=7.8, 1.4 Hz, 1 H) 8.22 (d, J=4.6 Hz, 1 H) 11.95 (s, 1 H).

Example 9(21)

7-[9-(4-fluorobenzyl)-5,6,8,9-tetrahydro-7H-pyrido[4',3':4,5]pyrrolo[2,3-b]pyridin-7-yl]-7-oxoheptanoic acid TLC: Rf 0.41 (methylene chloride:methanol=9:1);
$^1$H-NMR (DMSO-$d_6$): δ 1.15-1.58 (m, 6 H) 2.11-2.53 (m, 4 H) 2.63-2.82 (m, 2 H) 3.70-3.82 (m, 2 H) 4.62 (s, 2 H) 5.41-5.50 (m, 2 H) 7.06-7.24 (m, 5 H) 7.86-7.91 (m, 1 H) 8.18-8.24 (m, 1 H) 11.94 (s, 1 H).

Example 9(22)

7-[9-(3-chloro-4-fluorobenzyl)-5,6,8,9-tetrahydro-7H-pyrido[4',3':4,5]pyrrolo[2,3-b]pyridin-7-yl]-7-oxoheptanoic acid TLC: Rf 0.42 (methylene chloride:methanol=9:1);
$^1$H-NMR (DMSO-$d_6$): δ 1.16-1.57 (m, 6 H) 2.11-2.53 (m, 4 H) 2.63-2.83 (m, 2 H) 3.70-3.83 (m, 2 H) 4.64 (s, 2 H) 5.43-5.50 (m, 2 H) 7.02-7.15 (m, 2 H) 7.29-7.48 (m, 2 H) 7.86-7.94 (m, 1 H) 8.18-8.25 (m, 1 H) 11.93 (s, 1 H).

Example 9(23)

6-oxo-6-[9-(3-phenylpropyl)-5,6,8,9-tetrahydro-7H-pyrido[4',3':4,5]pyrrolo[2,3-b]pyridin-7-yl]hexanoic acid TLC: Rf 0.47 (methylene chloride:methanol=9:1);
$^1$H-NMR (DMSO-$d_6$): δ 1.48-1.60 (m, 4 H) 1.95-2.09 (m, 2 H) 2.15-2.28 (m, 2 H) 2.40-2.81 (m, 6 H) 3.73-3.84 (m, 2 H) 4.16-4.28 (m, 2 H) 4.69-4.77 (m, 2 H) 7.04 (dd, J=7.7, 4.6 Hz, 1 H) 7.10-7.29 (m, 5 H) 7.82 (dd, J=7.7, 1.1 Hz, 1 H) 8.18 (dd, J=4.6, 1.1 Hz, 1 H).

Example 9(24)

7-[9-(3-chlorobenzyl)-5,6,8,9-tetrahydro-7H-pyrido[4',3':4,5]pyrrolo[2,3-b]pyridin-7-yl]-7-oxoheptanoic acid TLC: Rf 0.47 (methylene chloride:methanol=9:1);
$^1$H-NMR (DMSO-$d_6$): δ 1.14-1.59 (m, 6 H) 2.11-2.52 (m, 4 H) 2.63-2.87 (m, 2 H) 3.70-3.82 (m, 2 H) 4.63 (s, 2 H) 5.43-5.52 (m, 2 H) 6.98-7.07 (m, 1 H) 7.10 (dd, J=7.8, 4.7 Hz, 1 H) 7.18-7.36 (m, 3 H) 7.87-7.93 (m, 1 H) 8.19-8.24 (m, 1 H) 11.93 (s, 1 H).

Example 9(26)

5-oxo-5-[9-(3-phenylpropyl)-5,6,8,9-tetrahydro-7H-pyrido[4',3':4,5]pyrrolo[2,3-b]pyridin-7-yl]pentanoic acid

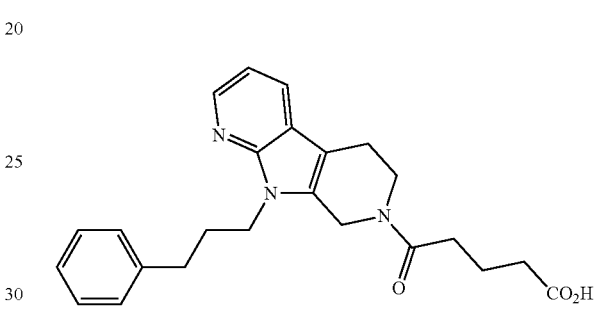

TLC: Rf 0.44 (ethyl acetate);
$^1$H-NMR (CDCl$_3$): δ 1.90-2.23 (m, 4 H) 2.39-2.92 (m, 8 H) 3.71-3.98 (m, 2 H) 4.17-4.33 (m, 2 H) 4.52-4.86 (m, 2 H) 6.99-7.32 (m, 6 H) 7.69-7.80 (m, 1 H) 8.24-8.34 (m, 1 H).

Example 9(27)

7-oxo-7-[9-(3-phenylpropyl)-5,6,8,9-tetrahydro-7H-pyrido[4',3':4,5]pyrrolo[2,3-b]pyridin-7-yl]heptanoic acid TLC: Rf 0.49 (ethyl acetate);
$^1$H-NMR (CDCl$_3$): δ 1.32-1.83 (m, 4 H) 2.01-2.92 (m, 12 H) 3.68-3.99 (m, 2 H) 4.14-4.35 (m, 2 H) 4.42-4.87 (m, 2 H) 6.99-7.09 (m, 1 H) 7.10-7.33 (m, 5 H) 7.69-7.81 (m, 1 H) 8.22-8.34 (m, 1 H).

Example 9(28)

6-oxo-6-[9-(2-phenoxyethyl)-5,6,8,9-tetrahydro-7H-pyrido[4',3':4,5]pyrrolo[2,3-b]pyridin-7-yl]hexanoic acid

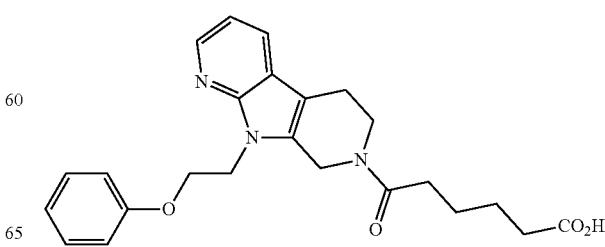

TLC: Rf 0.62 (chloroform:methanol:water=50:10:1);
$^1$H-NMR (DMSO-d$_6$): δ 1.45-1.68 (m, 4 H) 2.15-2.31 (m, 2 H) 2.36-2.60 (m, 2 H) 2.61-2.83 (m, 2 H) 3.71-3.85 (m, 2 H) 4.17-4.34 (m, 2 H) 4.47-4.66 (m, 2 H) 4.82-5.03 (m, 2 H) 6.81-6.95 (m, 3 H) 7.02-7.11 (m, 1 H) 7.15-7.28 (m, 2 H) 7.80-7.87 (m, 1 H) 8.14-8.22 (m, 1 H) 11.98 (s, 1 H).

Example 9(29)

6-[9-(cyclopentylmethyl)-5,6,8,9-tetrahydro-7H-pyrido[4',3':4,5]pyrrolo[2,3-b]pyridin-7-yl]-6-oxohexanoic acid HPLC retention time (min): 3.94;
MS (ESI, Pos. 20 V): m/z=384 (M+H)$^+$.

Example 9(30)

6-[9-(3-cyclohexen-1-ylmethyl)-5,6,8,9-tetrahydro-7H-pyrido[4',3':4,5]pyrrolo[2,3-b]pyridin-7-yl]-6-oxohexanoic acid HPLC retention time (min): 4.02;
MS (ESI, Pos. 20 V): m/z=396 (M+H)$^+$.

Example 9(31)

6-oxo-6-{9-[2-(phenylthio)ethyl]-5,6,8,9-tetrahydro-7H-pyrido[4',3':4,5]pyrrolo[2,3-b]pyridin-7-yl}hexanoic acid

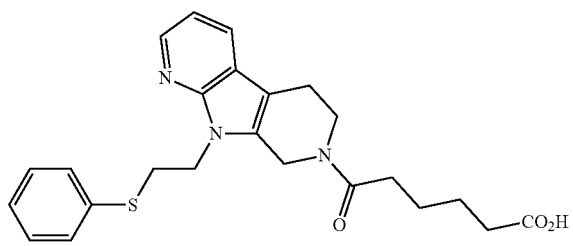 [SMILES: O=C(O)CCCCC(=O)N1CCc2c(n(CCSc3ccccc3)c3ncccc23)C1]

HPLC retention time (min): 3.95;
MS (ESI, Pos. 20 V): m/z=438 (M+H)$^+$.

Example 9(34)

methyl 6-[9-(3-chlorobenzyl)-5,6,8,9-tetrahydro-7H-pyrido[4',3':4,5]pyrrolo[2,3-b]pyridin-7-yl]-6-oxohexanoate TLC: Rf 0.25 (hexane:ethyl acetate=1:1);
$^1$H-NMR (CDCl$_3$): δ 1.66-1.76 (m, 4 H) 2.15-2.52 (m, 4 H) 2.76-2.92 (m, 2 H) 3.64-3.67 (m, 3 H) 3.75-3.95 (m, 2 H) 4.40-4.70 (m, 2 H) 5.41-5.49 (m, 2 H) 6.93-7.15 (m, 3 H) 7.16-7.27 (m, 2 H) 7.76-7.85 (m, 1 H) 8.27-8.33 (m, 1 H).

Example 9(35)

methyl 6-oxo-6-[9-(3-phenylpropyl)-5,6,8,9-tetrahydro-7H-pyrido[4',3':4,5]pyrrolo[2,3-b]pyridin-7-yl]hexanoate TLC: Rf 0.30 (hexane:ethyl acetate=1:1);
$^1$H-NMR (CDCl$_3$): δ 1.63-1.82 (m, 4 H) 2.05-2.91 (m, 10 H) 3.67 (s, 3 H) 3.72-3.97 (m, 2 H) 4.17-4.32 (m, 2 H) 4.45-4.84 (m, 2 H) 6.97-7.34 (m, 6 H) 7.69-7.81 (m, 1 H) 8.24-8.31 (m, 1 H).

Example 9(37)

ethyl 7-[9-(3-chlorobenzyl)-5,6,8,9-tetrahydro-7H-pyrido[4',3':4,5]pyrrolo[2,3-b]pyridin-7-yl]-7-oxoheptanoate TLC: Rf 0.38 (hexane:ethyl acetate=1:1);
$^1$H-NMR (CDCl$_3$): δ 1.20-1.32 (m, 3 H) 1.29-1.78 (m, 6 H) 2.11-2.50 (m, 4 H) 2.76-2.91 (m, 2 H) 3.69-3.96 (m, 2 H) 4.12 (q, J=7.50 Hz, 2 H) 4.40-4.71 (m, 2 H) 5.39-5.51 (m, 2 H) 6.92-7.23 (m, 5 H) 7.75-7.87 (m, 1 H) 8.23-8.35 (m, 1 H).

Example 9(38)

methyl 6-[9-(3-fluorobenzyl)-5,6,8,9-tetrahydro-7H-pyrido[4',3':4,5]pyrrolo[2,3-b]pyridin-7-yl]-6-oxohexanoate TLC: Rf 0.35 (hexane:ethyl acetate=1:1);
$^1$H-NMR (CDCl$_3$): δ 1.50-1.82 (m, 4 H) 2.12-2.53 (m, 4 H) 2.74-2.91 (m, 2 H) 3.65 (s, 3 H) 3.69-3.97 (m, 2 H) 4.39-4.72 (m, 2 H) 5.39-5.54 (m, 2 H) 6.72-6.82 (m, 1 H) 6.84-7.01 (m, 2 H) 7.01-7.16 (m, 1 H) 7.17-7.34 (m, 1 H) 7.73-7.86 (m, 1 H) 8.24-8.34 (m, 1 H).

Example 9(39)

methyl 5-oxo-5-[9-(3-phenylpropyl)-5,6,8,9-tetrahydro-7H-pyrido[4',3':4,5]pyrrolo[2,3-b]pyridin-7-yl]pentanoate TLC: Rf 0.51 (hexane:ethyl acetate=1:1);
$^1$H-NMR (CDCl$_3$): δ 1.92-2.22 (m, 4 H) 2.37-2.91 (m, 8 H) 3.62-3.71 (m, 3 H) 3.74-3.98 (m, 2 H) 4.19-4.31 (m, 2 H) 4.51-4.84 (m, 2 H) 6.97-7.31 (m, 6 H) 7.68-7.80 (m, 1 H) 8.22-8.32 (m, 1 H).

Example 9(40)

6-[9-(4-fluorobenzyl)-5,6,8,9-tetrahydro-7H-pyrido[4',3':4,5]pyrrolo[2,3-b]pyridin-7-yl]-6-oxohexanoic acid TLC: Rf 0.39 (methylene chloride:methanol=9:1);
$^1$H-NMR (DMSO-d$_5$): δ 1.40-1.57 (m, 4 H) 2.11-2.53 (m, 4 H) 2.62-2.83 (m, 2 H) 3.68-3.84 (m, 2 H) 4.62 (s, 2 H) 5.40-5.50 (m, 2 H) 7.05-7.25 (m, 5 H) 7.89 (d, J=7.5 Hz, 1 H) 8.21 (d, J=4.4 Hz, 1 H) 11.96 (s, 1 H).

Example 9(41)

6-oxo-6-[9-(4-phenylbutyl)-5,6,8,9-tetrahydro-7H-pyrido[4',3':4,5]pyrrolo[2,3-b]pyridin-7-yl]hexanoic acid TLC: Rf 0.41 (ethyl acetate);
$^1$H-NMR (CDCl$_3$): δ 1.59-1.91 (m, 6 H) 2.32-2.90 (m, 10 H) 3.72-3.99 (m, 2 H) 4.21 (t, J=7.50 Hz, 2 H) 4.54-4.85 (m, 2 H) 6.98-7.08 (m, 1 H) 7.08-7.30 (m, 5 H) 7.69-7.82 (m, 1 H) 8.23-8.32 (m, 1 H).

Example 9(42)

7-oxo-7-[9-(4-phenylbutyl)-5,6,8,9-tetrahydro-7H-pyrido[4',3':4,5]pyrrolo[2,3-b]pyridin-7-yl]heptanoic acid TLC: Rf 0.49 (ethyl acetate);
$^1$H-NMR (CDCl$_3$): δ 1.57-1.92 (m, 8 H) 2.28-2.90 (m, 10 H) 3.73-3.99 (m, 2 H) 4.21 (t, J=7.41 Hz, 2 H) 4.54-4.86 (m, 2 H) 6.98-7.08 (m, 1 H) 7.07-7.30 (m, 5 H) 7.69-7.81 (m, 1 H) 8.22-8.33 (m, 1 H).

Example 9(43)

6-oxo-6-[9-(3-phenoxypropyl)-5,6,8,9-tetrahydro-7H-pyrido[4',3':4,5]pyrrolo[2,3-b]pyridin-7-yl]hexanoic acid TLC: Rf 0.58 (chloroform:methanol:water=50:10:1);
$^1$H-NMR (DMSO-d$_6$): δ 1.39-1.64 (m, 4 H) 2.08-2.49 (m, 6 H) 2.59-2.84 (m, 2 H) 3.65-3.82 (m, 2 H) 3.94 (t, J=6.00 Hz, 2 H) 4.26-4.42 (m, 2 H) 4.66-4.85 (m, 2 H) 6.83-6.95 (m, 3 H) 7.04 (dd, J=7.50, 5.00 Hz, 1 H) 7.19-7.30 (m, 2 H) 7.83 (dd, J=7.50, 1.50 Hz, 1 H) 8.13-8.20 (m, 1 H) 11.96 (s, 1 H).

Example 9(44)

6-[9-(cyclobutylmethyl)-5,6,8,9-tetrahydro-7H-pyrido[4',3':4,5]pyrrolo[2,3-b]pyridin-7-yl]-6-oxohexanoic acid HPLC retention time (min): 3.82;
MS (ESI, Pos. 20 V): m/z=370 (M+H)$^+$.

Example 9(45)

ethyl 7-oxo-7-[9-(3-phenylpropyl)-5,6,8,9-tetrahydro-7H-pyrido[4',3':4,5]pyrrolo[2,3-b]pyridin-7-yl]heptanoate TLC: Rf 0.70 (hexane:ethyl acetate=1:1);
$^1$H-NMR (CDCl$_3$): δ 1.17-1.33 (m, 3 H) 1.34-1.51 (m, 2 H) 1.59-1.81 (m, 4 H) 2.07-2.91 (m, 10 H) 3.70-3.97 (m, 2 H) 4.12 (q, J=7.00 Hz, 2 H) 4.17-4.31 (m, 2 H) 4.43-4.86 (m, 2 H) 6.97-7.34 (m, 6 H) 7.68-7.84 (m, 1 H) 8.22-8.39 (m, 1 H).

Example 9(46)

6-oxo-6-[9-(2-phenylethyl)-5,6,8,9-tetrahydro-7H-pyrido[4',3':4,5]pyrrolo[2,3-b]pyridin-7-yl]hexanoic acid TLC: Rf 0.35 (ethyl acetate);
$^1$H-NMR (CDCl$_3$): δ 1.56-1.81 (m, 4 H) 2.02-2.52 (m, 4 H) 2.64-2.86 (m, 2 H) 3.02-3.22 (m, 2 H) 3.57-3.81 (m, 2 H) 3.81-4.30 (m, 2 H) 4.32-4.44 (m, 2 H) 6.81-7.30 (m, 6 H) 7.70-7.83 (m, 1 H) 8.27-8.37 (m, 1 H).

Example 9(47)

7-oxo-7-[9-(2-phenylethyl)-5,6,8,9-tetrahydro-7H-pyrido[4',3':4,5]pyrrolo[2,3-b]pyridin-7-yl]heptanoic acid TLC: Rf 0.40 (ethyl acetate);
$^1$H-NMR (CDCl$_3$): δ 1.28-1.80 (m, 6 H) 1.99-2.49 (m, 2 H) 2.63-2.86 (m, 2 H) 3.05-3.20 (m, 2 H) 3.57-3.81 (m, 2 H) 3.82-4.32 (m, 2 H) 4.33-4.45 (m, 2 H) 6.81-7.30 (m, 6 H) 7.70-7.83 (m, 1 H) 8.28-8.36 (m, 1 H).

Example 9(48)

6-[9-(cyclopropylmethyl)-5,6,8,9-tetrahydro-7H-pyrido[4',3':4,5]pyrrolo[2,3-b]pyridin-7-yl]-6-oxo-hexanoic acid HPLC retention time (min): 3.64;
MS (ESI, Pos. 20 V): m/z=356 (M+H)$^+$.

Example 9(49)

methyl 5-oxo-5-[9-(4-phenylbutyl)-5,6,8,9-tetrahydro-7H-pyrido[4',3':4,5]pyrrolo[2,3-b]pyridin-7-yl]pentanoate TLC: Rf 0.25 (hexane:ethyl acetate=1:1);
$^1$H-NMR (CDCl$_3$): δ 1.60-2.12 (m, 8 H) 2.36-2.93 (m, 8 H) 3.63-3.71 (m, 3 H) 3.74-3.99 (m, 2 H) 4.13-4.30 (m, 2 H) 4.59-4.87 (m, 1 H) 6.95-7.33 (m, 5 H) 7.67-7.81 (m, 1 H) 8.17-8.39 (m, 1 H).

Example 9(50)

methyl 6-oxo-6-[9-(4-phenylbutyl)-5,6,8,9-tetrahydro-7H-pyrido[4',3':4,5]pyrrolo[2,3-b]pyridin-7-yl]hexanoate TLC: Rf 0.24 (hexane:ethyl acetate=1:1);
$^1$H-NMR (CDCl$_3$): δ 1.60-1.94 (m, 8 H) 2.28-2.91 (m, 8 H) 3.61-3.70 (m, 3 H) 3.71-3.99 (m, 2 H) 4.21 (t, J=7.50 Hz, 2 H) 4.52-4.87 (m, 2 H) 6.97-7.32 (m, 6 H) 7.68-7.82 (m, 1 H) 8.21-8.32 (m, 1 H).

Example 9(51)

methyl 6-oxo-6-[9-(2-phenoxyethyl)-5,6,8,9-tetrahydro-7H-pyrido[4',3':4,5]pyrrolo[2,3-b]pyridin-7-yl]hexanoate TLC: Rf 0.35 (hexane:ethyl acetate=1:2);
$^1$H-NMR (CDCl$_3$): δ 1.61-1.85 (m, 4 H) 2.30-2.44 (m, 2 H) 2.43-2.58 (m, 2 H) 2.71-2.91 (m, 2 H) 3.61-3.70 (m, 3 H) 3.73-4.02 (m, 2 H) 4.24-4.40 (m, 2 H) 4.60 (t, J=5.00 Hz, 2 H) 4.82-5.09 (m, 2 H) 6.75-6.98 (m, 3 H) 6.99-7.11 (m, 1 H) 7.16-7.25 (m, 2 H) 7.70-7.81 (m, 1 H) 8.21-8.30 (m, 1 H).

Example 9(52)

5-oxo-5-[9-(4-phenylbutyl)-5,6,8,9-tetrahydro-7H-pyrido[4',3':4,5]pyrrolo[2,3-b]pyridin-7-yl]pentanoic acid TLC: Rf 0.35 (ethyl acetate);
$^1$H-NMR (CDCl$_3$): δ 1.53-2.15 (m, 4 H) 2.35-2.92 (m, 10 H) 3.76-3.99 (m, 2 H) 4.14-4.29 (m, 2 H) 4.62-4.84 (m, 2 H) 6.98-7.30 (m, 6 H) 7.70-7.82 (m, 1 H) 8.22-8.32 (m, 1 H).

Example 9(53)

ethyl 7-oxo-7-[9-(4-phenylbutyl)-5,6,8,9-tetrahydro-7H-pyrido[4',3':4,5]pyrrolo[2,3-b]pyridin-7-yl]heptanoate TLC: Rf 0.33 (hexane:ethyl acetate=1:1);
$^1$H-NMR (CDCl$_3$): δ 1.18-1.30 (m, 3 H) 1.33-1.93 (m, 10 H) 2.21-2.90 (m, 8 H) 3.71-3.98 (m, 2 H) 4.03-4.27 (m, 4 H) 4.53-4.87 (m, 2 H) 6.97-7.31 (m, 6 H) 7.69-7.81 (m, 1 H) 8.21-8.31 (m, 1 H).

Example 9(54)

methyl 5-oxo-5-[9-(2-phenylethyl)-5,6,8,9-tetrahydro-7H-pyrido[4',3':4,5]pyrrolo[2,3-b]pyridin-7-yl]pentanoate TLC: Rf 0.20 (hexane:ethyl acetate=1:1);
$^1$H-NMR (CDCl$_3$): δ 1.80-2.07 (m, 2 H) 2.09-2.57 (m, 4 H) 2.66-2.87 (m, 2 H) 3.02-3.21 (m, 2 H) 3.57-3.82 (m, 5 H) 3.89-4.32 (m, 2 H) 4.32-4.45 (m, 2 H) 6.86-7.30 (m, 6 H) 7.70-7.82 (m, 1 H) 8.25-8.36 (m, 1 H).

Example 9(55)

methyl 6-oxo-6-[9-(2-phenylethyl)-5,6,8,9-tetrahydro-7H-pyrido[4',3':4,5]pyrrolo[2,3-b]pyridin-7-yl]hexanoate TLC: Rf 0.20 (hexane:ethyl acetate=1:1);
$^1$H-NMR (CDCl$_3$): δ 1.61-1.78 (m, 4 H) 2.01-2.51 (m, 4 H) 2.62-2.87 (m, 2 H) 3.01-3.24 (m, 2 H) 3.56-3.81 (m, 5 H) 3.81-4.32 (m, 2 H) 4.33-4.45 (m, 2 H) 6.83-7.32 (m, 6 H) 7.70-7.83 (m, 1 H) 8.27-8.35 (m, 1 H).

Example 9(56)

ethyl 7-oxo-7-[9-(2-phenylethyl)-5,6,8,9-tetrahydro-7H-pyrido[4',3':4,5]pyrrolo[2,3-b]pyridin-7-yl]heptanoate TLC: Rf 0.31 (hexane:ethyl acetate=1:1);
$^1$H-NMR (CDCl$_3$): δ 1.20-1.30 (m, 3 H) 1.31-1.80 (m, 8 H) 2.00-2.48 (m, 4 H) 2.63-2.86 (m, 2 H) 3.00-3.24 (m, 2 H) 3.56-3.82 (m, 2 H) 3.81-4.34 (m, 2 H) 4.06-4.44 (m, 2 H) 6.83-7.30 (m, 6 H) 7.69-7.82 (m, 1 H) 8.25-8.35 (m, 1 H).

Example 9(57)

5-oxo-5-[9-(2-phenylethyl)-5,6,8,9-tetrahydro-7H-pyrido[4',3':4,5]pyrrolo[2,3-b]pyridin-7-yl]pentanoic acid TLC: Rf 0.28 (ethyl acetate);
$^1$H-NMR (CDCl$_3$): δ 1.77-2.10 (m, 2 H) 2.20-2.60 (m, 4 H) 2.66-2.86 (m, 2 H) 2.99-3.17 (m, 2 H) 3.58-3.84 (m, 2 H) 3.95-4.30 (m, 2 H) 4.33-4.48 (m, 2 H) 6.83-7.29 (m, 6 H) 7.69-7.88 (m, 1 H) 8.32 (dd, J=5.00, 1.50 Hz, 1 H).

Example 9(58)

6-[9-(3,5-difluorobenzyl)-5,6,8,9-tetrahydro-7H-pyrido[4',3':4,5]pyrrolo[2,3-b]pyridin-7-yl]-6-oxohexanoic acid HPLC retention time (min): 4.18;
MS (ESI, Pos. 20 V): m/z=428 (M+H)$^+$.

Example 9(59)

6-oxo-6-[9-(2-thienylmethyl)-5,6,8,9-tetrahydro-7H-pyrido[4',3':4,5]pyrrolo[2,3-b]pyridin-7-yl]hexanoic acid

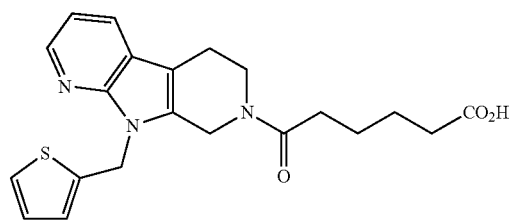 [SMILES: O=C(O)CCCCC(=O)N1CCc2c(n(Cc3cccs3)c3ncccc23)C1]

HPLC retention time (min): 3.94;
MS (ESI, Pos. 20 V): m/z=398 (M+H)$^+$.

Example 9(60)

6-oxo-6-[9-(3-thienylmethyl)-5,6,8,9-tetrahydro-7H-pyrido[4',3':4,5]pyrrolo[2,3-b]pyridin-7-yl]hexanoic acid HPLC retention time (min): 3.90;
MS (ESI, Pos. 20 V): m/z=398 (M+H)$^+$.

Example 9(61)

6-{9-[(5,6-dichloro-3-pyridinyl)methyl]-5,6,8,9-tetrahydro-7H-pyrido[4',3':4,5]pyrrolo[2,3-b]pyridin-7-yl}-6-oxohexanoic acid HPLC retention time (min): 4.26;
MS (ESI, Pos. 20 V): m/z=461 (M+H)$^+$.

Example 9(62)

6-{9-[(6-chloro-3-pyridinyl)methyl]-5,6,8,9-tetrahydro-7H-pyrido[4',3':4,5]pyrrolo[2,3-b]pyridin-7-yl}-6-oxohexanoic acid HPLC retention time (min): 3.97;
MS (ESI, Pos. 20 V): m/z=427 (M+H)$^+$.

Example 9(67)

methyl 6-(9-benzyl-5,6,8,9-tetrahydro-7H-pyrido[4',3':4,5]pyrrolo[2,3-b]pyridin-7-yl)-6-oxohexanoate TLC: Rf 0.22 (hexane:ethyl acetate=1:1);
$^1$H-NMR (CDCl$_3$): δ 1.45-1.81 (m, 4 H) 2.06-2.54 (m, 4 H) 2.71-2.93 (m, 2 H) 3.66 (s, 3 H) 3.68-3.95 (m, 2 H) 4.38-4.70 (m, 2 H) 5.43-5.53 (m, 2 H) 7.02-7.36 (m, 6 H) 7.74-7.86 (m, 1 H) 8.26-8.35 (m, 1 H).

Example 9(68)

6-{9-[(1-methyl-1H-indol-4-yl)methyl]-5,6,8,9-tetrahydro-7H-pyrido[4',3':4,5]pyrrolo[2,3-b]pyridin-7-yl}-6-oxohexanoic acid HPLC retention time (min): 4.02;
MS (ESI, Pos. 20 V): m/z=445 (M+H)$^+$.

Example 9(69)

6-oxo-6-[9-(3-pyridinylmethyl)-5,6,8,9-tetrahydro-7H-pyrido[4',3':4,5]pyrrolo[2,3-b]pyridin-7-yl]hexanoic acid TLC: Rf 0.44 (chloroform:methanol:water=50:10:1);
$^1$H-NMR (DMSO-d$_6$): δ 1.38-1.62 (m, 4 H) 2.12-2.50 (m, 4 H) 2.62-2.86 (m, 2 H) 3.68-3.84 (m, 2 H) 4.61-4.76 (m, 2 H) 5.44-5.57 (m, 2 H) 7.09 (dd, J=7.50, 4.50 Hz, 1 H) 7.30 (dd, J=7.50, 4.50 Hz, 1 H) 7.44-7.56 (m, 1 H) 7.85-7.93 (m, 1 H) 8.18-8.24 (m, 1 H) 8.39-8.50 (m, 2 H) 11.96 (s, 1 H).

Example 9(70)

6-[9-(2-furylmethyl)-5,6,8,9-tetrahydro-7H-pyrido[4',3':4,5]pyrrolo[2,3-b]pyridin-7-yl]-6-oxohexanoic acid HPLC retention time (min): 3.76;
MS (ESI, Pos. 20 V): m/z=382 (M+H)$^+$.

Example 9(71)

6-[9-(3-furylmethyl)-5,6,8,9-tetrahydro-7H-pyrido[4',3':4,5]pyrrolo[2,3-b]pyridin-7-yl]-6-oxohexanoic acid HPLC retention time (min): 3.77;
MS (ESI, Pos. 20 V): m/z=382 (M+H)$^+$.

Example 9(73)

6-oxo-6-[9-(4-pyridinylmethyl)-5,6,8,9-tetrahydro-7H-pyrido[4',3':4,5]pyrrolo[2,3-b]pyridin-7-yl]hexanoic acid TLC: Rf 0.44 (chloroform:methanol:water=50:10:1);
$^1$H-NMR (DMSO-d$_6$): δ 1.32-1.65 (m, 4 H) 2.11-2.49 (m, 4 H) 2.63-2.89 (m, 2 H) 3.68-3.87 (m, 2 H) 4.51-4.73 (m, 2 H) 5.41-5.61 (m, 2 H) 6.96-7.07 (m, 2 H) 7.10 (dd, J=8.00, 5.00 Hz, 1 H) 7.87-7.95 (m, 1 H) 8.14-8.22 (m, 1 H) 8.43-8.49 (m, 2 H) 11.95 (s, 1 H).

Example 9(74)

6-{9-[(5-methyl-3-isoxazolyl)methyl]-5,6,8,9-tetrahydro-7H-pyrido[4',3':4,5]pyrrolo[2,3-b]pyridin-7-yl}-6-oxohexanoic acid HPLC retention time (min): 3.79
MS (ESI, Pos. 20 V): m/z=397 (M+H)$^+$.

Example 9(76)

6-oxo-6-[9-(2-pyridinylmethyl)-5,6,8,9-tetrahydro-7H-pyrido[4',3':4,5]pyrrolo[2,3-b]pyridin-7-yl]hexanoic acid TLC: Rf 0.47 (chloroform:methanol:water=50:10:1);
$^1$H-NMR (DMSO-d$_6$): δ 1.34-1.67 (m, 4 H) 2.10-2.48 (m, 4 H) 2.62-2.87 (m, 2 H) 3.66-3.88 (m, 2 H) 4.58-4.87 (m, 2 H) 5.43-5.62 (m, 2 H) 6.97-7.14 (m, 2 H) 7.20-7.29 (m, 1 H) 7.63-7.76 (m, 1 H) 7.81-7.91 (m, 1 H) 8.15 (dd, J=4.50, 1.50 Hz, 1 H) 8.44-8.50 (m, 1 H) 11.96 (s, 1 H).

Example 9(76)

6-{9-[(1-methyl-1H-imidazol-5-yl)methyl]-5,6,8,9-tetrahydro-7H-pyrido[4',3':4,5]pyrrolo[2,3-b]pyridin-7-yl}-6-oxohexanoic acid HPLC retention time (min): 3.44;
MS (ESI, Pos. 20 V): m/z=396 (M+H)$^+$.

Example 9(79)

6-{9-[(1-methyl-1H-imidazol-2-yl)methyl]-5,6,8,9-tetrahydro-7H-pyrido[4',3':4,5]pyrrolo[2,3-b]pyridin-7-yl}-6-oxohexanoic acid HPLC retention time (min): 3.42;
MS (ESI, Pos. 20 V): m/z=396 (M+H)$^+$.

Example 9(82)

methyl 5-(9-benzyl-5,6,8,9-tetrahydro-7H-pyrido[4',3':4,5]pyrrolo[2,3-b]pyridin-7-yl)-5-oxopentanoate TLC: Rf 0.29 (hexane:ethyl acetate=1:2).

Example 9(83)

6-{9-[(5-chloro-2-thienyl)methyl]-5,6,8,9-tetrahydro-7H-pyrido[4',3':4,5]pyrrolo[2,3-b]pyridin-7-yl}-6-oxohexanoic acid TLC: Rf 0.42 (methylene chloride:methanol=9:1);
$^1$H-NMR (DMSO-d$_6$): δ 1.38-1.66 (m, 4 H), 2.10-2.44 (m, 4 H), 2.57-2.84 (m, 2 H), 3.61-3.87 (m, 2 H), 4.75 (s, 2 H), 5.44-5.64 (m, 2 H), 6.88-7.04 (m, 2 H), 7.10 (dd, J=7.8, 4.8 Hz, 1 H), 7.87 (d, J=7.8 Hz, 1 H), 8.17-8.32 (m, 1 H), 11.97 (s, 1 H).

Example 10

6-methoxy-5,5-dimethyl-6-oxohexanoic acid

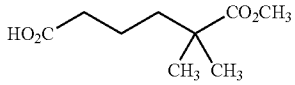

To tetrahydrofuran (THF) (180 mL) was added a 2.0M lithium diisopropylamide/THF-ethylbenzene-heptane solution (272 mL), the mixture was cooled to −68° C. in a dry ice-methanol bath, and a solution of methyl isobutyrate (55.38 g) in THF (180 mL) was added dropwise at −64° C. or lower for 50 minutes. The mixture was stirred at around −65° C. for 1 hour, and then a solution of [(4-bromobutoxy)methyl]benzene (40.0 g) and hexamethylphosphoric acid triamide (29.48 g) in THF (90 mL) was added dropwise at −62° C. or lower for about 30 minutes. After the mixture was stirred at the same temperature for 30 minutes, the dry ice bath was removed, followed by stirring for about 1.5 hours. The reaction solution was placed into an aqueous saturated ammonium chloride solution (1.4 L), followed by extraction with a mixed solution (1.6 L) of hexane:ethyl acetate (3:1). The extract solution was washed with water and an aqueous saturated sodium chloride solution, dried with anhydrous sodium sulfate, and concentrated under reduced pressure. The resulting orange liquid was treated with a silica gel column (hexane:ethyl acetate=15:1). The resulting compound (82.0 g) was dissolved in methanol (820 mL), a 4N hydrogen chloride/1,4-dioxane solution (82 mL) and 10% palladium carbon (50% hydrous product, 8.2 g) were added, and hydrogen was blown into the solution for 3.5 hours while stirring on a hot bath at 50° C. After cooled to room temperature, the system was replaced with nitrogen, and the catalyst was filtered off using Celite, followed by concentration under reduced pressure. Operation of adding toluene to the residue, and concentrating this again under reduced pressure was performed two times, followed by purification with a silica gel column (hexane:ethyl acetate=4:1→2:1). The resulting compound (23.88 g), carbon tetrachloride (170 mL) and sodium periodate (65.9 g) were added to a mixed solution of water (255 mL) and acetonitrile (170 mL), and then ruthenium trichloride (n-hydrate) (716 mg) was added for about 3 minutes in portions. After stirred at room temperature for 4 hours, the reaction mixture was dispersed in water (0.8 L), followed by extraction with ethyl acetate. After the extract solution was washed with water, an aqueous saturated sodium chloride solution was added, the mixture was stirred and filtered with Celite, and layers were separated. The organic layer was dried with anhydrous sodium sulfate, and concentrated under reduced pressure. The resulting residue was dissolved in toluene, and concentration operation was performed two times to obtain the title compound (27.2 g) having the following physical property values.

TLC: Rf 0.36 (hexane:ethyl acetate=1:1);

$^1$H-NMR (CDCl$_3$): δ 1.18 (s, 6 H) 1.51-1.64 (m, 4 H) 2.30-2.39 (m, 2 H) 3.66 (s, 3 H).

Example 11 methyl 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoate To a solution of the compound produced in Example 10 (77 mg), and 9-(3-fluorobenzyl)-6,7,8,9-tetrahydro-5H-pyrido[4',3':4,5]pyrrolo[2,3-b]pyridine (120 mg) in N,N-dimethylformamide (2.5 mL) were added triethylamine (0.075 mL), EDC (115 mg) and HOBt (67 mg) at room temperature, and the mixture was stirred for 3 hours. To the reaction mixture were added an aqueous saturated sodium hydroxide solution and water, followed by extraction with ethyl acetate. The extract was sequentially washed with water and an aqueous saturated sodium chloride solution, dried with anhydrous magnesium sulfate, and concentrated. The residue was purified by silica gel column chromatography (hexane:ethyl acetate=6:4) to obtain the title compound (133 mg) having the following physical property values.

TLC: Rf 0.55 ((hexane:ethyl acetate=1:1);

$^1$H-NMR (CDCl$_3$): δ 1.11-1.23 (m, 6 H) 1.42-1.72 (m, 4 H) 2.09-2.49 (m, 2 H) 2.71-2.93 (m, 2 H) 3.57-3.68 (m, 3 H) 3.68-3.96 (m, 2 H) 4.39-4.71 (m, 2 H) 5.39-5.52 (m, 2 H) 6.71-6.82 (m, 1 H) 6.83-7.01 (m, 2 H) 7.02-7.14 (m, 1 H) 7.17-7.31 (m, 1 H) 7.73-7.86 (m, 1 H) 8.25-8.34 (m, 1 H).

Example 12

6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoic acid

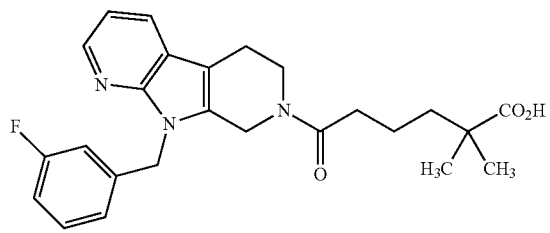 [SMILES: CC(C)(CCCC(=O)N1CCc2c(n(Cc3cccc(F)c3)c3ncccc23)C1)C(=O)O]

The compound produced in Example 11 was subjected to operation in accordance with Example 3 to obtain the title compound having the following physical property values.

TLC: Rf 0.49 (chloroform:methanol:water=50:10:1);

$^1$H-NMR (DMSO-d$_6$): δ 0.96-1.13 (m, 6 H) 1.32-1.53 (m, 4 H) 2.22-2.46 (m, 2 H) 2.62-2.84 (m, 2 H) 3.67-3.83 (m, 2 H) 4.62 (s, 2 H) 5.39-5.56 (m, 2 H) 6.85-7.14 (m, 4 H) 7.27-7.39 (m, 1 H) 7.84-7.94 (m, 1 H) 8.18-8.23 (m, 1 H) 12.00 (s, 1 H).

Examples 12(1)-Example 12(198)

β-carboline derivative produced by operation in accordance with Example 1 or a tetrahydropyridopyrrolopyridine derivative produced by operation in accordance with Example 4→Example 5→Example 6→Example 7→Example 1, and a corresponding carboxylic acid derivative in place of 6-methoxy-5,5-dimethyl-6-oxohexanoic acid were used, which were subjected to operation in accordance with Example 11 and, if necessary, subjected to operation in accordance with Example 12 to obtain the following compounds.

Example 12(1)

6-[9-(cyclohexylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.32;
MS (ESI, Pos. 20 V): m/z=426 (M+H)$^+$.

Example 12(2)

6-[9-(2-cyclohexylethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.49;
MS (ESI, Pos. 20 V): m/z=440 (M+H)$^+$.

Example 12(3)

6-[9-(3-cyclohexylpropyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.58;
MS (ESI, Pos. 20 V): m/z=454 (M+H)$^+$.

Example 12(4)

6-[9-(4-cyclohexylbutyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.68;
MS (ESI, Pos. 20 V): m/z=468 (M+H)$^+$.

Example 12(5)

6-[9-(3,4-dichlorobenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.59;
MS (ESI, Pos. 20 V): m/z=488 (M+H)$^+$.

Example 12(6)

6-[9-(3,5-dichlorobenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.64;
MS (ESI, Pos. 20 V): m/z=488 (M+H)$^+$.

Example 12(7)

6-[9-(3,4-dimethylbenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.41;
MS (ESI, Pos. 20 V): m/z=448 (M+H)$^+$.

Example 12(8)

6-[9-(3,5-dimethylbenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.43;
MS (ESI, Pos. 20 V): m/z=448 (M+H)$^+$.

Example 12(9)

6-[9-(3,5-difluorobenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.39;
MS (ESI, Pos. 20 V): m/z=456 (M+H)$^+$.

Example 12(10)

6-[9-(3,4-difluorobenzyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.37;
MS (ESI, Pos. 20 V): m/z=456 (M+H)$^+$.

Example 12(11)

2,2-dimethyl-6-oxo-6-[9-(3,4,5-trifluorobenzyl)-5,6,8,9-tetrahydro-7H-pyrido[4',3':4,5]pyrrolo[2,3-b]pyridin-7-yl]hexanoic acid HPLC retention time (min): 4.49;
MS (ESI, Pos. 20 V): m/z=474 (M+H)$^+$.

Example 12(12)

ethyl 6-(9-benzyl-5,6,8,9-tetrahydro-7H-pyrido[4',3':4,5]pyrrolo[2,3-b]pyridin-7-yl)-2,2-dimethyl-6-oxohexanoate TLC: Rf 0.24 (hexane:ethyl acetate=3:2);
$^1$H-NMR (CDCl$_3$): δ 1.06-1.33 (m, 9 H), 1.41-1.78 (m, 4 H), 2.04-2.49 (m, 2 H), 2.72-2.91 (m, 2 H), 3.65-3.96 (m, 2 H), 4.01-4.18 (m, 2 H), 4.36-4.70 (m, 2 H), 5.41-5.54 (m, 2 H), 7.00-7.37 (m, 6 H), 7.73-7.86 (m, 1 H), 8.26-8.35 (m, 1 H).

Example 12(13)

methyl 6-[9-(3-chloro-4-fluorobenzyl)-5,6,8,9-tetrahydro-7H-pyrido[4',3':4,5]pyrrolo[2,3-b]pyridin-7-yl]-2,2-dimethyl-6-oxohexanoate TLC: Rf 0.49 (hexane:ethyl acetate=1:1);
$^1$H-NMR (CDCl$_3$): δ 1.09-1.24 (m, 6 H) 1.50-1.68 (m, 4 H) 2.14-2.49 (m, 2 H) 2.85 (t, J=5.49 Hz, 2 H) 3.59-3.68 (m, 3 H) 3.69-3.97 (m, 2 H) 4.42-4.71 (m, 2 H) 5.35-5.47 (m, 2 H) 6.93-7.14 (m, 3 H) 7.16-7.24 (m, 1 H) 7.75-7.88 (m, 1 H) 8.26-8.34 (m, 1 H).

Example 12(15)

6-(9-benzyl-5,6,8,9-tetrahydro-7H-pyrido[4',3':4,5]pyrrolo[2,3-b]pyridin-7-yl)-2,2-dimethyl-6-oxohexanoic acid TLC: Rf 0.27 (chloroform:methanol:water=90:10:1);
$^1$H-NMR (DMSO-d$_6$): δ 0.98-1.11 (m, 6 H), 1.30-1.54 (m, 4 H), 2.16-2.45 (m, 2 H), 2.58-2.86 (m, 2 H), 3.65-3.83 (m, 2 H), 4.61 (s, 2 H), 5.39-5.53 (m, 2 H), 7.04-7.17 (m, 3 H), 7.17-7.35 (m, 3 H), 7.84-7.93 (m, 1 H), 8.16-8.24 (m, 1 H), 12.01 (s, 1 H).

Example 12(16)

6-[9-(3-chlorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.48 (methylene chloride:methanol=9:1);
$^1$H-NMR (DMSO-d$_6$): δ 1.01-1.10 (m, 6 H) 1.37-1.50 (m, 4 H) 2.24-2.51 (m, 2 H) 2.64-2.83 (m, 2 H) 3.70-3.82 (m, 2 H) 4.63 (s, 2 H) 5.43-5.53 (m, 2 H) 6.98-7.07 (m, 1 H) 7.11 (dd, J=7.8, 4.8 Hz, 1 H) 7.18-7.36 (m, 3 H) 7.90 (dd, J=7.8, 1.4 Hz, 1 H) 8.19-8.24 (m, 1 H) 12.02 (s, 1 H).

Example 12(17)

6-[9-(3-chloro-4-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.72 (ethyl acetate);
$^1$H-NMR (CDCl$_3$): δ 1.16-1.30 (m, 6 H), 1.45-1.81 (m, 4 H), 2.09-2.59 (m, 2 H), 2.70-2.94 (m, 2 H), 3.68-4.00 (m, 2 H), 4.41-4.76 (m, 2 H), 5.29-5.52 (m, 2 H), 6.90-7.15 (m, 3 H), 7.14-7.24 (m, 1 H), 7.70-7.90 (m, 1 H), 8.21-8.40 (m, 1 H).

Example 12(19)

6-[9-(cyclopropylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 3.99;
MS (ESI, Pos. 20 V): m/z=384 (M+H)$^+$.

Example 12(20)

6-[9-(cyclobutylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.12;
MS (ESI, Pos. 20 V): m/z=398 (M+H)$^+$.

Example 12(21)

6-[9-(cyclopentylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.21;
MS (ESI, Pos. 20 V): m/z=412 (M+H)$^+$.

Example 12(22)

6-[9-(3-cyclohexen-1-ylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.27;
MS (ESI, Pos. 20 V): m/z=424 (M+H)$^+$.

Example 12(23)

2,2-dimethyl-6-oxo-6-{9-[2-(phenylthio)ethyl]-5,6,8,9-tetrahydro-7H-pyrido[4',3':4,5]pyrrolo[2,3-b]pyridin-7-yl}hexanoic acid HPLC retention time (min): 4.23;
MS (ESI, Pos. 20 V): m/z=466 (M+H)$^+$.

Example 12(26)

ethyl 6-(9-benzyl-1,3,4,9-tetrahydro-2H-beta-carbolin-2-yl)-2,2-dimethyl-6-oxohexanoate TLC: Rf 0.72 (hexane:ethyl acetate=1:1);
$^1$H-NMR (CDCl$_3$): δ 1.06-1.34 (m, 9 H) 1.45-1.83 (m, 4 H) 2.11-2.53 (m, 2 H) 2.76-2.99 (m, 2 H) 3.69-3.98 (m, 2 H) 4.00-4.19 (m, 2 H) 4.43-4.75 (m, 2 H) 5.21-5.31 (m, 2 H) 6.97-7.08 (m, 2 H) 7.08-7.37 (m, 6 H) 7.47-7.60 (m, 1 H).

Example 12(27)

6-(9-benzyl-1,3,4,9-tetrahydro-2H-beta-carbolin-2-yl)-2,2-dimethyl-6-oxohexanoic acid

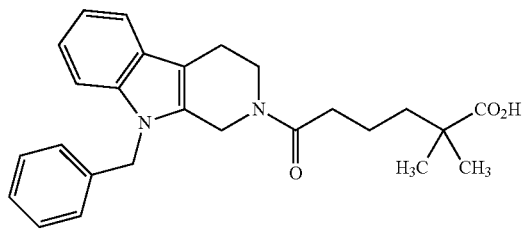 [SMILES: CC(C)(CCCC(=O)N1CCc2c(n(Cc3ccccc3)c3ccccc23)C1)C(=O)O]

TLC: Rf 0.35 (hexane:ethyl acetate=1:2);
$^1$H-NMR (DMSO-d$_6$): δ 0.99-1.09 (m, 6 H) 1.31-1.54 (m, 4 H) 2.10-2.46 (m, 2 H) 2.62-2.83 (m, 2 H) 3.65-3.85 (m, 2 H) 4.63 (s, 2 H) 5.29-5.45 (m, 2 H) 6.93-7.49 (m, 9 H) 12.04 (s, 1 H).

Example 12(28)

2,2-dimethyl-6-oxo-6-[9-(3-phenylpropyl)-1,3,4,9-tetrahydro-2H-beta-carbolin-2-yl]hexanoic acid TLC: Rf 0.36 (chloroform:methanol:water=90:10:1);
$^1$H-NMR (DMSO-d$_6$): δ 1.00-1.11 (m, 6 H) 1.37-1.55 (m, 4 H) 1.85-2.81 (m, 8 H) 3.66-3.83 (m, 2 H) 4.00-4.17 (m, 2 H) 4.58-4.76 (m, 2 H) 6.98 (t, J=7.5 Hz, 1 H) 7.07 (t, J=7.5 Hz, 1 H) 7.12-7.30 (m, 5 H) 7.33 (d, J=7.5 Hz, 1 H) 7.40 (d, J=7.5 Hz, 1 H) 12.05 (s, 1 H).

Example 12(29)

ethyl 2,2-dimethyl-6-oxo-6-[9-(3-phenylpropyl)-1,3,4,9-tetrahydro-2H-beta-carbolin-2-yl]hexanoate TLC: Rf 0.50 (hexane:ethyl acetate=2:1);
$^1$H-NMR (CDCl$_3$): δ 1.11-1.32 (m, 9 H) 1.52-1.79 (m, 4 H) 1.98-2.22 (m, 2 H) 2.27-2.55 (m, 2 H) 2.60-2.93 (m, 4 H) 3.68-3.98 (m, 2 H) 3.96-4.21 (m, 4 H) 4.42-4.83 (m, 2 H) 7.05-7.36 (m, 8 H) 7.42-7.55 (m, 1 H).

Example 12(30)

2,2-dimethyl-6-oxo-6-[9-(2-thienylmethyl)-5,6,8,9-tetrahydro-7H-pyrido[4',3':4,5]pyrrolo[2,3-b]pyridin-7-yl]hexanoic acid HPLC retention time (min): 4.20;
MS (ESI, Pos. 20 V): m/z=426 (M+H)$^+$.

Example 12(31)

2,2-dimethyl-6-oxo-6-[9-(3-thienylmethyl)-5,6,8,9-tetrahydro-7H-pyrido[4',3':4,5]pyrrolo[2,3-b]pyridin-7-yl]hexanoic acid HPLC retention time (min): 4.18;
MS (ESI, Pos. 20 V): m/z=426 (M+H)$^+$.

Example 12(32)

6-{9-[(5,6-dichloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid HPLC retention time (min): 4.47;
MS (ESI, Pos. 20 V): m/z=489 (M+H)$^+$.

Example 12(33)

6-{9-[(6-chloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid HPLC retention time (min): 4.23;
MS (ESI, Pos. 20 V): m/z=455 (M+H)$^+$.

Example 12(40)

6-{9-[(1,3-dimethyl-1H-pyrazol-5-yl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.44 (chloroform:methanol:water=50:10:1);
$^1$H-NMR (DMSO-d$_6$): δ 0.99-1.14 (m, 6 H) 1.37-1.56 (m, 4 H) 1.98-2.06 (m, 3 H) 2.30-2.47 (m, 2 H) 2.62-2.85 (m, 2 H) 3.67-3.86 (m, 5 H) 4.62-4.77 (m, 2 H) 5.44-5.52 (m, 2 H) 5.71 (s, 1 H) 7.09 (dd, J=8.00, 5.00 Hz, 1 H) 7.83-7.94 (m, 1 H) 8.16-8.25 (m, 1 H) 12.05 (br. s., 1 H).

Example 12(42)

6-{9-[(5-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid

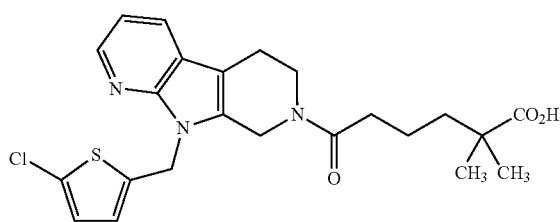 [SMILES: CC(C)(CCCC(=O)N1CCc2c(n(Cc3ccc(Cl)s3)c3ncccc23)C1)C(=O)O]

TLC: Rf 0.44 (ethyl acetate);
$^1$H-NMR (DMSO-d$_6$): δ 1.00-1.13 (m, 6 H) 1.38-1.55 (m, 4 H) 2.33-2.47 (m, 2 H) 2.58-2.85 (m, 2 H) 3.63-3.87 (m, 2 H) 4.76 (s, 2 H) 5.47-5.64 (m, 2 H) 6.91-7.04 (m, 2 H) 7.11 (dd, J=7.50, 5.00 Hz, 1 H) 7.88 (d, J=7.50 Hz, 1 H) 8.20-8.30 (m, 1 H) 12.07 (s, 1 H).

Example 12(43)

6-[9-(2-furylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.05;
MS (ESI, Pos. 20 V): m/z=410 (M+H)$^+$.

Example 12(44)

6-[9-(3-furylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.08;
MS (ESI, Pos. 20 V): m/z=410 (M+H)$^+$.

Example 12(47)

methyl 6-{9-[(1,3-dimethyl-1H-pyrazol-5-yl)methyl]-5,6,8,9-tetrahydro-7H-pyrido[4',3':4,5]pyrrolo[2,3-b]pyridin-7-yl}-2,2-dimethyl-6-oxohexanoate TLC: Rf 0.30 (ethyl acetate);
$^1$H-NMR (CDCl$_3$): δ 1.16-1.23 (m, 6 H) 1.53-1.73 (m, 4 H) 2.15-2.24 (m, 3 H) 2.20-2.51 (m, 2 H) 2.73-2.91 (m, 2 H) 3.61-3.68 (m, 3 H) 3.71-3.97 (m, 2 H) 3.74 (s, 3 H) 4.48-4.78 (m, 2 H) 5.38-5.53 (m, 2 H) 5.89 (s, 1 H) 7.03-7.14 (m, 1 H) 7.74-7.85 (m, 1 H) 8.26-8.34 (m, 1 H).

Example 12(49)

2,2-dimethyl-6-{9-[(5-methyl-3-isoxazolyl)methyl]-5,6,8,9-tetrahydro-7H-pyrido[4',3':4,5]pyrrolo[2,3-b]pyridin-7-yl}-6-oxohexanoic acid HPLC retention time (min): 4.06;
MS (ESI, Pos. 20 V): m/z=425 (M+H)$^+$.

Example 12(51)

methyl 2,2-dimethyl-6-{9-[(1-methyl-1H-pyrazol-5-yl)methyl]-5,6,8,9-tetrahydro-7H-pyrido[4',3':4,5]pyrrolo[2,3-b]pyridin-7-yl}-6-oxohexanoate TLC: Rf 0.24 (ethyl acetate);
$^1$H-NMR (CDCl$_3$): δ 1.13-1.23 (m, 6 H) 1.51-1.68 (m, 4 H) 2.31-2.49 (m, 2 H) 2.71-2.89 (m, 2 H) 3.60-3.69 (m, 3 H) 3.71-3.97 (m, 5 H) 4.69-4.89 (m, 2 H) 5.39-5.48 (m, 2 H) 5.97-6.09 (m, 1 H) 7.01-7.10 (m, 1 H) 7.17-7.25 (m, 1 H) 7.72-7.81 (m, 1 H) 8.27-8.33 (m, 1 H).

Example 12(52)

2,2-dimethyl-6-{9-[(1-methyl-1H-imidazol-5-yl)methyl]-5,6,8,9-tetrahydro-7H-pyrido[4',3':4,5]pyrrolo[2,3-b]pyridin-7-yl}-6-oxohexanoic acid HPLC retention time (min): 3.70;
MS (ESI, Pos. 20 V): m/z=424 (M+H)$^+$.

Example 12(55)

2,2-dimethyl-6-{9-[(1-methyl-1H-pyrazol-5-yl)methyl]-5,6,8,9-tetrahydro-7H-pyrido[4',3':4,5]pyrrolo[2,3-b]pyridin-7-yl}-6-oxohexanoic acid TLC: Rf 0.14 (chloroform:methanol:water=50:10:1);
$^1$H-NMR (DMSO-d$_6$): δ 0.99-1.13 (m, 6 H) 1.47 (m, 4 H) 2.31-2.47 (m, 2 H) 2.59-2.84 (m, 2 H) 3.64-3.86 (m, 5 H) 4.71-4.89 (m, 2 H) 5.29-5.42 (m, 2 H) 5.92-6.04 (m, 1 H) 7.07 (dd, J=8.00, 5.00 Hz, 1 H) 7.51-7.59 (m, 1 H) 7.80-7.89 (m, 1 H) 8.15-8.25 (m, 1 H) 12.07 (s, 1 H).

Example 12(57)

2,2-dimethyl-6-{9-[(1-methyl-1H-imidazol-2-yl)methyl]-5,6,8,9-tetrahydro-7H-pyrido[4',3':4,5]pyrrolo[2,3-b]pyridin-7-yl}-6-oxohexanoic acid HPLC retention time (min): 3.67;
MS (ESI, Pos. 20 V): m/z=424 (M+H)$^+$.

Example 12(60)

6-{9-[(6-chloro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.47 (chloroform:methanol:water=50:10:1)
$^1$H-NMR (DMSO-d$_6$): δ 0.97-1.13 (m, 6 H) 1.35-1.54 (m, 4 H) 2.29-2.47 (m, 2 H) 2.61-2.86 (m, 2 H) 3.66-3.86 (m, 2 H) 4.69 (br. s., 2 H) 5.44-5.57 (m, 2 H) 7.12 (dd, J=7.90, 4.80 Hz, 1 H) 7.40-7.48 (m, 1 H) 7.51-7.63 (m, 1 H) 7.87-7.95 (m, 1 H) 8.18-8.39 (m, 2 H) 12.06 (s, 1 H).

Example 12(61)

6-{9-[(5-fluoro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.21 (methylene chloride:ethyl acetate:methanol=8:4:1);
MS (ESI, Pos.): m/z=439(M+H)$^+$.

Example 12(62)

2,2-dimethyl-6-{9-[(1-methyl-1H-pyrazol-4-yl)methyl]-5,6,8,9-tetrahydro-7H-pyrido[4',3':4,5]pyrrolo[2,3-b]pyridin-7-yl}-6-oxohexanoic acid TLC: Rf 0.46 (chloroform:methanol:water=10:2:0.2);
MS (ESI, Pos.): m/z=424 (M+H)$^+$.

Example 12(63)

6-{9-[(1,3-dimethyl-1H-pyrazol-4-yl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.23 (methylene chloride:ethyl acetate:methanol=8:4:1);
$^1$H-NMR (DMSO-d$_6$): δ 1.00-1.12 (m, 6 H), 1.36-1.53 (m, 4 H), 2.01-2.11 (m, 3 H), 2.29-2.81 (m, 4 H), 3.58-3.67 (m, 3 H), 3.67-3.83 (m, 2 H), 4.68 (s, 2 H), 5.15-5.30 (m, 2 H), 7.06 (dd, J=7.7, 4.6 Hz, 1 H), 7.33-7.49 (m, 1 H), 7.79-7.88 (m, 1 H), 8.17-8.25 (m, 1 H), 12.05 (s, 1 H).

Example 12(64)

6-{9-[(3-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.26 (hexane:ethyl acetate=1:1);
MS (ESI, Pos.): m/z=460 (M+H)$^+$.

Example 12(65)

6-[9-(3-cyanobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.58 (ethyl acetate:methanol=9:1);
MS (ESI, Pos. 20 V): m/z=445 (M+H)$^+$.

Example 12(66)

6-[9-(4-cyanobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.58 (ethyl acetate:methanol=9:1);
MS (ESI, Pos. 20 V): m/z=445 (M+H)$^+$.

Example 12(67)

6-{9-[(6-chloro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.48 (chloroform:methanol:water=50:10:1);
$^1$H-NMR (DMSO-d$_6$): δ 1.01-1.15 (m, 6 H) 1.36-1.58 (m, 4 H) 2.34-2.47 (m, 2 H) 2.63-2.90 (m, 2 H) 3.67-3.90 (m, 2 H) 4.61-4.91 (m, 2 H) 5.43-5.63 (m, 2 H) 6.86-7.17 (m, 2 H) 7.40 (d, J=7.87 Hz, 1 H) 7.72-7.83 (m, 1 H) 7.84-7.95 (m, 1 H) 8.17 (dd, J=4.67, 1.37 Hz, 1 H) 12.03 (br. s., 1 H).

Example 12(68)

6-{9-[(2,5-dimethyl-1,3-thiazol-4-yl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.39 (chloroform:methanol=10:1);
MS (FAB, Pos.): m/z=445 (M+H)$^+$.

Example 12(69)

6-{9-[(3-fluoro-4-pyridinyl)methyl]-5,6,8,9-tetrahydro-7H-pyrido[4',3':4,5]pyridin-[2,3-b]pyridin-7-yl}-2,2-dimethyl-6-oxohexanoic acid TLC: Rf 0.43 (chloroform:methanol=10:1);
MS (ESI, Pos.): m/z=439 (M+H)$^+$.

Example 12(70)

6-{9-[(5-fluoro-3-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.55 (ethyl acetate:methanol=9:1);
$^1$H-NMR (DMSO-d$_6$): δ 1.00-1.11 (m, 6 H), 1.36-1.53 (m, 4 H), 2.31-2.53 (m, 2 H), 2.63-2.85 (m, 2 H), 3.70-3.86 (m, 2 H), 4.66-4.76 (m, 2 H), 5.54 (s, 2 H), 7.11 (dd, J=7.8, 4.8 Hz, 1 H), 7.40-7.55 (m, 1 H), 7.91 (dd, J=7.8, 1.3 Hz, 1 H), 8.18-8.24 (m, 1 H), 8.24-8.35 (m, 1 H), 8.47 (d, J=2.6 Hz, 1H), 12.04 (s, 1 H).

Example 12(71)

6-{9-[(3-fluoro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.55 (ethyl acetate:methanol=9:1);
$^1$H-NMR (DMSO-$d_6$): δ 1.00-1.12 (m, 6 H), 1.35-1.54 (m, 4 H), 2.27-2.45 (m, 2 H), 2.64-2.85 (m, 2 H), 3.66-3.87 (m, 2 H), 4.64-4.83 (m, 2 H), 5.57-5.72 (m, 2 H), 7.05 (dd, J=7.8, 4.5 Hz, 1 H), 7.33-7.44 (m, 1 H), 7.69-7.80 (m, 1 H), 7.80-7.89 (m, 1 H), 8.12 (dd, J=4.5, 1.1 Hz, 1 H), 8.20-8.27 (m, 1 H), 12.05 (s, 1 H).

Example 12(72)

6-{9-[(4-chloro-2-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.34 (hexane:ethyl acetate=1:2);
$^1$H-NMR (DMSO-$d_6$): δ 0.95-1.14 (m, 6 H) 1.31-1.56 (m, 4 H) 2.29-2.46 (m, 2 H) 2.62-2.86 (m, 2 H) 3.66-3.86 (m, 2 H) 4.61-4.84 (m, 2 H) 5.44-5.61 (m, 2 H) 7.03-7.11 (m, 1 H) 7.23-7.35 (m, 1 H) 7.42 (dd, J=5.00, 2.00 Hz, 1 H) 7.82-7.92 (m, 1 H) 8.15 (dd, J=5.00, 1.50 Hz, 1 H) 8.43 (d, J=5.00 Hz, 1 H) 12.04 (s, 1 H).

Example 12(73)

6-[9-(4-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.44 (chloroform:methanol:water=50:10:1);
$^1$H-NMR (DMSO-$d_6$): δ 0.92-1.17 (m, 6 H) 1.27-1.54 (m, 4 H) 2.18-2.45 (m, 2 H) 2.61-2.83 (m, 2 H) 3.62-3.84 (m, 2 H) 4.61 (s, 2 H) 5.34-5.54 (m, 2 H) 7.03-7.26 (m, 5 H) 7.84-7.93 (m, 1 H) 8.17-8.24 (m, 1 H) 12.04 (s, 1 H).

Example 12(74)

6-[9-(4-chlorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.44 ((chloroform:methanol:water=50:10:1);
$^1$H-NMR (DMSO-$d_6$): δ 0.94-1.15 (m, 6 H) 1.28-1.54 (m, 4 H) 2.19-2.45 (m, 2 H) 2.60-2.85 (m, 2 H) 3.64-3.83 (m, 2 H) 4.60 (s, 2 H) 5.38-5.53 (m, 2 H) 7.04-7.19 (m, 3 H) 7.35 (d, J=8.5 Hz, 2 H) 7.83-7.93 (m, 1 H) 8.16-8.23 (m, 1 H) 12.03 (s, 1 H).

Example 12(75)

6-{9-[(2,4-dimethyl-1,3-thiazol-5-yl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.49 (ethyl acetate:methanol=9:1);
$^1$H-NMR (CDCl$_3$): δ 1.08-1.33 (m, 6 H), 1.52-1.81 (m, 4 H), 2.17-2.67 (m, 8 H), 2.69-2.91 (m, 2 H), 3.64-3.98 (m, 2 H), 4.39-4.86 (m, 2 H), 5.40-5.60 (m, 2 H), 6.99-7.17 (m, 1 H), 7.67-7.86 (m, 1 H), 8.24-8.39 (m, 1 H).

Example 12(76)

6-{9-[(2-chloro-4-pyridinyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.50 (methylene chloride:methanol=9:1);
$^1$H-NMR (DMSO-$d_6$): δ 0.96-1.13 (m, 6 H), 1.36-1.54 (m, 4 H), 2.27-2.45 (m, 2 H), 2.63-2.88 (m, 2 H), 3.68-3.87 (m, 2 H), 4.57-4.71 (m, 2 H), 5.53 (s, 2 H), 6.92-7.03 (m, 1 H), 7.12 (dd, J=7.8, 4.8 Hz, 1 H), 7.17-7.30 (m, 1 H), 7.93 (dd, J=7.8, 1.6 Hz, 1 H), 8.19 (dd, J=4.8, 1.6 Hz, 1 H), 8.30 (d, J=5.1 Hz, 1 H), 12.05 (s, 1 H).

Example 12(79)

6-{9-[(5-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.52 (hexane:methanol:water=50:10:1);
$^1$H-NMR (DMSO-$d_6$): δ 0.97-1.13 (m, 6 H), 1.33-1.54 (m, 4 H), 2.29-2.46 (m, 2 H), 2.61-2.82 (m, 2 H), 3.68-3.82 (m, 2 H), 4.60-4.77 (m, 2 H), 5.26-5.42 (m, 2 H), 6.88-6.97 (m, 1 H), 7.04-7.20 (m, 2 H), 7.83-7.91 (m, 1 H), 8.16-8.25 (m, 1 H), 12.02 (s, 1 H).

Example 12(80)

6-{9-[(2,5-dimethyl-3-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.24 (hexane:ethyl acetate=1:2);
$^1$H-NMR (DMSO-$d_6$): δ 0.98-1.12 (m, 6 H), 1.34-1.53 (m, 4 H), 2.15-2.46 (m, 8 H), 2.60-2.82 (m, 2 H), 3.66-3.81 (m, 2 H), 4.55-4.68 (m, 2 H), 5.20-5.33 (m, 2 H), 6.21-6.29 (m, 1 H), 7.08 (dd, J=7.7, 4.8 Hz, 1 H), 7.86 (dd, J=7.9, 1.3 Hz, 1 H), 8.19-8.26 (m, 1 H), 12.05 (s, 1 H).

Example 12(81)

6-[9-(3-chlorobenzyl)-1,3,4,9-tetrahydro-2H-beta-carbolin-2-yl]-2,2-dimethyl-6-oxohexanoic acid TLC: Rf 0.59 (chloroform:methanol:water=50:10:1);
$^1$H-NMR (DMSO-$d_6$): δ 0.93-1.14 (m, 6 H), 1.33-1.55 (m, 4 H), 2.23-2.45 (m, 2 H), 2.62-2.84 (m, 2 H), 3.67-3.84 (m, 2 H), 4.62 (s, 2 H), 5.32-5.47 (m, 2 H), 6.86-7.18 (m, 4 H), 7.24-7.36 (m, 2 H), 7.36-7.49 (m, 2 H), 12.03 (s, 1 H).

Example 12(82)

6-[9-(3-chloro-4-fluorobenzyl)-1,3,4,9-tetrahydro-2H-beta-carbolin-2-yl]-2,2-dimethyl-6-oxohexanoic acid TLC: Rf 0.59 (chloroform:methanol:water=50:10:1);
$^1$H-NMR (DMSO-$d_6$): δ 0.98-1.12 (m, 6 H), 1.31-1.57 (m, 4 H), 2.22-2.46 (m, 2 H), 2.61-2.85 (m, 2 H), 3.64-3.85 (m, 2 H), 4.63 (s, 2 H), 5.29-5.45 (m, 2 H), 6.88-7.13 (m, 3 H), 7.25-7.49 (m, 4 H), 12.03 (s, 1 H).

Example 12(88)

2,2-dimethyl-6-oxo-6-[9-(2,4,6-trifluorobenzyl)-5,6,8,9-tetrahydro-7H-pyrido[4',3':4,5]pyrrolo[2,3-b]pyridin-7-yl]hexanoic acid TLC: Rf 0.49 (chloroform:methanol:water=50:10:1);
$^1$H-NMR (DMSO-$d_6$): δ 0.94-1.19 (m, 6 H), 1.29-1.60 (m, 4 H), 2.28-2.47 (m, 2 H), 2.58-2.83 (m, 2 H), 3.61-3.85 (m, 2 H), 4.66 (s, 2 H), 5.34-5.56 (m, 2 H), 7.04 (dd, J=8.0, 5.0 Hz, 1 H), 7.08-7.25 (m, 2 H), 7.76-7.87 (m, 1 H), 8.10-8.21 (m, 1 H), 12.04 (s, 1 H).

Example 12(89)

6-[9-(4-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.49 (chloroform:methanol:water=50:10:1);
$^1$H-NMR (DMSO-$d_6$): δ 0.98-1.12 (m, 6 H), 1.30-1.58 (m, 4 H), 2.23-2.49 (m, 2 H), 2.59-2.89 (m, 2 H), 3.62-3.87 (m, 2 H), 4.64 (s, 2 H), 5.37-5.58 (m, 2 H), 6.83 (dd, J=8.0 Hz, 1 H), 7.09 (dd, J=8.0, 4.5 Hz, 1 H), 7.16 (dd, J=8.0, 2.0 Hz, 1 H), 7.46 (dd, J=10.0, 2.0 Hz, 1 H), 7.88 (d, J=8.0 Hz, 1 H), 8.18 (dd, J=4.5, 2.0 Hz, 1 H), 12.00 (s, 1 H).

Example 12(90)

6-{9-[(4-chloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.36 (methylene chloride:ethyl acetate:methanol=8:4:1);
$^1$H-NMR (DMSO-$d_6$): δ 0.99-1.13 (m, 6 H), 1.38-1.54 (m, 4 H), 2.30-2.51 (m, 2 H), 2.61-2.83 (m, 2 H), 3.68-3.84 (m, 2 H), 4.74 (s, 2 H), 5.53-5.65 (m, 2 H), 6.99-7.16 (m, 2 H), 7.36-7.43 (m, 1 H), 7.83-7.93 (m, 1 H), 8.19-8.27 (m, 1 H), 12.05 (s, 1 H).

Example 12(92)

6-{9-[(5-carbamoyl-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.38 (methylene chloride:methanol=9:1);
$^1$H-NMR (DMSO-$d_6$): δ 0.95-1.14 (m, 6 H), 1.35-1.56 (m, 4 H), 2.30-2.50 (m, 2 H), 2.60-2.86 (m, 2 H), 3.65-3.87 (m, 2 H), 4.73 (s, 2 H), 6.54-6.70 (m, 2 H), 6.96-7.16 (m, 2 H), 7.30 (brs, 1 H), 7.53 (d, J=3.6 Hz, 1 H), 7.76-7.98 (m, 2 H), 8.23 (d, J=4.8 Hz, 1 H), 12.04 (s, 1 H).

Example 12(93)

6-{9-[(5-cyano-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.46 (methylene chloride:ethyl acetate:methanol=8:4:1);
$^1$H-NMR (DMSO-$d_6$): δ 1.00-1.10 (m, 6 H), 1.35-1.55 (m, 4 H), 2.30-2.50 (m, 2 H), 2.60-2.85 (m, 2 H), 3.68-3.85 (m, 2 H), 4.74 (s, 2 H), 5.65-5.75 (m, 2 H), 7.12 (dd, J=7.5, 4.5 Hz, 1 H), 7.15-7.26 (m, 1 H), 7.81 (d, J=3.6 Hz, 1 H), 7.89 (d J=7.5 Hz, 1 H), 8.24 (d, J=4.5 Hz, 1 H), 12.06 (s, 1 H).

Example 12(94)

6-[9-(2,3-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.51 (chloroform:methanol:water=50:10:1);
$^1$H-NMR (DMSO-$d_6$): δ 0.96-1.13 (m, 6 H), 1.31-1.56 (m, 4 H), 2.27-2.46 (m, 2 H), 2.62-2.86 (m, 2 H), 3.66-3.85 (m, 2 H), 4.65 (s, 2 H), 5.46-5.64 (m, 2 H), 6.56-6.66 (m, 1 H), 7.02-7.09 (m, 1 H), 7.09 (dd, J=7.5, 4.5 Hz, 1 H), 7.26-7.40 (m, 1 H), 7.89 (dd, J=7.5, 1.5 Hz, 1 H), 8.18 (dd, J=4.5, 1.5 Hz, 1 H), 12.04 (s, 1 H).

Example 12(95)

2,2-dimethyl-6-oxo-6-[9-(2,3,6-trifluorobenzyl)-5,6,8,9-tetrahydro-7H-pyrido[4',3':4,5]pyrrolo[2,3-b]pyridin-7-yl]hexanoic acid TLC: Rf 0.49 (chloroform:methanol:water=50:10:1);
$^1$H-NMR (DMSO-$d_6$): δ 0.96-1.16 (m, 6 H), 1.33-1.56 (m, 4 H), 2.30-2.46 (m, 2 H), 2.60-2.81 (m, 2 H), 3.63-3.84 (m, 2 H), 4.60-4.76 (m, 2 H), 5.46-5.58 (m, 2 H), 7.05 (dd, J=7.5, 4.5 Hz, 1 H), 7.07-7.17 (m, 1 H), 7.39-7.53 (m, 1 H), 7.83 (dd, J=7.5, 1.5 Hz, 1 H), 8.16 (dd, J=4.5, 1.5 Hz, 1 H), 11.93 (s, 1 H).

Example 12(96)

6-[9-(3-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.50 (chloroform:methanol:water=50:10:1);
$^1$H-NMR (DMSO-$d_6$): δ 0.99-1.10 (m, 6 H), 1.35-1.53 (m, 4 H), 2.26-2.45 (m, 2 H), 2.65-2.83 (m, 2 H), 3.67-3.85 (m, 2 H), 4.59-4.70 (m, 2 H), 5.48-5.62 (m, 2 H), 6.69-6.79 (m, 1 H), 7.04-7.14 (m, 2 H), 7.43-7.53 (m, 1 H), 7.90 (dd, J=7.5, 1.5 Hz, 1 H), 8.18 (dd, J=4.5, 1.5 Hz, 1 H), 12.04 (s, 1 H).

Example 12(97)

6-[9-(2,4-difluorobenzyl)-5,6,8,9-tetrahydro-7H-pyrido[4',3':4,5]pyrrolo[2,3-b]pyridin-7-yl]-2,2-dimethyl-6-oxohexanoic acid

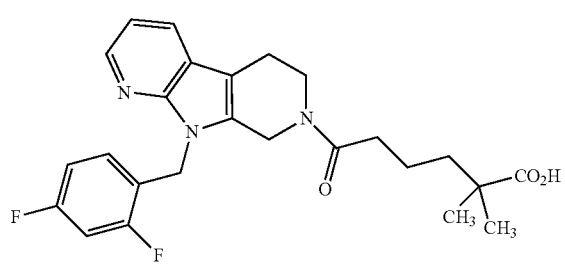 [SMILES: CC(C)(CCCC(=O)N1CCc2c(n(Cc3ccc(F)cc3F)c3ncccc23)C1)C(=O)O]

TLC: Rf 0.38 (methylene chloride:ethyl acetate:methanol=8:4:1);
$^1$H-NMR (DMSO-$d_6$): δ 0.98-1.14 (m, 6 H), 1.35-1.52 (m, 4 H), 2.25-2.82 (m, 4 H), 3.67-3.84 (m, 2 H), 4.64 (s, 2 H), 5.41-5.54 (m, 2 H), 6.85-7.02 (m, 2 H), 7.09 (dd, J=7.9, 4.8 Hz, 1 H), 7.21-7.33 (m, 1 H), 7.89 (dd, J=7.9, 1.4 Hz, 1 H), 8.19 (dd, J=4.8, 1.4 Hz, 1 H), 12.04 (s, 1 H).

Example 12(98)

6-[9-(3-chloro-2,4-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.38 (methylene chloride:ethyl acetate:methanol=8:4:1);
$^1$H-NMR (DMSO-$d_6$): δ 1.00-1.12 (m, 6 H), 1.37-1.52 (m, 4 H), 2.24-2.81 (m, 4 H), 3.68-3.84 (m, 2 H), 4.66 (s, 2 H), 5.47-5.58 (m, 2 H), 6.82-6.96 (m, 1 H), 7.09 (dd, J=7.8, 4.8 Hz, 1 H), 7.15-7.25 (m, 1 H), 7.89 (dd, J=7.8, 1.5 Hz, 1 H), 8.18 (dd, J=4.8, 1.5 Hz, 1 H), 12.04 (s, 1 H).

Example 12(99)

6-[9-(4-chloro-3-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.19 (hexane:ethyl acetate=1:2);
$^1$H-NMR (DMSO-$d_6$): δ 0.98-1.11 (m, 6 H), 1.34-1.53 (m, 4 H), 2.24-2.82 (m, 4 H), 3.68-3.84 (m, 2 H), 4.63 (s, 2 H), 5.43-5.53 (m, 2 H), 6.84-6.97 (m, 1 H), 7.05-7.28 (m, 2 H), 7.46-7.55 (m, 1 H), 7.86-7.94 (m, 1 H), 8.18-8.24 (m, 1 H), 12.05 (s, 1 H).

Example 12(100)

6-[9-(3-chloro-5-fluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.23 (hexane:ethyl acetate=1:2);
$^1$H-NMR (DMSO-$d_6$): δ 1.00-1.11 (m, 6 H), 1.36-1.53 (m, 4 H), 2.28-2.84 (m, 4 H), 3.69-3.84 (m, 2 H), 4.60-4.69 (m, 2 H), 5.44-5.52 (m, 2 H), 6.85-7.00 (m, 1 H), 7.00-7.15 (m, 2 H), 7.29-7.36 (m, 1 H), 7.87-7.95 (m, 1 H), 8.18-8.25 (m, 1 H), 12.05 (s, 1 H).

Example 12(101)

2,2-dimethyl-6-oxo-6-[9-(2,3,4-trifluorobenzyl)-5,6,8,9-tetrahydro-7H-pyrido[4',3':4,5]pyrrolo[2,3-b]pyridin-7-yl]hexanoic acid TLC: Rf 0.48 (chloroform:methanol:water=50:10:1);
$^1$H-NMR (DMSO-$d_6$): δ 0.97-1.14 (m, 6 H), 1.32-1.55 (m, 4 H), 2.28-2.46 (m, 2 H), 2.63-2.84 (m, 2 H), 3.65-3.84 (m, 2 H), 4.66 (s, 2 H), 5.44-5.60 (m, 2 H), 6.66-6.79 (m, 1 H), 7.09 (dd, J=7.5, 4.5 Hz, 1 H), 7.12-7.26 (m, 1 H), 7.89 (dd, J=7.5, 1.5 Hz, 1 H), 8.19 (dd, J=4.5, 1.5 Hz, 1 H), 12.04 (s, 1 H).

Example 12(102)

2,2-dimethyl-6-oxo-6-[9-(2,3,4,6-tetrafluorobenzyl)-5,6,8,9-tetrahydro-7H-pyrido[4',3':4,5]pyrrolo[2,3-b]pyridin-7-yl]hexanoic acid TLC: Rf 0.46 (chloroform:methanol:water=50:10:1);
$^1$H-NMR (DMSO-$d_6$): δ 0.97-1.17 (m, 6 H), 1.34-1.57 (m, 4 H), 2.32-2.46 (m, 2 H), 2.58-2.81 (m, 2 H), 3.65-3.82 (m, 2 H), 4.69 (s, 2 H), 5.41-5.56 (m, 2 H), 7.05 (dd, J=7.5, 4.5 Hz, 1 H), 7.43-7.57 (m, 1 H), 7.83 (dd, J=7.5, 1.5 Hz, 1 H), 8.16 (dd, J=4.5, 1.5 Hz, 1 H), 12.05 (s, 1 H).

Example 12(103)

2,2-dimethyl-6-oxo-6-[9-(pentafluorobenzyl)-5,6,8,9-tetrahydro-7H-pyrido[4',3':4,5]pyrrolo[2,3-b]pyridin-7-yl]hexanoic acid TLC: Rf 0.47 (chloroform:methanol:water=50:10:1);
$^1$H-NMR (DMSO-$d_6$): δ 1.00-1.16 (m, 6 H), 1.35-1.58 (m, 4 H), 2.35-2.48 (m, 2 H), 2.61-2.80 (m, 2 H), 3.66-3.82 (m, 2 H), 4.72 (s, 2 H), 5.48-5.65 (m, 2 H), 7.06 (dd, J=7.5, 4.5 Hz, 1 H), 7.84 (dd, J=7.5, 1.5 Hz, 1 H), 8.15-8.20 (m, 1 H), 12.04 (s, 1 H).

Example 12(107)

6-[9-(2,5-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.20 (chloroform:methanol:28% aqueous ammonia=85:13:2);
$^1$H-NMR (DMSO-$d_6$): δ 0.96-1.14 (m, 6 H), 1.36-1.56 (m, 4 H), 2.24-2.48 (m, 2 H), 2.62-2.87 (m, 2 H), 3.66-3.87 (m, 2 H), 4.60-4.75 (m, 2 H), 5.40-5.57 (m, 2 H), 6.51-6.69 (m, 1 H), 7.03-7.37 (m, 3 H), 7.81-7.97 (m, 1 H), 8.12-8.25 (m, 1 H), 12.04 (s, 1 H).

Example 12(108)

6-{9-[(2-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.56 (ethyl acetate);
$^1$H-NMR (DMSO-$d_6$): δ 1.00-1.13 (m, 6 H), 1.36-1.54 (m, 4 H), 2.28-2.45 (m, 2 H), 2.62-2.81 (m, 2 H), 3.66-3.83 (m, 2 H), 4.67 (s, 2 H), 5.30-5.44 (m, 2 H), 6.56-6.65 (m, 1 H), 7.10 (dd, J=7.7, 4.6 Hz, 1 H), 7.30-7.39 (m, 1 H), 7.88 (dd, J=7.7, 1.3 Hz, 1 H), 8.22 (dd, J=4.6, 1.3 Hz, 1 H), 12.05 (s, 1 H).

Example 12(109)

2,2-dimethyl-6-oxo-6-[9-(2,4,5-trifluorobenzyl)-5,6,8,9-tetrahydro-7H-pyrido[4',3':4,5]pyrrolo[2,3-b]pyridin-7-yl]hexanoic acid TLC: Rf 0.50 (chloroform:methanol:water=50:10:1);
$^1$H-NMR (DMSO-$d_6$): δ 0.95-1.16 (m, 6 H), 1.33-1.56 (m, 4 H), 2.30-2.46 (m, 2 H), 2.64-2.83 (m, 2 H), 3.68-3.85 (m, 2 H), 4.67 (s, 2 H), 5.37-5.55 (m, 2 H), 6.93-7.06 (m, 1 H), 7.09 (dd, 4.5 Hz, 1 H), 7.52-7.66 (m, 1 H), 7.84-7.94 (m, 1 H), 8.16-8.24 (m, 1 H), 12.03 (s, 1 H).

Example 12(110)

6-[9-(2-fluoro-3-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.52 (chloroform:methanol:water=50:10:1);
$^1$H-NMR (DMSO-$d_6$): δ 0.98-1.12 (m, 6 H), 1.32-1.54 (m, 4 H), 2.17-2.47 (m, 5 H), 2.64-2.86 (m, 2 H), 3.67-3.85 (m, 2 H), 4.62 (s, 2 H), 5.40-5.57 (m, 2 H), 6.51-6.63 (m, 1 H), 6.88-6.98 (m, 1 H), 7.08 (dd, J=7.5, 4.5 Hz, 1 H), 7.12-7.21 (m, 1 H), 7.89 (dd, J=7.5, 1.5 Hz, 1 H), 8.18 (dd, J=4.5, 1.5 Hz, 1 H), 12.01 (s, 1 H).

Example 12(113)

2,2-dimethyl-6-oxo-6-[9-(2,3,4,5-tetrafluorobenzyl)-5,6,8,9-tetrahydro-7H-pyrido[4',3':4,5]pyrrolo[2,3-b]pyridin-7-yl]hexanoic acid TLC: Rf 0.51 (chloroform:methanol:water=50:10:1);
$^1$H-NMR (DMSO-$d_6$): δ 0.97-1.14 (m, 6 H), 1.32-1.55 (m, 4 H), 2.28-2.46 (m, 2 H), 2.63-2.84 (m, 2 H), 3.65-3.84 (m, 2 H), 4.68 (s, 2 H), 5.44-5.60 (m, 2 H), 6.83-6.95 (m, 1 H), 7.10 (dd, J=7.5, 4.5 Hz, 1 H), 7.89 (dd, J=7.5, 1.5 Hz, 1 H), 8.19 (dd, J=4.5, 1.5 Hz, 1 H), 12.04 (s, 1 H).

Example 12(115)

2,2-dimethyl-6-oxo-6-[9-(2,3,5,6-tetrafluorobenzyl)-5,6,8,9-tetrahydro-7H-pyrido[4',3':4,5]pyrrolo[2,3-b]pyridin-7-yl]hexanoic acid TLC: Rf 0.59 (chloroform:methanol:water=50:10:1);
$^1$H-NMR (DMSO-$d_6$): δ 1.00-1.16 (m, 6 H), 1.33-1.60 (m, 4 H), 2.32-2.47 (m, 2 H), 2.62-2.83 (m, 2 H), 3.66-3.84 (m, 2 H), 4.71 (s, 2 H), 5.47-5.66 (m, 2 H), 7.06 (dd, J=7.5, 4.5 Hz, 1 H), 7.78-7.93 (m, 2 H), 8.16 (dd, J=4.5, 1.5 Hz, 1 H), 12.05 (s, 1 H).

Example 12(116)

6-[9-(2-fluoro-4-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.54 (chloroform:methanol:water=50:10:1);
$^1$H-NMR (DMSO-$d_6$): δ 0.97-1.13 (m, 6 H), 1.31-1.53 (m, 4 H), 2.24 (s, 3 H), 2.35-2.46 (m, 2 H), 2.62-2.84 (m, 2 H), 3.66-3.83 (m, 2 H), 4.62 (s, 2 H), 5.38-5.52 (m, 2 H), 6.66-6.78 (m, 1 H), 6.83-6.91 (m, 1 H), 7.00-7.13 (m, 2 H), 7.88 (d, J=8.0 Hz, 1 H), 8.18 (dd, J=4.5, 1.5 Hz, 1 H), 12.04 (s, 1 H).

Example 12(119)

6-[9-(4-fluoro-3-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.24 (hexane:ethyl acetate=1:2);
$^1$H-NMR (DMSO-$d_6$): δ 0.98-1.13 (m, 6 H), 1.33-1.53 (m, 4 H), 2.10-2.83 (m, 7 H), 3.66-3.82 (m, 2 H), 4.62 (s, 2 H), 5.34-5.46 (m, 2 H), 6.84-7.22 (m, 4 H), 7.83-7.92 (m, 1 H), 8.18-8.26 (m, 1 H), 12.02 (br s, 1 H).

Example 12(123)

6-[9-(3-fluoro-5-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.49 (chloroform:methanol:water=50:10:1);
$^1$H-NMR (DMSO-$d_5$): δ 0.95-1.13 (m, 6 H), 1.31-1.53 (m, 4 H), 2.18-2.46 (m, 2 H), 2.22 (s, 3 H), 2.63-2.84 (m, 2 H), 3.67-3.82 (m, 2 H), 4.62 (s, 2 H), 5.35-5.50 (m, 2 H), 6.60-6.94 (m, 3 H), 7.09 (dd, J=7.5, 4.5 Hz, 1 H), 7.84-7.93 (m, 1 H), 8.17-8.24 (m, 1 H), 12.04 (s, 1 H).

Example 12(130)

6-[9-(3-fluoro-4-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.44 (methylene chloride:ethyl acetate:methanol=8:4:1);
$^1$H-NMR (DMSO-$d_6$): δ 0.99-1.11 (m, 6 H) 1.32-1.52 (m, 4 H) 2.16 (s, 3 H) 2.21-2.84 (m, 4 H) 3.67-3.83 (m, 2 H) 4.62 (s, 2 H) 5.38-5.49 (m, 2 H) 6.77-6.98 (m, 2 H) 7.09 (dd, J=7.9, 4.8 Hz, 1 H) 7.14-7.23 (m, 1 H) 7.84-7.92 (m, 1 H) 8.17-8.24 (m, 1 H) 12.04 (br. s., 1 H).

Example 12(133)

6-[9-(4-chloro-3-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.29 (hexane:ethyl acetate=1:2);
$^1$H-NMR (DMSO-$d_6$): δ 0.96-1.14 (m, 6 H), 1.28-1.56 (m, 4 H), 2.18-2.29 (m, 3 H), 2.34-2.83 (m, 4 H), 3.66-3.86 (m, 2 H), 4.61 (s, 2 H), 5.33-5.51 (m, 2 H), 6.80-6.97 (m, 1 H), 7.09 (dd, J=7.9, 4.8 Hz, 1 H), 7.14-7.25 (m, 1 H), 7.26-7.37 (m, 1 H), 7.83-7.94 (m, 1 H), 8.15-8.26 (m, 1 H), 12.05 (s, 1 H).

Example 12(137)

6-[9-(2-fluoro-5-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.47 (methylene chloride:ethyl acetate:methanol=8:4:1);
$^1$H-NMR (DMSO-$d_6$): δ 1.01-1.11 (m, 6 H) 1.35-1.54 (m, 4 H) 2.08-2.17 (m, 3 H) 2.24-2.84 (m, 4 H) 3.68-3.84 (m, 2 H) 4.64 (s, 2 H) 5.40-5.53 (m, 2 H) 6.65-6.76 (m, 1 H) 7.04-7.17 (m, 3 H) 7.84-7.94 (m, 1 H) 8.15-8.24 (m, 1 H) 12.05 (br. s., 1 H).

Example 12(138)

6-{9-[(4-chloro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.54 (chloroform:methanol=10:1);
$^1$H-NMR (DMSO-$d_6$): δ 0.98-1.14 (m, 6 H), 1.33-1.54 (m, 4 H), 2.21-2.51 (m, 2 H), 2.62-2.85 (m, 2 H), 3.65-3.88 (m, 2 H), 3.66-3.87 (m, 2 H), 4.64 (s, 2 H), 5.30-5.47 (m, 2 H), 6.81-7.16 (m, 2 H), 7.59-7.69 (m, 1 H), 7.82-7.94 (m, 1 H), 8.13-8.23 (m, 1 H).

Example 12(139)

6-[9-(2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.50 (chloroform:methanol=10:1);
$^1$H-NMR (DMSO-$d_6$): δ 0.98-1.16 (m, 6 H), 1.35-1.54 (m, 4 H), 2.22-2.49 (m, 2 H), 2.57-2.82 (m, 2 H), 3.64-3.82 (m, 2 H), 4.64 (s, 2 H), 5.42-5.57 (m, 2 H), 6.97-7.14 (m, 3 H), 7.31-7.46 (m, 1 H), 7.76-7.89 (m, 1 H), 8.11-8.21 (m, 1 H), 12.04 (s, 1 H).

Example 12(142)

6-[9-(5-chloro-2-fluorobenzyl)-5,6,8,9-tetrahydro-7H-pyrido[4',3':4,5]pyrrolo[2,3-b]pyridin-7-yl]-2,2-dimethyl-6-oxohexanoic acid

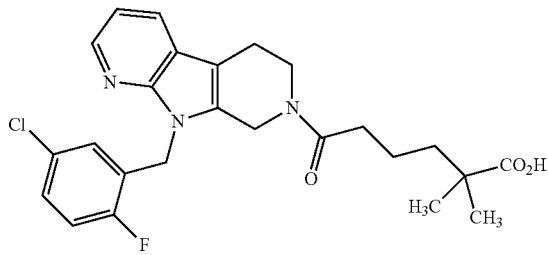 [SMILES: CC(C)(CCCC(=O)N1CCc2c(n(Cc3cc(Cl)ccc3F)c3ncccc23)C1)C(=O)O]

TLC: Rf 0.42 (methylene chloride:ethyl acetate:methanol=8:4:1);
$^1$H-NMR (DMSO-d$_6$): δ 1.02-1.09 (m, 6 H) 1.37-1.53 (m, 4 H) 2.24-2.83 (m, 4 H) 3.70-3.84 (m, 2 H) 4.64-4.71 (m, 2 H) 5.45-5.53 (m, 2 H) 6.87-6.94 (m, 1 H) 7.10 (dd, J=7.7, 4.8 Hz, 1 H) 7.26-7.34 (m, 1 H) 7.35-7.43 (m, 1 H) 7.85-7.94 (m, 1 H) 8.16-8.23 (m, 1 H) 12.02 (br. s., 1 H).

Example 12(143)

2,2-dimethyl-6-oxo-6-[9-(2,3,5-trifluorobenzyl)-5,6,8,9-tetrahydro-7H-pyrido[4',3':4,5]pyrrolo[2,3-b]pyridin-7-yl]hexanoic acid TLC: Rf 0.47 (methylene chloride:ethyl acetate:methanol=8:4:1);
$^1$H-NMR (DMSO-d$_6$): δ 0.96-1.14 (m, 6 H) 1.37-1.56 (m, 4 H) 2.22-2.86 (m, 4 H) 3.70-3.85 (m, 2 H) 4.63-4.75 (m, 2 H) 5.50-5.60 (m, 2 H) 6.44-6.55 (m, 1 H) 7.10 (dd, J=7.8, 4.9 Hz, 1 H) 7.41-7.51 (m, 1 H) 7.87-7.92 (m, 1 H) 8.17-8.21 (m, 1 H) 12.04 (br. s., 1 H).

Example 12(145)

6-[9-(3-fluorobenzyl)-1,3,4,9-tetrahydro-2H-beta-carbolin-2-yl]-2,2-dimethyl-6-oxohexanoic acid TLC: Rf 0.59 (chloroform:methanol:water=50:10:1);
$^1$H-NMR (DMSO-d$_6$): δ 0.94-1.16 (m, 6 H) 1.31-1.55 (m, 4 H) 2.24-2.46 (m, 2 H) 2.78 (br. s., 2 H) 3.65-3.87 (m, 2 H) 4.63 (s, 2 H) 5.31-5.49 (m, 2 H) 6.81 (m, 2 H) 6.95-7.15 (m, 3 H) 7.25-7.51 (m, 3 H) 12.03 (s, 1 H).

Example 12(146)

6-{9-[(2,5-dimethyl-1,3-thiazol-4-yl)methyl]-1,3,4,9-tetrahydro-2H-beta-carbolin-2-yl}-2,2-dimethyl-6-oxohexanoic acid TLC: Rf 0.53 (chloroform:methanol:water=50:10:1);
$^1$H-NMR (DMSO-d$_6$): δ 0.97-1.16 (m, 6 H) 1.34-1.58 (m, 4 H) 2.27-2.47 (m, 8 H) 2.58-2.82 (m, 2 H) 3.63-3.81 (m, 2 H) 4.57-4.74 (m, 2 H) 5.36-5.56 (m, 2 H) 6.97-7.05 (m, 1 H) 7.06-7.15 (m, 1 H) 7.36-7.50 (m, 1 H) 12.05 (s, 1 H).

Example 12(147)

6-[9-(4-cyanobenzyl)-1,3,4,9-tetrahydro-2H-beta-carbolin-2-yl]-2,2-dimethyl-6-oxohexanoic acid TLC: Rf 0.56 (chloroform:methanol:water=50:10:1);
$^1$H-NMR (DMSO-d$_6$): δ 0.95-1.14 (m, 6 H) 1.30-1.56 (m, 4 H) 2.19-2.48 (m, 2 H) 2.61-2.87 (m, 2 H) 3.65-3.85 (m, 2 H) 4.60 (s, 2 H) 5.41-5.57 (m, 2 H) 6.96-7.22 (m, 4 H) 7.33-7.40 (m, 1 H) 7.45 (d, J=7.50 Hz, 1 H) 7.69-7.82 (m, 2 H) 12.04 (s, 1 H).

Example 12(148)

6-[9-(4-carbamoylbenzyl)-1,3,4,9-tetrahydro-2H-beta-carbolin-2-yl]-2,2-dimethyl-6-oxohexanoic acid TLC: Rf 0.42 (chloroform:methanol:water=50:10:1);
$^1$H-NMR (DMSO-d$_6$): δ 0.96-1.14 (m, 6 H) 1.29-1.58 (m, 4 H) 2.20-2.46 (m, 2 H) 2.61-2.87 (m, 2 H) 3.66-3.86 (m, 2 H) 4.62 (s, 2 H) 5.33-5.52 (m, 2 H) 6.96-7.14 (m, 4 H) 7.31 (br. s., 1 H) 7.34-7.49 (m, 2 H) 7.71-7.81 (m, 2 H) 7.87 (br. s., 1 H) 12.04 (br. s., 1 H).

Example 12(150)

6-[9-(4-chloro-2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.17 (hexane:ethyl acetate=1:2);
$^1$H-NMR (DMSO-d$_6$): δ 1.00-1.16 (m, 6 H) 1.37-1.56 (m, 4 H) 2.23-2.82 (m, 4 H) 3.64-3.86 (m, 2 H) 4.69 (s, 2 H) 5.38-5.56 (m, 2 H) 6.99-7.12 (m, 1 H) 7.28-7.46 (m, 2 H) 7.79-7.90 (m, 1 H) 8.11-8.22 (m, 1 H) 12.07 (s, 1 H).

Example 12(152)

6-[9-(3-chloro-2,6-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.53 (methylene chloride:ethyl acetate:methanol=8:4:1);
$^1$H-NMR (DMSO-d$_6$): δ 1.00-1.10 (m, 6 H) 1.38-1.56 (m, 4 H) 2.23-2.84 (m, 4 H) 3.67-3.83 (m, 2 H) 4.65-4.73 (m, 2 H) 5.46-5.57 (m, 2 H) 7.05 (dd, J=7.8, 4.7 Hz, 1 H) 7.13-7.21 (m, 1 H) 7.55-7.65 (m, 1 H) 7.83 (dd, J=7.7, 1.5 Hz, 1 H) 8.16 (dd, J=4.8, 1.7 Hz, 1 H) 12.05 (br. s., 1 H).

Example 12(159)

6-{9-[(6-chloro-3-pyridinyl)methyl]-1,3,4,9-tetrahydro-2H-beta-carbolin-2-yl}-2,2-dimethyl-6-oxohexanoic acid TLC: Rf 0.44 (chloroform:methanol:water=50:10:1);
MS (ESI, Pos. 20 V): m/z=545 (M+H)$^+$.

Example 12(160)

6-{9-[(1,3-dimethyl-1H-pyrazol-5-yl)methyl]-1,3,4,9-tetrahydro-2H-beta-carbolin-2-yl}-2,2-dimethyl-6-oxohexanoic acid TLC: Rf 0.36 (chloroform:methanol:water=50:10:1);
MS (ESI, Pos. 20 V): m/z=437 (M+H)$^+$.

Example 12(163)

6-[9-(4-chloro-3,5-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.45 (methylene chloride:ethyl acetate:methanol=8:4:1);
MS (ESI, Pos. 20 V): m/z=490 (M+H)$^+$.

Example 12(164)

6-[9-(4-chloro-2,5-difluorobenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.46 (methylene chloride:ethyl acetate:methanol=8:4:1);
MS (ESI, Pos. 20 V): m/z=490 (M+H)$^+$.

Example 12(166)

6-{9-[(5-fluoro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.42 (methylene chloride:ethyl acetate:methanol=8:4:1);
MS (ESI, Pos. 20 V): m/z=444 (M+H)$^+$.

Example 12(172)

6-{9-[(4,5-dichloro-2-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.44 (chloroform:methanol:water=50:10:1);
MS (ESI, Pos. 20 V): m/z=494 (M+H)$^+$.

Example 12(174)

6-{9-[(5-fluoro-3-thienyl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.36 (methylene chloride:ethyl acetate:methanol=8:4:1);
MS (ESI, Pos. 20 V): m/z=444 (M+H)$^+$.

Example 12(178)

6-[9-(3-chloro-4-methoxybenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.61 (ethyl acetate);
MS (FAB, Pos.): m/z=484 (M+H)$^+$.

Example 12(181)

6-[9-(3-chloro-4-methylbenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.43 (hexane:ethyl acetate=1:2);
MS (ESI, Pos. 20 V): m/z=468 (M+H)$^+$.

Example 12(182)

6-[9-(3-fluoro-4-methoxybenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.43 (hexane:ethyl acetate=1:2);
MS (ESI, Pos. 20 V): m/z=468 (M+H)$^+$.

Example 12(187)

6-[9-(3-fluoro-5-methoxybenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.48 (methylene chloride:methanol=9:1);
MS (ESI, Pos. 20 V): m/z=468 (M+H)$^+$.

Example 12(188)

6-[9-(2-fluoro-3-methoxybenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.43 (methylene chloride:methanol=9:1);
MS (ESI, Pos. 20 V): m/z=468 (M+H)$^+$.

Example 12(195)

6-[9-(4-fluoro-3-methoxybenzyl)-5,6,8,9-tetrahydro-7H-pyrido[4',3':4,5]pyrrolo[2,3-b]pyridin-7-yl]-2,2-dimethyl-6-oxohexanoic acid TLC: Rf 0.50 (chloroform:methanol=10:1);
MS (FAB, Pos.): m/z=468 (M+H)$^+$.

Example 12(198)

2,2-dimethyl-6-{9-[(2-methyl-1,3-thiazol-5-yl)methyl]-5,6,8,9-tetrahydro-7H-pyrido[4',3':4,5]pyrrolo[2,3-b]pyridin-7-yl}-2,2-dimethyl-6-oxohexanoic acid TLC: Rf 0.45 (methylene chloride:methanol:water=90:10:1);
MS (FAB, Pos.): m/z=441 (M+H)$^+$.

Example 13 ethyl 6-diazo-3,3-dimethyl-5-oxohexanoate

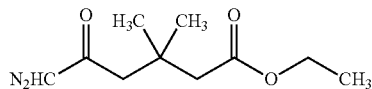

4,4-Dimethyldihydro-2H-pyran-2,6-(3H)-dione (7.11 g) was dissolved in ethanol (50 ml), and the solution was stirred at 100° C. for 16 hours. After cooled to room temperature, the reaction solution was concentrated under reduced pressure. The reaction mixture was diluted with ethyl acetate, and extracted with an aqueous saturated sodium bicarbonate solution. To the aqueous layer was added 5N hydrochloric acid to make the solution acidic, followed by extraction with ethyl acetate. The organic layer was dried with anhydrous magnesium sulfate, and concentrated. The residue was purified by silica gel column chromatography (hexane:ethyl acetate=7:3). The resulting compound (1.50 g) was dissolved in ethyl acetate (13.3 mL), thionyl chloride (1.16 mL) was added, and the mixture was stirred at 60° C. for 8 hours. After cooled to room temperature, the reaction solution was concentrated under reduced pressure. To a mixed solution (15 mL) of THF:acetonitrile (1:1) was added a 2.0M trimethylsilyldiazomethane/hexane solution (8.8 mL), this was cooled to 0° C., a THF:acetonitrile (1:1) mixed solution (6 mL) of the acid chloride was added, a temperature was raised to room temperature, and the mixture was stirred for 1 hour. The reaction solution was concentrated under reduced pressure, and the resulting yellow oil was treated with a silica gel column (hexane:ethyl acetate=90:10→70:30) to obtain the title compound (1.21 g) having the following physical property values.

TLC: Rf 0.28 (hexane:ethyl acetate=4:1);

$^1$H-NMR (CDCl$_3$): δ 1.12 (s, 6 H), 1.26 (t, J=7.1 Hz, 3 H), 2.34-2.47 (m, 4 H), 4.13 (q, J=7.1 Hz, 2 H), 5.38 (s, 1 H).

Example 14

6-ethoxy-4,4-dimethyl-6-oxohexanoic acid

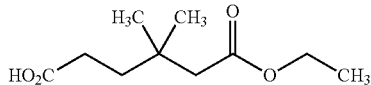

The compound (1.06 g) produced in Example 13 was dissolved in benzyl alcohol (5.0 mL), triethylamine (1.39 mL) and silver acetate (17 mg) were sequentially added, and the mixture was stirred at room temperature for 15 minutes. Further, a temperature was raised to 60° C., the mixture was stirred for 1 hour, and cooled to room temperature, and the reaction solution was placed into 1N hydrochloric acid (10 mL), followed by extraction with hexane (30 mL). The extract solution was washed with 1N hydrochloric acid (5 mL) and an aqueous saturated sodium chloride solution (10 mL), dried with anhydrous magnesium sulfate, and concentrated under reduced pressure. The resulting pale yellow liquid was treated with a silica gel column (hexane:ethyl acetate=100:0→90:10→85:15). The resulting compound (728 mL) was dissolved in ethanol (5.0 mL), 10% palladium carbon (50% hydrous product, 73 mg) was added under the nitrogen atmosphere, and hydrogen was blown into the solution for 1.5 hours while stirred at room temperature. After the system was replaced with nitrogen, the catalyst was filtered off using Celite, followed by concentration under reduced pressure, to obtain the title compound (459 mg) having the following physical property values.

TLC: Rf 0.39 (hexane:ethyl acetate=2:1);

$^1$H-NMR (CDCl$_3$): δ 1.02 (s, 6 H), 1.26 (t, J=7.1 Hz, 3 H), 1.63-1.76 (m, 2 H), 2.20 (s, 2 H), 2.31-2.44 (m, 2 H), 4.12 (q, J=7.1 Hz, 2 H).

Example 15

6-(9-benzyl-1,3,4,9-tetrahydro-2H-beta-carbolin-2-yl)-3,3-dimethyl-6-oxohexanoic acid

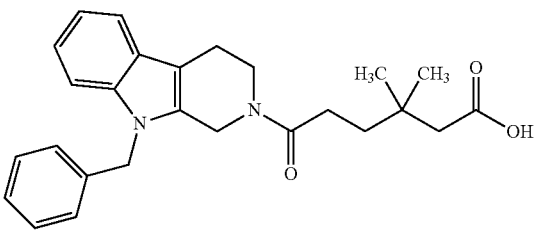 [SMILES: CC(C)(CCC(=O)N1CCc2c(n(Cc3ccccc3)c3ccccc23)C1)CC(=O)O]

The compound produced in Example 14 and a β-carboline derivative produced by operation in accordance with Example 1 were used, which were subjected to operations in accordance with Example 11 and Example 12 to obtain the following compound.

TLC: Rf 0.38 (hexane:ethyl acetate=2:3);

$^1$H-NMR (DMSO-d$_6$): δ 0.86-1.01 (m, 6 H) 1.43-1.62 (m, 2 H) 2.03-2.52 (m, 4 H) 2.64-2.85 (m, 2 H) 3.72-3.84 (m, 2 H) 4.60-4.69 (m, 2 H) 5.31-5.44 (m, 2 H) 6.96-7.12 (m, 4 H) 7.17-7.33 (m, 3 H) 7.37-7.48 (m, 2 H) 11.94 (s, 1 H).

Example 15(1)-Example 15(29)

A corresponding ester in place of 6-ethoxy-4,4-dimethyl-6-oxohexanoic acid, and a β-carboline derivative produced by operation in accordance with Example 1 or a tetrahydropyridopyrrolopyridine derivative produced by operation in accordance with Example 4→Example 5→Example 6→Example 7→Example 1 were used, which were subjected to operation in accordance with Example 11 and, if necessary, subjected to operation in accordance with Example 12 to obtain the following compounds.

Example 15(1)

ethyl 6-(9-benzyl-1,3,4,9-tetrahydro-2H-beta-carbolin-2-yl)-3,3-dimethyl-6-oxohexanoate TLC: Rf 0.36 (hexane:ethyl acetate=3:2);

$^1$H-NMR (CDCl$_3$): δ 0.88-1.11 (m, 6 H) 1.17-1.31 (m, 3 H) 1.54-1.81 (m, 2 H) 2.08-2.27 (m, 2 H) 2.21-2.54 (m, 2 H) 2.78-2.99 (m, 2 H) 3.74-3.98 (m, 2 H) 4.00-4.19 (m, 2 H) 4.53-4.76 (m, 2 H) 5.22-5.36 (m, 2 H) 6.97-7.34 (m, 8 H) 7.47-7.57 (m, 1 H).

Example 15(2)

ethyl 6-[9-(3-fluorobenzyl)-5,6,8,9-tetrahydro-7H-pyrido[4',3':4,5]pyrrolo[2,3-b]pyridin-7-yl]-3,3-dimethyl-6-oxohexanoate TLC: Rf 0.18 (hexane:ethyl acetate=2:1);

$^1$H-NMR (CDCl$_3$): δ 5.31-5.50 (m, 6 H) 5.60-5.71 (m, 3 H) 5.95-6.16 (m, 2 H) 6.52-6.63 (m, 2 H) 6.64-6.92 (m, 2 H) 7.14-7.35 (m, 2 H) 8.13-8.36 (m, 2 H) 8.52 (q, J=7.50 Hz, 2 H) 8.92-9.11 (m, 2 H) 9.81-9.99 (m, 2 H) 11.08-11.39 (m, 3 H) 11.43-11.53 (m, 1 H) 11.58-11.63 (m, 1 H) 12.14-12.25 (m, 1 H) 12.66-12.74 (m, 1 H).

Example 15(3)

6-[9-(3-fluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.23 (hexane:ethyl acetate=2:3);
$^1$H-NMR (CDCl$_3$): δ 0.95-1.15 (m, 6 H) 1.62-1.84 (m, 2 H) 2.17-2.30 (m, 2 H) 2.24-2.56 (m, 2 H) 2.77-2.95 (m, 2 H) 3.76-3.99 (m, 2 H) 4.51-4.72 (m, 2 H) 5.43-5.57 (m, 2 H) 6.73-6.83 (m, 1 H) 6.85-7.00 (m, 2 H) 7.06-7.17 (m, 1 H) 7.21-7.25 (m, 1 H) 7.76-7.90 (m, 1 H) 8.28-8.36 (m, 1 H).

Example 15(4)

6-{9-[(5-chloro-3-thienyl)methyl]-5,6,8,9-tetrahydro-7H-pyrido[4',3':4,5]pyrrolo[2,3-b]pyridin-7-yl}-3,3-dimethyl-6-oxohexanoic acid TLC: Rf 0.26 (hexane:ethyl acetate=1:2);
$^1$H-NMR (DMSO-d$_6$): δ 0.88-1.02 (m, 6 H), 1.45-1.63 (m, 2 H), 2.08-2.18 (m, 2 H), 2.23-2.85 (m, 4 H), 3.72-3.88 (m, 2 H), 4.65-4.78 (m, 2 H), 5.29-5.43 (m, 2 H), 6.87-7.01 (m, 1 H), 7.04-7.19 (m, 2 H), 7.83-7.92 (m, 1 H), 8.16-8.27 (m, 1 H), 11.97 (s, 1 H).

Example 15(6)

6-[9-(4-chloro-2-fluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.52 (ethyl acetate);
$^1$H-NMR (DMSO-d$_6$): δ 0.87-1.03 (m, 6 H) 1.43-1.64 (m, 2 H) 2.03-2.19 (m, 2 H) 2.23-2.88 (m, 4 H) 3.72-3.87 (m, 2 H) 4.62-4.74 (m, 2 H) 5.44-5.57 (m, 2 H) 6.77-6.88 (m, 1 H) 7.11 (dd, J=7.8, 4.8 Hz, 1 H) 7.15-7.22 (m, 1 H) 7.43-7.53 (m, 1 H) 7.91 (dd, J=7.8, 1.6 Hz, 1 H) 8.20 (dd, J=4.8, 1.6 Hz, 1 H) 11.97 (s, 1 H).

Example 15(7)

6-[9-(2,4-difluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.43 (ethyl acetate);
$^1$H-NMR (DMSO-d$_6$): δ 0.85-1.05 (m, 6 H) 1.42-1.65 (m, 2 H) 2.03-2.22 (m, 2 H) 2.24-2.89 (m, 4 H) 3.72-3.87 (m, 2 H) 4.61-4.76 (m, 2 H) 5.39-5.57 (m, 2 H) 6.83-7.04 (m, 2 H) 7.11 (dd, J=7.7, 4.8 Hz, 1 H) 7.20-7.37 (m, 1 H) 7.90 (dd, J=7.7, 1.5 Hz, 1 H) 8.20 (dd, J=4.8, 1.5 Hz, 1 H) 11.97 (s, 1 H).

Example 15(8)

6-[9-(3-chloro-2,4-difluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.46 (ethyl acetate);
$^1$H-NMR (DMSO-d$_6$): δ 0.86-1.05 (m, 6 H) 1.41-1.64 (m, 2 H) 2.05-2.19 (m, 2 H) 2.25-2.87 (m, 4 H) 3.71-3.88 (m, 2 H) 4.59-4.76 (m, 2 H) 5.43-5.62 (m, 2 H) 6.81-6.98 (m, 1 H) 7.11 (dd, J=7.7, 4.8 Hz, 1 H) 7.16-7.28 (m, 1 H) 7.84-7.96 (m, 1 H) 8.16-8.25 (m, 1 H) 11.97 (s, 1 H).

Example 15(10)

6-[9-(4-fluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.22 (ethyl acetate:methanol=19:1);
$^1$H-NMR (DMSO-d$_6$): δ 0.84-1.05 (m, 6 H) 1.41-1.63 (m, 2 H) 2.04-2.18 (m, 2 H) 2.18-2.32 (m, 2 H) 2.62-2.88 (m, 2 H) 3.69-3.86 (m, 2 H) 4.57-4.72 (m, 2 H) 5.38-5.54 (m, 2 H) 7.01-7.27 (m, 5 H) 7.83-7.95 (m, 1 H) 8.16-8.27 (m, 1 H) 11.97 (br s, 1 H).

Example 15(11)

3,3-dimethyl-6-oxo-6-[9-(3,4,5-trifluorobenzyl)-5,6,8,9-tetrahydro-7H-pyrido[4',3':4,5]pyrrolo[2,3-b]pyridin-7-yl]hexanoic acid TLC: Rf 0.28 (ethyl acetate:methanol=19:1);
$^1$H-NMR (DMSO-d$_6$): δ 0.87-1.04 (m, 6 H) 1.43-1.65 (m, 2 H) 2.05-2.19 (m, 2 H) 2.22-2.47 (m, 2 H) 2.65-2.87 (m, 2 H) 3.73-3.87 (m, 2 H) 4.60-4.74 (m, 2 H) 5.41-5.53 (m, 2 H) 6.96-7.20 (m, 3 H) 7.88-7.96 (m, 1 H) 8.18-8.26 (m, 1 H) 11.97 (s, 1 H).

Example 15(12)

6-[9-(4-chlorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.25 (ethyl acetate:methanol=19:1);
$^1$H-NMR (DMSO-d$_6$): δ 0.87-1.04 (m, 6 H) 1.41-1.61 (m, 2 H) 2.04-2.17 (m, 2 H) 2.19-2.47 (m, 2 H) 2.63-2.87 (m, 2 H) 3.72-3.86 (m, 2 H) 4.56-4.71 (m, 2 H) 5.42-5.54 (m, 2 H) 7.05-7.22 (m, 3 H) 7.28-7.43 (m, 2 H) 7.85-7.96 (m, 1 H) 8.17-8.27 (m, 1 H) 11.97 (s, 1 H).

Example 15(13)

3,3-dimethyl-6-oxo-6-[9-(2,4,5-trifluorobenzyl)-5,6,8,9-tetrahydro-7H-pyrido[4',3':4,5]pyrrolo[2,3-b]pyridin-7-yl]hexanoic acid TLC: Rf 0.47 (ethyl acetate:methanol=19:1);
$^1$H-NMR (DMSO-d$_6$): δ 0.88-1.04 (m, 6 H) 1.45-1.63 (m, 2 H) 2.07-2.18 (m, 2 H) 2.29-2.47 (m, 2 H) 2.65-2.86 (m, 2 H) 3.74-3.86 (m, 2 H) 4.65-4.76 (m, 2 H) 5.41-5.54 (m, 2 H) 7.01 (ddd, J=10.70, 8.87, 7.14 Hz, 1 H) 7.11 (dd, J=7.68, 4.76 Hz, 1 H) 7.52-7.68 (m, 1 H) 7.91 (dd, J=7.68, 1.28 Hz, 1 H) 8.21 (dd, J=4.76, 1.46 Hz, 1 H) 11.97 (s, 1 H).

Example 15(15)

6-{9-[(5-chloro-2-thienyl)methyl]-5,6,8,9-tetrahydro-7H-pyrido[4',3':4,5]pyrrolo[2,3-b]pyridin-7-yl}-3,3-dimethyl-6-oxohexanoic acid TLC: Rf 0.42 (ethyl acetate:methanol=19:1);
$^1$H-NMR (DMSO-d$_6$): δ 0.87-1.04 (m, 6 H) 1.47-1.66 (m, 2 H) 2.09-2.18 (m, 2 H) 2.28-2.47 (m, 2 H) 2.62-2.84 (m, 2 H) 3.70-3.86 (m, 2 H) 4.70-4.84 (m, 2 H) 5.48-5.64 (m, 2 H) 6.90-7.05 (m, 2 H) 7.12 (dd, J=7.68, 4.76 Hz, 1 H) 7.82-7.95 (m, 1 H) 8.20-8.30 (m, 1 H) 12.00 (br s, 1 H).

Example 15(16)

6-{9-[(2,5-dimethyl-3-thienyl)methyl]-5,6,8,9-tetrahydro-7H-pyrido[4',3':4,5]pyrrolo[2,3-b]pyridin-7-yl}-3,3-dimethyl-6-oxohexanoic acid TLC: Rf 0.47 (ethyl acetate:methanol=19:1);
$^1$H-NMR (DMSO-$d_6$): δ 0.90-1.03 (m, 6 H) 1.46-1.63 (m, 2 H) 2.10-2.17 (m, 2 H) 2.18-2.25 (m, 3 H) 2.25-2.47 (m, 5 H) 2.62-2.85 (m, 2 H) 3.70-3.84 (m, 2 H) 4.58-4.70 (m, 2 H) 5.18-5.36 (m, 2 H) 6.17-6.35 (m, 1 H) 7.01-7.16 (m, 1 H) 7.88 (dd, J=7.87, 1.46 Hz, 1 H) 8.15-8.32 (m, 1 H) 11.98 (s, 1 H).

Example 15(17)

6-[9-(3,5-dichlorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.52 (chloroform:methanol:water=50:10:1);
MS (ESI, Pos. 20 V): m/z=488 (M+H)$^+$.

Example 15(20)

6-{9-[(4-chloro-2-thienyl)methyl]-5,6,8,9-tetrahydro-7H-pyrido[4',3':4,5]pyrrolo[2,3-b]pyridin-7-yl}-3,3-dimethyl-6-oxohexanoic acid TLC: Rf 0.52 (chloroform:methanol:water=50:10:1);
MS (ESI, Pos. 20 V): m/z=460 (M+H)$^+$.

Example 15(21)

6-[9-(4-chloro-3-fluorobenzyl)-5,6,8,9-tetrahydro-7H-pyrido[4',3':4,5]pyrrolo[2,3-b]pyridin-7-yl]-3,3-dimethyl-6-oxohexanoic acid TLC: Rf 0.38 (methylene chloride:ethyl acetate:methanol=8:4:1);
MS (ESI, Pos. 20 V): m/z=472 (M+H)$^+$.

Example 15(23)

6-[9-(4-cyanobenzyl)-1,3,4,9-tetrahydro-2H-beta-carbolin-2-yl]-3,3-dimethyl-6-oxohexanoic acid TLC: Rf 0.55 (chloroform:methanol:water=50:10:1);
MS (ESI, Pos. 20 V): m/z=444 (M+H)$^+$.

Example 15(24)

6-{9-[(6-chloro-3-pyridinyl)methyl]-1,3,4,9-tetrahydro-2H-beta-carbolin-2-yl}-3,3-dimethyl-6-oxohexanoic acid TLC: Rf 0.43 (chloroform:methanol=10:1);
MS (FAB, Pos.): m/z=454 (M+H)$^+$.

Example 15(26)

6-{9-[(1,3-dimethyl-1H-pyrazol-5-yl)methyl]-1,3,4,9-tetrahydro-2H-beta-carbolin-2-yl}-3,3-dimethyl-6-oxohexanoic acid TLC: Rf 0.36 (chloroform:methanol=10:1);
MS (FAB, Pos.): m/z=437 (M+H)$^+$.

Example 15(27)

6-{9-[(2,5-dimethyl-1,3-thiazol-4-yl)methyl]-1,3,4,9-tetrahydro-2H-beta-carbolin-2-yl}-3,3-dimethyl-6-oxohexanoic acid TLC: Rf 0.40 (chloroform:methanol=10:1);
MS (FAB, Pos.): m/z=454 (M+H)$^+$.

Example 15(29)

3,3-dimethyl-6-oxo-6-[9-(2,3,4,6-tetrafluorobenzyl)-5,6,8,9-tetrahydro-7H-pyrido[4',3':4,5]pyrrolo[2,3-b]pyridin-7-yl]hexanoic acid TLC: Rf 0.41 (chloroform:methanol:water=50:10:1);
MS (ESI, Pos. 20 V): m/z=983 (2M+H)$^+$, 492 (M+H)$^+$.

Example 16

7-(chloroacetyl)-9-(3-fluorobenzyl)-6,7,8,9-tetrahydro-5H-pyrido[4',3':4,5]pyrrolo[2,3-b]pyridine

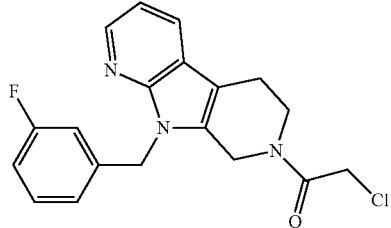 [SMILES: O=C(CCl)N1CCc2c(n(Cc3cccc(F)c3)c3ncccc23)C1]

To a suspension of 9-(3-fluorobenzyl)-6,7,8,9-tetrahydro-5H-pyrido[4',3':4,5]pyrrolo[2,3-b]pyridine (500 mg) produced by operation in accordance with Example 1 in THF (10 mL) were sequentially added triethylamine (0.59 mL) and chloroacetyl chloride (0.135 mL), and the mixture was stirred for 30 minutes. The reaction mixture was poured into an aqueous saturated sodium bicarbonate solution, followed by extraction with ethyl acetate. The organic layer was washed with an aqueous saturated sodium chloride solution, dried with anhydrous magnesium sulfate, and concentrated. The residue was purified by silica gel column chromatography (hexane:ethyl acetate=1:1) to obtain the title compound (459 mg) having the following physical property values.

TLC: Rf 0.29 (hexane:ethyl acetate=3:2);
$^1$H-NMR (CDCl$_3$): δ 2.80-3.02 (m, 2 H) 3.76-4.23 (m, 4 H) 4.50-4.75 (m, 2 H) 5.42-5.52 (m, 2 H) 6.71-6.85 (m, 1 H) 6.86-7.03 (m, 2 H) 7.06-7.15 (m, 1 H) 7.19-7.34 (m, 1 H) 7.77-7.88 (m, 1 H) 8.26-8.37 (m, 1 H).

Example 17 methyl 3-{2-[9-(3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoate

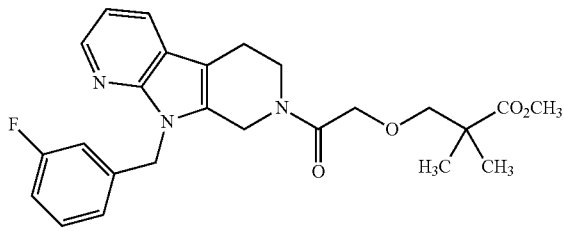 [SMILES: COC(=O)C(C)(C)COCC(=O)N1CCc2c(n(Cc3cccc(F)c3)c3ncccc23)C1]

To a solution of methyl 3-hydroxy-2,2-dimethylpropanoate (0.04 mL) in N,N-dimethylformamide (2 mL) was added sodium hydride (60% in oil, 12 mg) at 0° C., and the mixture was stirred for 20 minutes. To the reaction mixture was added dropwise a solution of the compound (54 mg) produced in Example 16 in N,N-dimethylformamide (1 mL), and the mixture was stirred for 1 hour. The reaction mixture was poured into ice water, followed by extraction with ethyl acetate. The organic layer was sequentially washed with water, and an aqueous saturated sodium chloride solution, dried with anhydrous magnesium sulfate, and concentrated. The residue was purified by silica gel column chromatography (hexane:ethyl acetate=1:2) to obtain the title compound (28 mg) having the following physical property values.

TLC: Rf 0.48 (hexane:ethyl acetate=1:2);
$^1$H-NMR (CDCl$_3$): δ 1.04-1.33 (m, 6 H) 2.77-2.92 (m, 2 H) 3.38-3.57 (m, 2 H) 3.57-3.70 (m, 3 H) 3.74-3.96 (m, 2 H) 4.01-4.27 (m, 2 H) 4.53-4.67 (m, 2 H) 5.43-5.51 (m, 2 H) 6.71-7.00 (m, 3 H) 7.05-7.14 (m, 1 H) 7.18-7.31 (m, 1 H) 7.76-7.86 (m, 1 H) 8.26-8.34 (m, 1 H).

Example 18

3-{2-[9-(3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid To the compound (28 mg) produced in Example 17 in a mixture solution of ethylene glycol dimethyl ether (1 mL) and methanol (1 mL) was added a 1N aqueous sodium hydroxide solution (1 mL) at room temperature, and the mixture was stirred overnight. To the reaction mixture were added 1N hydrochloric acid (1 mL) and water, followed by extraction with ethyl acetate. The extract was washed with an aqueous saturated sodium chloride solution, dried with anhydrous sodium sulfate, and concentrated. The residue was purified by silica gel column chromatography (chloroform:methanol:water=50:10:1) to obtain the title compound (11 mg) having the following physical property values.

TLC: Rf 0.51 (chloroform:methanol:water=50:10:1);
$^1$H-NMR (DMSO-d$_6$): δ 0.97-1.14 (m, 6 H) 2.66-2.88 (m, 2 H) 3.35-3.50 (m, 2 H) 3.62-3.85 (m, 2 H) 4.07-4.29 (m, 2 H) 4.61 (s, 2 H) 5.48 (s, 2 H) 6.84-7.01 (m, 2 H) 7.02-7.11 (m, 1 H) 7.11 (dd, J=8.00, 4.50 Hz, 1 H) 7.33 (ddd, J=8.00, 8.00, 6.00 Hz, 1 H) 7.90 (dd, J=8.00, 1.50 Hz, 1 H) 8.21 (dd, J=4.50, 1.50 Hz, 1 H) 12.19 (s, 1 H).

Example 18(1)-18(23)

A corresponding ester in place of methyl 3-hydroxy-2,2-dimethylpropanoate, and a β-carboline derivative produced by operation in accordance with Example 1 or a tetrahydropyridopyrrolopyridine derivative produced by operation in accordance with Example 4→Example 5→Example 6→Example 7→Example 1 were used, which were subjected to operation in accordance with Example 17 and, if necessary, subjected to operation in accordance with Example 18 to obtain the following compounds.

Example 18(1)

2-{2-[9-(3-fluorobenzyl)-5,6,8,9-tetrahydro-7H-pyrido[4',3':4,5]pyrrolo[2,3-b]pyridin-7-yl]-2-oxoethoxy}-2-methylpropanoic acid

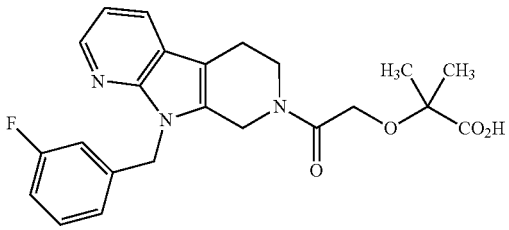 [SMILES: CC(C)(OCC(=O)N1CCc2c(n(Cc3cccc(F)c3)c3ncccc23)C1)C(=O)O]

TLC: Rf 0.33 (chloroform:methanol:water=50:10:1);
$^1$H-NMR (DMSO-d$_6$): δ 1.17-1.42 (m, 6 H) 2.61-2.90 (m, 2 H) 3.65-3.96 (m, 2 H) 4.02-4.34 (m, 2 H) 4.49-5.07 (m, 2 H) 5.36-5.64 (m, 2 H) 6.78-7.16 (m, 4 H) 7.24-7.38 (m, 1 H) 7.81-7.95 (m, 1 H) 8.14-8.27 (m, 1 H).

Example 18(2)

3-{2-[9-(4-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.24 (chloroform:methanol:water=10:1:0.1);
MS (ESI, Pos.): m/z=440(M+H)$^+$.

Example 18(3)

3-{2-[9-(2,4-difluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.19 (chloroform:methanol:water=10:1:0.1);
MS (ESI, Pos.): m/z=453 (M+H)$^+$.

Example 18(4)

2,2-dimethyl-3-{2-oxo-2-[9-(3,4,5-trifluorobenzyl)-5,6,8,9-tetrahydro-7H-pyrido[4',3':4,5]pyrrolo[2,3-b]pyridin-7-yl]ethoxy}propanoic acid TLC: Rf 0.26 (chloroform:methanol:water=10:1:0.1);
MS (ESI, Pos.): m/z=476 (M+H)$^+$.

Example 18(5)

2,2-dimethyl-3-{2-oxo-2-[9-(2,4,5-trifluorobenzyl)-5,6,8,9-tetrahydro-7H-pyrido[4',3':4,5]pyrrolo[2,3-b]pyridin-7-yl]ethoxy}propanoic acid TLC: Rf 0.20 (chloroform:methanol:water=10:1:0.1);
MS (ESI, Pos.): m/z=476 (M+H)$^+$.

Example 18(6)

3-{2-[9-(4-chlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.18 (chloroform:methanol:water=10:1:0.1);
MS (ESI, Pos.): m/z=456 (M+H)$^+$.

Example 18(7)

3-{2-[9-(4-chloro-2-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.16 (chloroform:methanol:water=10:1:0.1);
MS (ESI, Pos.): m/z=474 (M+H)$^+$.

Example 18(8)

3-{2-[9-(4-chloro-3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.13 (chloroform:methanol:water=10:1:0.1);
MS (ESI, Pos.): m/z=474 (M+H)$^+$.

Example 18(9)

3-{2-[9-(3-chloro-4-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.15 (chloroform:methanol:water=10:1:0.1);
MS (ESI, Pos.): m/z=474 (M+H)$^+$.

Example 18(11)

2,2-dimethyl-3-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethoxy}propanoic acid TLC: Rf 0.15 (chloroform:methanol:water=10:1:0.1);
MS (ESI, Pos.): m/z=494 (M+H)$^+$.

Example 18(13)

3-{2-[9-(3-chloro-2,4-difluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.19 (chloroform:methanol:water=10:1:0.1);
MS (ESI, Pos.): m/z=492 (M+H)$^+$.

Example 18(16)

3-{2-[9-(3,4-dichlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.21 (chloroform:methanol:water=10:1:0.1);
MS (FAB, Pos.): m/z=490 (M+H)$^+$.

Example 18(17)

3-{2-[9-(3,5-dichlorobenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC: Rf 0.24 (chloroform:methanol:water=10:1:0.1);
MS (FAB, Pos.): m/z=490 (M+H)$^+$.

Example 18(20)

3-(2-{9-[(4-chloro-2-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid TLC: Rf 0.22 (chloroform:methanol:water=10:1:0.1);
MS (FAB, Pos.): m/z=462 (M+H)$^+$.

Example 18(21)

3-(2-{9-[(5-chloro-3-thienyl)methyl]-5,6,8,9-tetrahydro-7H-pyrido[4',3':4,5]pyrrolo[2,3-b]pyridin-7-yl}-2-oxoethoxy-2,2-dimethylpropanoic acid TLC: Rf 0.24 (chloroform:methanol:water=10:1:0.1);
MS (FAB, Pos.): m/z=462 (M+H)$^+$.

Example 18(22)

3-(2-{9-[(5-chloro-2-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid TLC: Rf 0.33 (chloroform:methanol:water=10:1:0.1);
MS (FAB, Pos.): m/z=462 (M+H)$^+$.

Example 18(23)

3-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethoxy)-2,2-dimethylpropanoic acid TLC: Rf 0.22 (chloroform:methanol:water=10:1:0.1);
MS (FAB, Pos.): m/z=456 (M+H)$^+$.

Example 19 methyl 3-[(2-{9-[(3-fluorbenzyl)methyl]-5,6,8,9-tetrahydro-7H-pyrido[4',3':4,5]pyrrolo[2,3-b]pyridin-7-yl}-2-oxoethoxy)amino-2,2-dimethylpropanoate To the compound (72 mg) produced in Example 16 and methyl 3-amino-2,2-dimethylpropanoate hydrochloride (67 mg) in THF solution (5 mL) was added triethylamine (0.14 mL) at 0°C. After stirred at room temperature for 1 hour, tetrabutylammonium bromide (10 mg) was added, and the mixture was stirred at 60°C. for 14 hours. The reaction solution was cooled to room temperature, and to the reaction solution was added an aqueous saturated sodium bicarbonate solution, followed by extraction with ethyl acetate. After the extract solution was washed with an aqueous saturated sodium chloride solution (2 L), dried using anhydrous magnesium sulfate, and concentrated under reduced pressure. The resulting residue was purified with a silica gel column (ethyl acetate:methanol=9:1) to obtain the title compound (80 mg) having the following physical property values.
TLC:Rf 0.47 (chloroform: methanol:water=50:10:1);

¹H-NMR(CDCl₃):δ 1.08-1.26 (m, 6 H), 2.60-2.73(m, 2 H), 2.74-2.90(m, 2 H), 3.24-3.58 (m, 2 H), 3.59-3.68 (m, 3 H), 3.66-3.96 (m, 2 H), 4.38-4.71 (m, 2 H), 5.38-5.51 (m, 2 H), 6.69-6.99 (m, 3 H), 7.02-7.13 (m, 1 H), 7.16-7.31 (m, 1 H), 7.73-7.86 (m, 1 H), 8.21-8.36 (m, 1 H).

Example 20

3-({2-[9-(3-fluorobenzyl)-5,6,8,9-tetrahydro-7H-pyrido[4',3':4,5]pyrrolo[2,3-b]pyridin-7-yl]-2-oxoethyl}amino)-2,2-dimethylpropanoic acid hydrochloride

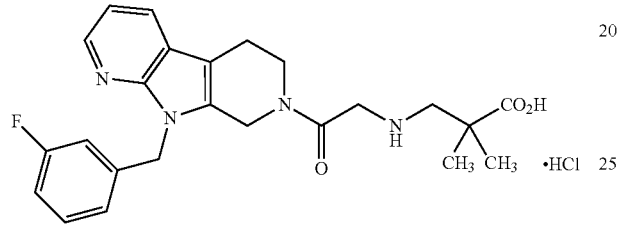

The compound (10 mg) produced in Example 19 was dissolved in 5 mol/L hydrochloric acid (0.5 mL), and the solution was stirred at 60° C. for 4 hours. The reaction solution was distilled off and concentrated under reduced pressure to obtain the title compound (8 mg) having the following physical property values.

TLC: Rf 0.30 (chloroform:methanol:water=50:10:1);
¹H-NMR (DMSO-d₆): δ 1.17-1.29 (m, 6 H) 2.73-2.92 (m, 2 H) 2.98-3.17 (m, 2 H) 3.65-3.93 (m, 2 H) 4.13-4.26 (m, 2 H) 4.62-4.75 (m, 2 H) 5.44-5.59 (m, 2 H) 6.86-7.20 (m, 4 H) 7.27-7.41 (m, 1 H) 7.90-8.02 (m, 1 H) 8.18-8.29 (m, 1 H) 8.64-8.93 (m, 2 H).

Example 20(1)-Example 20(2)

A corresponding carboxylic acid ester derivative in place of methyl 3-amino-2,2-dimethylpropanoate was used, which was subjected to operation in accordance with Example 17 and Example 18 to obtain the following compounds.

Example 20(1)

2-({2-[9-(3-fluorobenzyl)-5,6,8,9-tetrahydro-7H-pyrido[4',3':4,5]pyrrolo[2,3-b]pyridin-7-yl]-2-oxoethyl}amino)-2-methylpropanoic acid hydrochloride TLC: Rf 0.34 (chloroform:methanol:water=50:10:1);
¹H-NMR (DMSO-d₆): δ 1.45-1.60 (m, 6 H) 2.72-2.93 (m, 2 H) 3.72-3.97 (m, 2 H) 4.05-4.22 (m, 2 H) 4.67-4.78 (m, 2 H) 5.45-5.59 (m, 2 H) 6.82-7.22 (m, 4 H) 7.25-7.40 (m, 1 H) 7.88-8.03 (m, 1 H) 8.17-8.29 (m, 1 H) 8.97-9.38 (m, 2 H).

Example 20(2)

3-[{2-[9-(3-fluorobenzyl)-5,6,8,9-tetrahydro-7H-pyrido[4',3':4,5]pyrrolo[2,3-b]pyridin-7-yl]-2-oxoethyl}(methyl)amino]-2,2-dimethylpropanoic acid hydrochloride TLC: Rf 0.43 (chloroform:methanol:water=50:10:1);
¹H-NMR (DMSO-d₆): δ 1.09-1.39 (m, 6 H) 2.72-2.98 (m, 5 H) 3.22-4.03 (m, 4 H) 4.39-4.58 (m, 2 H) 4.57-4.79 (m, 2 H) 5.52 (s, 2 H) 6.87-7.20 (m, 4 H) 7.27-7.41 (m, 1 H) 7.91-8.02 (m, 1 H) 8.20-8.30 (m, 1 H) 9.04-9.43 (m, 1 H).

Example 21

2-(1H-indol-3-yl)propanenitrile

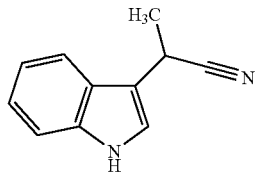

1H-pyrrolo[2,3-b]pyridin-3-ylacetonitrile (100 mg) was dissolved in THF (1.5 mL), the solution was cooled to −30° C., lithium diisopropylamide (2.0M heptane:THF:ethylbenzene mixed solution, 0.01 mL) was added dropwise, and the mixture was stirred at 0° C. for 30 minutes. After the reaction mixture was cooled to −30° C., methyl iodide (199 mg) was added dropwise, and the mixture was stirred for 2 hours. The reaction mixture was poured into an aqueous saturated ammonium chloride solution, followed by extraction with ethyl acetate. The organic layer was sequentially washed with an aqueouse saturated sodium bicarbonate solution and an aqueous saturated sodium chloride solution, dried with anhydrous magnesium sulfate, and concentrated. The residue was purified by silica gel column chromatography (hexane:ethyl acetate=1:4) to obtain the title compound (103 mg) having the following physical property values.

TLC: Rf 0.42 (ethyl acetate);
¹H-NMR (CDCl₃): δ 1.77 (d, J=7.0 Hz, 3 H), 4.16 (q, J=7.0 Hz, 1 H), 7.16 (dd, J=8.0, 5.0 Hz, 1 H), 7.33 (d, J=3.0 Hz, 1 H), 8.03 (dd, J=8.0, 1.0 Hz, 1 H), 8.37 (dd, J=5.0, 1.0 Hz, 1 H), 9.18 (s, 1 H).

Example 22 tert-butyl 4-methyl-1,3,4,9-tetrahydro-2H-beta-carboline-2-carboxylate

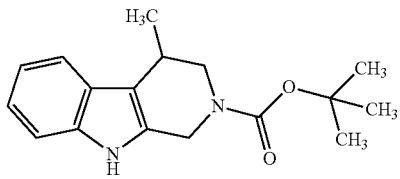 [SMILES: CC1CN(C(=O)OC(C)(C)C)Cc2[nH]c3ccccc3c21]

To a suspension of lithium aluminum hydride (51 mg) in anhydrous THF (3 mL) was added dropwise a solution of the compound (77 mg) produced in Example 21 in anhydrous THF (1 mL) at room temperature, and the mixture was stirred until the raw materials disappeared. To the reaction mixture was added a 2N aqueous sodium hydroxide solution (0.5 mL), and the mixture was stirred at room temperature. The reaction mixture was filtered through a cotton plug, and the filtrate was concentrated. The residue was dissolved in ethanol (3 mL), a 4N solution of hydrogen chloride in dioxane (0.142 mL) and a 37% aqueous formaldehyde solution (0.047 mL) were added, and the mixture was stirred at 90° C. for 5 hours. The reaction mixture was concentrated, to the resulting residue was added 1,4-dioxane (2.5 mL) to suspend the residue, and a 1N aqueous sodium hydroxide solution (0.56 mL) and di-tert-butyl dicarbonate (130 mg) were added at room temperature, and the mixture was stirred for 17 hours. The reaction mixture was poured into an aqueous saturated sodium bicarbonate solution, followed by extraction with ethyl acetate. The organic layer was sequentially washed with an aqueous saturated sodium chloride solution, dried with anhydrous sodium sulfate, and concentrated to obtain the title compound (47 mg) having the following physical property values.

TLC: Rf 0.17 (hexane:ethyl acetate=2:1);
$^1$H-NMR (CDCl$_3$): δ 1.34 (d, J=7.0 Hz, 3 H), 1.51 (s, 9 H), 3.08-3.89 (m, 3 H), 4.60-4.95 (m, 2 H), 7.08 (dd, J=8.0, 5.0 Hz, 1 H), 7.86 (d, J=8.0, 1 H), 8.21 (dd, J=5.0, 1.0 Hz, 1 H), 11.40-11.90 (m, 1 H).

Example 23

6-[9-(3-fluorobenzyl)-5-methyl-5,6,8,9-tetrahydro-7H-pyrido[4',3':4,5]pyrrolo[2,3-b]pyridin-7-yl]-2,2-dimethyl-6-oxohexanoic acid

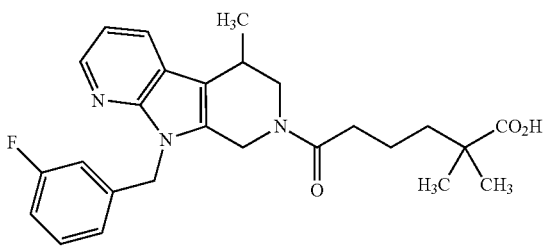 [SMILES: CC1CN(C(=O)CCCC(C)(C)C(=O)O)Cc2c1c1cccnc1n2Cc1cccc(F)c1]

The compound produced in Example 22 was used, which was subjected to operation in accordance with Example 1 and, further, subjected to operation in accordance with Example 11 and Example 12 to obtain the title compound having the following physical property values.

TLC: Rf 0.24 (hexane:ethyl acetate=2:3);
$^1$H-NMR (CDCl$_3$): δ 1.16-1.24 (m, 6 H) 1.31-1.41 (m, 3 H) 1.45-1.81 (m, 4 H) 2.29-2.51 (m, 2 H) 3.12-3.32 (m, 1 H) 3.40-3.98 (m, 2 H) 4.39-4.84 (m, 2 H) 5.32-5.62 (m, 2 H) 6.72-7.01 (m, 3 H) 7.03-7.16 (m, 1 H) 7.19-7.26 (m, 1 H) 7.83-7.96 (m, 1 H) 8.27-8.34 (m, 1 H).

Example 23(1)-Example 23(14)

A corresponding carboxylic acid derivative in place of 6-ethoxy-4,4-dimethyl-6-oxohexanoic acid, and a tetrahydropyridopyrrolopyridine derivative produced by operation in accordance with Examples 21 and 22 were used, which were subjected to operation in accordance with Example 11 and, if necessary, subjected to operation in accordance with Example 12 to obtain the following compounds.

Example 23(1)

6-[9-(3-fluorobenzyl)-5,5-dimethyl-5,6,8,9-tetrahydro-7H-pyrido[4',3':4,5]pyrrolo[2,3-b]pyridin-7-yl]-2,2-dimethyl-6-oxohexanoic acid TLC: Rf 0.27 (hexane:ethyl acetate=2:3);
$^1$H-NMR (CDCl$_3$): δ 1.17-1.28 (m, 6 H) 1.38-1.47 (m, 6 H) 1.52-1.79 (m, 4 H) 2.20-2.51 (m, 2 H) 3.40-3.70 (m, 2 H) 4.40-4.71 (m, 2 H) 5.41-5.51 (m, 2 H) 6.75-6.83 (m, 1 H) 6.84-7.02 (m, 2 H) 7.04-7.14 (m, 1 H) 7.18-7.26 (m, 1 H) 7.91-8.01 (m, 1 H) 8.27-8.33 (m, 1 H).

Example 23(2)

6-[9-(3-fluorobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoic acid TLC: Rf 0.27 (hexane:ethyl acetate=2:3);
$^1$H-NMR (CDCl$_3$): δ 0.99-1.11 (m, 6 H) 1.36-1.50 (m, 6 H) 1.61-1.84 (m, 2 H) 2.17-2.29 (m, 2 H) 2.30-2.56 (m, 2 H) 3.45-3.68 (m, 2 H) 4.49-4.70 (m, 2 H) 5.42-5.55 (m, 2 H) 6.74-6.99 (m, 3 H) 7.04-7.15 (m, 1 H) 7.19-7.25 (m, 1 H) 7.92-8.03 (m, 1 H) 8.27-8.34 (m, 1 H).

Example 23(3)

ethyl 6-[9-(3-fluorobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoate TLC: Rf 0.29 (hexane:ethyl acetate=2:1);
$^1$H-NMR (CDCl$_3$): δ 0.94-1.11 (m, 6 H) 1.22-1.31 (m, 3 H) 1.37-1.51 (m, 6 H) 1.58-1.79 (m, 2 H) 2.14-2.26 (m, 2 H) 2.30-2.53 (m, 2 H) 3.45-3.67 (m, 2 H) 4.14 (q, J=7.50 Hz, 2 H) 4.55-4.69 (m, 2 H) 5.40-5.62 (m, 2 H) 6.74-7.01 (m, 3 H) 7.03-7.13 (m, 1 H) 7.21-7.26 (m, 1 H) 7.91-8.02 (m, 1 H) 8.26-8.34 (m, 1 H).

Example 23(4)

6-(9'-benzyl-8',9'-dihydrospiro[cyclopropane-1,5'-pyrido[4',3':4,5]pyrrolo[2,3-b]pyridin]-7'(6'H)-yl)-6-oxohexanoic acid TLC: Rf 0.26 (ethyl acetate);
$^1$H-NMR (CDCl$_3$): δ 0.85-1.02 (m, 2 H) 1.29-1.45 (m, 2 H) 1.46-1.82 (m, 4 H) 2.07-2.49 (m, 4 H) 3.47-3.74 (m, 2 H) 4.45-4.79 (m, 2 H) 5.43-5.54 (m, 2 H) 6.93-7.39 (m, 6 H) 7.54-7.66 (m, 1 H) 8.22-8.31 (m, 1 H).

Example 23(5)

methyl 6-(9'-benzyl-8',9'-dihydrospiro[cyclopropane-1,5'-pyrido[4',3':4,5]pyrrolo[2,3-b]pyridin]-7'(6'H)-yl)-6-oxohexanoate TLC: Rf 0.34 (hexane:ethyl acetate=1:1);
$^1$H-NMR (CDCl$_3$): δ 0.86-1.01 (m, 2 H) 1.28-1.45 (m, 2 H) 1.61-1.77 (m, 4 H) 2.05-2.48 (m, 4 H) 3.46-3.74 (m, 2 H) 3.66 (s, 3 H) 4.44-4.77 (m, 2 H) 5.43-5.55 (m, 2 H) 6.91-7.37 (m, 6 H) 7.52-7.66 (m, 1 H) 8.20-8.31 (m, 1 H).

Example 23(6)

methyl 6-(9-benzyl-6,6-dimethyl-5,6,8,9-tetrahydro-7H-pyrido[4',3':4,5]pyrrolo[2,3-b]pyridin-7-yl)-6-oxohexanoate TLC: Rf 0.52 (hexane:ethyl acetate=1:1);
$^1$H-NMR (CDCl$_3$): δ 1.41-1.65 (m, 4 H) 1.55 (s, 6 H) 2.00 (t, J=7.00 Hz, 2 H) 2.26 (t, J=7.00 Hz, 2 H) 2.83 (s, 2 H) 3.66 (s, 3 H) 4.35 (s, 2 H) 5.51 (s, 2 H) 7.00-7.12 (m, 3 H) 7.19-7.34 (m, 3 H) 7.77-7.82 (m, 1 H) 8.27-8.34 (m, 1 H).

Example 23(7)

methyl 6-(9-benzyl-6-methyl-5,6,8,9-tetrahydro-7H-pyrido[4',3':4,5]pyrrolo[2,3-b]pyridin-7-yl)-6-oxohexanoate TLC: Rf 0.27 (hexane:ethyl acetate=1:1);
$^1$H-NMR (CDCl$_3$): δ 1.03-1.25 (m, 3 H) 1.61-1.78 (m, 4 H) 2.02-3.14 (m, 7 H) 3.66 (s, 3 H) 3.75-4.60 (m, 2 H) 5.32-5.74 (m, 2 H) 7.00-7.36 (m, 6 H) 7.73-7.86 (m, 1 H) 8.24-8.36 (m, 1 H).

Example 23(8)

6-(9-benzyl-6-methyl-5,6,8,9-tetrahydro-7H-pyrido[4',3':4,5]pyrrolo[2,3-b]pyridin-7-yl)-6-oxohexanoic acid TLC: Rf 0.33 (ethyl acetate);
$^1$H-NMR (CDCl$_3$): δ 1.06-1.22 (m, 3 H) 1.50-1.81 (m, 2 H) 2.23-3.15 (m, 5 H) 3.70-4.64 (m, 4 H) 5.24-5.74 (m, 4 H) 6.98-7.35 (m, 6 H) 7.73-7.86 (m, 1 H) 8.26-8.36 (m, 1 H).

Example 23(9)

6-[9-(4-cyanobenzyl)-5,5-dimethyl-5,6,8,9-tetrahydro-7H-pyrido[4',3':4,5]pyrrolo[2,3-b]pyridin-7-yl]-2,2-dimethyl-6-oxohexanoic acid TLC: Rf 0.45 (methylene chloride:ethyl acetate:methanol=8:4:1);
$^1$H-NMR (DMSO-d$_6$): δ 0.92-1.15 (m, 6 H), 1.20-1.55 (m, 10 H), 2.25-2.50 (m, 2 H), 3.40-3.60 (m, 2 H), 4.45-4.65 (m, 2 H), 5.45-5.65 (m, 2 H), 7.08 (dd, J=4.8, 7.8 Hz, 1 H), 7.18-7.33 (m, 2 H), 7.77 (d, J=8.1 Hz, 2 H), 8.08 (d, J=7.8 Hz, 1 H), 8.17 (d, J=4.8 Hz, 1 H), 12.03 (s, 1 H).

Example 23(10)

6-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2,2-dimethyl-6-oxohexanoic acid TLC: Rf 0.35 (methylene chloride:ethyl acetate:methanol=8:4:1);
$^1$H-NMR (DMSO-d$_6$): δ 0.95-1.15 (m, 6 H), 1.20-1.40 (m, 6 H), 1.40-1.60 (m, 4 H), 2.25-2.60 (m, 8 H), 3.35-3.55 (m, 2 H), 4.69 (s, 2 H), 5.40-5.65 (m, 2 H), 7.07 (dd, J=7.8, 4.8 Hz, 1 H), 8.04 (d, J=7.8 Hz, 1 H), 8.21 (d, J=4.8 Hz, 1 H), 12.05 (s, 1 H).

Example 23(11)

6-[9-(4-cyanobenzyl)-5,5-dimethyl-5,6,8,9-tetrahydro-7H-pyrido[4',3':4,5]pyrrolo[2,3-b]pyridin-7-yl]-3,3-dimethyl-6-oxohexanoic acid TLC: Rf 0.44 (chloroform:methanol=10:1);
MS (FAB, Pos.): m/z=473 (M+H)$^+$.

Example 23(12)

6-{9-[(6-chloro-3-pyridinyl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid TLC: Rf 0.41 (chloroform:methanol=10:1);
MS (FAB, Pos.): m/z=483 (M+H)$^+$.

Example 23(13)

6-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid TLC: Rf 0.38 (chloroform:methanol=10:1);
MS (FAB, Pos.): m/z=466 (M+H)$^+$.

Example 23(14)

6-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-3,3-dimethyl-6-oxohexanoic acid TLC:Rf 0.44 (chloroform:methanol=10:1);
MS (FAB, Pos.) : m/z=483 (M+H)$^+$.

Example 24 ethyl 5-((chlorocarbonyl)oxy)pentanoate

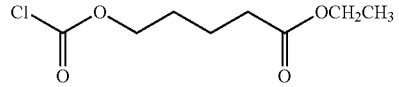 [SMILES: CCOC(=O)CCCCOC(=O)Cl]

Ethyl 5-hydroxypentanoate (1.12 g, 7.66 mmol) was dissolved in 25 mL of methylene chloride, triphosgene (772 mg, 0.34 equivalent), and pyridine (0.743 mL, 1.2 equivalent) were sequentially added while stirred at 0° C., and the mixture was stirred at room temperature for 1 hour. After completion of the reaction, water was added, and extraction operation (methylene chloride) was performed. The separated organic layer was washed using an aqueous saturated sodium chloride solution, and dried with magnesium sulfate, and the solvent was distilled off under reduced pressure to obtain the crude product. This was purified by column chromatography (ethyl acetate:n-hexane=1:10) to obtain the title compound (972 mg) having the following physical property values.

TLC: Rf 0.29 (ethyl acetate:n-hexane=1:10);
$^1$H-NMR (CDCl$_3$): δ 1.22-1.29 (m, 3 H) 1.65-1.84 (m, 4 H) 2.32-2.38 (m, 2 H) 4.10-4.18 (m, 2 H) 4.29-4.36 (m, 2 H).

Example 25

5-ethoxy-5-oxypentyl 9-(3-Fluorbenzyl)-5,6,8,9-tetrahydro-7H-pyrido[4',3':4,5]pyrrolo[2,3-b]pyridine-7-carboxylate

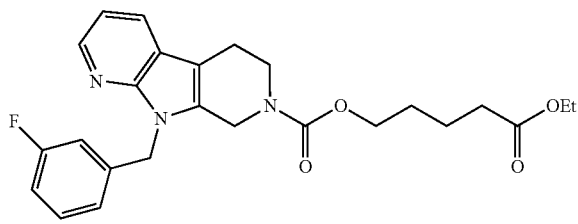 [SMILES: CCOC(=O)CCCCOC(=O)N1CCc2c(n(Cc3cccc(F)c3)c3ncccc23)C1]

9-(3-Fluorobenzyl)-6,7,8,9-tetrahydro-5H-pyrido[4',3':4,5]pyrrolo[2,3-b]pyridine dihydrochloride (100 mg, 0.28 mmol) produced by operation in accordance with Example 4→Example 5→Example 6→Example 7→Example 1 was dissolved in 2.8 mL of methylene chloride, pyridine (0.136 mL, 6.0 equivalent) and the compound (175 mg, 3.0 equivalent) produced in Example 24 were sequentially added while stirred at room temperature, and the mixture was stirred at room temperature for 1 hour. After completion of the reaction, water was added, and extraction operation (methylene chloride) was performed. The separated organic layer was washed using an aqueous saturated sodium chloride solution, dried with magnesium sulfate, and the solvent was distilled off under reduced pressure to obtain the crude product. This was purified by column chromatography (ethyl acetate:n-hexane; 12%→33%→45%) to obtain the title compound (111 mg) having the following physical property values.

TLC: Rf 0.66 (ethyl acetate:n-hexane=1:1);
$^1$H-NMR (CDCl$_3$): δ 1.21-1.28 (m, 3 H) 1.60-1.78 (m, 4 H) 2.31-2.38 (m, 2 H) 2.77-2.86 (m, 2 H) 3.62-3.84 (m, 2 H) 4.06-4.18 (m, 4 H) 4.49-4.56 (m, 2 H) 5.41-5.46 (m, 2 H) 6.72-6.97 (m, 3 H) 7.05-7.11 (m, 1 H) 7.20-7.29 (m, 1 H) 7.78-7.83 (m, 1 H) 8.28-8.31 (m, 1 H).

Example 26

5-({[9-(3-fluorobenzyl)-5,6,8,9-tetrahydro-7H-pyrido[4',3':4,5]pyrrolo[2,3-b]pyridin-7-yl]carbonyl}oxy)pentanoic acid

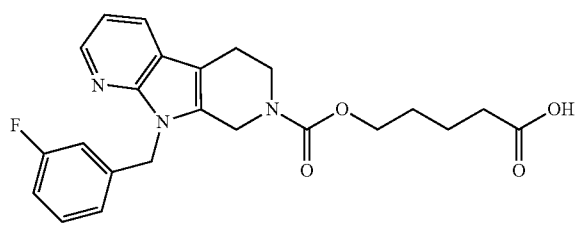 [SMILES: O=C(O)CCCCOC(=O)N1CCc2c(n(Cc3cccc(F)c3)c3ncccc23)C1]

The compound produced in Example 25 was used, which was subjected to operation in accordance with Example 3 to obtain the title compound having the following physical property values.

TLC: Rf 0.46 (chloroform:methanol=10:1);
$^1$H-NMR (DMSO-d$_6$): δ 1.37-1.66 (m, 4 H), 2.13-2.31 (m, 2 H), 2.66-2.80 (m, 2 H), 3.65-3.76 (m, 2 H), 3.90-4.10 (m, 2 H), 4.56 (s, 2 H), 5.47 (s, 2 H), 6.86-7.16 (m, 4 H), 7.27-7.40 (m, 1 H), 7.85-7.96 (m, 1 H), 8.15-8.26 (m, 1 H), 12.03 (s, 1 H).

Example 26(1)-Example 26(2)

A corresponding ester in place of ethyl 5-((chlorocarbonyl)oxy) pentanoate was used, which was subjected to operation in accordance with Example 25→Example 26 to obtain the following compounds.

Example 26(1)

5-({[9-(3-fluorobenzyl)-5,6,8,9-tetrahydro-7H-pyrido[4',3':4,5]pyrrolo[2,3-b]pyridin-7-yl]carbonyl}oxy)-2,2-dimethylpentanoic acid TLC: Rf 0.51 (chloroform:methanol=10:1);
$^1$H-NMR (CDCl$_3$): δ 1.07-1.36 (m, 6 H), 1.49-1.74 (m, 4 H), 2.73-2.88 (m, 2 H), 3.68-3.86 (m, 2 H), 3.99-4.18 (m, 2 H), 4.44-4.59 (m, 2 H), 5.44 (s, 2 H), 6.70-7.00 (m, 3 H), 7.04-7.13 (m, 1 H), 7.16-7.31 (m, 1 H), 7.74-7.87 (m, 1 H), 8.25-8.35 (m, 1 H).

Example 26(2)

4-({[9-(3-fluorobenzyl)-5,6,8,9-tetrahydro-7H-pyrido[4',3':4,5]pyrrolo[2,3-b]pyridin-7-yl]carbonyl}oxy)-2,2-dimethylbutanoic acid TLC: Rf 0.50 (chloroform:methanol=10:1);
$^1$H-NMR (CDCl$_3$): δ 1.08-1.36 (m, 6 H), 1.85-2.07 (m, 2 H), 2.60-2.81 (m, 2 H), 3.58-3.85 (m, 2 H), 4.17-4.32 (m, 2 H), 4.39-4.61 (m, 2 H), 5.26-5.61 (m, 2 H), 6.64-7.09 (m, 4 H), 7.14-7.28 (m, 1 H), 7.55-7.70 (m, 1 H), 8.04-8.40 (m, 1 H).

Example 27 methyl 5-({[9-(3-fluorobenzyl)-5,6,8,9-tetrahydro-7H-pyrido[4',3':4,5]pyrrolo[2,3-b]pyridin-7-yl]carbonyl}amino)-2,2-dimethylpentanoate

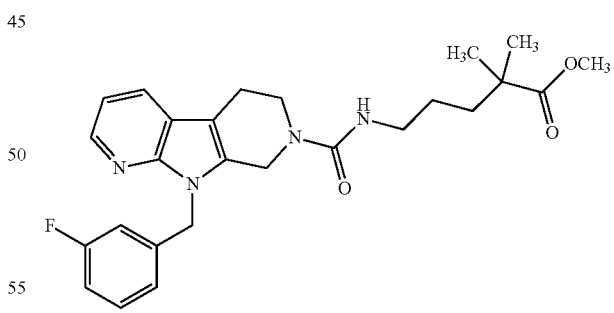

The compound (211 mg, 1.12 mmol) produced in Example 10 was dissolved in 1.2 mL of toluene, diphenylphosphoryl azide (0.241 mL, 1.12 mmol) and triethylamine (0.156 mL, 1.12 mmol) were sequentially added while stirred at room temperature, and the mixture was stirred at 120° C. for 2 hours, and allowed to cool to room temperature (this is defined as solution A). On the other hand, 9-(3-fluorobenzyl)-6,7,8,9-tetrahydro-5H-pyrido[4',3':4,5]pyrrolo[2,3-b]pyridine dihydrochloride (200 mg, 0.56 mmol) produced by operation in accordance with Example 1 and pyridine (0.234 mL, 1.68 mmol) were dissolved in 2.8 mL of methylene chloride, the solution A was added while stirred at room temperature, and the mixture was stirred at room temperature for 1 hour. To this reaction solution was added an aqueous saturated sodium bicarbonate solution, and extraction operation (ethyl acetate) was performed. After the separated organic layer was dried with sodium sulfate, the solvent was distilled off under reduced pressure to obtain the crude product. This was purified by column chromatography (ethyl acetate:n-hexane; 50%→70%) to obtain the title compound (256 mg) having the following physical property values.

TLC: Rf 0.55 (methanol:chloroform=1:10);
$^1$H-NMR (CDCl$_3$): δ 1.18 (s, 6 H) 1.23-1.58 (m, 4 H) 2.79-2.90 (m, 2 H) 3.15-3.28 (m, 2 H) 3.58-3.74 (m, 5 H) 4.51 (s, 2 H) 4.66-4.78 (m, 1 H) 5.46 (s, 2 H) 6.74-6.84 (m, 1 H) 6.86-6.99 (m, 2 H) 7.04-7.13 (m, 1 H) 7.18-7.28 (m, 1 H) 7.75-7.85 (m, 1 H) 8.25-8.33 (m, 1 H).

Example 28

5-({[9-(3-fluorobenzyl)-5,6,8,9-tetrahydro-7H-pyrido[4',3':4,5]pyrrolo[2,3-b]pyridin-7-yl]carbonyl}amino)-2,2-dimethylpentanoic acid

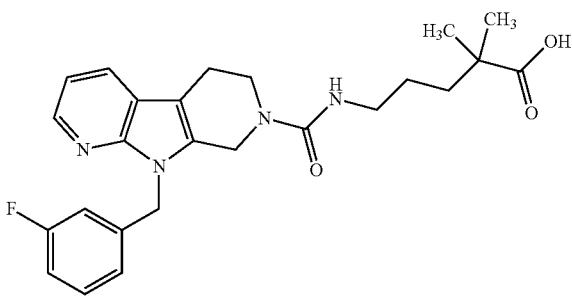 [SMILES: CC(C)(CCCNC(=O)N1CCc2c(n(Cc3cccc(F)c3)c3ncccc23)C1)C(=O)O]

The compound produced in Example 27 was used, which was subjected to operation in accordance with Example 3 to obtain the title compound (68 mg) having the following physical property values.

TLC: Rf 0.29 (chloroform:methanol=10:1);
$^1$H-NMR (DMSO-d$_6$): δ 1.05 (s, 6 H) 1.25-1.48 (m, 4 H) 2.64-2.76 (m, 2 H) 2.92-3.07 (m, 2 H) 3.57-3.72 (m, 2 H) 4.51 (s, 2 H) 5.44 (s, 2 H) 6.66-6.77 (m, 1 H) 6.87-7.16 (m, 4 H) 7.26-7.42 (m, 1 H) 7.84-7.94 (m, 1 H) 8.14-8.26 (m, 1 H) 12.04 (s, 1 H).

Example 28(1)

A corresponding ester in place of the compound produced in Example 10 was used, which was subjected to operation in accordance with Example 27→Example 28 to obtain the following compound.

Example 28(1)

4-({[9-(3-fluorobenzyl)-5,6,8,9-tetrahydro-7H-pyrido[4',3':4,5]pyrrolo[2,3-b]pyridin-7-yl]carbonyl}amino)-2,2-dimethylbutanoic acid TLC: Rf 0.48 (chloroform:methanol=10:1);
$^1$H-NMR (DMSO-d$_6$): δ 1.10 (s, 6 H) 1.55-1.69 (m, 2 H) 2.63-2.77 (m, 2 H) 2.95-3.10 (m, 2 H) 3.57-3.68 (m, 2 H) 4.50 (s, 2 H) 5.43 (s, 2 H) 6.58-6.68 (m, 1 H) 6.88-7.15 (m, 4 H) 7.28-7.40 (m, 1 H) 7.84-7.93 (m, 1 H) 8.15-8.23 (m, 1 H) 12.13 (s, 1 H).

Example 29 methyl cis-4-(diazoacetyl)cyclohexanecarboxylate

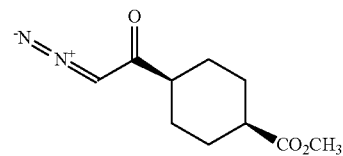

To an ethyl acetate solution (5.0 mL) of cis-4-(methoxycarbonyl)cyclohexanecarboxylic acid (5.89 g) was added thionyl chloride (4.6 mL), and the mixture was stirred at 60° C. for 6 hours. After cooled to room temperature, the reaction was concentrated, and azeotroped with toluene. A THF:acetonitrile (1:1) solution (26 mL) of the resulting oil was added to a 2.0 M solution (100 mL) of trimethylsilyldiazomethane (32 mL) in a mixture of THF:acetonitrile (1:1), and the mixture was stirred at room temperature overnight. After acetic acid (5 mL) and water (20 mL) were added, THF and acetonitrile were distilled off, and an aqueous saturated sodium bicarbonate solution was added. This was extracted with ethyl acetate, and the organic layer was washed with an aqueous saturated sodium chloride solution, dried with anhydrous sodium sulfate, and concentrated. The resulting residue was isolation-purified by column chromatography (hexane:ethyl acetate=80:20→65:35→50:50) to obtain the title compound (5.16 g) having the following physical property values.

TLC: 0.33 (ethyl acetate);
$^1$H-NMR (CDCl$_3$): δ 1.52-1.79 (m, 6 H) 2.00-2.16 (m, 2 H) 2.26-2.42 (m, 1 H) 2.56 (quin, J=4.94 Hz, 1 H) 3.69 (s, 3 H) 5.30 (s, 1 H).

Example 30

[cis-4-(methoxycarbonyl)cyclohexyl]acetic acid

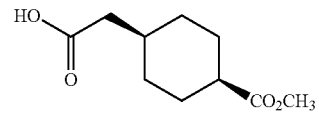

A solution (41 mL) of the compound (6.06 g) produced in Example 29 in a mixture of THF:water (10:1) was added dropwise to a solution (80 mL) of silver trifluoroacetate (318 mg) and triethylamine (12.1 mL) in a mixture of THF:water (10:1) at room temperature over 1 hour, and the mixture was stirred at room temperature overnight. After THF was distilled off, t-butyl methyl ether (120 mL) was added, and this was filtered with Celite, and extracted with an aqueous saturated sodium bicarbonate solution (350 mL). The aqueous phase was separated, and 5N hydrochloric acid (65 mL) was added, followed by extraction with ethyl acetate. The organic layer was washed with an aqueous saturated sodium chloride solution, dried with anhydrous sodium sulfate, and concentrated to obtain the title compound (3.75 g) having the following physical property values.

TLC: Rf 0.70 (ethyl acetate);
$^1$H-NMR (CDCl$_3$): δ 1.25-1.40 (m, 2 H) 1.50-1.74 (m, 4 H) 1.87-2.07 (m, 3 H) 2.30 (d, J=7.32 Hz, 2 H) 2.57 (quin, J=5.03 Hz, 1 H) 3.69 (s, 3 H).

Example 31 cis-4-{2-[9-(4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid

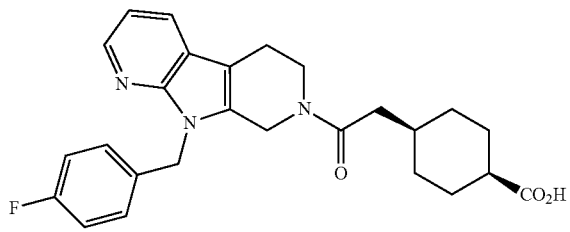 [SMILES: O=C(C[C@H]1CC[C@@H](C(=O)O)CC1)N1CCc2c(n(Cc3ccc(F)cc3)c3ncccc23)C1]

The compound produced in Example 30 and a tetrahydropyridopyrrolopyridine derivative produced by operation in accordance with Example 4→Example 5→Example 6→Example 7→Example 1 were used, which were subjected to operation in accordance with Example 11 and Example 3 to obtain the title compound (53 mg) having the following physical property values.

TLC: Rf 0.34 (ethyl acetate:methanol=19:1);
$^1$H-NMR (DMSO-d$_6$): δ 1.04-1.29 (m, 2 H) 1.32-1.63 (m, 4 H) 1.65-1.96 (m, 3 H) 2.13-2.47 (m, 3 H) 2.62-2.85 (m, 2 H) 3.70-3.84 (m, 2 H) 4.64 (s, 2 H) 5.39-5.54 (m, 2 H) 7.02-7.30 (m, 5 H) 7.81-7.94 (m, 1 H) 8.16-8.28 (m, 1 H) 12.04 (s, 1 H).

Example 31(1)-Example 31(198)

A corresponding ester in place of cis-4-(methoxycarbonyl)cyclohexanecarboxylic acid, and corresponding halide in place of 4-fluorobenzyl chloride were used, which were subjected to operation in accordance with Example 29→Example 30→Example 31 to obtain the following compounds.

Example 31(1)

cis-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid

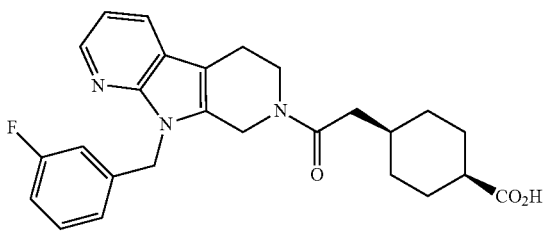 [SMILES: O=C(C[C@H]1CC[C@@H](C(=O)O)CC1)N1CCc2c(n(Cc3cccc(F)c3)c3ncccc23)C1]

TLC: Rf 0.49 (methylene chloride:ethyl acetate:methanol=8:4:1);
$^1$H-NMR (DMSO-d$_6$): δ 1.10-1.31 (m, 2 H), 1.34-1.60 (m, 4 H), 1.63-1.96 (m, 3 H), 2.11-2.45 (m, 3 H), 2.61-2.84 (m, 2 H), 3.68-3.87 (m, 2 H), 4.63 (s, 2 H), 5.42-5.57 (m, 2 H), 6.85-7.15 (m, 4 H), 7.26-7.40 (m, 1 H), 7.84-7.96 (m, 1 H), 8.16-8.26 (m, 1 H), 12.03 (s, 1 H).

Example 31(2)

trans-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.45 (methylene chloride:ethyl acetate:methanol=8:4:1);
$^1$H-NMR (DMSO-d$_6$): δ 0.73-1.37 (m, 4 H), 1.45-1.92 (m, 5 H), 1.94-2.36 (m, 3 H), 2.62-2.85 (m, 2 H), 3.69-3.85 (m, 2 H), 4.64 (s, 2 H), 5.43-5.56 (m, 2 H), 6.85-7.17 (m, 4 H), 7.27-7.41 (m, 1 H), 7.85-7.95 (m, 1 H), 8.16-8.26 (m, 1 H), 11.97 (s, 1 H).

Example 31(3)

cis-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.39 (ethyl acetate:methanol=19:1);
$^1$H-NMR (DMSO-d$_6$): δ 1.08-1.31 (m, 2 H) 1.35-1.61 (m, 4 H) 1.69-1.96 (m, 3 H) 2.16-2.46 (m, 3 H) 2.62-2.86 (m, 2 H) 3.69-3.87 (m, 2 H) 4.60-4.73 (m, 2 H) 5.41-5.58 (m, 2 H) 6.86-7.04 (m, 2 H) 7.05-7.16 (m, 1 H) 7.21-7.36 (m, 1 H) 7.83-7.96 (m, 1 H) 8.16-8.26 (m, 1 H) 12.04 (s, 1 H).

Example 31(4)

cis-4-{2-oxo-2-[9-(3,4,5-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.37 (ethyl acetate:methanol=19:1);
$^1$H-NMR (DMSO-d$_6$): δ 1.08-1.29 (m, 2 H) 1.34-1.63 (m, 4 H) 1.70-1.96 (m, 3 H) 2.22-2.46 (m, 3 H) 2.63-2.83 (m, 2 H) 3.70-3.87 (m, 2 H) 4.61-4.75 (m, 2 H) 5.38-5.54 (m, 2 H) 6.95-7.20 (m, 3 H) 7.85-7.97 (m, 1 H) 8.17-8.27 (m, 1 H) 12.03 (br s, 1 H).

Example 31(5)

cis-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.34 (ethyl acetate:methanol=19:1);
$^1$H-NMR (DMSO-d$_6$): δ 1.05-1.29 (m, 2 H) 1.33-1.61 (m, 4 H) 1.68-1.94 (m, 3 H) 2.14-2.47 (m, 3 H) 2.63-2.84 (m, 2 H) 3.70-3.84 (m, 2 H) 4.58-4.68 (m, 2 H) 5.41-5.54 (m, 2 H) 7.05-7.23 (m, 3 H) 7.30-7.41 (m, 2 H) 7.85-7.95 (m, 1 H) 8.18-8.25 (m, 1 H) 12.04 (s, 1 H).

Example 31(6)

cis-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.49 (ethyl acetate:methanol=19:1);
$^1$H-NMR (DMSO-d$_6$): δ 1.07-1.30 (m, 2 H) 1.35-1.62 (m, 4 H) 1.71-1.96 (m, 3 H) 2.21-2.47 (m, 3 H) 2.62-2.84 (m, 2 H) 3.71-3.86 (m, 2 H) 4.63-4.79 (m, 2 H) 5.37-5.57 (m, 2 H)

6.93-7.06 (m, 1 H) 7.07-7.17 (m, 1 H) 7.52-7.70 (m, 1 H) 7.86-7.96 (m, 1 H) 8.15-8.25 (m, 1 H) 12.04 (s, 1 H).

Example 31(7)

cis-4-{2-[9-(4-chloro-2-fluorobenzyl)-5,6,8,9-tetrahydro-7H-pyrido[4',3':4,5]pyrrolo[2,3-b]pyridin-7-yl]-2-oxoethoxy}cyclohexanecarboxylic acid TLC: Rf 0.53 (ethyl acetate:methanol=19:1);
$^1$H-NMR (DMSO-$d_6$): δ 1.09-1.30 (m, 2 H) 1.37-1.61 (m, 4 H) 1.74-1.94 (m, 3 H) 2.18-2.47 (m, 3 H) 2.65-2.84 (m, 2 H) 3.72-3.86 (m, 2 H) 4.61-4.71 (m, 2 H) 5.44-5.56 (m, 2 H) 6.81-6.91 (m, 1 H) 7.07-7.14 (m, 1 H) 7.15-7.23 (m, 1 H) 7.43-7.53 (m, 1 H) 7.87-7.94 (m, 1 H) 8.17-8.23 (m, 1 H) 12.04 (s, 1 H).

Example 31(9)

cis-4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethoxy}cyclohexanecarboxylic acid TLC: Rf 0.47 (ethyl acetate:methanol=19:1);
$^1$H-NMR (DMSO-$d_6$): δ 1.10-1.30 (m, 2 H) 1.35-1.64 (m, 4 H) 1.68-1.95 (m, 3 H) 2.22-2.47 (m, 3 H) 2.63-2.83 (m, 2 H) 3.72-3.85 (m, 2 H) 4.58-4.72 (m, 2 H) 5.46-5.60 (m, 2 H) 6.84-6.99 (m, 1 H) 7.07-7.15 (m, 1 H) 7.16-7.28 (m, 1 H) 7.86-7.95 (m, 1 H) 8.16-8.24 (m, 1 H) 12.04 (s, 1 H).

Example 31(10)

cis-4-{2-[9-(4-chloro-3-fluorobenzyl)-5,6,8,9-tetrahydro-7H-Pyrido[4',3':4,5]pyrrolo[2,3-b]pyridin-7-yl]-2-oxoethyl}cyclohexanecarboxylic acid TLC: Rf 0.43 (methylene chloride:ethyl acetate:methanol=8:4:1);
MS (ESI, Pos. 20 V): m/z=484 (M+H)$^+$.

Example 31(13)

cis-4-{2-[9-(3,5-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.43 (methylene chloride:ethyl acetate:methanol=8:4:1);
MS (ESI, Pos. 20 V): m/z=500 (M+H)$^+$.

Example 31(14)

cis-4-{2-[9-(4-cyanobenzyl)-1,3,4,9-tetrahydro-2H-beta-carbolin-2-yl]-2-oxoethyl}cyclohexanecarboxylic acid TLC: Rf 0.48 (methylene chloride:ethyl acetate:methanol=8:4:1);
$^1$H-NMR (DMSO-$d_6$): δ 1.05-1.31 (m, 2 H) 1.33-1.63 (m, 4 H) 1.66-1.96 (m, 3 H) 2.14-2.47 (m, 3 H) 2.64-2.85 (m, 2 H) 3.70-3.85 (m, 2 H) 4.57-4.67 (m, 2 H) 5.46-5.58 (m, 2 H) 6.98-7.22 (m, 4 H) 7.32-7.42 (m, 1 H) 7.44-7.51 (m, 1 H) 7.72-7.82 (m, 2 H) 12.04 (s, 1 H).

Example 31(15)

cis-4-(2-{9-[(6-chloro-3-pyridinyl)methyl]-1,3,4,9-tetrahydro-2H-beta-carbolin-2-yl}-2-oxoethyl)cyclohexanecarboxylic acid TLC: Rf 0.44 (methylene chloride:ethyl acetate:methanol=8:4:1);
$^1$H-NMR (DMSO-$d_6$): δ 1.07-1.30 (m, 2 H) 1.34-1.61 (m, 4 H) 1.72-1.95 (m, 3 H) 2.21-2.47 (m, 3 H) 2.62-2.84 (m, 2 H) 3.72-3.87 (m, 2 H) 4.63-4.75 (m, 2 H) 5.41-5.51 (m, 2 H) 6.98-7.16 (m, 2 H) 7.35-7.51 (m, 4 H) 8.14-8.28 (m, 1 H) 12.04 (br s, 1 H).

Example 31(17)

cis-4-(2-{9-[(1,3-dimethyl-1H-pyrazol-5-yl)methyl]-1,3,4,9-tetrahydro-2H-beta-carbolin-2-yl}-2-oxoethyl)cyclohexanecarboxylic acid TLC: Rf 0.31 (methylene chloride:ethyl acetate:methanol=8:4:1);
$^1$H-NMR (DMSO-$d_6$): δ 1.09-1.31 (m, 2 H) 1.34-1.61 (m, 4 H) 1.70-1.93 (m, 3 H) 1.93-2.04 (m, 3 H) 2.18-2.47 (m, 3 H) 2.61-2.82 (m, 2 H) 3.61-3.84 (m, 5 H) 4.57-4.70 (m, 2 H) 5.26-5.48 (m, 3 H) 6.93-7.15 (m, 2 H) 7.35-7.49 (m, 2 H) 12.03 (br s, 1 H).

Example 31(18)

cis-4-(2-{9-[(2,5-dimethyl-1,3-thiazol-4-yl)methyl]-1,3,4,9-tetrahydro-2H-beta-carbolin-2-yl}-2-oxoethyl)cyclohexanecarboxylic acid

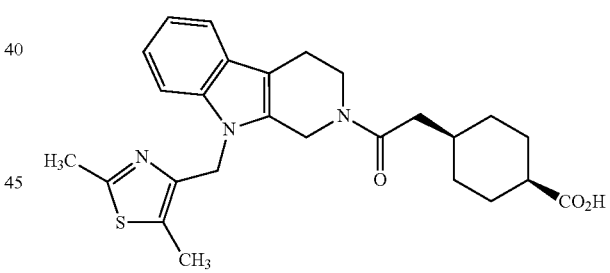

TLC: Rf 0.36 (methylene chloride:ethyl acetate:methanol=8:4:1);
$^1$H-NMR (DMSO-$d_6$): δ 1.08-1.32 (m, 2 H) 1.36-1.64 (m, 4 H) 1.69-1.97 (m, 3 H) 2.21-2.47 (m, 9 H) 2.59-2.81 (m, 2 H) 3.66-3.83 (m, 2 H) 4.64-4.75 (m, 2 H) 5.41-5.56 (m, 2 H) 6.97-7.07 (m, 1 H) 7.07-7.18 (m, 1 H) 7.37-7.52 (m, 2 H) 12.04 (s, 1 H).

Example 31(21)

cis-4-(2-{9-[(4-chloro-2-thienyl)methyl]-5,6,8,9-tetrahydro-7H-pyrido[4',3':4,5]pyrrolo[2,3-b]pyridin-7-yl}-2-oxoethoxy)cyclohexanecarboxylic acid TLC: Rf 0.38 (chloroform:methanol=10:1);
MS (FAB, Pos.): m/z=472 (M+H)$^+$.

Example 31(22)

cis-4-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.40 (chloroform:methanol=10:1);
MS (FAB, Pos.): m/z=466 (M+H)+.

Example 31(23)

trans-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.39 (methylene chloride:ethyl acetate:methanol=8:4:1);
$^1$H-NMR (DMSO-$d_6$): δ 0.81-1.09 (m, 2 H) 1.20-1.38 (m, 2 H) 1.53-1.94 (m, 5 H) 2.02-2.16 (m, 1 H) 2.20-2.39 (m, 2 H) 2.64-2.84 (m, 2 H) 3.70-3.87 (m, 2 H) 4.65-4.74 (m, 2 H) 5.41-5.54 (m, 2 H) 7.01 (ddd, J=10.79, 8.87, 7.04 Hz, 1 H) 7.11 (dd, J=7.78, 4.67 Hz, 1 H) 7.54-7.69 (m, 1 H) 7.87-7.95 (m, 1 H) 8.21 (dd, J=4.67, 1.37 Hz, 1 H) 11.98 (s, 1 H).

Example 31(24)

trans-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}cyclohexanecarboxylic acid

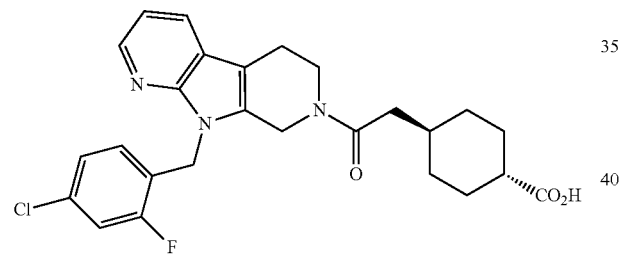

TLC: Rf 0.38 (methylene chloride:ethyl acetate:methanol=8:4:1);
$^1$H-NMR (DMSO-$d_6$): δ 0.77-1.10 (m, 2 H) 1.13-1.38 (m, 2 H) 1.48-1.94 (m, 5 H) 2.00-2.39 (m, 3 H) 2.62-2.86 (m, 2 H) 3.70-3.87 (m, 2 H) 4.61-4.72 (m, 2 H) 5.43-5.57 (m, 2 H) 6.78-6.91 (m, 1 H) 7.11 (dd, J=7.68, 4.76 Hz, 1 H) 7.16-7.23 (m, 1 H) 7.43-7.54 (m, 1 H) 7.86-7.96 (m, 1 H) 8.20 (dd, J=4.76, 1.46 Hz, 1 H) 11.98 (s, 1 H).

Example 31(26)

trans-4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethoxy}cyclohexanecarboxylic acid TLC: Rf 0.38 (methylene chloride:ethyl acetate:methanol=8:4:1);
$^1$H-NMR (DMSO-$d_6$): δ 0.77-1.11 (m, 2 H) 1.12-1.42 (m, 2 H) 1.54-1.93 (m, 5 H) 2.01-2.18 (m, 1 H) 2.18-2.40 (m, 2 H) 2.61-2.88 (m, 2 H) 3.68-3.87 (m, 2 H) 4.60-4.74 (m, 2 H) 5.44-5.63 (m, 2 H) 6.84-7.01 (m, 1 H) 7.11 (dd, J=7.87, 4.76 Hz, 1 H) 7.22 (td, J=8.83, 1.74 Hz, 1 H) 7.85-7.96 (m, 1 H) 8.15-8.25 (m, 1 H) 11.98 (s, 1 H).

Example 31(27)

trans-4-{2-[9-(4-chloro-3-fluorobenzyl)-5,6,8,9-tetrahydro-7H-pyrido[4',3':4,5]pyrrolo[2,3-b]pyridin-7-yl]-2-oxoethoxy}cyclohexanecarboxylic acid TLC: Rf 0.57 (chloroform:methanol:water=50:10:1);
MS (ESI, Pos. 20 V): m/z=967 (2M+H)+, 484 (M+H)+.

Example 31(30)

trans-4-{2-[9-(3,5-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.57 (chloroform:methanol:water=50:10:1);
MS (ESI, Pos. 20 V): m/z=500 (M+H)+.

Example 31(31)

trans-4-{2-[9-(4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.34 (methylene chloride:ethyl acetate:methanol=8:4:1);
MS (ESI, Pos. 20 V): m/z=450 (M+H)+.

Example 31(32)

trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid

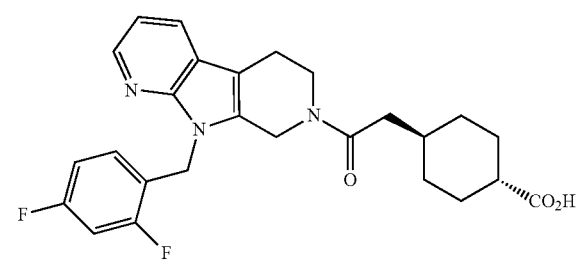 [SMILES: O=C(C[C@H]1CC[C@H](C(=O)O)CC1)N1CCc2c(n(Cc3ccc(F)cc3F)c3ncccc23)C1]

TLC: Rf 0.37 (methylene chloride:ethyl acetate:methanol=8:4:1);
$^1$H-NMR (DMSO-$d_6$): δ 0.75-1.37 (m, 4 H), 1.45-1.92 (m, 5 H), 1.92-2.38 (m, 3 H), 2.62-2.84 (m, 2 H), 3.68-3.84 (m, 2 H), 4.65 (s, 2 H), 5.38-5.56 (m, 2 H), 6.86-7.03 (m, 2 H), 7.10 (dd, J=7.8, 4.8 Hz), 7.21-7.36 (m, 1 H), 7.84-7.94 (m, 1 H), 8.20 (dd, J=4.8, 1.2 Hz, 1 H), 11.97 (s, 1 H).

Example 31(33)

trans-4-{2-oxo-2-[9-(3,4,5-trifluorobenzyl)-5,6,8,9-tetrahydro-7H-pyrido[4',3';4,5]pyrrolo[2,3-b]pyridin-7-yl]ethyl}cyclohexanecarboxylic acid TLC: Rf 0.34 (methylene chloride:ethyl acetate:methanol=8:4:1);
MS (ESI, Pos. 20 V): m/z=486 (M+H)+.

Example 31(34)

trans-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid

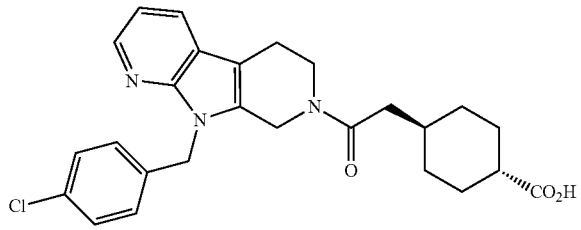 [SMILES: O=C(C[C@H]1CC[C@H](C(=O)O)CC1)N1CCc2c(n(Cc3ccc(Cl)cc3)c3ncccc23)C1]

TLC: Rf 0.36 (methylene chloride:ethyl acetate:methanol=8:4:1);
$^1$H-NMR (DMSO-$d_6$): δ 0.75-1.38 (m, 4 H), 1.40-1.92 (m, 5 H), 1.96-2.40 (m, 3 H), 2.63-2.84 (m, 2 H), 3.65-3.84 (m, 2 H), 4.62 (s, 2 H), 5.39-5.54 (m, 2 H), 7.04-7.23 (m, 3 H), 7.30-7.43 (m, 2 H), 7.89 (d, J=7.8 Hz, 1 H), 8.16-8.26 (m, 1 H), 11.96 (s, 1 H).

Example 31(36)

trans-4-(2-{9-[(4-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.40 (methylene chloride:ethyl acetate:methanol=8:4:1);
$^1$H-NMR (DMSO-$d_6$): δ 0.78-1.10 (m, 2 H) 1.12-1.39 (m, 2 H) 1.51-1.93 (m, 5 H) 2.00-2.18 (m, 1 H) 2.20-2.39 (m, 2 H) 2.60-2.83 (m, 2 H) 3.69-3.86 (m, 2 H) 4.70-4.82 (m, 2 H) 5.54-5.67 (m, 2 H) 7.02-7.18 (m, 2 H) 7.39-7.45 (m, 1 H) 7.85-7.94 (m, 1 H) 8.19-8.28 (m, 1 H) 11.98 (s, 1 H).

Example 31(37)

trans-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.41 (methylene chloride:ethyl acetate:methanol=8:4:1);
$^1$H-NMR (DMSO-$d_6$): δ 0.80-1.10 (m, 2 H) 1.13-1.39 (m, 2 H) 1.53-1.95 (m, 5 H) 2.00-2.18 (m, 1 H) 2.21-2.38 (m, 2 H) 2.60-2.81 (m, 2 H) 3.69-3.85 (m, 2 H) 4.72-4.81 (m, 2 H) 5.50-5.63 (m, 2 H) 6.90-7.05 (m, 2 H) 7.07-7.15 (m, 1 H) 7.84-7.92 (m, 1 H) 8.20-8.28 (m, 1 H) 11.97 (br s, 1 H).

Example 31(38)

trans-4-(2-{9-[(2,5-dimethyl-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.44 (methylene chloride:ethyl acetate:methanol=8:4:1);
$^1$H-NMR (DMSO-$d_6$): δ 0.75-1.09 (m, 2 H) 1.14-1.38 (m, 2 H) 1.47-1.93 (m, 5 H) 2.02-2.37 (m, 6 H) 2.38-2.46 (m, 3 H) 2.61-2.82 (m, 2 H) 3.68-3.83 (m, 2 H) 4.57-4.70 (m, 2 H) 5.21-5.34 (m, 2 H) 6.19-6.29 (m, 1 H) 7.04-7.15 (m, 1 H) 7.83-7.92 (m, 1 H) 8.19-8.28 (m, 1 H) 11.98 (s, 1 H).

Example 31(39)

cis-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.39 (methylene chloride:ethyl acetate:methanol=8:4:1);
$^1$H-NMR (DMSO-$d_6$): δ 1.09-1.31 (m, 2 H) 1.33-1.62 (m, 4 H) 1.65-1.96 (m, 3 H) 2.19-2.48 (m, 3 H) 2.61-2.81 (m, 2 H) 3.71-3.85 (m, 2 H) 4.66-4.75 (m, 2 H) 5.30-5.42 (m, 2 H) 6.89-6.96 (m, 1 H) 7.05-7.24 (m, 2 H) 7.85-7.92 (m, 1 H) 8.18-8.25 (m, 1 H) 12.04 (br s, 1 H).

Example 31(41)

cis-4-(2-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid TLC: Rf 0.19 (methylene chloride:ethyl acetate:methanol=8:4:1);
$^1$H-NMR (DMSO-$d_6$): δ 1.08-1.65 (m, 9 H) 1.70-2.07 (m, 6 H) 2.28-2.47 (m, 3 H) 3.47-3.58 (m, 2 H) 3.72-3.79 (m, 3 H) 4.62-4.71 (m, 2 H) 5.40-5.55 (m, 2 H) 5.56-5.74 (m, 1 H) 7.04-7.13 (m, 1 H) 8.02-8.11 (m, 1 H) 8.16-8.25 (m, 1 H) 12.04 (s, 1 H).

Example 31(42)

cis-4-(2-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid TLC: Rf 0.21 (methylene chloride:ethyl acetate:methanol=8:4:1);
$^1$H-NMR (DMSO-$d_6$): δ 1.07-1.65 (m, 9 H) 1.69-2.02 (m, 3 H) 2.30-2.50 (m, 9 H) 3.45-3.57 (m, 2 H) 4.64-4.75 (m, 2 H) 5.47-5.62 (m, 2 H) 7.03-7.14 (m, 1 H) 8.01-8.09 (m, 1 H) 8.18-8.26 (m, 1 H) 12.04 (br s, 1 H).

Example 31(44)

trans-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.39 (methylene chloride:ethyl acetate:methanol=8:4:1);
MS (ESI, Pos. 20 V): m/z=472 (M+H)$^+$.

Example 31(46)

cis-4-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.41 (chloroform:methanol:water=50:10:1);
MS (ESI, Pos. 20 V): m/z=504 (M+H)$^+$.

Example 31(47)

trans-4-{2-oxo-2-[9-(2,3,4,6-tetrafluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.41 (chloroform:methanol:water=50:10:1);
MS (ESI, Pos. 20 V): m/z=504 (M+H)$^+$.

Example 31(48)

cis-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethoxy)cyclohexanecarboxylic acid TLC: Rf 0.37 (methylene chloride:ethyl acetate:methanol=8:4:1);
$^1$H-NMR (DMSO-d$_6$): δ 1.09-1.32 (m, 2 H) 1.37-1.63 (m, 4 H) 1.71-1.95 (m, 3 H) 2.22-2.49 (m, 3 H) 2.59-2.82 (m, 2 H) 3.70-3.84 (m, 2 H) 4.68-4.83 (m, 2 H) 5.48-5.64 (m, 2 H) 6.90-7.05 (m, 2 H) 7.06-7.16 (m, 1 H) 7.83-7.92 (m, 1 H) 8.20-8.29 (m, 1 H) 12.04 (s, 1 H).

Example 31(50)

trans-4-{2-[9-(4-cyanobenzyl)-5,5-dimethyl-5,6,8,9-tetrahydro-7H-pyrido[4',3':4,5]pyrrolo[2,3-b]pyridin-7-yl]-2-oxoethyl}cyclohexanecarboxylic acid TLC: Rf 0.43 (chloroform:methanol=10:1);
MS (FAB, Pos.): m/z=485 (M+H)$^+$.

Example 31(51)

trans-4-(2-{9-[(6-chloro-3-pyridinyl)methyl]-5,5-dimethyl-5,6,8,9-tetrahydro-7H-pyrido[4',3':4,5]pyrrolo[2,3-b]pyridin-7-yl}-2-oxoethoxy)cyclohexanecarboxylic acid TLC: Rf 0.38 (chloroform:methanol=10:1);
MS (FAB, Pos.): m/z=495 (M+H)$^+$.

Example 31(52)

trans-4-(2-{9-[(1,3-dimethyl-1H-pyrazol-5-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid TLC: Rf 0.35 (chloroform:methanol=10:1);
MS (FAB, Pos.): m/z=478 (M+H)$^+$.

Example 31(53)

trans-4-(2-{9-[(2,5-dimethyl-1,3-thiazol-4-yl)methyl]-5,5-dimethyl-5,6,8,9-tetrahydro-7H-pyrido[4',3':4,5]pyrrolo[2,3-b]pyridin-7-yl}-2-oxoethyl)cyclohexanecarboxylic acid TLC: Rf 0.35 (chloroform:methanol=10:1);
MS (FAB, Pos.): m/z=495 (M+H)$^+$.

Example 31(54)

trans-4-{2-[9-(3,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.47 (chloroform:methanol:water=50:10:1);
MS (ESI, Pos. 20 V): m/z=468 (M+H)$^+$.

Example 31(55)

trans-4-{2-oxo-2-[9-(2,3,4-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.47 (chloroform:methanol:water=50:10:1);
MS (ESI, Pos. 20 V): m/z=468 (M+H)$^+$.

Example 31(56)

trans-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.47 (chloroform:methanol:water=50:10:1);
MS (ESI, Pos. 20 V): m/z=967 (2M+H)$^+$, 484 (M+H)$^+$.

Example 31(59)

cis-4-{2-[9-(3,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.54 (chloroform:methanol:water=50:10:1);
MS (ESI, Pos. 20 V): m/z=935 (2M+H)$^+$, 468 (M+H)$^+$.

Example 31(60)

cis-4-{2-oxo-2-[9-(2,3,4-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.54 (chloroform:methanol:water=50:10:1);
MS (ESI, Pos. 20 V): m/z=971 (2M+H)$^+$, 486 (M+H)$^+$.

Example 31(61)

cis-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.54 (chloroform:methanol:water=50:10:1);
MS (ESI, Pos. 20 V): m/z=967 (2M+H)$^+$, 484 (M+H)$^+$.

Example 31(62)

cis-4-{2-[9-(3,4-dichlorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.54 (chloroform:methanol:water=50:10:1);
MS (ESI, Pos. 20 V): m/z=999 (2M+H)$^+$, 500 (M+H)$^+$.

Example 31(63)

trans-4-{2-[9-(3,5-difluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.39 (chloroform:methanol:water=50:10:1);
MS (ESI, Pos. 20 V): m/z=468 (M+H)$^+$.

Example 31(64)

trans-4-{2-[9-(3-chloro-5-fluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.39 (chloroform:methanol:water=50:10:1);
MS (ESI, Pos. 20 V): m/z=484 (M+H)$^+$.

Example 31(65)

cis-4-{2-[9-(3,5-difluorobenzyl)-5,6,8,9-tetrahydro-7H-pyrido[4',3':4,5]pyrrolo[2,3-b]pyridin-7-yl]-2-oxoethyl}cyclohexanecarboxylic acid TLC: Rf 0.39 (chloroform:methanol:water=50:10:1);
MS (ESI, Pos. 20 V): m/z=935 (2M+H)$^+$, 468 (M+H)$^+$.

Example 31(66)

cis-4-{2-[9-(3-chloro-5-fluorobenzyl)-5,6,8,9-tetrahydro-7H-pyrido[4',3':4,5]pyrrolo[2,3-b]pyridin-7-yl]-2-oxoethoxy}cyclohexanecarboxylic acid TLC: Rf 0.39 (chloroform:methanol:water=50:10:1);
MS (ESI, Pos. 20 V): m/z=967 (2M+H)$^+$, 484 (M+H)$^+$.

Example 31(75)

trans-4-(2-{9-[(5-fluoro-2-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.34 (methylene chloride:ethyl acetate:methanol=8:4:1);
MS (ESI, Pos. 20 V): m/z=456 (M+H)$^+$.

Example 31(76)

cis-4-(2-{9-[(5-fluoro-2-thienyl)methyl]-5,6,8,9-tetrahydro-7H-pyrido[4',3':4,5]pyrrolo[2,3-b]pyridin-7-yl}-2-oxoethoxy)cyclohexanecarboxylic acid TLC: Rf 0.35 (methylene chloride:ethyl acetate:methanol=8:4:1);
MS (ESI, Pos. 20 V): m/z=456 (M+H)$^+$.

Example 31(77)

trans-4-(2-{9-[(5-fluoro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.33 (methylene chloride:ethyl acetate:methanol=8:4:1);
MS (ESI, Pos. 20 V): m/z=456 (M+H)$^+$.

Example 31(78)

cis-4-(2-{9-[(5-fluoro-3-thienyl)methyl]-5,6,8,9-tetrahydro-7H-pyrido[4',3':4,5]pyrrolo[2,3-b]pyridin-7-yl}-2-oxoethyl)cyclohexanecarboxylic acid TLC: Rf 0.36 (methylene chloride:ethyl acetate:methanol=8:4:1);
MS (ESI, Pos. 20 V): m/z=456 (M+H)$^+$.

Example 31(79)

(cis-4-{[9-(3-fluorobenzyl)-5,6,8,9-tetrahydro-7H-pyrrolo[4',3':4,5]pyrrolo[2,3-b]pyridin-7-yl]carbonyl}cyclohexyl)acetic acid TLC: Rf 0.45 (methylene chloride:ethyl acetate:methanol=8:4:1);
$^1$H-NMR (DMSO-d$_6$): δ 1.16-1.69 (m, 9 H), 1.88-2.23 (m, 3 H), 2.59-2.89 (m, 2 H), 3.69-3.85 (m, 2 H), 4.55-4.70 (m, 2 H), 5.42-5.57 (m, 2 H), 6.87-7.00 (m, 2 H), 7.00-7.16 (m, 2 H), 7.27-7.40 (m, 1 H), 7.90 (d, J=7.7 Hz, 1 H), 8.21 (d, J=4.0 Hz, 1 H), 11.99 (s, 1 H).

Example 31(80)

(trans-4-{[9-(3-fluorobenzyl)-5,6,8,9-tetrahydro-7H-pyrrolo[4',3':4,5]pyrrolo[2,3-b]pyridin-7-yl]carbonyl}cyclohexyl)acetic acid TLC: Rf 0.45 (methylene chloride:ethyl acetate:methanol=8:4:1);
$^1$H-NMR (DMSO-d$_6$): δ 0.77-1.15 (m, 2 H), 1.19-1.81 (m, 7 H), 2.01-2.15 (m, 2 H), 2.58-2.86 (m, 3 H), 3.78 (t, J=5.2 Hz, 2 H), 4.55-4.72 (m, 2 H), 5.40-5.58 (m, 2 H), 6.85-7.02 (m, 2 H), 7.02-7.16 (m, 2 H), 7.28-7.40 (m, 1 H), 7.90 (d, J=7.7 Hz, 1 H), 8.16-8.28 (m, 1 H), 12.00 (s, 1 H).

Example 31(81)

3-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid TLC: Rf 0.33 (ethyl acetate);
$^1$H-NMR (DMSO-d$_6$): δ 2.66-2.80 (m, 2 H) 3.75-3.98 (m, 4 H) 4.62-4.77 (m, 2 H) 5.48 (s, 2 H) 6.87-7.01 (m, 2 H) 7.01-7.17 (m, 2 H) 7.23-7.56 (m, 3 H) 7.70-7.98 (m, 3 H) 8.17-8.28 (m, 1 H) 12.90 (br s, 1 H).

Example 31(82)

4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid TLC: Rf 0.19 (ethyl acetate);
$^1$H-NMR (DMSO-d$_6$): δ 2.62-2.80 (m, 2 H) 3.73-4.00 (m, 4 H) 4.61-4.77 (m, 2 H) 5.42-5.53 (m, 2 H) 6.85-7.00 (m, 2 H) 7.00-7.16 (m, 2 H) 7.21-7.43 (m, 3 H) 7.73-797 (m, 3 H) 8.16-8.26 (m, 1 H) 12.82 (br s, 1 H).

Example 31(83)

4-{2-[9-(4-cyanobenzyl)-5,6,8,9-tetrahydro-7H-pyrido[4',3':4,5]pyrrolo[2,3-b]pyridin-7-yl]-2-oxoethyl}benzoic acid TLC: Rf 0.24 (methylene chloride:ethyl acetate:methanol=8:4:1);
MS (ESI, Pos.): m/z=451 (M+H)$^+$.

Example 31(84)

4-(2-{9-[(6-chloro-3-pyridinyl)methyl]-5,6,8,9-tetrahydro-7H-pyrido[4',3':4,5]pyrrolo[2,3-b]pyridin-7-yl}-2-oxoethyl)benzoic acid TLC: Rf 0.20 (methylene chloride:ethyl acetate:methanol=8:4:1);
MS (ESI, Pos.): m/z=461 (M+H)$^+$.

Example 31(86)

4-(2-{9-[(1,3-dimethyl-1H-pyrazol-5-yl)methyl]-5,6,
8,9-tetrahydro-7H-pyrido[4',3':4,5]pyrrolo[2,3-b]
pyridin-7-yl}-2-oxoethyl)benzoic acid TLC: Rf 0.14 (methylene chloride:ethyl acetate:methanol=8:4:1);
MS (ESI, Pos.): m/z=444 (M+H)$^+$.

Example 31(87)

4-(2-{9-[(2,5-dimethyl-1,3-thiazol-4-yl)methyl]-5,6,
8,9-tetrahydro-7H-pyrido[4',3':4,5]pyrrolo[2,3-b]
pyridin-7-yl}-2-oxoethyl)benzoic acid TLC: Rf 0.15 (methylene chloride:ethyl acetate:methanol=8:4:1);
MS (ESI, Pos.): m/z=461 (M+H)$^+$.

Example 31(88)

4-(2-{9-[(5-chloro-2-thienyl)methyl]-5,6,8,9-tetrahydro-7H-pyrido[4',3':4,5]pyrrolo[2,3-b]pyridin-7-yl}-
2-oxoethoxy)benzoic acid TLC: Rf 0.36 (chloroform:methanol:water=50:10:1);
MS (ESI, Pos. 20 V): m/z=466 (M+H)$^+$.

Example 31(90)

4-{[9-(3-fluorobenzyl)-5,6,8,9-tetrahydro-7H-pyrido
[4',3':4,5]pyrrolo[2,3-b]pyridin-7-yl]
carbonyl}benzoic acid TLC: Rf 0.17 (ethyl acetate);
$^1$H-NMR (DMSO-d$_6$): δ 2.75-2.92 (m, 2 H) 3.50-4.08 (m, 2 H) 4.43-4.88 (m, 2 H) 5.20-5.64 (m, 2 H) 6.49-7.67 (m, 7 H) 7.79-8.09 (m, 3 H) 8.18-8.29 (m, 1 H) 13.17 (br s, 1 H).

Example 31(91)

(4-{2-[9-(4-chloro-2-fluorobenzyl)-5,5-dimethyl-5,6,
8,9-tetrahydro-7H-pyrido[4',3':4,5]pyrrolo[2,3-b]
pyridin-7-yl]-2-oxoethyl}-1-piperidinyl)acetic acid
hydrochloride TLC: Rf 0.41 (methylene chloride:methanol:28% aqueous ammonia=15:5:1);
MS (ESI, Pos. 20 V): m/z=527 (M+H)$^+$.

Example 31(93)

(4-{[9-(3-fluorobenzyl)-5,6,8,9-tetrahydro-7H-pyrido[4',3':4,5]pyrrolo[2,3-b]pyridin-7-yl]carbonyl}-
1-piperidinyl)acetic acid hydrochloride TLC: Rf 0.09 (chloroform:methanol:28% aqueous ammonia=85:13:2);
$^1$H-NMR (DMSO-d$_6$): δ 1.62-2.11 (m, 4 H) 2.63-3.63 (m, 7 H) 3.73-4.18 (m, 4 H) 4.55-4.82 (m, 2 H) 4.87-5.34 (m, 1 H) 5.47-5.67 (m, 2 H) 6.87-7.25 (m, 4 H) 7.27-7.42 (m, 1 H) 7.90-8.07 (m, 1 H) 8.20-8.32 (m, 1 H) 9.97-10.37 (m, 1 H).

Example 31(94)

4-{2-[9-(2,4-difluorobenzyl)-5,6,8,9-tetrahydro-7H-
pyrido[4',3':4,5]pyrrolo[2,3-b]pyridin-7-yl]-2-oxoethyl}-2-ethoxybenzoic acid TLC: Rf 0.60 (chloroform:methanol:water=50:10:1);
MS (ESI, Pos. 20 V): m/z=506 (M+H)$^+$.

Example 31(95)

2-ethoxy-4-{2-[9-(3-fluorobenzyl)-5,6,8,9-tetrahydro-7H-pyrido[4',3':4,5]pyrrolo[2,3-b]pyridin-7-yl]-
2-oxoethyl}benzoic acid TLC: Rf 0.60 (chloroform:methanol:water=50:10:1);
MS (ESI, Pos. 20 V): m/z=975 (2M+H)$^+$, 488 (M+H)$^+$.

Example 31(98)

4-{2-[9-(2,4-difluorobenzyl)-5,6,8,9-tetrahydro-7H-
pyrido[4',3':4,5]pyrrolo[2,3-b]pyridin-7-yl]-2-
oxoethyl}bicyclo[2.2.2]octane-1-carboxylic acid TLC: Rf 0.20 (hexane:ethyl acetate=1:1);
MS (FAB, Pos.): m/z=494 (M+H)$^+$.

Example 31(99)

(3-{2-[9-(3-fluorobenzyl)-5,6,8,9-tetrahydro-7H-
pyrido[4',3':4,5]pyrrolo[2,3-b]pyridin-7-yl]-2-
oxoethyl}phenyl)acetic acid TLC: Rf 0.65 (chloroform:methanol:water=50:10:1);
MS (ESI, Pos. 20 V): m/z=915 (2M+H)$^+$, 458 (M+H)$^+$.

Example 31(100)

(3-{2-[9-(2,4-difluorobenzyl)-5,6,8,9-tetrahydro-7H-
pyrido[4',3':4,5]pyrrolo[2,3-b]pyridin-7-yl]-2-
oxoethyl}phenyl)acetic acid TLC: Rf 0.65 (chloroform:methanol:water=50:10:1);
MS (ESI, Pos. 20 V): m/z=951 (2M+H)$^+$, 476 (M+H)$^+$.

Example 31(102)

cis-3-{2-[9-(3-fluorobenzyl)-5,6,8,9-tetrahydro-7H-
pyrido[4',3':4,5]pyrrolo[2,3-b]pyridin-7-yl]-2-
oxoethyl}cyclobutanecarboxylic acid TLC: Rf 0.52 (ethyl acetate);
MS (ESI, Pos. 20 V): m/z=422 (M+H)$^+$.

Example 31(103)

4-{3-[9-(3-fluorobenzyl)-5,6,8,9-tetrahydro-7H-pyrido[4',3':4,5]pyrrolo[2,3-b]pyridin-7-yl]-3-
oxopropyl}benzoic acid TLC: Rf 0.40 (methylene chloride:ethyl acetate:methanol=8:4:1);
$^1$H-NMR (DMSO-d$_6$): δ 2.60-2.98 (m, 6 H), 3.68-3.86 (m, 2 H), 4.64 (s, 2 H), 5.48 (s, 2 H), 6.84-7.14 (m, 4 H), 7.22-7.42 (m, 3 H), 7.75-7.85 (m, 1 H), 7.89 (dd, J=7.5, 1.5 Hz, 1 H), 8.20 (dd, J=4.5, 1.5 Hz, 1 H), 12.8 (brs, 1 H).

Example 31(104)

4-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid TLC: Rf 0.40 (methylene chloride:ethyl acetate:methanol=8:4:1);
$^1$H-NMR (DMSO-d$_6$): δ 2.63-2.96 (m, 6 H), 3.66-3.84 (m, 2 H), 4.66 (s, 2 H), 5.46 (s, 2 H), 6.78-7.03 (m, 2 H), 7.09 (dd, J=7.5, 4.8 Hz, 1 H), 7.16-7.42 (m, 3 H), 7.67-7.86 (m, 2 H), 7.88 (d, J=7.5 Hz, 1 H), 8.15-8.22 (m, 1 H), 12.7 (brs, 1 H).

Example 31(106)

3-{3-[9-(3-fluorobenzyl)-5,6,8,9-tetrahydro-7H-pyrido[4',3':4,5]pyrrolo[2,3-b]pyridin-7-yl]-3-oxopropyl}benzoic acid TLC: Rf 0.38 (methylene chloride:ethyl acetate:methanol=8:4:1);
$^1$H-NMR (DMSO-d$_6$): δ 2.60-2.92 (m, 6 H), 3.70-3.84 (m, 2 H), 4.58-4.68 (m, 2 H), 5.43-5.50 (m, 2 H), 6.84-7.14 (m, 4 H), 7.22-7.55 (m, 3 H), 7.63-7.92 (m, 3 H), 8.20 (dd, J=4.8, 1.8 Hz, 1 H), 12.8 (brs, 1 H).

Example 31(107)

3-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid TLC: Rf 0.38 (methylene chloride:ethyl acetate:methanol=8:4:1);
$^1$H-NMR (DMSO-d$_6$): δ 2.60-2.96 (m, 6 H), 3.68-3.84 (m, 2 H), 4.60-4.72 (m, 2 H), 5.45 (s, 2 H), 6.80-7.02 (m, 2 H), 7.08 (dd, J=7.5, 4.8 Hz, 1 H), 7.15-7.54 (m, 3 H), 7.63-7.91 (m, 3 H), 8.15-8.21 (m, 1 H), 12.8 (brs, 1 H).

Example 31(109)

cis-3-{2-[9-(2,4-difluorobenzyl)-5,6,8,9-tetrahydro-7H-pyrido[4',3':4,5]pyrrolo[2,3-b]pyridin-7-yl]-2-oxoethyl}cyclobutanecarboxylic acid TLC: Rf 0.49 (ethyl acetate);
MS (FAB, Pos.): m/z=440 (M+H)$^+$.

Example 31(111)

trans-3-{2-[9-(3-fluorobenzyl)-5,6,8,9-tetrahydro-7H-pyrido[4',3':4,5]pyrrolo[2,3-b]pyridin-7-yl]-2-oxoethyl}cyclobutanecarboxylic acid TLC: Rf 0.32 (ethyl acetate);
MS (FAB, Pos.): m/z=422 (M+H)$^+$.

Example 31(112)

trans-3-{2-[9-(2,4-difluorobenzyl)-5,6,8,9-tetrahydro-7H-pyrido[4',3':4,5]pyrrolo[2,3-b]pyridin-7-yl]-2-oxoethyl}cyclobutanecarboxylic acid TLC: Rf 0.25 (ethyl acetate);
MS (ESI, Pos. 20 V): m/z=440 (M+H)$^+$.

Example 31(114)

2-{3-[9-(3-fluorobenzyl)-5,6,8,9-tetrahydro-7H-pyrido[4',3':4,5]pyrrolo[2,3-b]pyridin-7-yl]-3-oxopropyl}benzoic acid TLC: Rf 0.38 (methylene chloride:ethyl acetate:methanol=8:4:1);
MS (ESI, Pos. 20V): m/z=458 (M+H)$^+$.

Example 31(115)

2-{3-[9-(2,4-difluorobenzyl)-5,6,8,9-tetrahydro-7H-pyrido[4',3':4,5]pyrrolo[2,3-b]pyridin-7-yl]-3-oxopropyl}benzoic acid TLC: Rf 0.38 (methylene chloride:ethyl acetate:methanol=8:4:1);
MS (ESI, Pos. 20V): m/z=476 (M+H)$^+$.

Example 31(120)

5-{3-[9-(3-fluorobenzyl)-5,6,8,9-tetrahydro-7H-pyrido[4',3':4,5]pyrrolo[2,3-b]pyridin-7-yl]-3-oxopropyl}-2-thiophenecarboxylic acid TLC: Rf 0.13 (ethyl acetate);
MS (ESI, Pos. 20 V): m/z=464 (M+H)$^+$.

Example 31(121)

5-{3-[9-(2,4-difluorobenzyl)-5,6,8,9-tetrahydro-7H-pyrido[4',3':4,5]pyrrolo[2,3-b]pyridin-7-yl]-3-oxopropyl}-2-thiophenecarboxylic acid TLC: Rf 0.20 (ethyl acetate);
MS (ESI, Pos. 20 V): m/z=482 (M+H)$^+$.

Example 31(123)

4-{2-[9-(2-cyclohexylethyl)-5,6,8,9-tetrahydro-7H-pyrido[4',3':4,5]pyrrolo[2,3-b]pyridin-7-yl]-2-oxoethyl}benzoic acid TLC: Rf 0.45 (methylene chloride:methanol=9:1);
MS (APCI, Pos. 20 V): m/z=446 (M+H)$^+$.

Example 31(124)

(4-{2-[9-(3-fluorobenzyl)-5,6,8,9-tetrahydro-7H-pyrido[4',3':4,5]pyrrolo[2,3-b]pyridin-7-yl]-2-oxoethyl}phenyl)acetic acid TLC: Rf 0.36 (methylene chloride:methanol=9:1);
MS (FAB, Pos.): m/z=458 (M+H)$^+$.

Example 31(125)

(4-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)acetic acid TLC: Rf 0.36 (methylene chloride:methanol=9:1);
MS (FAB, Pos.): m/z=476 (M+H)$^+$.

Example 31(127)

4-{2-[9-(3-fluorobenzyl)-5,6,8,9-tetrahydro-7H-py-rido[4',3':4,5]pyrrolo[2,3-b]pyridin-7-yl]-2-oxoethyl}bicyclo[2.2.2]octane-1-carboxylic acid

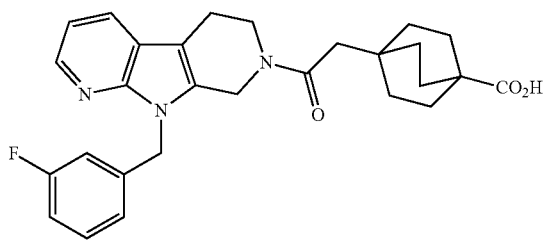 [SMILES: O=C(CC12CCC(C(=O)O)(CC1)CC2)N1CCc2c(n(Cc3cccc(F)c3)c3ncccc23)C1]

TLC: Rf 0.35 (chloroform:methanol=10:1);
MS (FAB, Pos.): m/z=476 (M+H)+.

Example 31(128)

4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid

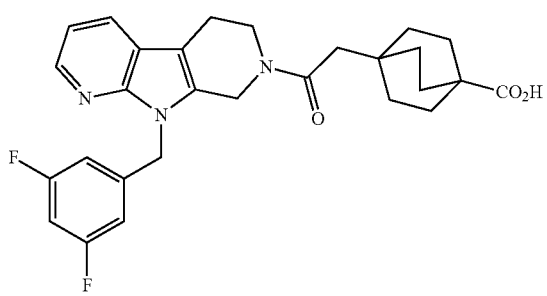 [SMILES: O=C(CC12CCC(C(=O)O)(CC1)CC2)N1CCc2c(n(Cc3cc(F)cc(F)c3)c3ncccc23)C1]

TLC: Rf 0.46 (chloroform:methanol=10:1);
MS (FAB, Pos.): m/z=494 (M+H)+.

Example 31(129)

4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}bicyclo[2.2.2]octane-1-carboxylic acid

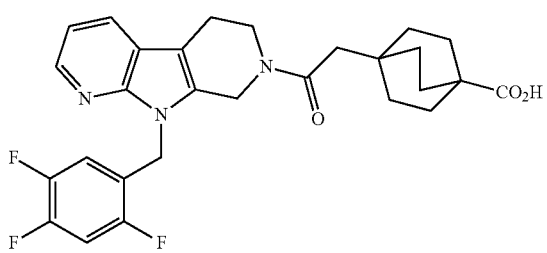 [SMILES: O=C(CC12CCC(C(=O)O)(CC1)CC2)N1CCc2c(n(Cc3cc(F)c(F)cc3F)c3ncccc23)C1]

TLC: Rf 0.46 (chloroform:methanol=10:1);
MS (FAB, Pos.): m/z=512 (M+H)+.

Example 31(130)

4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid TLC: Rf 0.44 (chloroform:methanol=10:1);
MS (FAB, Pos.): m/z=498 (M+H)+.

Example 31(131)

(2-{2-[9-(3-fluorobenzyl)-5,6,8,9-tetrahydro-7H-pyrido[4',3':4,5]pyrrolo[2,3-b]pyridin-7-yl]-2-oxoethyl}phenyl)acetic acid TLC: Rf 0.30 (methylene chloride:methanol=9:1);
MS (FAB, Pos.): m/z=458 (M+H)+.

Example 31(132)

(2-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)acetic acid TLC: Rf 0.30 (methylene chloride:methanol=9:1);
MS (FAB, Pos.): m/z=476 (M+H)+.

Example 31(134)

4-{(1E)-3-[9-(3-fluorobenzyl)-5,6,8,9-tetrahydro-7H-pyrido[4',3':4,5]pyrrolo[2,3-b]pyridin-7-yl]-3-oxo-1-propen-1-yl}benzoic acid TLC: Rf 0.15 (ethyl acetate);
MS (ESI, Pos. 20 V): m/z=456 (M+H)+.

Example 31(135)

(1R,3R)-3-{2-[9-(3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.45 (chloroform:methanol:water=10:1:0.1);
MS (FAB, Pos.): m/z=478 (M+H)+.

Example 31(137)

(1R,3R)-3-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.49 (chloroform:methanol:water=10:1:0.1);
MS (FAB, Pos.): m/z=496 (M+H)+.

Example 31(139)

4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid TLC: Rf 0.48 (ethyl acetate);
MS (FAB, Pos.): m/z=476 (M+H)+.

Example 31(140)

4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid

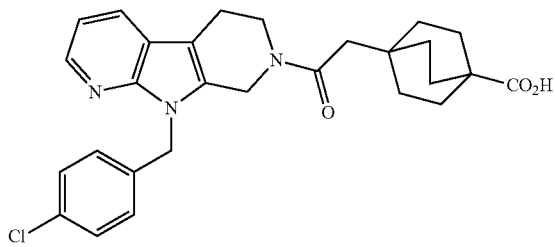 [SMILES: O=C(CC12CCC(C(=O)O)(CC1)CC2)N1CCc2c(n(Cc3ccc(Cl)cc3)c3ncccc23)C1]

TLC: Rf 0.50 (ethyl acetate);
MS (FAB, Pos.): m/z=492 (M+H)$^+$.

Example 31(141)

4-{2-[9-(3-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid TLC: Rf 0.50 (ethyl acetate);
MS (FAB, Pos.): m/z=492 (M+H)$^+$.

Example 31(142)

4-{2-[9-(4-chloro-2-fluorobenzyl)-5,6,8,9-tetrahydro-7H-pyrido[4',3':4,5]pyrrolo[2,3-b]pyridin-7-yl]-2-oxoethoxy}bicyclo[2.2.2]octane-1-carboxylic acid

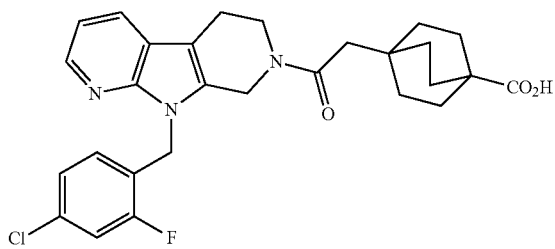 [SMILES: O=C(CC12CCC(C(=O)O)(CC1)CC2)N1CCc2c(n(Cc3ccc(Cl)cc3F)c3ncccc23)C1]

TLC: Rf 0.57 (ethyl acetate);
MS (FAB, Pos.): m/z=510 (M+H)$^+$.

Example 31(143)

4-{2-[9-(4-chloro-3-fluorobenzyl)-5,6,8,9-tetrahydro-7H-pyrido[4',3':4,5]pyrrolo[2,3-b]pyridin-7-yl]-2-oxoethoxy}bicyclo[2.2.2]octane-1-carboxylic acid TLC: Rf 0.45 (ethyl acetate);
MS (FAB, Pos.): m/z=510 (M+H)$^+$.

Example 31(145)

4-(2-{9-[(5-chloro-3-thienyl)methyl]-5,6,8,9-tetrahydro-7H-pyrido[4',3':4,5]pyrrolo[2,3-b]pyridin-7-yl}-2-oxoethoxy)bicyclo[2.2.2]octane-1-carboxylic acid TLC: Rf 0.48 (ethyl acetate);
MS (FAB, Pos.): m/z=498 (M+H)$^+$.

Example 31(146)

(1S,3S)-3-{2-[9-(3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.45 (chloroform:methanol:water=10:1:0.1);
MS (ESI, Pos. 20V): m/z=478 (M+H)$^+$.

Example 31(151)

4-{2-[9-(3-chloro-4-fluorobenzyl)-5,6,8,9-tetrahydro-7H-pyrido[4',3':4,5]pyrrolo[2,3-b]pyridin-7-yl]-2-oxoethoxy}bicyclo[2.2.2]octane-1-carboxylic acid TLC: Rf 0.71 (ethyl acetate);
MS (ESI, Pos. 20 V): m/z=510 (M+H)$^+$.

Example 31(156)

(1R,3R)-3-{2-[9-(3,5-difluorobenzyl)-5,6,8,9-tetrahydro-7H-pyrido[4',3':4,5]pyrrolo[2,3-b]pyridin-7-yl]-2-oxoethoxy}-1,2,2-trimethylcyclopentanecarboxylic acid TLC: Rf 0.43 (chloroform:methanol:water=100:10:1);
MS (ESI, Pos. 20 V): m/z=496 (M+H)$^+$.

Example 31(158)

(1R,3R)-3-{2-[9-(4-chlorobenzyl)-5,6,8,9-tetrahydro-7H-pyrido[4',3':4,5]pyrrolo[2,3-b]pyridin-7-yl]-2-oxoethoxy}-1,2,2-trimethylcyclopentanecarboxylic acid TLC: Rf 0.34 (chloroform:methanol:water=100:10:1);
MS (ESI, Pos. 20V): m/z=494 (M+H)$^+$, 460.

Example 31(159)

(1R,3R)-3-{2-[9-(3-chlorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.34 (chloroform:methanol:water=100:10:1);
MS (ESI, Pos. 20V): m/z=494 (M+H)$^+$, 460.

Example 31(160)

(1R,3R)-3-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid

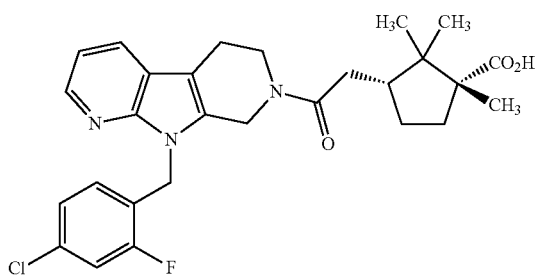 [SMILES: CC1(C)[C@@H](CC(=O)N2CCc3c(n(Cc4ccc(Cl)cc4F)c4ncccc34)C2)CC[C@@]1(C)C(=O)O]

TLC: Rf 0.34 (chloroform:methanol:water=100:10:1);
MS (ESI, Pos. 20V): m/z=512 (M+H)$^+$, 478.

Example 31(161)

(1R,3R)-3-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.34 (chloroform:methanol:water=10:1:0.1);
MS (ESI, Pos. 20V): m/z=512 (M+H)$^+$, 478.

Example 31(162)

(1R,3R)-3-{2-[9-(4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid

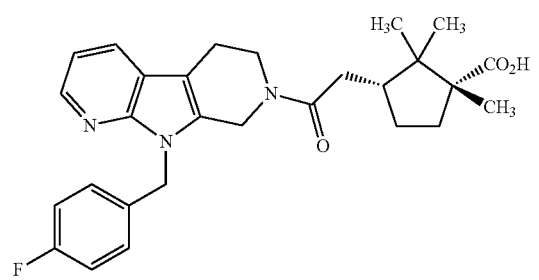 [SMILES: CC1(C)[C@@H](CC(=O)N2CCc3c(n(Cc4ccc(F)cc4)c4ncccc34)C2)CC[C@@]1(C)C(=O)O]

TLC: Rf 0.41 (chloroform:methanol:water=100:10:1);
MS (ESI, Pos. 20 V): m/z=478 (M+H)$^+$.

Example 31(163)

(1R,3R)-3-{2-[9-(3,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.43 (chloroform:methanol:water=100:10:1);
MS (ESI, Pos. 20 V): m/z=496 (M+H)$^+$.

Example 31(166)

(1R,3R)-1,2,2-trimethyl-3-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclopentanecarboxylic acid TLC: Rf 0.50 (chloroform:methanol:water=100:10:1);
MS (ESI, Pos. 20 V): m/z=514 (M+H)$^+$.

Example 31(169)

(1R,3R)-3-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid

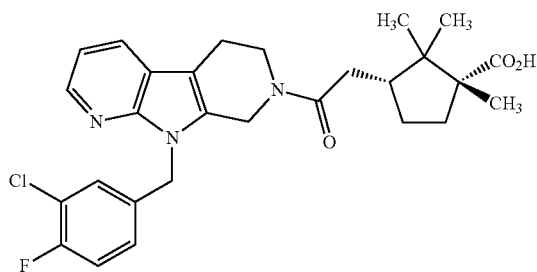 [SMILES: CC1(C)[C@@H](CC(=O)N2CCc3c(n(Cc4ccc(F)c(Cl)c4)c4ncccc34)C2)CC[C@@]1(C)C(=O)O]

TLC: Rf 0.33 (chloroform:methanol:water=100:10:1);
MS (ESI, Pos. 20 V): m/z=512 (M+H)$^+$.

Example 31(170)

4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid

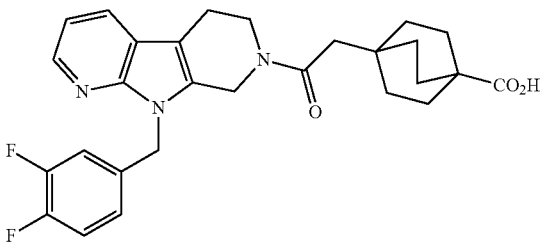 [SMILES: O=C(CC12CCC(C(=O)O)(CC1)CC2)N1CCc2c(n(Cc3ccc(F)c(F)c3)c3ncccc23)C1]

TLC: Rf 0.22 (hexane:ethyl acetate=1:2);
MS (ESI, Pos. 20 V): m/z=494 (M+H)$^+$.

Example 31(173)

(1S,3S)-3-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid TLC: Rf 0.41 (chloroform:methanol:water=100:10:1);
MS (ESI, Pos. 20 V): m/z=496 (M+H)$^+$.

Example 31(177)

(1R,3R)-3-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid TLC: Rf 0.31 (chloroform:methanol:water=100:10:1);
MS (ESI, Pos. 20 V): m/z=500 (M+H)$^+$.

Example 31(178)

(1R,3R)-3-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid TLC: Rf 0.31 (chloroform:methanol:water=100:10:1);
MS (ESI, Pos. 20 V): m/z=500 (M+H)$^+$.

Example 31(181)

4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid

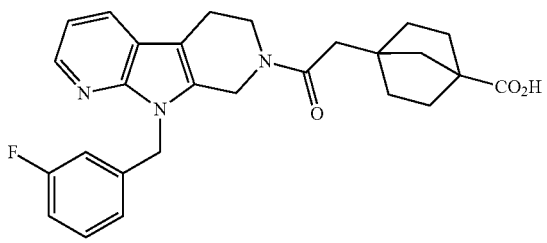 [SMILES: O=C(CC12CCC(C(=O)O)(CC1)C2)N1CCc2c(n(Cc3cccc(F)c3)c3ncccc23)C1]

TLC: Rf 0.51 (chloroform:methanol=9:1);
MS (ESI, Pos. 20 V): m/z=462 (M+H)$^+$.

Example 31(182)

4-{2-[9-(2,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid

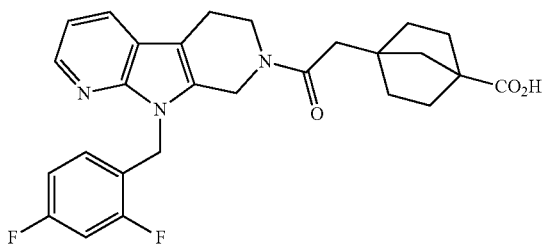 [SMILES: O=C(CC12CCC(C(=O)O)(CC1)C2)N1CCc2c(n(Cc3ccc(F)cc3F)c3ncccc23)C1]

TLC: Rf 0.48 (chloroform:methanol=9:1);
MS (ESI, Pos. 20 V): m/z=480 (M+H)$^+$.

Example 31(183)

4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid TLC: Rf 0.65 (chloroform:methanol:water=50:10:1);
MS (ESI, Pos. 20 V): m/z=480 (M+H)$^+$.

Example 31(184)

4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid TLC: Rf 0.33 (methylene chloride:methanol=9:1);
MS (ESI, Pos. 20V): m/z=498 (M+H)$^+$.

Example 31(188)

4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid

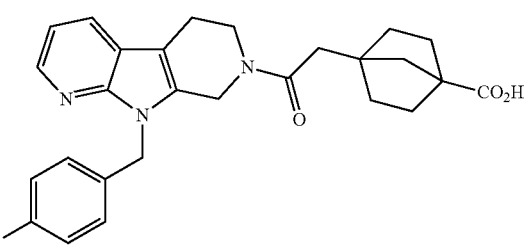

TLC: Rf 0.38 (methylene chloride:methanol=9:1);
MS (ESI, Pos. 20 V): m/z=462 (M+H)$^+$.

Example 31(189)

4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid

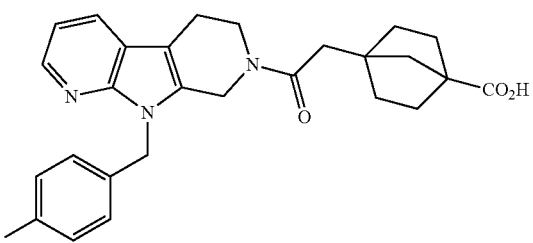

TLC:Rf 0.48 (chloroform:methanol:water=100:10:1);
MS (ESI, Pos. 20 V): m/z=478 (M+H)+.

Example 31(190)

4-{2-[9-(3-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid TLC: Rf 0.49 (methylene chloride:methanol=9:1);
MS (APCI, Pos. 40 V): m/z=478 (M+H)$^+$.

Example 31(191)

4-{2-[9-(4-chloro-2-fluorobenzyl)-5,6,8,9-tetrahydro-7H-pyrido[4',3':4,5]pyrrolo[2,3-b]pyridin-7-yl]-2-oxoethoxy}bicyclo[2.2.1]heptane-1-carboxylic acid TLC: Rf 0.50 (chloroform:methanol:water=100:10:1);
MS (ESI, Pos. 20 V): m/z=496 (M+H)$^+$.

Example 31(192)

4-{2-[9-(4-chloro-3-fluorobenzyl)-5,6,8,9-tetrahydro-7H-pyrido[4',3':4,5]pyrrolo[2,3-b]pyridin-7-yl]-2-oxoethoxy}bicyclo[2.2.1]heptane-1-carboxylic acid TLC: Rf 0.54 (methylene chloride:methanol=9:1);
MS (APCI, Pos. 40 V): m/z=496 (M+H)$^+$.

Example 31(193)

4-{2-[9-(3-chloro-4-fluorobenzyl)-5,6,8,9-tetrahydro-7H-pyrido[4',3':4,5]pyrrolo[2,3-b]pyridin-7-yl]-2-oxoethoxy}bicyclo[2.2.1]heptane-1-carboxylic acid TLC: Rf 0.61 (chloroform:methanol:water=50:10:1);
MS (ESI, Pos. 20 V): m/z=496 (M+H)$^+$.

Example 31(195)

4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid TLC: Rf 0.61 (methylene chloride:methanol=9:1);
MS (ES, Pos.): m/z=480 (M+H)$^+$.

Example 32 tert-butyl 1-[2-(benzyloxy)-2-oxoethyl]piperidine-4-carboxylate

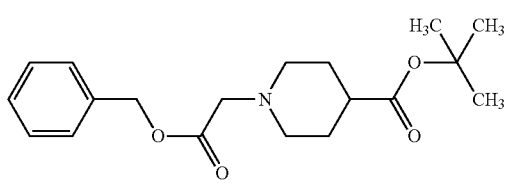 [SMILES: CC(C)(C)OC(=O)C1CCN(CC(=O)OCc2ccccc2)CC1]

To a suspension (39 mL) of tert-butyl piperidine-4-carboxylate (2.6 g) in acetonitrile was added diisopropylethylamine (4.4 mL), subsequently, benzyl bromoacetate (2.0 mL) was added at room temperature in portions, and the mixture was stirred for 4 hours. To the reaction mixture was added water, followed by extraction with ethyl acetate. This was washed with an aqueous saturated sodium chloride solution, dried with anhydrous sodium sulfate, and concentrated. The residue was purified by silica gel column chromatography (hexane:ethyl acetate=1:3→0:1) to obtain the title compound (3.4 g) having the following physical property values.
TLC: Rf 0.66 (hexane:ethyl acetate=2:1);
$^1$H-NMR (CDCl$_3$): δ 1.44 (s, 9 H) 1.68-1.92 (m, 4 H) 2.10-2.35 (m, 3 H) 2.83-2.96 (m, 2 H) 3.26 (s, 2 H) 5.16 (s, 2 H) 7.25-7.41 (m, 5 H).

Example 33

[4-(tert-butoxycarbonyl)piperidin-1-yl]acetic acid

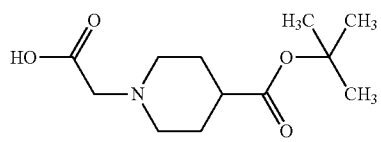 [SMILES: CC(C)(C)OC(=O)C1CCN(CC(=O)O)CC1]

The compound (3.4 g) produced in Example 32 was dissolved in ethanol (41 mL), 5% Pd/C (50% hydrous product, 340 mg) was added under the argon atmosphere, and hydrogen was blown into the solution for 2.5 hours while stirred at room temperature. After the system was replaced with argon, the catalyst was filtered off using Celite, and this was concentrated under reduced pressure to obtain the title compound (2.5 g) having the following physical property values.
TLC: Rf 0.30 (chloroform:methanol:28% aqueous ammonia=85:13:2);
$^1$H-NMR (CDCl$_3$): δ 1.44 (s, 9 H) 1.97-2.25 (m, 4 H) 2.40-2.54 (m, 1 H) 2.95-3.45 (m, 4 H) 3.46 (s, 2 H) 7.43-7.96 (br.s, 1 H).

Example 34 tert-butyl 1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}piperidine-4-carboxylate

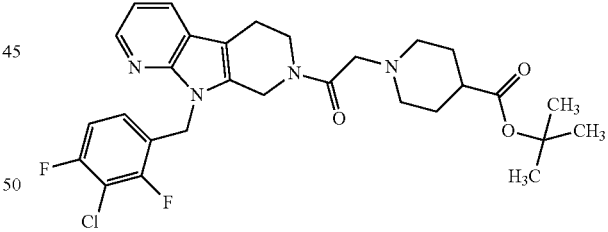

The compound produced in Example 33 and a tetrahydropyridopyrrolopyridine derivative produced by operation in accordance with Example 4→Example 5 Example 6→Example 7→Example 1 were used, which were subjected to operation in accordance with Example 11 to obtain the title compound (50 mg) having the following physical property values.
TLC: Rf 0.58 (dichloromethane:ethyl acetate:methanol=8:4:1);
$^1$H-NMR (CDCl$_3$): δ 1.42-1.44 (m, 9 H) 1.48-1.95 (m, 4 H) 2.00-2.28 (m, 3 H) 2.68-2.96 (m, 4 H) 3.13-3.30 (m, 2 H) 3.84-3.98 (m, 2 H) 4.65-4.88 (m, 2 H) 5.47 (s, 2 H) 6.70-7.16 (m, 3 H) 7.81 (dd, J=7.8, 1.5 Hz, 1 H) 8.23-8.34 (m, 1 H).

Example 35

1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-4-piperidinecarboxylic acid hydrochloride

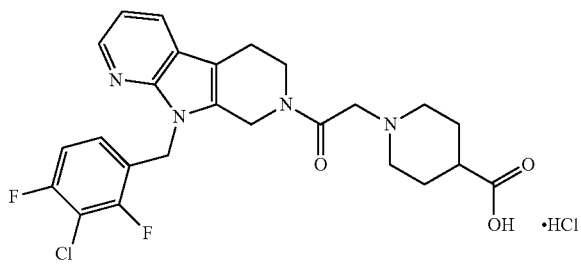 [SMILES: O=C(O)C1CCN(CC(=O)N2CCc3c(n(Cc4ccc(F)c(Cl)c4F)c4ncccc34)C2)CC1 ; Cl]

To the compound (30 mg) produced in Example 34 were sequentially added a 4N solution (4 mL) of hydrogen chloride in dioxane, and water (0.1 mL) at room temperature, and the mixture was stirred overnight. The reaction mixture was concentrated, and the resulting solid was washed with ethyl acetate, filtered off and dried to obtain the title compound (25 mg) having the following physical property values.

TLC: Rf 0.23 (chloroform:methanol:water=50:10:1);
$^1$H-NMR (DMSO-d$_6$): δ 1.71-2.31 (m, 4 H) 2.64-4.53 (m, 12 H) 4.63-4.80 (m, 2 H) 5.51-5.63 (m, 2 H) 6.91-7.04 (m, 1 H) 7.14 (dd, J=7.7, 4.8 Hz, 1 H) 7.18-7.28 (m, 1 H) 7.87-8.02 (m, 1 H) 8.23 (dd, J=4.7, 1.4 Hz, 1 H) 9.47-9.77 (m, 1 H).

Example 35(1)-Example 35(122) and Reference Example 1

A tetrahydropyridopyrrolopyridine derivative produced by operation in accordance with Example 4→Example 5→Example 6→Example 7→Example 1 and a corresponding ester in place of [4-(tert-butoxycarbonyl)piperidin-1-yl]acetic acid were used, which were subjected to operation in accordance with Example 11→Example 34→Example 35 to obtain the following compounds.

Example 35(1)

1-{2-[9-(3-fluorobenzyl)-5,6,8,9-tetrahydro-7H-pyrido[4',3':4,5]pyrrolo[2,3-b]pyridin-7-yl]-2-oxoethyl}-2-piperidinecarboxylic acid TLC: Rf 0.22 (chloroform:methanol=10:1);
$^1$H-NMR (DMSO-d$_6$): δ 0.93-2.37 (m, 6 H), 2.60-4.20 (m, 9 H), 4.44-5.36 (m, 2 H), 5.39-5.61 (m, 2 H), 6.85-7.17 (m, 4 H), 7.23-7.44 (m, 1 H), 7.82-7.98 (m, 1 H), 8.13-8.26 (m, 1 H), 8.83-13.71 (m, 1 H).

Example 35(2)

1-{2-[9-(3-fluorobenzyl)-5,6,8,9-tetrahydro-7H-pyrido[4',3':4,5]pyrrolo[2,3-b]pyridin-7-yl]-2-oxoethyl}-3-piperidinecarboxylic acid

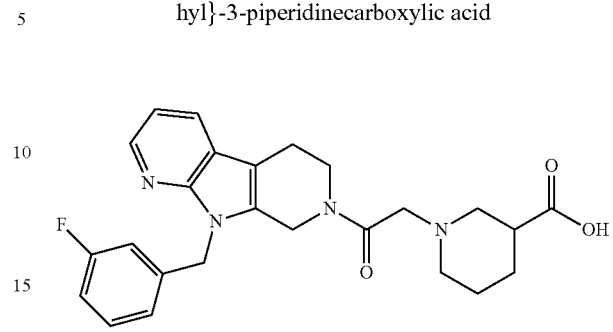

TLC: Rf 0.09 (chloroform:methanol=10:1);
$^1$H-NMR (DMSO-d$_6$): δ 1.29-2.23 (m, 4 H), 2.64-4.29 (m, 11 H), 4.58-4.84 (m, 2 H), 5.34-5.67 (m, 2 H), 6.80-7.21 (m, 4 H), 7.26-7.43 (m, 1 H), 7.80-8.04 (m, 1 H), 8.15-8.30 (m, 1 H), 9.30-13.65 (m, 1 H).

Example 35(3)

1-{3-[9-(3-fluorobenzyl)-5,6,8,9-tetrahydro-7H-pyrido[4',3':4,5]pyrrolo[2,3-b]pyridin-7-yl]-3-oxopropyl}-3-piperidinecarboxylic acid TLC: Rf 0.11 (chloroform:methanol=10:1);
$^1$H-NMR (CDCl$_3$): δ 1.56-2.09 (m, 4 H), 2.53-3.31 (m, 11 H), 3.70-3.94 (m, 2 H), 4.51-4.70 (m, 2 H), 5.36-5.57 (m, 2 H), 6.68-6.98 (m, 3 H), 7.01-7.13 (m, 1 H), 7.15-7.28 (m, 1 H), 7.74-7.85 (m, 1 H), 8.21-8.35 (m, 1 H).

Example 35(4)

1-{3-[9-(3-fluorobenzyl)-5,6,8,9-tetrahydro-7H-pyrido[4',3':4,5]pyrrolo[2,3-b]pyridin-7-yl]-3-oxopropyl}-1,2,3,6-tetrahydro-4-pyridinecarboxylic acid TLC: Rf 0.44 (chloroform:methanol:water=50:10:1);
$^1$H-NMR (CDCl$_3$): δ 2.27-3.42 (m, 12 H), 3.67-3.96 (m, 2 H), 4.47-4.71 (m, 2 H), 5.38-5.53 (m, 2 H), 6.52-6.66 (m, 1 H), 6.70-6.99 (m, 3 H), 7.03-7.15 (m, 1 H), 7.15-7.33 (m, 1 H), 7.73-7.86 (m, 1 H), 8.24-8.35 (m, 1 H).

Example 35(5)

(1-{2-[9-(3-fluorobenzyl)-5,6,8,9-tetrahydro-7H-pyrido[4',3':4,5]pyrrolo[2,3-b]pyridin-7-yl]-2-oxoethyl}-4-piperidinyl)acetic acid TLC: Rf 0.24 (chloroform:methanol:water=50:10:1);
$^1$H-NMR (DMSO-d$_6$): δ 0.78-2.18 (m, 9 H), 2.56-2.87 (m, 4 H), 3.00-3.26 (m, 2 H), 3.71-4.20 (m, 2 H), 4.54-4.85 (m, 2 H), 5.40-5.54 (m, 2 H), 6.85-7.16 (m, 4 H), 7.27-7.40 (m, 1 H), 7.84-7.97 (m, 1 H), 8.16-8.25 (m, 1 H).

Example 35(6)

1-{3-[9-(3-fluorobenzyl)-5,6,8,9-tetrahydro-7H-pyrido[4',3':4,5]pyrrolo[2,3-b]pyridin-7-yl]-3-oxopropyl}-4-piperidinecarboxylic acid hydrochloride TLC: Rf 0.05 (chloroform:methanol:28% aqueous ammonia=85:13:2);

¹H-NMR (DMSO-d₆): δ 1.70-2.43 (m, 4 H) 2.64-3.88 (m, 13 H) 4.08-4.79 (m, 3 H) 5.45-5.59 (m, 2 H) 6.85-7.19 (m, 4 H) 7.29-7.40 (m, 1 H) 7.91-8.02 (m, 1 H) 8.23 (dd, J=4.8, 1.3 Hz, 1 H) 10.26 (br. s., 1 H).

Example 35(7)

1-{2-[9-(4-chloro-2-fluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid hydrochloride TLC: Rf 0.53 (methylene chloride:methanol:28% aqueous ammonia=15:5:1);
¹H-NMR (DMSO-d₆): δ 1.25-1.55 (m, 6 H), 1.70-2.15 (m, 5 H), 2.90-3.22 (m, 2 H), 3.35-3.70 (m, 4 H), 4.25-4.52 (m, 2 H), 4.55-4.80 (m, 2 H), 5.40-5.60 (m, 2 H), 6.82-7.04 (m, 1 H), 7.10 (dd, J=7.8, 4.5 Hz, 1 H), 7.20 (d, J=8.4 Hz, 1 H), 7.49 (d, J=9.9 Hz, 1 H), 8.11 (d, J=7.8 Hz, 1 H), 8.16-8.26 (m, 1 H), 9.52-9.74 (br, 1 H), 12.2-13.0 (br, 1 H).

Example 35(9)

(1-{3-[9-(3-fluorobenzyl)-5,6,8,9-tetrahydro-7H-pyrido[4',3':4,5]pyrrolo[2,3-b]pyridin-7-yl]-3-oxopropyl}-4-piperidinyl)acetic acid TLC: Rf 0.06 (chloroform:methanol:28% aqueous ammonia=85:13:2);
¹H-NMR (DMSO-d₆): δ 0.98-1.73 (m, 5 H) 1.81-3.52 (m, 13 H) 3.72-3.82 (m, 2 H) 4.59-4.70 (m, 2 H) 5.44-5.54 (m, 2 H) 6.85-7.14 (m, 4 H) 7.27-7.38 (m, 1 H) 7.86-7.94 (m, 1 H) 8.18-8.23 (m, 1 H).

Example 35(10)

1-{3-[9-(3-fluorobenzyl)-5,6,8,9-tetrahydro-7H-pyrido[4',3':4,5]pyrrolo[2,3-b]pyridin-7-yl]-3-oxopropyl}-2-piperidinecarboxylic acid TLC: Rf 0.16 (chloroform:methanol:28% aqueous ammonia=85:13:2);
¹H-NMR (CD₃OD): δ 0.82-2.33 (m, 6 H) 2.76-3.98 (m, 11 H) 4.58-4.74 (m, 2 H) 5.42-5.60 (m, 2 H) 6.69-7.36 (m, 5 H) 7.92-7.99 (m, 1 H) 8.19-8.25 (m, 1 H).

Example 35(11)

(1-{2-[9-(4-chloro-2-fluorobenzyl)-5,5-dimethyl-5,6,8,9-tetrahydro-7H-pyrido[4',3':4,5]pyrrolo[2,3-b]pyridin-7-yl]-2-oxoethoxy}-4-piperidin)acetic acid TLC: Rf 0.55 (methylene chloride:methanol:28% aqueous ammonia=15:5:1);
MS (ESI, Pos. 20 V): m/z=527 (M+H)⁺.

Example 35(14)

1-{2-[9-(4-chloro-2-fluorobenzyl)-1,3,4,9-tetrahydro-2H-beta-carbolin-2-yl]-2-oxoethyl}-4-piperidinecarboxylic acid TLC: Rf 0.23 (chloroform:methanol:water=50:10:1);
MS (ESI, Pos. 20 V): m/z=484 (M+H)⁺.

Example 35(16)

1-{2-[9-(3,5-dichlorobenzyl)-5,6,8,9-tetrahydro-7H-pyrido[4',3':4,5]pyrrolo[2,3-b]pyridin-7-yl]-2-oxoethyl}-4-piperidinecarboxylic acid hydrochloride TLC: Rf 0.23 (chloroform:methanol:water=50:10:1);
MS (FAB, Pos.): m/z=501 (M+H)⁺.

Example 35(19)

1-{2-[9-(3-chloro-2,4-difluorobenzyl)-1,3,4,9-tetrahydro-2H-beta-carbolin-2-yl]-2-oxoethyl}-4-piperidinecarboxylic acid hydrochloride TLC: Rf 0.24 (chloroform:methanol:water=50:10:1);
MS (ESI, Pos. 20 V): m/z=502 (M+H)⁺.

Example 35(20)

1-{2-[9-(3,5-dichlorobenzyl)-1,3,4,9-tetrahydro-2H-beta-carbolin-2-yl]-2-oxoethyl}-4-piperidinecarboxylic acid hydrochloride TLC: Rf 0.24 (chloroform:methanol:water=50:10:1);
MS (ESI, Pos. 20 V): m/z=500 (M+H)⁺.

Example 35(23)

1-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid hydrochloride TLC: Rf 0.27 (chloroform:methanol:water=50:10:1);
MS (ESI, Pos. 20 V): m/z=531 (M+H)⁺.

Example 35(24)

1-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-4-piperidinecarboxylic acid hydrochloride TLC: Rf 0.27 (chloroform:methanol:water=50:10:1);
MS (ESI, Pos. 20 V): m/z=529 (M+H)⁺.

Example 35(26)

(1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethoxy}-4-piperidin)acetic acid hydrochloride TLC: Rf 0.35 (chloroform:methanol:water=50:10:1);
MS (ESI, Pos. 20 V): m/z=517 (M+H)⁺.

Example 35(28)

(1-{2-[9-(3,5-dichlorobenzyl)-5,6,8,9-tetrahydro-7H-pyrido[4',3':4,5]pyrrolo[2,3-b]pyridin-7-yl]-2-oxoethyl}-4-piperidinyl)acetic acid hydrochloride TLC: Rf 0.40 (chloroform:methanol:water=50:10:1);
MS (ESI, Pos. 20 V): m/z=515 (M+H)⁺.

Example 35(30)

(1-{2-[9-(3-chloro-2,4-difluorobenzyl)-1,3,4,9-tetrahydro-2H-beta-carbolin-2-yl]-2-oxoethyl}-4-piperidinyl)acetic acid hydrochloride TLC: Rf 0.40 (chloroform:methanol:water=50:10:1);
MS (ESI, Pos. 20 V): m/z=516 (M+H)$^+$.

Example 35(32)

(1-{2-[9-(3,5-dichlorobenzyl)-1,3,4,9-tetrahydro-2H-beta-carbolin-2-yl]-2-oxoethyl}-4-piperidinyl)acetic acid hydrochloride TLC: Rf 0.42 (chloroform:methanol:water=50:10:1);
MS (ESI, Pos. 20 V): m/z=514 (M+H)$^+$.

Example 35(37)

(1-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethoxy}-4-piperidin)acetic acid hydrochloride TLC: Rf 0.30 (chloroform:methanol:water=50:10:1);
MS (ESI, Pos. 20 V): m/z=545 (M+H)$^+$.

Example 35(38)

(1-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-4-piperidinyl)acetic acid hydrochloride TLC: Rf 0.31 (chloroform:methanol:water=50:10:1);
MS (ESI, Pos. 20 V): m/z=543 (M+H)$^+$.

Example 35(55)

[1-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-4-piperidinyl]acetic acid hydrochloride TLC: Rf 0.44 (chloroform:methanol:water=50:10:1);
MS (ESI, Pos. 20 V): m/z=487 (M+H)$^+$.

Example 35(56)

[1-(2-{9-[(5-chloro-2-thienyl)methyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid hydrochloride TLC: Rf 0.50 (chloroform:methanol:water=50:10:1);
MS (ESI, Pos. 20 V): m/z=515 (M+H)$^+$.

Example 35(57)

(4-{3-[9-(3-fluorobenzyl)-5,6,8,9-tetrahydro-7H-pyrido[4',3':4,5]pyrrolo[2,3-b]pyridin-7-yl]-3-oxopropyl}-1-piperazinyl)acetic acid dihydrochloride TLC: Rf 0.10 (chloroform:methanol:28% aqueous ammonia=85:13:2);
$^1$H-NMR (DMSO-d$_6$): δ 2.66-4.06 (m, 18 H), 4.32-4.94 (m, 4 H), 5.44-5.64 (m, 2 H), 6.84-7.19 (m, 4 H), 7.27-7.42 (m, 1 H), 7.89-8.02 (m, 1 H), 8.17-8.31 (m, 1 H), 9.47-11.85 (m, 1 H).

Example 35(58)

(4-{2-[9-(3-fluorobenzyl)-5,6,8,9-tetrahydro-7H-pyrido[4',3':4,5]pyrrolo[2,3-b]pyridin-7-yl]-2-oxoethyl}-1-piperazinyl)acetic acid dihydrochloride TLC: Rf 0.14 (chloroform:methanol:water=50:10:1);
$^1$H-NMR (DMSO-d$_6$): δ 2.65-2.96 (m, 2 H), 3.34-5.33 (m, 18 H), 5.49-5.66 (m, 2 H), 6.85-7.23 (m, 4 H), 7.27-7.42 (m, 1 H), 7.92-8.06 (m, 1 H), 8.19-8.31 (m, 1 H).

Example 35(59)

(4-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-1-piperazinyl)acetic acid dihydrochloride TLC: Rf 0.09 (chloroform:methanol:28% aqueous ammonia=85:13:2);
$^1$H-NMR (DMSO-d$_6$): δ ppm 2.66-2.96 (m, 2 H) 3.22-6.05 (m, 21 H) 6.94-7.09 (m, 1 H) 7.11-7.28 (m, 2 H) 7.92-8.02 (m, 1 H) 8.19-8.26 (m, 1 H).

Example 35(61)

(4-{2-[9-(3,5-dichlorobenzyl)-5,6,8,9-tetrahydro-7H-pyrido[4',3':4,5]pyrrolo[2,3-b]pyridin-7-yl]-2-oxoethyl}-1-piperazinyl)acetic acid dihydrochloride TLC: Rf 0.05 (chloroform:methanol:28% aqueous ammonia=85:13:2);
$^1$H-NMR (DMSO-d$_6$): δ 2.68-3.00 (m, 2 H) 3.35-5.91 (m, 21 H) 7.10-7.34 (m, 3 H) 7.50-7.54 (m, 1 H) 7.92-8.04 (m, 1 H) 8.21-8.30 (m, 1 H).

Example 35(64)

(4-{2-[9-(3-chloro-2,4-difluorobenzyl)-1,3,4,9-tetrahydro-2H-beta-carbolin-2-yl]-2-oxoethyl}-1-piperazinyl)acetic acid dihydrochloride TLC: Rf 0.50 (chloroform:methanol:water=50:10:1);
MS (ESI, Pos. 20 V): m/z=517 (M+H)$^+$.

Example 35(66)

(4-{2-[9-(3,5-dichlorobenzyl)-1,3,4,9-tetrahydro-2H-beta-carbolin-2-yl]-2-oxoethyl}-1-piperazinyl)acetic acid dihydrochloride TLC: Rf 0.47 (chloroform:methanol:water=50:10:1);
MS (ESI, Pos. 20 V): m/z=515 (M+H)$^+$.

Example 35(69)

(4-{2-[9-(3-chloro-2,4-difluorobenzyl)-5,5-dimethyl-5,6,8,9-tetrahydro-7H-pyrido[4',3':4,5]pyrrolo[2,3-b]pyridin-7-yl]-2-oxoethoxy}-1-piperazinyl)acetic acid dihydrochloride TLC: Rf 0.18 (chloroform:methanol:water=50:10:1);
MS (ESI, Pos. 20 V): m/z=546 (M+H)$^+$.

Example 35(71)

(4-{2-[9-(3,5-dichlorobenzyl)-5,5-dimethyl-5,6,8,9-tetrahydro-7H-pyrido[4',3':4,5]pyrrolo[2,3-b]pyridin-7-yl]-2-oxoethyl}-1-piperazinyl)acetic acid dihydrochloride TLC: Rf 0.18 (chloroform:methanol:water=50:10:1);
MS (FAB Pos.): m/z=544 (M+H)$^+$.

Example 35(79)

(1-{3-[9-(3-fluorobenzyl)-5,6,8,9-tetrahydro-7H-pyrido[4',3':4,5]pyrrolo[2,3-b]pyridin-7-yl]-3-oxopropyl}-3-pyrrolidinyl)acetic acid hydrochloride TLC: Rf 0.13 (chloroform:methanol:28% aqueous ammonia=85:13:2);
$^1$H-NMR (DMSO-d$_6$): δ 1.40-2.31 (m, 2 H), 2.61-3.91 (m, 15 H), 4.33-5.16 (m, 3 H), 5.44-5.60 (m, 2 H), 6.83-7.22 (m, 4 H), 7.26-7.40 (m, 1 H), 7.91-8.02 (m, 1 H), 8.19-8.28 (m, 1 H), 10.27-10.94 (m, 1 H).

Example 35(80)

(1-{2-[9-(3-fluorobenzyl)-5,6,8,9-tetrahydro-7H-pyrido[4',3':4,5]pyrrolo[2,3-b]pyridin-7-yl]-2-oxoethyl}-3-pyrrolidinyl)acetic acid TLC: Rf 0.18 (chloroform:methanol:water=50:10:1);
$^1$H-NMR (DMSO-d$_6$): δ 1.17-2.96 (m, 11 H), 3.23-4.20 (m, 4 H), 4.57-4.81 (m, 2 H), 5.36-5.58 (m, 2 H), 6.83-7.15 (m, 4 H), 7.26-7.41 (m, 1 H), 7.84-7.97 (m, 1 H), 8.08-8.25 (m, 1 H).

Example 35(81)

1-{2-[9-(3-fluorobenzyl)-5,6,8,9-tetrahydro-7H-pyrido[4',3':4,5]pyrrolo[2,3-b]pyridin-7-yl]-2-oxoethyl}-3-pyrrolidinecarboxylic acid TLC: Rf 0.13 (chloroform:methanol=10:1);
$^1$H-NMR (DMSO-d$_6$): δ 1.74-2.03 (m, 2 H) 2.58-3.70 (m, 10 H) 3.73-3.86 (m, 2 H) 4.56-4.84 (m, 2 H) 5.37-5.57 (m, 2 H) 6.84-7.18 (m, 4 H) 7.27-7.40 (m, 1 H) 7.84-7.96 (m, 1 H) 8.16-8.27 (m, 1 H).

Example 35(82)

(1-{2-[9-(3-fluorobenzyl)-5,6,8,9-tetrahydro-7H-pyrido[4',3':4,5]pyrrolo[2,3-b]pyridin-7-yl]-2-oxoethyl}-2-pyrrolidinyl)acetic acid hydrochloride TLC: Rf 0.11 (chloroform:methanol:28% aqueous ammonia=85:13:2);
$^1$H-NMR (DMSO-d$_6$): δ 1.58-2.36 (m, 4 H) 2.61-4.83 (m, 14 H) 5.41-5.65 (m, 2 H) 6.85-7.22 (m, 4 H) 7.28-7.44 (m, 1 H) 7.91-8.03 (m, 1 H) 8.19-8.31 (m, 1 H) 9.65-9.92 (m, 1 H).

Example 35(83)

(2S)-1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinecarboxylic acid hydrochloride TLC: Rf 0.18 (chloroform:methanol:28% aqueous ammonia=85:13:2);
$^1$H-NMR (DMSO-d$_6$): δ 1.76-2.46 (m, 4 H) 2.65-4.48 (m, 11 H) 4.49-4.93 (m, 3 H) 5.48-5.57 (m, 2 H) 6.85-7.20 (m, 4 H) 7.28-7.40 (m, 1 H) 7.92-8.00 (m, 1 H) 8.19-8.28 (m, 1 H) 9.82 (br. s., 1 H).

Example 35(84)

(2R)-1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinecarboxylic acid hydrochloride TLC: Rf 0.19 (chloroform:methanol:28% aqueous ammonia=85:13:2);
$^1$H-NMR (CD$_3$OD): δ 0.79-2.50 (m, 6 H) 2.77-4.01 (m, 9 H) 4.55-4.76 (m, 2 H) 5.46-5.58 (m, 2 H) 6.69-7.04 (m, 3 H) 7.15 (dd, J=7.78, 4.85 Hz, 1 H) 7.24-7.36 (m, 1 H) 7.89-7.99 (m, 1 H) 8.18-8.24 (m, 1 H).

Example 35(85)

(1-{3-[9-(3-fluorobenzyl)-5,6,8,9-tetrahydro-7H-pyrido[4',3':4,5]pyrrolo[2,3-b]pyridin-7-yl]-3-oxopropyl}-2-pyrrolidinyl)acetic acid hydrochloride TLC: Rf 0.09 (chloroform:methanol:28% aqueous ammonia=85:13:2);
$^1$H-NMR (DMSO-d$_6$): δ 1.56-2.05 (m, 4 H) 2.15-4.37 (m, 15 H) 4.61-4.77 (m, 2 H) 5.46-5.57 (m, 2 H) 6.84-7.21 (m, 4 H) 7.27-7.41 (m, 1 H) 7.90-7.99 (m, 1 H) 8.19-8.27 (m, 1 H).

Example 35(86)

1-{3-[9-(3-fluorobenzyl)-5,6,8,9-tetrahydro-7H-pyrido[4',3':4,5]pyrrolo[2,3-b]pyridin-7-yl]-3-oxopropyl}-3-pyrrolidinecarboxylic acid hydrochloride TLC: Rf 0.05 (chloroform:methanol:28% aqueous ammonia=85:13:2);
$^1$H-NMR (DMSO-d$_6$): δ 1.95-4.42 (m, 17 H) 4.60-4.78 (m, 2 H) 5.46-5.76 (m, 2 H) 6.84-7.19 (m, 4 H) 7.27-7.41 (m, 1 H) 7.89-8.00 (m, 1 H) 8.19-8.26 (m, 1 H).

Example 35(87)

1-{2-[9-(3-fluorobenzyl)-5,6,8,9-tetrahydro-7H-pyrido[4',3':4,5]pyrrolo[2,3-b]pyridin-7-yl]-2-oxoethyl}-1H-pyrazole-4-carboxylic acid TLC: Rf 0.24 (chloroform:methanol=10:1);
MS (FAB, Pos): m/z=434 (M+H)$^+$.

Example 35(88)

1-{2-[9-(3-fluorobenzyl)-5,6,8,9-tetrahydro-7H-pyrido[4',3':4,5]pyrrolo[2,3-b]pyridin-7-yl]-2-oxoethyl}-5-methyl-1H-imidazole-4-carboxylic acid TLC: Rf 0.27 (chloroform:methanol:water=50:10:1);
MS (FAB, Pos): m/z=496 (M+H)$^+$.

Example 35(89)

(3-{2-[9-(3-fluorobenzyl)-5,6,8,9-tetrahydro-7H-pyrido[4',3':4,5]pyrrolo[2,3-b]pyridin-7-yl]-2-oxoethyl}-2-oxo-1-imidazolidinyl)acetic acid TLC: Rf 0.10 (chloroform:methanol:water=50:10:1);
$^1$H-NMR (DMSO-$d_6$): δ 2.64-2.89 (m, 2 H), 3.27-3.41 (m, 4 H), 3.65-3.88 (m, 4 H), 3.98-4.19 (m, 2 H), 4.53-4.74 (m, 2 H), 5.47 (s, 2 H), 6.84-7.16 (m, 4 H), 7.26-7.39 (m, 1 H), 7.85-7.95 (m, 1 H), 8.16-8.26 (m, 1 H), 12.66 (s, 1 H).

Example 35(90)

1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazole-4-carboxylic acid TLC: Rf 0.58 (chloroform:methanol:water=5:2:1);
$^1$H-NMR (DMSO-$d_6$): δ 2.70-2.97 (m, 2 H), 3.74-3.92 (m, 2 H), 4.59-4.89 (m, 2 H), 5.42-5.57 (m, 2 H), 5.60-5.74 (m, 2 H), 6.84-7.18 (m, 4 H), 7.25-7.40 (m, 1 H), 7.89-8.00 (m, 1 H), 8.19-8.27 (m, 1 H), 8.49-8.59 (m, 1 H), 13.07 (s, 1 H).

Example 35(91)

3-(1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazol-4-yl)propanoic acid TLC: Rf 0.30 (chloroform:methanol:water=50:10:1)
$^1$H-NMR (DMSO-$d_6$): δ 2.51-2.61 (m, 2 H), 2.67-2.95 (m, 4 H), 3.75-3.88 (m, 2 H), 4.58-4.86 (m, 2 H), 5.42-5.60 (m, 4 H), 6.84-7.16 (m, 4 H), 7.25-7.40 (m, 1 H), 7.69-7.76 (m, 1 H), 7.89-7.98 (m, 1 H), 8.18-8.27 (m, 1 H), 12.12 (s, 1 H).

Example 35(92)

(1-{2-[9-(3-fluorobenzyl)-5,6,8,9-tetrahydro-7H-pyrido[4',3':4,5]pyrrolo[2,3-b]pyridin-7-yl]-2-oxoethyl}-1H-1,2,3-triazol-4-yl)acetic acid TLC: Rf 0.72 (chloroform:methanol:water=5:2:1);
$^1$H-NMR (DMSO-$d_6$): δ 2.68-2.96 (m, 2 H), 3.66 (s, 2 H), 3.76-3.90 (m, 2 H), 4.60-4.85 (m, 2 H), 5.41-5.65 (m, 4 H), 6.85-7.17 (m, 4 H), 7.25-7.41 (m, 1 H), 7.86 (s, 1 H), 7.89-7.99 (m, 1 H), 8.18-8.27 (m, 1 H), 12.31 (s, 1 H).

Example 35(93)

(4-{3-[9-(3-fluorobenzyl)-5,6,8,9-tetrahydro-7H-pyrido[4',3':4,5]pyrrolo[2,3-b]pyridin-7-yl]-3-oxopropyl}-1H-1,2,3-triazol-1-yl)acetic acid TLC: Rf 0.25 (chloroform:methanol:water=9:3:0.2);
$^1$H-NMR (DMSO-$d_6$): δ 2.62-2.89 (m, 6 H), 3.70-3.87 (m, 2 H), 4.50-4.58 (m, 2 H), 4.66 (s, 2 H), 5.48 (s, 2 H), 6.84-7.15 (m, 4 H), 7.24-7.39 (m, 1 H), 7.57-7.68 (m, 1 H), 7.85-7.94 (m, 1 H), 8.16-8.25 (m, 1 H).

Example 35(94)

1-{2-[9-(3-fluorobenzyl)-5,6,8,9-tetrahydro-7H-pyrido[4',3':4,5]pyrrolo[2,3-b]pyridin-7-yl]-2-oxoethyl}-4-methyl-4-piperidinecarboxylic acid TLC: Rf 0.49 (chloroform:methanol=4:1);
MS (FAB, Pos.): m/z=465 (M+H)$^+$.

Example 35(95)

1-{2-[9-(2,4-difluorobenzyl)-5,6,8,9-tetrahydro-7H-pyrido[4',3':4,5]pyrrolo[2,3-b]pyridin-7-yl]-2-oxoethyl}-4-methyl-4-piperidinecarboxylic acid TLC: Rf 0.49 (chloroform:methanol=4:1);
MS (FAB, Pos.): m/z=483 (M+H)$^+$.

Example 35(97)

1-{2-[9-(3-fluorobenzyl)-5,6,8,9-tetrahydro-7H-pyrido[4',3':4,5]pyrrolo[2,3-b]pyridin-7-yl]-2-oxoethyl}-4-hydroxy-4-piperidinecarboxylic acid TLC: Rf 0.26 (chloroform:methanol:water=50:10:1);
MS (FAB, Pos.): m/z=467 (M+H)$^+$.

Example 35(98)

1-{2-[9-(2,4-difluorobenzyl)-5,6,8,9-tetrahydro-7H-pyrido[4',3':4,5]pyrrolo[2,3-b]pyridin-7-yl]-2-oxoethyl}-4-hydroxy-4-piperidinecarboxylic acid TLC: Rf 0.26 (chloroform:methanol:water=50:10:1);
MS (FAB, Pos.): m/z=485 (M+H)$^+$.

Example 35(100)

rel-[(2R,6S)-4-{2-[9-(3-fluorobenzyl)-5,6,8,9-tetrahydro-7H-pyrido[4',3':4,5]pyrrolo[2,3-b]pyridin-7-yl]-2-oxoethyl}-2,6-dimethyl-1-piperazinyl]acetic acid dihydrochloride TLC: Rf 0.20 (chloroform:methanol:28% aqueous ammonia=85:13:2);
MS (ESI, Pos. 20 V): m/z=494 (M+H)$^+$.

Example 35(101)

rel-[(2R,6S)-4-{2-[9-(2,4-difluorobenzyl)-5,6,8,9-tetrahydro-7H-pyrido[4',3':4,5]pyrrolo[2,3-b]pyridin-7-yl]-2-oxoethyl}-2,6-dimethyl-1-piperazinyl]acetic acid dihydrochloride TLC: Rf 0.19 (chloroform:methanol:28% aqueous ammonia=85:13:2);
MS (ESI, Pos. 20 V): m/z=512 (M+H)$^+$.

Example 35(103)

rel-[(3R,5S)-4-{2-[9-(3-fluorobenzyl)-5,6,8,9-tetrahydro-7H-pyrido[4',3':4,5]pyrrolo[2,3-b]pyridin-7-yl]-2-oxoethoxy}-3,5-dimethyl-1-piperazinyl]acetic acid TLC: Rf 0.07 (chloroform:methanol:28% aqueous ammonia=85:13:2);
MS (ESI, Pos. 20 V): m/z=494 (M+H)$^+$.

Example 35(104)

rel-[(3R,5S)-4-{2-[9-(2,4-difluorobenzyl)-5,6,8,9-tetrahydro-7H-pyrido[4',3':4,5]pyrrolo[2,3-b]pyridin-7-yl]-2-oxoethyl}-3,5-dimethyl-1-piperazinyl]acetic acid TLC: Rf 0.09 (chloroform:methanol:28% aqueous ammonia=85:13:2);
MS (ESI, Pos. 20 V): m/z=512 (M+H)$^+$.

Example 35(105)

1-{2-[9-(3-fluorobenzyl)-5,6,8,9-tetrahydro-7H-pyrido[4',3':4,5]pyrrolo[2,3-b]pyridin-7-yl]-2-oxoethyl}-4-methoxy-4-piperidinecarboxylic acid TLC: Rf 0.16 (chloroform:methanol:water=80:20:1);
MS (FAB, Pos.): m/z=481 (M+H)+.

Example 35(106)

1-{2-[9-(2,4-difluorobenzyl)-5,6,8,9-tetrahydro-7H-pyrrolo[2,3-b]pyridin-7-yl]-2-oxoethyl}-4-methoxy-4-piperidinecarboxylic acid TLC: Rf 0.17 (chloroform:methanol:water=80:20:1);
MS (FAB, Pos.): m/z=499 (M+H)+.

Example 35(109)

[1-(2-{9-[(5-chloro-2-thienyl)methyl]-1,3,4,9-tetrahydro-2H-beta-carbolin-2-yl}-2-oxoethyl)-4-piperidinyl]acetic acid hydrochloride TLC: Rf 0.30 (chloroform:methanol:water=50:10:1);
MS (ESI, Pos. 20 V): m/z=486 (M+H)+.

Example 35(111)

1-{2-[9-(3-fluorobenzyl)-5,6,8,9-tetrahydro-7H-pyrido[4',3':4,5]pyrrolo[2,3-b]pyridin-7-yl]-2-oxoethyl}-1,2,3,6-tetrahydro-4-pyridinecarboxylic acid TLC: Rf 0.28 (chloroform:methanol:water=90:10:1);
MS (FAB, Pos.): m/z=449 (M+H)+.

Example 35(112)

1-{2-[9-(2,4-difluorobenzyl)-5,6,8,9-tetrahydro-7H-pyrido[4',3':4,5]pyrrolo[2,3-b]pyridin-7-yl]-2-oxoethyl}-1,2,3,6-tetrahydro-4-pyridinecarboxylic acid TLC: Rf 0.27 (chloroform:methanol:water=90:10:1);
MS (FAB, Pos.): m/z=467 (M+H)+.

Example 35(114)

1-(2-{9-[(5-chloro-2-thienyl)methyl]-1,3,4,9-tetrahydro-2H-beta-carbolin-2-yl}-2-oxoethyl)-4-piperidinecarboxylic acid hydrochloride TLC: Rf 0.15 (chloroform:methanol:water=50:10:1);
MS (ESI, Pos. 20 V): m/z=472 (M+H)+.

Example 35(116)

[4-(2-{9-[(5-chloro-2-thienyl)methyl]-1,3,4,9-tetrahydro-2H-beta-carbolin-2-yl}-2-oxoethyl)-1-piperazinyl]acetic acid dihydrochloride TLC: Rf 0.09 (chloroform:methanol:water=50:10:1);
MS (ESI, Pos. 20 V): m/z=487 (M+H)+.

Example 35(118)

(2S)-2-amino-6-[9-(3-fluorobenzyl)-5,6,8,9-tetrahydro-7H-pyrido[4',3':4,5]pyrrolo[2,3-b]pyridin-7-yl]-6-oxohexanoic acid hydrochloride TLC: Rf 0.13 (chloroform:methanol:water=80:20:1);
MS (FAB, Pos.): m/z=425 (M+H)+.

Example 35(119)

(2S)-2-amino-6-[9-(2,4-difluorobenzyl)-5,6,8,9-tetrahydro-7H-pyrido[4',3':4,5]pyrrolo[2,3-b]pyridin-7-yl]-6-oxohexanoic acid hydrochloride TLC: Rf 0.17 (chloroform:methanol:water=80:20:1);
MS (FAB, Pos.): m/z=443 (M+H)+.

Example 35(122)

rel-[(2R,6S)-4-(2-{9-[(5-chloro-2-thienyl)methyl]-1,3,4,9-tetrahydro-2H-beta-carbolin-2-yl}-2-oxoethyl)-2,6-dimethyl-1-piperazinyl]acetic acid dihydrochloride

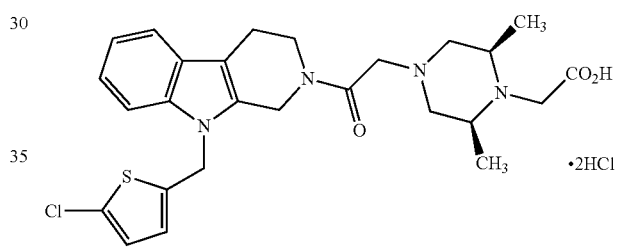

TLC: Rf 0.51 (chloroform:methanol:water=50:10:1);
MS (ESI, Pos. 20 V): m/z=515 (M+H)+.

Example 35(125)

1-(2-{9-[(5-chloro-2-thienyl)methyl]-1,3,4,9-tetrahydro-2H-beta-carbolin-2-yl}-2-oxoethyl)-4-methyl-4-piperidinecarboxylic acid TLC:Rf 0.30 (methylene chloride:methanol:water=90:10:1);
MS (FAB, Pos.): m/z=486 (M+H)+.

Reference Example 1

3-{2-[9-(3-fluorobenzyl)-5,6,8,9-tetrahydro-7H-pyrido[4',3':4,5]pyrrolo[2,3-b]pyridin-7-yl]-2-oxoethoxy}-1,2-oxazole-5-carboxylic acid TLC: Rf 0.19 (chloroform:methanol:water=8:2:0.2);
$^1$H-NMR (CD$_3$OD): δ 2.80-2.99 (m, 2 H), 3.76-3.98 (m, 2 H), 4.59-4.74 (m, 2 H), 4.92-5.17 (m, 2 H), 5.47-5.56 (m, 2 H), 6.35-6.42 (m, 1 H), 6.74-7.02 (m, 3 H), 7.15 (dd, J=7.8, 4.8 Hz, 1 H), 7.23-7.34 (m, 1 H), 7.96 (dd, J=7.8, 1.5 Hz, 1 H), 8.18-8.24 (m, 1 H).

Example 36 tert-butyl 2-methyl-2-[3-(tetrahydro-2H-pyran-2-yloxy)propoxy]propanoate

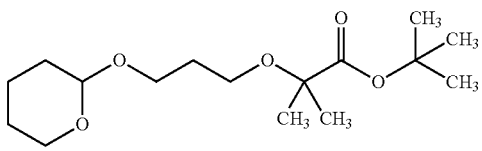 [SMILES: CC(C)(C)OC(=O)C(C)(C)OCCCOC1CCCCO1]

To a solution (22 mL) of tert-butyl 2-hydroxy-2-methylpropanoate (1.0 g) in N,N-dimethylformamide was added sodium hydride (250 mg) under an ice bath, and the mixture was stirred at room temperature for 1 hour. Thereafter, under an ice bath, 2-(3-bromopropoxy)tetrahydro-2H-pyran (0.88 mL) was added dropwise, and the mixture was stirred at room temperature overnight. To the reaction mixture were added water and 1N hydrochloric acid under an ice bath, followed by extraction with t-butyl methyl ether. The organic layer was sequentially washed with an aqueous saturated sodium bicarbonate solution and an aqueous saturated sodium chloride solution, dried with anhydrous sodium sulfate, and concentrated. The residue was purified by silica gel column chromatography (hexane:ethyl acetate=8:1) to obtain the title compound having the following physical property values, as a mixture (400 mg) with tert-butyl 2-hydroxy-2-methylpropanoate.

TLC: Rf 0.23 (hexane:ethyl acetate=8:1);
$^1$H-NMR (CDCl$_3$): δ 1.37 (s, 6 H) 1.47 (s, 9 H) 1.31-1.93 (m, 8 H) 3.42-3.56 (m, 4 H) 3.77-3.91 (m, 2 H) 4.55-4.60 (m, 1 H).

Example 37 tert-butyl 2-(3-hydroxypropoxy)-2-methylpropanoate

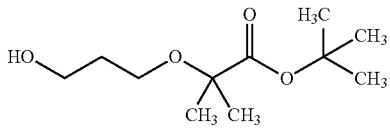

To a solution (4.3 mL) of the compound produced in Example 36 (400 mg: mixture with tert-butyl 2-hydroxy-2-methylpropanoate) in methanol was added p-toluenesulfonic acid monohydrate (26 mg) at room temperature, and the mixture was stirred at room temperature for 2 hours. To the reaction mixture was added triethylamine (18 L), this was concentrated, and the resulting residue was purified by silica gel column chromatography (hexane:ethyl acetate=8:1→4:1→2:1) to obtain the title compound (130 mg) having the following physical property values.

TLC: Rf 0.22 (hexane:ethyl acetate=4:1);
$^1$H-NMR (CDCl$_3$): δ 1.37 (s, 6 H) 1.46 (s, 9 H) 1.64-1.84 (m, 2 H) 3.31 (br.s, 1 H) 3.51-3.60 (m, 2 H) 3.73-3.84 (m, 2 H).

Example 38

3-(2-tert-butoxy-1,1-dimethyl-2-oxoethoxy)propionic acid

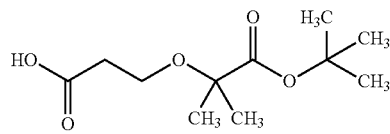 [SMILES: CC(C)(C)OC(=O)C(C)(C)OCCC(=O)O]

To a solution of the compound (116 mg) produced in Example 37 in acetonitrile were sequentially added a buffer solution of sodium dihydrogen phosphate (2.7 mL, pH: 6.58), 2,2,6,6-tetramethylpiperidine 1-oxyl (9 mg) and an aqueous solution (1.2 mL) of sodium chlorite (97 mg) and a sodium hypochlorite solution (50 μL) at room temperature, a temperature was raised to 50° C., and the mixture was stirred for 2.5 hours. To the reaction mixture was added an aqueous saturated sodium sulfite solution under an ice bath, and it was confirmed that the solution became colorless and transparent, followed by concentration. To the resulting residue was added 5N hydrochloric acid, this was extracted with ethyl acetate two times, and the extract was dried with anhydrous sodium sulfate, and concentrated to obtain the title compound (118 mg) having the following physical property values.

TLC: Rf 0.23 (hexane:ethyl acetate=2:1);
$^1$H-NMR (CDCl$_3$): δ 1.41 (s, 6 H) 1.48 (s, 9 H) 2.69 (t, J=6.0 Hz, 2 H) 3.69 (t, J=6.0 Hz, 2 H).

Example 39

2-{3-[9-(3-fluorobenzyl)-5,6,8,9-tetrahydro-7H-pyrido[4',3':4,5]pyrrolo[2,3-b]pyridin-7-yl]-3-oxopropoxy}-2-methylpropanoic acid hydrochloride

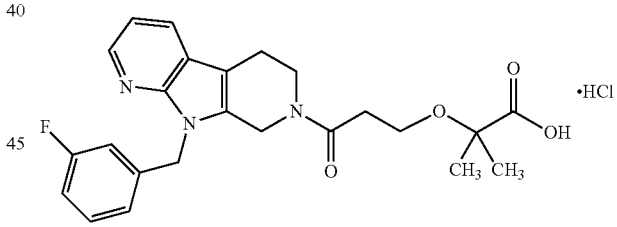

The compound produced in Example 38 and tetrahydropyridopyrrolopyridine produced by operation in accordance with Example 4→Example 5→Example 6→Example 7→Example 1 were used, which were subjected to operation in accordance with Example 11→Example 35 to obtain the title compound (59 mg) having the following physical property values.

TLC: Rf 0.09 (chloroform:methanol:28% aqueous ammonia=85:13:2);
$^1$H-NMR (DMSO-d$_6$): δ 1.20-1.34 (m, 6 H) 2.23-2.87 (m, 4 H) 3.50-3.84 (m, 4 H) 4.21-5.05 (m, 4 H) 5.47-5.57 (m, 2 H) 6.87-7.17 (m, 4 H) 7.28-7.39 (m, 1 H) 7.90-7.98 (m, 1 H) 8.20-8.25 (m, 1 H).

Example 39(1)-Example 39(16)

A corresponding ester in place of 3-(2-tert-butoxy-1,1-dimethyl-2-oxoethoxy)propanoic acid, and a tetrahydropyridopyrrolopyridine derivative produced by operation in accordance with Example 4→Example 5→Example 6→Example 7→Example 1 were used, which were subjected to operation in accordance with Example 39 to obtain the following compounds.

Example 39(1)

{3-[9-(3-fluorobenzyl)-5,6,8,9-tetrahydro-7H-pyrido[4',3':4,5]pyrrolo[2,3-b]pyridin-7-yl]-3-oxopropoxy}acetic acid TLC: Rf 0.22 (chloroform:methanol:water=50:10:1);
$^1$H-NMR (DMSO-$d_6$): δ 2.60-2.88 (m, 4 H) 3.60-3.85 (m, 4 H) 3.90-4.05 (m, 2 H) 4.56-4.75 (m, 2 H) 5.38-5.58 (m, 2 H) 6.84-7.15 (m, 4 H) 7.26-7.38 (m, 1 H) 7.85-7.93 (m, 1 H) 8.20 (dd, J=5.00, 1.50 Hz, 1 H) 12.56 (br. s., 1 H).

Example 39(2)

{4-[9-(3-fluorobenzyl)-5,6,8,9-tetrahydro-7H-pyrido[4',3':4,5]pyrrolo[2,3-b]pyridin-7-yl]-4-oxobutoxy}acetic acid TLC: Rf 0.34 (chloroform:methanol:water-=10:2:0.2);
$^1$H-NMR (DMSO-$d_6$): δ 1.61-1.83 (m, 2 H), 2.32-2.50 (m, 2 H), 2.63-2.86 (m, 2 H), 3.35-3.51 (m, 2 H), 3.69-3.84 (m, 2 H), 3.91-3.99 (m, 2 H), 4.59-4.70 (m, 2 H), 5.43-5.54 (m, 2 H), 6.85-7.15 (m, 4 H), 7.27-7.40 (m, 1 H), 7.86-7.95 (m, 1 H), 8.21 (d, J=4.6 Hz, 1 H).

Example 39(3)

2-{3-[9-(4-fluorobenzyl)-5,6,8,9-tetrahydro-7H-pyrido[4',3':4,5]pyrrolo[2,3-b]pyridin-7-yl]-3-oxopropoxy}-2-methylpropanoic acid TLC: Rf 0.20 (chloroform:methanol:28% aqueous ammonia=85:13:2);
MS (ESI, Pos.): m/z=440 (M+H)$^+$.

Example 39(4)

2-{3-[9-(2,4-difluorobenzyl)-5,6,8,9-tetrahydro-7H-pyrido[4',3':4,5]pyrrolo[2,3-b]pyridin-7-yl]-3-oxopropoxy}-2-methylpropanoic acid TLC: Rf 0.21 (chloroform:methanol:28% aqueous ammonia=85:13:2);
MS (ESI, Pos.): m/z=458 (M+H)$^+$.

Example 39(5)

2-methyl-2-{3-oxo-3-[9-(3,4,5-trifluorobenzyl)-5,6,8,9-tetrahydro-7H-pyrido[4',3':4,5]pyrrolo[2,3-b]pyridin-7-yl]propoxy}propanoic acid TLC: Rf 0.19 (chloroform:methanol:28% aqueous ammonia=85:13:2);
MS (ESI, Pos.): m/z=476 (M+H)$^+$.

Example 39(6)

2-methyl-2-{3-oxo-3-[9-(2,4,5-trifluorobenzyl)-5,6,8,9-tetrahydro-7H-pyrido[4',3':4,5]pyrrolo[2,3-b]pyridin-7-yl]propoxy}propanoic acid TLC: Rf 0.19 (chloroform:methanol:28% aqueous ammonia=85:13:2);
MS (ESI, Pos.): m/z=476 (M+H)$^+$.

Example 39(7)

2-methyl-2-{3-oxo-3-[9-(2,3,4,6-tetrafluorobenzyl)-5,6,8,9-tetrahydro-7H-pyrido[4',3':4,5]pyrrolo[2,3-b]pyridin-7-yl]propoxy}propanoic acid TLC: Rf 0.19 (chloroform:methanol:28% aqueous ammonia=85:13:2);
MS (ESI, Pos.): m/z=494 (M+H)$^+$.

Example 39(8)

2-{3-[9-(4-chlorobenzyl)-5,6,8,9-tetrahydro-7H-pyrido[4',3':4,5]pyrrolo[2,3-b]pyridin-7-yl]-3-oxopropoxy}-2-methylpropanoic acid TLC: Rf 0.17 (chloroform:methanol:28% aqueous ammonia=85:13:2);
MS (ESI, Pos.): m/z=456 (M+H)$^+$.

Example 39(9)

2-{3-[9-(4-chloro-2-fluorobenzyl)-5,6,8,9-tetrahydro-7H-pyrido[4',3':4,5]pyrrolo[2,3-b]pyridin-7-yl]-3-oxopropoxy}-2-methylpropanoic acid TLC: Rf 0.19 (chloroform:methanol:28% aqueous ammonia=85:13:2);
MS (ESI, Pos. 20 V): m/z=474 (M+H)$^+$.

Example 39(10)

2-{3-[9-(4-chloro-3-fluorobenzyl)-5,6,8,9-tetrahydro-7H-pyrido[4',3':4,5]pyrrolo[2,3-b]pyridin-7-yl]-3-oxopropoxy}-2-methylpropanoic acid TLC: Rf 0.17 (chloroform:methanol:28% aqueous ammonia=85:13:2);
MS (ESI, Pos. 20 V): m/z=474 (M+H)$^+$.

Example 39(14)

2-(3-{9-[(4-chloro-2-thienyl)methyl]-5,6,8,9-tetrahydro-7H-pyrido[4',3':4,5]pyrrolo[2,3-b]pyridin-7-yl}-3-oxopropoxy)-2-methylpropanoic acid MS (ESI, Pos.): m/z=462 (M+H)$^+$.

Example 39(15)

2-(3-{9-[(5-chloro-2-thienyl)methyl]-5,6,8,9-tetrahydro-7H-pyrido[4',3':4,5]pyrrolo[2,3-b]pyridin-7-yl}-3-oxopropoxy)-2-methylpropanoic acid TLC: Rf 0.16 (chloroform:methanol:28% aqueous ammonia=85:13:2);
MS (ESI, Pos.): m/z=462 (M+H)$^+$.

Example 39(16)

2-(3-{9-[(5-chloro-2-thienyl)methyl]-5,6,8,9-tetrahydro-7H-pyrido[4',3':4,5]pyrrolo[2,3-b]pyridin-7-yl}-3-oxopropoxy)-2-methylpropanoic acid TLC: Rf 0.16 (chloroform:methanol:28% aqueous ammonia=85:13:2);
MS (ESI, Pos. 20 V): m/z=462 (M+H)$^+$.

Example 40

3-({1-[9-(3-fluorobenzyl)-5,6,8,9-tetrahydro-7H-pyrido[4',3':4,5]pyrrolo[2,3-b]pyridin-7-yl]-1-oxo-2-propanyl}amino)-2,2-dimethylpropanoic acid dihydrochloride

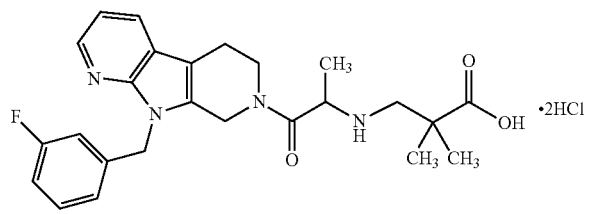 [SMILES: CC(NCC(C)(C)C(=O)O)C(=O)N1CCc2c(n(Cc3cccc(F)c3)c3ncccc23)C1 ; "·2HCl"]

2-chloropropionyl chloride in place of chloroacetyl chloride in Example 16 was used, which was subjected to operation in accordance with Example 19 and Example 20 to obtain the following compound.

TLC: Rf 0.61 (chloroform:methanol:water=50:10:1);

$^1$H-NMR (DMSO-d$_6$): δ 0.93-1.59 (m, 9 H), 2.65-3.22 (m, 4 H), 3.57-4.12 (m, 3 H), 4.47-5.00 (m, 2 H), 5.35-5.79 (m, 2 H), 6.86-7.43 (m, 5 H), 7.84-8.06 (m, 1 H), 8.17-8.37 (m, 1 H), 8.42-9.89 (m, 3 H).

Example 41 tert-butyl 1-[4-(tetrahydro-2H-pyran-2-yloxy)butyl]cyclopropanecarboxylate

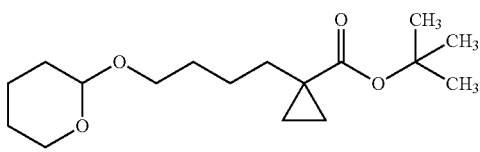 [SMILES: CC(C)(C)OC(=O)C1(CCCCOC2CCCCO2)CC1]

Under the argon atmosphere, tert-butyl cyclopropylcarboxylate (3.76 g) and 2-(4-bromobutoxy)tetrahydro-2H-pyran (7.52 g) were dissolved in anhydrous/THF (106 mL), followed by cooling to an inner temperature of −65° C. A lithium diisopropylamide solution (2.0M, THF:heptane:ethylbenzene solution) (19.8 mL) was added dropwise over 15 minutes. After completion of addition, the mixture was stirred at room temperature for 8 hours. An aqueous saturated ammonium chloride solution was added to stop the reaction, and water, and hexane:ethyl acetate (1:1) were added, followed by extraction. The organic layer was washed with dilute hydrochloric acid, water and an aqueous saturated sodium chloride solution, and dried with anhydrous sodium sulfate. The residue obtained by concentration was purified by silica gel column chromatography (hexane:ethyl acetate, 98:2→90:10) to obtain the title compound (3.86 g) having the following physical property values.

TLC: Rf 0.40 (hexane:ethyl acetate=9:1);

$^1$H-NMR (CDCl$_3$): δ 0.60 (2 H), 1.10 (2 H), 1.42 (9 H), 1.45 □ 1.90 (12 H), 3.34 □ 3.43 (1 H), 3.45 □ 3.54 (1 H), 3.68 □ 3.78 (1 H), 3.82 □ 3.91 (1 H), 4.54 □ 4.60 (1 H).

Example 42

4-[1-tert-butoxycarbonyl)cyclopropyl]butanoic acid

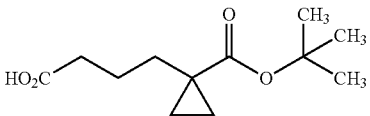 [SMILES: CC(C)(C)OC(=O)C1(CCCC(=O)O)CC1]

To a solution of the compound (4.32 g) produced in Example 41 in methanol (29 mL) was added p-toluenesulfonic acid monohydrate (28 mg), and the mixture was stirred at room temperature for 24 hours. Water and an aqueous saturated sodium bicarbonate solution were added, thereafter, methanol was distilled off, followed by extraction with ethyl acetate. The organic layer was washed with an aqueous saturated sodium chloride solution, dried with anhydrous sodium sulfate, and concentrated to obtain tert-butyl 1-(4-hydroxybutyl)cyclopropanecarboxylate (3.20 g). This was dissolved in acetonitrile (118 mL), a phosphate buffer (pH 6.6, 79 mL) was added, and the mixture was stirred at 40° C. A 2,2,6,6-tetramethylpiperidine 1-oxyl free radical (TEMPO, 227 mg), an aqueous sodium chlorite solution (sodium chlorite 2.62 g, water 16 mL) and an aqueous sodium hypochlorite solution (0.5%, 16 mL) were added, and the mixture was stirred for 15 hours. After allowing to cool, an aqueous sodium sulfite solution and 2N hydrochloric acid were added, followed by extraction with ethyl acetate. This was reverse-extracted with an aqueous saturated sodium bicarbonate solution, 2N hydrochloric acid was added to make the solution acidic, followed by extraction with ethyl acetate. This was washed with water and an aqueous saturated sodium chloride solution, dried with anhydrous sodium sulfate, and concentrated to obtain the title compound (3.08 g) having the following physical property values.

TLC: Rf 0.38 (hexane:ethyl acetate=2:1);

$^1$H-NMR (DMSO-d$_6$): δ 0.64 (2 H), 0.97 (2 H), 1.36 (s, 9 H), 1.36 □ 1.46 (2 H), 1.54 □ 1.70 (2 H), 2.16 (2 H), 12.0 (1 H).

Example 43

1-{4-[9-(3-fluorobenzyl)-5,6,8,9-tetrahydro-7H-pyrido[4',3':4,5]pyrrolo[2,3-b]pyridin-7-yl]-4-oxobutyl}cyclopropanecarboxylic acid

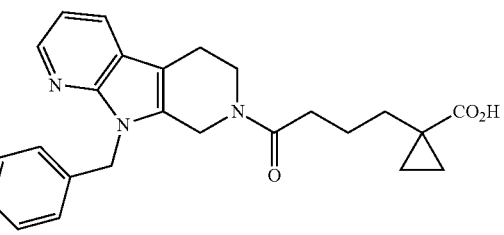

The compound produced in Example 42 and a tetrahydropyridopyrrolopyridine derivative produced by operation in accordance with Example 4→Example 5→Example 6→Example 7→Example 1 were used, which were subjected to operation in accordance with Example 11→Example 35 to obtain the title compound having the following physical property values.

TLC: Rf 0.46 (methylene chloride:ethyl acetate:methanol=8:4:1);
$^1$H-NMR (DMSO-d$_6$): δ 0.56-0.72 (m, 2 H), 0.95-1.06 (m, 2 H), 1.32-1.72 (m, 4 H), 2.22-2.45 (m, 2 H), 2.63-2.84 (m, 2 H), 3.68-3.82 (m, 2 H), 4.62 (s, 2 H), 5.42-5.54 (m, 2 H), 6.85-7.05 (m, 4 H), 7.28-7.38 (m, 1 H), 7.85-7.94 (m, 1 H), 8.20 (dd, J=4.8, 1.5 Hz, 1 H), 11.97 (brs, 1 H).

Example 43(1)

1-{4-[9-(2,4-difluorobenzyl)-5,6,8,9-tetrahydro-7H-pyrido[4'3':4,5]pyrrolo[2,3-b]pyridin-7-yl]-4-oxobutyl}cyclopropanecarboxylic acid The compound produced in Example 42 and a tetrahydropyridopyrrolopyridine derivative produced by operation in accordance with Example 4→Example 5→Example 6→Example 7→Example 1 were used, which were subjected to operation in accordance with Example 11→Example 35 to obtain the title compound having the following physical property values.

TLC: Rf 0.48 (methylene chloride:ethyl acetate:methanol=8:4:1);
$^1$H-NMR (DMSO-d$_6$): δ 0.59-0.71 (m, 2 H), 0.96-1.05 (m, 2 H), 1.36-1.75 (m, 4 H), 2.26-2.48 (m, 2 H), 2.63-2.84 (m, 2 H), 3.66-3.82 (m, 2 H), 4.64 (s, 2 H), 5.41-5.54 (m, 2 H), 6.86-7.02 (m, 2 H), 7.10 (dd, J=7.8, 4.8 Hz, 1 H), 7.22-7.33 (m, 1 H), 7.85-7.92 (m, 1 H), 8.20 (dd, J=4.8, 1.5 Hz, 1 H), 12.00 (brs, 1 H).

Example 44 ethyl 8-methyl-1,4-dioxaspiro[4.5]decane-8-carboxylate

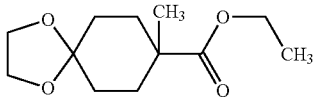 [SMILES: CCOC(=O)C1(C)CCC2(CC1)OCCO2]

Ethyl-4-oxocyclohexanecarboxylate (25.1 g) and ethylene glycol (32.3 g) were dissolved in 80 mL of toluene, p-toluenesulfonic acid monohydrate (563 mg) was added while stirring at room temperature, and the mixture was stirred at that temperature overnight. After completion of the reaction, a hexane:ethyl acetate=3:1 solution (150 mL) was added to dilute the reaction, thereafter, 100 mL of water was added, and extraction operation was performed. The resulting organic layer was sequentially washed with an aqueous saturated sodium bicarbonate solution and an aqueous saturated sodium chloride solution, dried with magnesium sulfate, and the solvent was distilled off under reduced pressure to obtain the crude product. This was azeotroped with toluene to obtain a ketal intermediate (32.1 g).

Lithium diisopropylamide (37.5 mL) was dissolved in 50 mL of THF, and a solution of the ketal intermediate (10.7 g) in 12 mL of THF was added dropwise over 5 minutes while stirring at an inner temperature of −30° C. After this solution was stirred at an inner temperature of −30° C. for 20 minutes, and a solution of methyl iodide (14.2 g) in 12 mL of THF was added dropwise at that temperature over 5 minutes. An inner temperature at that time was raised to −5° C. This solution was stirred for 1 hour until an inner temperature became 23° C., water was added to stop the reaction, extraction operation (THF, once) was performed, the aqueous layer was neutralized with 2N hydrochloric acid, and re-extraction operation (ethyl acetate, two times) was performed. The resulting organic layer was sequentially washed with water and an aqueous saturated sodium chloride solution, and dried with magnesium sulfate, and the solvent was distilled off under reduced pressure to obtain the title compound (12.8 g) having the following physical property values.

TLC: Rf 0.51 (hexane:ethyl acetate=4:1);
$^1$H-NMR (CDCl$_3$): δ 1.19 (s, 3 H), 1.25 (t, J=7.2 Hz, 3 H), 1.43-1.71 (m, 6 H), 2.09-2.17 (m, 2 H), 3.93 (s, 4 H), 4.15 (q, J=7.2 Hz, 2 H).

Example 45 ethyl 1-methyl-4-oxocyclohexanecarboxylate

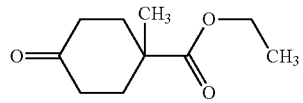

The compound (12.8 g) produced in Example 44 was dissolved in 100 mL of acetone, 50 mL of 2N hydrochloric acid was added while stirring at room temperature, and the mixture was stirred at that temperature overnight. After completion of the reaction, the solvent was distilled off under reduced pressure, 100 mL of tetrabutyl methyl ether was added, and extraction operation was performed. The resulting organic layer was sequentially washed with an aqueous saturated sodium bicarbonate solution and an aqueous saturated sodium chloride solution, and dried with magnesium sulfate, and the solvent was distilled off under reduced pressure to obtain 9.7 g of the crude product. The crude product was purified by silica gel column chromatography (ethyl acetate/hexane=3%→25%) to obtain the title compound (8.34 g) having the following physical property values.

TLC: Rf 0.41 (hexane:ethyl acetate=4:1);
$^1$H-NMR (CDCl$_3$): δ 1.25-1.32 (m, 6 H), 1.58-1.73 (m, 2 H), 2.27-2.51 (m, 6 H), 4.22 (q, J=7.2 Hz, 2 H).

Example 46 ethyl trans-4-(2,2-dimethyl-4,6-dioxo-1,3-dioxan-5-yl)-1-methylcyclohexanecarboxylate The compound (3.68 g) produced in Example 45 and Meldrum's acid (3.17 g) were dissolved in 40 mL of dimethylformamide, sodium triacetoxyborohydride (5.09 g) was added while stirring at room temperature, and the mixture was stirred at that temperature for 4 hours. After completion of the reaction, 300 mL of water was added, and extraction operation (hexane:ethyl acetate=3:1) was performed. The resulting organic layer was sequentially washed with an aqueous saturated sodium bicarbonate solution and an aqueous saturated sodium chloride solution, and dried with magnesium sulfate, and the solvent was distilled off under reduced pressure to obtain 6.8 g of the crude product. The crude product was purified by silica gel column chromatography (ethyl acetate/hexane=18%→29%) to obtain an isomer mixture (3.36 g) of trans:cis=10:11. The isomer mixture was dissolved in 4 mL of ethyl acetate, and the solution was allowed to stand at room temperature overnight. The precipitated crystal was filtered, and dried under reduced pressure to obtain the title compound (437 mg) having the following physical property values.

TLC: Rf 0.48 (hexane:ethyl acetate=2:1);

$^1$H-NMR (CDCl$_3$): δ 1.12-1.29 (m, 8 H), 1.48-1.60 (m, 2 H), 1.67-1.87 (m, 8 H), 2.24-2.46 (m, 3 H), 3.33 (d, J=3.3 Hz, 1 H), 4.17 (q, J=7.2 Hz, 2 H).

Example 47

[trans-4-(ethoxycarbonyl)-4-methylcyclohexyl]acetic acid

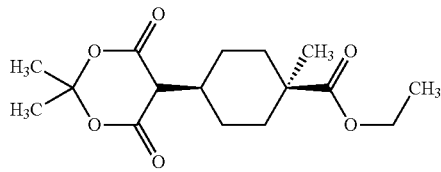 [SMILES: CCOC(=O)[C@]1(C)CC[C@H](C2C(=O)OC(C)(C)OC2=O)CC1]

The compound (370 mg) produced in Example 46 was dissolved in 2.5 mL of dimethylformamide and 0.25 mL of water, and the solution was stirred at 115° C. for 2 hours. After completion of the reaction, 30 mL of water was added, and extraction operation (hexane:ethyl acetate=1:1) was performed. The resulting organic layer was washed using an aqueous saturated sodium chloride solution, and dried with magnesium sulfate, and the solvent was distilled off under reduced pressure to obtain the title compound (274 mg) having the following physical property values.

TLC: Rf 0.41 (hexane:ethyl acetate=2:1);

$^1$H-NMR (CDCl$_3$): δ 0.98-1.29 (m, 10 H), 1.63-1.80 (m, 3 H), 2.15-2.27 (m, 4 H), 4.13 (q, J=7.2 Hz, 2 H).

Example 48 cis-4-{2-[9-(3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid

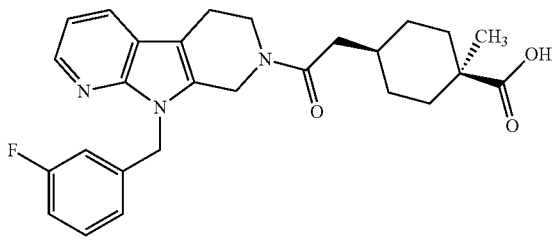 [SMILES: C[C@]1(C(=O)O)CC[C@@H](CC(=O)N2CCc3c(n(Cc4cccc(F)c4)c4ncccc34)C2)CC1]

The compound produced in Example 47 and a tetrahydropyridopyrrolopyridine derivative produced by operation in accordance with Example 4→Example 5→Example 6→Example 7→Example 1 were used, which were subjected to operation in accordance with Example 11→Example 3 to obtain the title compound having the following physical property values.

TLC: Rf 0.26 (n-hexane:ethyl acetate=1:1);

MS (FAB, Pos.): m/z=464 (M+H)$^+$.

Example 48(1)-Example 48(41)

The compound produced in Example 47 and a tetrahydropyridopyrrolopyridine derivative produced by operation in accordance with Example 4→Example 5→Example 6→Example 7→Example 1 were used, which were subjected to operation in accordance with Example 11→Example 3 to obtain the title compounds having the following physical property values.

Example 48(1)

cis-4-{2-[9-(2,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.35 (n-hexane:ethyl acetate=1:1);

MS (FAB, Pos.): m/z=482 (M+H)$^+$.

Example 48(3)

trans-4-{2-[9-(3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.46 (n-hexane:ethyl acetate=1:2);

MS (FAB, Pos.): m/z=464 (M+H)$^+$.

Example 48(4)

trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.54 (n-hexane:ethyl acetate=1:2);

MS (FAB, Pos.): m/z=482 (M+H)$^+$.

Example 48(6)

trans-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC: Rf 0.47 (ethyl acetate);

MS (ESI, Pos. 20 V): m/z=486 (M+H)$^+$.

Example 48(7)

trans-1-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.64 (ethyl acetate);

MS (ESI, Pos. 20 V): m/z=500 (M+H)$^+$.

Example 48(8)

trans-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid

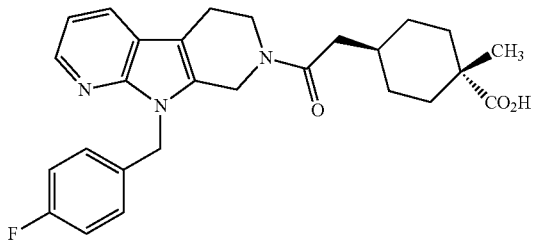 [SMILES: C[C@]1(C(=O)O)CC[C@H](CC(=O)N2CCc3c(n(Cc4ccc(F)cc4)c4ncccc34)C2)CC1]

TLC: Rf 0.43 (ethyl acetate);
MS (ESI, Pos. 20 V): m/z=464 (M+H)$^+$.

Example 48(9)

trans-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid

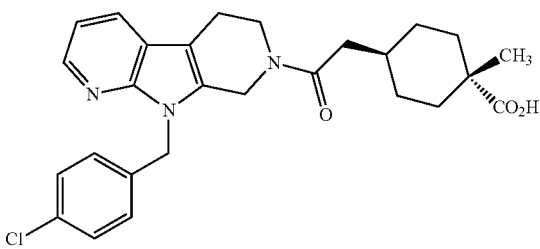 [SMILES: C[C@]1(C(=O)O)CC[C@H](CC(=O)N2CCc3c(n(Cc4ccc(Cl)cc4)c4ncccc34)C2)CC1]

TLC: Rf 0.43 (ethyl acetate);
MS (ESI, Pos. 20 V): m/z=480 (M+H)$^+$.

Example 48(10)

trans-4-{2-[9-(3-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.45 (ethyl acetate);
MS (ESI, Pos. 20 V): m/z=480 (M+H)$^+$.

Example 48(12)

trans-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC: Rf 0.30 (hexane:ethyl acetate=1:2);
MS (ESI, Pos. 20 V): m/z=486 (M+H)$^+$.

Example 48(13)

trans-4-{2-[9-(3,5-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.39 (hexane:ethyl acetate=1:2);
MS (ESI, Pos. 20 V): m/z=482 (M+H)$^+$.

Example 48(14)

trans-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.36 (hexane:ethyl acetate=1:2);
MS (ESI, Pos. 20 V): m/z=498 (M+H)$^+$.

Example 48(15)

trans-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.46 (hexane:ethyl acetate=1:2);
MS (ESI, Pos. 20 V): m/z=498 (M+H)$^+$.

Example 48(16)

trans-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.33 (hexane:ethyl acetate=1:2);
MS (ESI, Pos. 20 V): m/z=498 (M+H)$^+$.

Example 48(19)

cis-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.30 (ethyl acetate:n-hexane=2:1);
MS (ESI, Pos. 20V): m/z=464 (M+H)$^+$.

Example 48(20)

cis-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.28 (ethyl acetate:n-hexane=2:1)
MS (ESI, Pos. 20V): m/z=480 (M+H, 35Cl)$^+$.

Example 48(21)

cis-4-{2-[9-(3-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.33 (ethyl acetate:n-hexane=2:1);
MS (ESI, Pos. 20V): m/z=480 (M+H, 35Cl)$^+$.

Example 48(22)

cis-4-{2-[9-(3,5-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.42 (ethyl acetate:n-hexane=2:1);
MS (ESI, Pos. 20V): m/z=482 (M+H)+.

Example 48(23)

cis-1-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}cyclohexanecarboxylic acid TLC: Rf 0.43 (ethyl acetate:n-hexane);
MS (ESI, Pos. 20V): m/z=500 (M+H)+.

Example 48(24)

cis-4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.43 (ethyl acetate:n-hexane=2:1);
MS (ESI, Pos. 20V): m/z=498 (M+H, 35Cl)+.

Example 48(25)

cis-4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.32 (ethyl acetate:n-hexane=2:1);
MS (ESI, Pos. 20V): m/z=498 (M+H, 35Cl)+.

Example 48(26)

cis-4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.32 (ethyl acetate:n-hexane=2:1);
MS (ESI, Pos. 20V): m/z=498 (M+H, 35Cl)+.

Example 48(29)

cis-4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC: Rf 0.25 (ethyl acetate:n-hexane=2:1);
MS (ESI, Pos. 20V): m/z=486 (M+H, 35Cl)+.

Example 48(30)

cis-4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC: Rf 0.18 (ethyl acetate:n-hexane=2:1);
MS (ESI, Pos. 20V): m/z=486 (M+H, 35Cl)+.

Example 48(34)

cis-4-{2-[9-(3,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.59 (ethyl acetate);
MS (ESI, Pos. 20V): m/z=482 (M+H)+.

Example 48(41)

trans-4-{2-[9-(3,4-difluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid TLC: Rf 0.31 (hexane:ethyl acetate=1:2);
MS (ESI, Pos. 20 V): m/z=482 (M+H)+.

Example 49 methyl 4-(2-tert-butoxy-2-oxoethyl)-2-chlorobenzoate

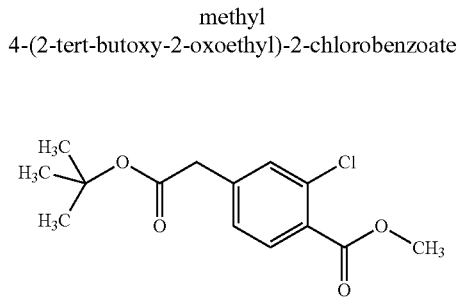

To anhydrous THF (4.5 mL) suspension containing active zinc (530 mg) were added tert-butyl bromoacetate (800 μL) and 1,2-dibromoethane (15 μL), and a reaction was performed at 90° C. for 3 minutes using a microwave synthesis apparatus initiator manufactured by Biotage. Centrifugation was performed to obtain the supernatant, to prepare a solution of 2-tert-butoxy-2-oxoethylzinc bromide in THF.

To methyl 2-chloro-4-iodobenzoate (296 mg) was added a solution (4.5 mL) of 2-tert-butoxy-2-oxoethylzinc bromide in THF, then, bis(tri-tert-butylphosphine)palladium (51 mg) was added, and a reaction was performed at 50 W and 80° C. for 10 minutes using a microwave synthesis apparatus manufactured by CEM Co. The reaction solution was poured into an aqueous saturated ammonium chloride solution, and ethyl acetate was added. Insolubles were filtered off with Celite, and layers were separated. The organic layer was washed with an aqueous saturated sodium chloride solution, dried with anhydrous sodium sulfate, and concentrated under reduced pressure. The resulting residue was purified by medium pressure preparative liquid chromatography W-prep 2XY (column:main column M, inject column S; automatic condition setting: n-hexane:ethyl acetate=4:1, Rf=0.60) to obtain the title compound (94 mg) having following physical property values.

TLC: Rf 0.58 (n-hexane:ethyl acetate=4:1);

$^1$H-NMR (CDCl$_3$): δ 7.80 (d, 1H), 7.38 (d, 1H), 7.22 (dd, 1H), 3.92 (s, 3H), 3.53 (s, 2H), 1.44 (s, 9H).

Example 50 methyl 4-(carboxymethyl)-2-chlorobenzoate

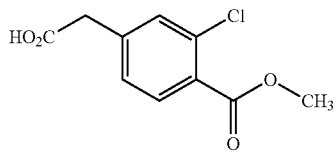

To a solution of the compound (87 mg) produced in Example 49 in methylene chloride (1.0 mL) was added trifluoroacetic acid (0.5 mL), and the mixture was stirred at room temperature for 1 hour. The reaction solution was concentrated to dryness under reduced pressure to obtain the title compound having the following physical property values.

TLC: Rf 0.28 (methylene chloride:methanol=9:1);

$^1$H-NMR (CDCl$_3$): δ 7.82 (d, 1H), 7.40 (d, 1H), 7.24 (dd, 1H), 3.93 (s, 3H), 3.68 (s, 2H).

Example 51

2-chloro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid

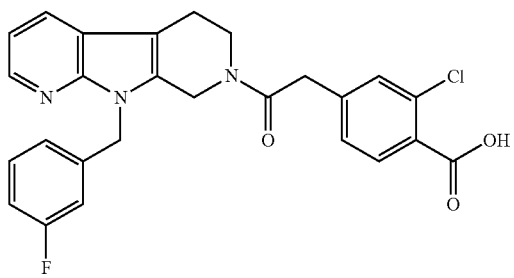 [SMILES: O=C(O)c1ccc(CC(=O)N2CCc3c(n(Cc4cccc(F)c4)c4ncccc34)C2)cc1Cl]

The compound produced in Example 50 and a tetrahydropyridopyrrolopyridine derivative produced by operation in accordance with Example 4→Example 5→Example 6→Example 7→Example 1 were used, which were subjected to operation in accordance with Example 11→Example 3 to obtain the title compound having the following physical property values.

TLC: Rf 0.26 (chloroform:methanol=9:1);

MS (ESI, Pos. 20 V): m/z=478 (M+H)$^+$.

Example 51(1)-Example 51(80)

A corresponding ester in place of the compound produced in Example 50 and a tetrahydropyridopyrrolopyridine derivative produced by operation in accordance with Example 4→Example 5→Example 6→Example 7→Example 1 were used, which were subjected to operation in accordance with Example 11→Example 3 to obtain the title compounds having the following physical property values.

Example 51(1)

3-fluoro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid TLC: Rf 0.43 (methylene chloride:methanol=9:1);
MS (ESI, Pos. 20 V): m/z=462 (M+H)$^+$.

Example 51(2)

3-chloro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid TLC: Rf 0.36 (methylene chloride:methanol=9:1);
MS (ESI, Pos. 20 V): m/z=478 (M+H)$^+$.

Example 51(3)

2-chloro-4-{2-[9-(2,4-difluorobenzyl)-5,6,8,9-tetrahydro-7H-pyrido[4',3':4,5]pyrrolo[2,3-b]pyridin-7-yl]-2-oxoethyl}carboxylic acid TLC:Rf 0.28 (methylene chloride:methanol=9:1);
MS (ESI, Pos. 20 V): m/z=496 (M+H)$^+$.

Example 51(5)

2-fluoro-4-{2-[9-(3-fluorobenzyl)-5,6,8,9-tetrahydro-7H-pyrido[4',3':4,5]pyrrolo[2,3-b]pyridin-7-yl]-2-oxoethyl}carboxylic acid TLC:Rf 0.29 (methylene chloride:methanol=9:1);
MS (ESI, Pos. 20 V): m/z=462 (M+H)$^+$.

Example 51(6)

4-{2-[9-(3-fluorobenzyl)-5,6,8,9-tetrahydro-7H-pyrido[4',3':4,5]pyrrolo[2,3-b]pyridin-7-yl]-2-oxoethyl}-3-methylcarboxylic acid TLC:Rf 0.40 (methylene chloride:methanol=9:1);
MS (ESI, Pos. 20 V): m/z=458 (M +H)$^+$.

Example 51(7)

4-{2-[9-(3-fluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.45 (methylene chloride:methanol=9:1);
MS (APCI, Pos. 20 V): m/z=474 (M+H)$^+$.

Example 51(8)

4-{2-[9-(3-fluorobenzyl)-5,6,8,9-tetrahydro-7H-pyrido[4',3':4,5]pyrrolo[2,3-b]pyridin-7-yl]-2-oxoethyl}-3-methoxybenzoic acid TLC: Rf 0.40 (methylene chloride:methanol=9:1);
MS (APCI, Pos. 20 V): m/z=474 (M+H)$^+$.

Example 51(9)

4-{2-[9-(3-fluorobenzyl)-5,6,8,9-tetrahydro-7H-py-rido[4',3':4,5]pyrrolo[2,3-b]pyridin-7-yl]-2-oxoethyl}-2-methylbenzoic acid TLC: Rf 0.52 (methylene chloride:methanol=9:1);
MS (APCI, Pos. 20 V): m/z=458 (M+H)+.

Example 51(10)

4-{2-[9-(2,4-difluorobenzyl)-5,6,8,9-tetrahydro-7H-pyrrolo[2,3-b]pyridin-7-yl]-2-oxoethyl}-2-fluorobenzoic acid TLC: Rf 0.28 (methylene chloride:methanol=9:1);
MS (APCI, Pos. 20 V): m/z=480 (M+H)+.

Example 51(12)

5-{2-[9-(3-fluorobenzyl)-5,6,8,9-tetrahydro-7H-py-rido[4',3':4,5]pyrrolo[2,3-b]pyridin-7-yl]-2-oxoethyl}-2-thiophenecarboxylic acid TLC: Rf 0.10 (ethyl acetate);
MS (ESI, Pos. 20 V): m/z=450 (M+H)+.

Example 51(13)

4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.50 (methylene chloride:methanol=9:1);
MS (APCI, Pos. 20 V): m/z=476 (M+H)+.

Example 51(15)

4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.54 (methylene chloride:methanol=9:1);
MS (APCI, Pos. 20 V): m/z=492 (M+H)+.

Example 51(17)

4-{2-[9-(2,4-difluorobenzyl)-5,6,8,9-tetrahydro-7H-pyrido[4',3':4,5]pyrrolo[2,3-b]pyridin-7-yl]-2-oxoethyl}-3-methoxybenzoic acid TLC: Rf 0.45 (methylene chloride:methanol=9:1);
MS (APCI, Pos. 20 V): m/z=492 (M+H)+.

Example 51(19)

2-(4-{2-[9-(3-fluorobenzyl)-5,6,8,9-tetrahydro-7H-pyrido[4',3':4,5]pyrrolo[2,3-b]pyridin-7-yl]-2-oxoethyl}phenyl)-2-methylpropanoic acid TLC: Rf 0.55 (methylene chloride:methanol=9:1);
MS (APCI, Pos. 20 V): m/z=486 (M+H)+.

Example 51(20)

2-(4-{2-[9-(2,4-difluorobenzyl)-5,6,8,9-tetrahydro-7H-pyrido[4',3':4,5]pyrrolo[2,3-b]pyridin-7-yl]-2-oxoethyl}phenyl)-2-methylpropanoic acid TLC: Rf 0.49 (methylene chloride:methanol=9:1);
MS (APCI, Pos. 20 V): m/z=504 (M+H)+.

Example 51(22)

2-(benzyloxy)-4-{2-[9-(2,4-difluorobenzyl)-5,6,8,9-tetrahydro-7H-pyrido[4',3':4,5]pyrrolo[2,3-b]pyridin-7-yl]-2-oxoethyl}benzoic acid TLC: Rf 0.56 (methylene chloride:methanol:water=90:10:1);
MS (FAB, Pos.): m/z=568 (M+H)+.

Example 51(23)

4-{2-[9-(3,5-difluorobenzyl)-5,6,8,9-tetrahydro-7H-pyrido[4',3':4,5]pyrrolo[2,3-b]pyridin-7-yl]-2-oxoethyl}-2-methoxybenzoic acid

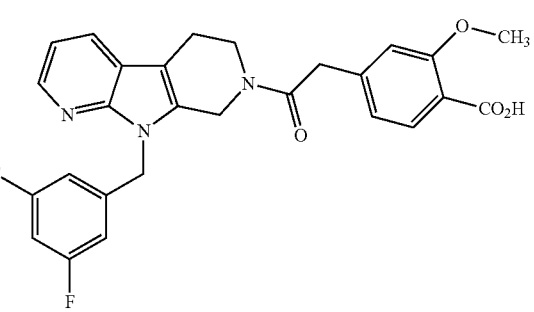

TLC: Rf 0.37 (methylene chloride:methanol=9:1);
MS (APCI, Pos. 20 V): m/z=492 (M+H)+.

Example 51(24)

2-methoxy-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid

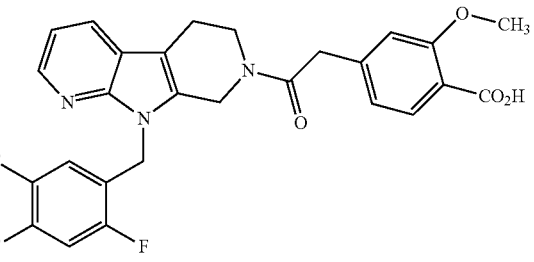

TLC: Rf 0.34 (methylene chloride:methanol=9:1);
MS (APCI, Pos. 20 V): m/z=510 (M+H)+.

Example 51(25)

4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2-methoxybenzoic acid TLC: Rf 0.38 (methylene chloride:methanol=9:1);
MS (APCI, Pos. 20 V): m/z=496 (M+H)$^+$.

Example 51(26)

4-{2-[9-(4-fluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.51 (methylene chloride:methanol=9:1);
MS (APCI, Pos. 20 V): m/z=474 (M+H)$^+$.

Example 51(27)

4-{2-[9-(4-chlorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.52 (methylene chloride:methanol=9:1);
MS (APCI, Pos. 20 V): m/z=490 (M+H)$^+$.

Example 51(28)

4-{2-[9-(3-chlorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.50 (methylene chloride:methanol=9:1);
MS (APCI, Pos. 20 V): m/z=490 (M+H)$^+$.

Example 51(29)

4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.51 (methylene chloride:methanol=9:1);
MS (APCI, Pos. 20 V): m/z=508 (M+H)$^+$.

Example 51(31)

4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.51 (methylene chloride:methanol=9:1);
MS (FAB, Pos.): m/z=508 (M+H)$^+$.

Example 51(32)

4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.48 (methylene chloride:methanol=9:1);
MS (FAB, Pos.): m/z=508 (M+H)$^+$.

Example 51(35)

4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methoxybenzoic acid TLC: Rf 0.44 (methylene chloride:methanol=9:1);
MS (FAB, Pos.): m/z=496 (M+H)$^+$.

Example 51(38)

4-{2-[9-(4-chlorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.40 (methylene chloride:methanol=9:1);
MS (FAB, Pos.): m/z=474 (M+H)$^+$.

Example 51(39)

4-{2-[9-(3-chlorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.38 (methylene chloride:methanol=9:1);
MS (FAB, Pos.): m/z=474 (M+H)$^+$.

Example 51(40)

4-{2-[9-(3,5-difluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.38 (methylene chloride:methanol=9:1);
MS (FAB, Pos.): m/z=476 (M+H)$^+$.

Example 51(41)

2-methyl-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid TLC: Rf 0.38 (methylene chloride:methanol=9:1);
MS (FAB, Pos.): m/z=494 (M+H)$^+$.

Example 51(42)

4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.43 (methylene chloride:methanol=9:1);
MS (FAB, Pos.): m/z=492 (M+H)$^+$.

Example 51(43)

4-{2-[9-(3,4-difluorobenzyl)-5,6,8,9-tetrahydro-7H-pyrido[4',3':4,5]pyrrolo[2,3-b]pyridin-7-yl]-2-oxoethyl}-2-methoxybenzoic acid TLC: Rf 0.50 (methylene chloride:methanol=9:1);
MS (FAB, Pos.): m/z=492 (M+H)$^+$.

Example 51(48)

4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methylbenzoic acid

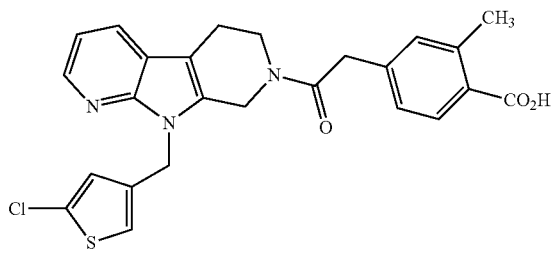 [SMILES: Cc1cc(CC(=O)N2CCc3c(n(Cc4csc(Cl)c4)c4ncccc34)C2)ccc1C(=O)O]

TLC: Rf 0.41 (methylene chloride:methanol:water=90:10:1);
MS (FAB, Pos.): m/z=480 (M+H)+.

Example 51(49)

4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2-methylbenzoic acid TLC: Rf 0.48 (methylene chloride:methanol:water);
MS (FAB, Pos.): m/z=480 (M+H)+.

Example 51(52)

4-{2-[9-(4-fluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.46 (methylene chloride:methanol:water=90:10:1);
MS (FAB, Pos.): m/z=458 (M+H)+.

Example 51(53)

4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.35 (methylene chloride:methanol:water=90:10:1);
MS (FAB, Pos.): m/z=492 (M+H)+.

Example 51(54)

4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.35 (methylene chloride:methanol:water=90:10:1);
MS (FAB, Pos.): m/z=492 (M+H)+.

Example 51(55)

4-{2-[9-(3,4-difluorobenzyl)-5,6,8,9-tetrahydro-7H-pyrido[4',3':4,5]pyrrolo[2,3-b]pyridin-7-yl]-2-oxoethyl}-2-methylbenzoic acid TLC: Rf 0.35 (methylene chloride:methanol:water=90:10:1);
MS (FAB, Pos.): m/z=476 (M+H)+.

Example 51(61)

4-{2-[9-(4-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.50 (chloroform:methanol:water=50:10:1);
MS (ESI, Pos. 20 V): m/z=504 (M+H)+.

Example 51(62)

4-{2-[9-(4-chlorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.50 (chloroform:methanol:water=50:10:1);
MS (ESI, Pos. 20 V): m/z=520 (M+H)+.

Example 51(64)

4-{2-[9-(2,4-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.23 (ethyl acetate:methanol=9:1);
MS (ESI, Pos. 20V): m/z=522 (M+H)+.

Example 51(70)

4-{2-[9-(3-chlorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.44 (methylene chloride:methanol:water=90:10:1);
MS (FAB, Pos.): m/z=520 (M+H)+.

Example 51(71)

4-{2-[9-(3,5-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.40 (methylene chloride:methanol:water=90:10:1);
MS (FAB, Pos.): m/z=522 (M+H)+.

Example 51(72)

2,6-dimethoxy-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid TLC: Rf 0.42 (methylene chloride:methanol:water=90:10:1);
MS (FAB, Pos.): m/z=540 (M+H)+.

Example 51(73)

4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.42 (methylene chloride:methanol:water=90:10:1);
MS (FAB, Pos.): m/z=538 (M+H)+.

Example 51(74)

4-{2-[9-(4-chloro-3-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.46 (methylene chloride:methanol:water=90:10:1);
MS (FAB, Pos.): m/z=538 (M+H)⁺.

Example 51(75)

4-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.42 (methylene chloride:methanol:water=90:10:1);
MS (FAB, Pos.): m/z=538 (M+H)⁺.

Example 51(77)

4-{2-[9-(3,4-difluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.48 (methylene chloride:methanol:water=90:10:1);
MS (FAB, Pos.): m/z=522 (M+H)⁺.

Example 51(78)

4-{2-[9-(3-fluorobenzyl)-5,6,8,9-tetrahydro-7H-pyrido[4',3':4,5]pyrrolo[2,3-b]pyridin-7-yl]-2-oxoethyl}-2,6-dimethoxybenzoic acid TLC: Rf 0.88 (ethyl acetate:acetic acid:water=3:1:1);
MS (ESI, Pos. 20 V): m/z=504 (M+H)⁺.

Example 51(79)

4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2,6-dimethoxybenzoic acid TLC: Rf 0.88 (ethyl acetate:acetic acid:water=3:1:1);
MS (ESI, Pos. 20 V): m/z=526 (M+H)⁺.

Example 51(80)

4-(2-{9-[(5-chloro-2-thienyl)methyl]-5,6,8,9-tetrahydro-7H-pyrido[4',3':4,5]pyrrolo[2,3-b]pyridin-7-yl}-2-oxoethyl)-2,6-dimethoxybenzoic acid TLC: Rf 0.88 (ethyl acetate:acetic acid:water=3:1:1);
MS (ESI, Pos. 20 V): m/z=526 (M+H)⁺.

Example 52

(4E)-6-methoxy-6-oxo-4-hexenoic acid

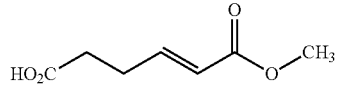

4-oxobutanoic acid (5.0 mL, about 15% aqueous solution) and trimethyl phosphoacetate (7.8 g) were dissolved in 10 mL of water, potassium carbonate (4.06 g) was added while stirring at 0° C., and the mixture was stirred at 60° C. overnight. To this solution was added 100 mL of an aqueous saturated sodium bicarbonate solution, reverse extraction operation (ethyl acetate, three times) was performed, the aqueous layer was made acidic (pH4) with 1N hydrochloric acid, and extraction operation (ethyl acetate, three times) was performed. The resulting organic layer was dried with magnesium sulfate, and the solvent was distilled off under reduced pressure to obtain the title compound (1.01 g) having the following physical property values.

TLC: Rf 0.45 (hexane:ethyl acetate=1:3);
¹H-NMR (CDCl₃): δ 2.52-2.57 (m, 4 H), 3.74 (s, 3 H), 5.83-5.91 (m, 1 H), 6.89-7.02 (m, 1 H).

Example 53

(2E)-6-[9-(3-fluorobenzyl)-5,6,8,9-tetrahydro-7H-pyrido[4',3':4,5]pyrrolo[2,3-b]pyridin-7-yl]-6-oxo-2-hexenoic acid

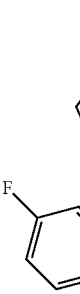

The compound produced in Example 52 and a tetrahydropyridopyrrolopyridine derivative produced by operation in accordance with Example 4→Example 5→Example 6→Example 7→Example 1 were used, which were subjected to operation in accordance with Example 11→Example 3 to obtain the title compound having the following physical property values.

TLC: Rf 0.29 (n-hexane:ethyl acetate=1:3);
MS (FAB, Pos.): m/z=408 (M+H)⁺.

Example 53(1)

(2E)-6-[9-(2,4-difluorobenzyl)-5,6,8,9-tetrahydro-7H-pyrido[4',3':4,5]pyrrolo[2,3-b]pyridin-7-yl]-6-oxo-2-hexenoic acid The compound produced in Example 52 and a tetrahydropyridopyrrolopyridine derivative produced by operation in accordance with Example 4 Example 5→Example 6→Example 7→Example 1 were used, which were subjected to operation in accordance with Example 11→Example 3 to obtain the title compound having the following physical property values.

TLC: Rf 0.37 (n-hexane:ethyl acetate=1:3);
MS (FAB, Pos.): m/z=426 (M+H)+.

Example 54

6-ethoxy-5,5-dimethyl-4,6-dioxohexanoic acid

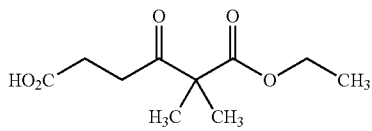

To dehydrated THF (20 mL) was added a 2.0M LDA/THF-ethylbenzene-heptane solution (7.88 mL), this was cooled to around −78° C. in a dry ice-methanol bath, and a solution of ethyl 2-methylpropanoate (1.74 g) in dehydrated THF (5 mL) was slowly added dropwise. After the mixture was stirred at around −78° C. for 1 hour, this solution was added dropwise to a suspension of succinic acid anhydride (1.50 g) in dehydrated THF (5 mL) over 5 minutes under an ice bath. After stirred at the same temperature for 40 minutes, the mixture was stirred at room temperature for 3 hours. Into the reaction solution was slowly placed water under an ice bath, ethyl acetate and an aqueous saturated sodium bicarbonate solution were added, followed by extraction. To the resulting aqueous phase was added 1N hydrochloric acid to adjust a pH at around 3, followed by extraction with ethyl acetate. The organic phase was dried with anhydrous sodium sulfate, and concentrated under reduced pressure. The resulting crude product was washed with dichloromethane, a compound derived from succinic acid anhydride was removed by filtration, and the resulting filtrate was concentrated under reduced pressure to obtain the title compound (2.22 g) having the following physical property values.

TLC: Rf 0.45 (chloroform:ethyl acetate:methanol=6:3:1);
$^1$H-NMR (DMSO-$d_6$): δ 1.17 (t, J=7.2 Hz, 3 H) 1.29 (s, 6 H) 2.39 (t, J=6.3 Hz, 2 H) 2.72 (t, J=6.3 Hz, 2 H) 4.10 (q, J=7.2 Hz, 2 H) 12.12 (s, 1 H).

Example 55 ethyl 6-[9-(3-fluorobenzyl)-5,6,8,9-tetrahydro-7H-pyrido[4',3':4,5]pyrrolo[2,3-b]pyridin-7-yl]-2,2-dimethyl-3,6-dioxohexanoate

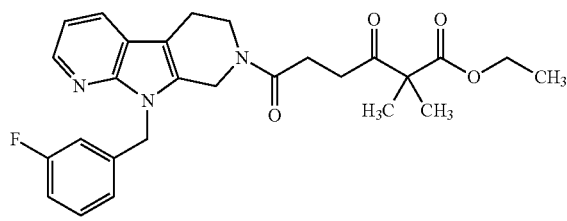 [SMILES: CCOC(=O)C(C)(C)C(=O)CCC(=O)N1CCc2c(n(Cc3cccc(F)c3)c3ncccc23)C1]

To a solution of the compound (259 mg) produced in Example 1 in N,N-dimethylformamide (5 ml) were sequentially added the compound (355 mg) produced in Example 54, triethylamine (433 μL), 1-hydroxybenzotriazole (199 mg), and 1-ethyl-3-(3-dimethylaminopropyl)carbodiimide hydrochloride (288 mg) at room temperature, and the mixture was stirred for 16 hours. To the reaction mixture was added water, and this was extracted with ethyl acetate, dried with anhydrous sodium sulfate, and concentrated under reduced pressure. The residue was purified by silica gel column chromatography (hexane:ethyl acetate=2:1→1:1) to obtain the title compound (381 mg) having the following physical property values.

TLC: Rf 0.49 (hexane:ethyl acetate=1:1);
$^1$H-NMR (CDCl$_3$): δ 1.26 (t, J=7.2 Hz, 3 H) 1.41 (s, 6 H) 2.48-2.96 (m, 6 H) 3.75-3.97 (m, 2 H) 4.19 (q, J=7.2 Hz, 2 H) 4.49-4.68 (m, 2 H) 5.43-5.52 (m, 2 H) 6.70-7.32 (m, 5 H) 7.76-7.87 (m, 1 H) 8.26-8.40 (m, 1 H).

Example 56 ethyl 6-[9-(3-fluorobenzyl)-5,6,8,9-tetrahydro-7H-pyrido[4',3':4,5]pyrrolo[2,3-b]pyridin-7-yl]-3-hydroxy-2,2-dimethyl-6-oxohexanoate

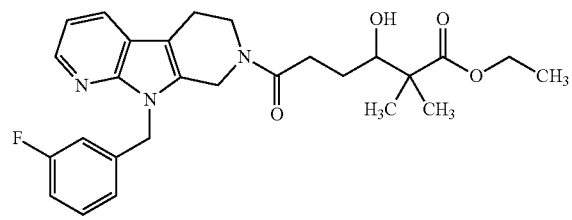 [SMILES: CCOC(=O)C(C)(C)C(O)CCC(=O)N1CCc2c(n(Cc3cccc(F)c3)c3ncccc23)C1]

To a solution of the compound (22 mg) produced in Example 55 in methanol (1 mL) was added sodium borohydride (3.5 mg) under an ice bath, and the mixture was stirred at room temperature for 2.5 hours. Thereafter, to the reaction mixture were added water and 1N hydrochloric acid under an ice bath, followed by extraction with ethyl acetate. The organic phase was dried with anhydrous sodium sulfate, and concentrated under reduced pressure to obtain the title compound (22 mg) having the following physical property values.

TLC: Rf 0.34 (hexane:ethyl acetate=1:1);
$^1$H-NMR (CDCl$_3$): δ 1.15-1.49 (m, 9 H) 1.50-3.74 (m, 8 H) 3.76-3.96 (m, 2 H) 4.14 (m, 2 H) 4.46-4.68 (m, 2 H) 5.42-5.50 (m, 2 H) 6.68-7.32 (m, 5 H) 7.77-7.92 (m, 1 H) 8.23-8.35 (m, 1 H).

Example 57

6-[9-(3-fluorobenzyl)-5,6,8,9-tetrahydro-7H-pyrido[4',3':4,5]pyrrolo[2,3-b]pyridin-7-yl]-3-hydroxy-2,2-dimethyl-6-oxahexanoic acid

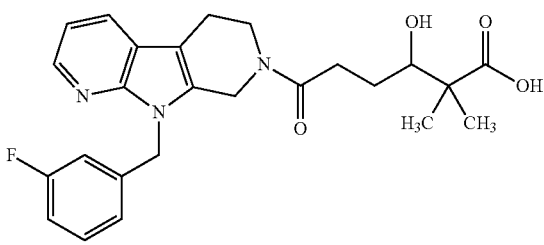 [SMILES: CC(C)(C(=O)O)C(O)CCC(=O)N1CCc2c(n(Cc3cccc(F)c3)c3ncccc23)C1]

The compound (20 mg) produced in Example 56 was dissolved in 1,2-dimethoxyethane (0.5 mL) and methanol (0.5 mL), a 1N aqueous sodium hydroxide solution (0.5 mL) was added, and the mixture was stirred at room temperature for 30 minutes. To the reaction solution were added water and tert-butyl methyl ether, followed by extraction, and to the resulting aqueous phase was added 1N hydrochloric acid to adjust a pH at around 3, followed by extraction using ethyl acetate. The organic phase was dried with anhydrous sodium sulfate, and concentrated under reduced pressure. The residue was purified by preparative thin layer chromatography (ethyl acetate) to obtain the title compound (4 mg) having the following physical property values.

TLC: Rf 0.38 (ethyl acetate);
$^1$H-NMR (CDCl$_3$): δ 1.16-1.39 (s, 6 H) 1.45-2.98 (m, 7 H) 3.22-4.10 (m, 3 H) 4.46-4.72 (m, 2 H) 5.42-5.55 (m, 2 H) 6.70-7.35 (m, 5 H) 7.78-7.85 (m, 1 H) 8.28-8.36 (m, 1 H).

Example 58

6-ethoxy-6-oxo-4-hexynoic acid

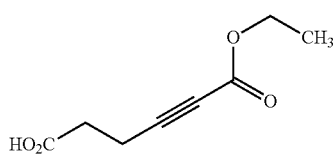

4-pentynoic acid (2.01 g) and hexamethylphosphoamide (6.99 mL) were dissolved in 80 mL of THF, and LDA (20.1 mL) was added dropwise over 20 minutes while stirring at −78° C. After this solution was stirred at −78° C. for 1 hour, a solution of ethyl chloroformate (2.18 g) in 20 mL of THF was added dropwise over 15 minutes, and the mixture was stirred at that temperature for 30 minutes. Thereafter, acetic acid (1.15 mL) was added, a temperature was raised to room temperature, a 10% aqueous potassium dihydrogen phosphate solution was added, and extraction operation (THF once, tetrabutyl methyl ether two times) was performed. After the resulting organic layer was dried with magnesium sulfate, the solvent was distilled off under reduced pressure to obtain the crude product. The crude product was purified by silica gel column chromatography (A/B=30%→45%, A=ethyl acetate: acetic acid=30:1, B=n-hexane) to obtain the title compound (641 mg) having the following physical property values.

TLC: Rf 0.50 (hexane:ethyl acetate:acetic acid=5:5:0.1);
$^1$H-NMR (CDCl$_3$): δ 1.31 (t, J=7.2 Hz, 3 H), 2.67 (s, 4 H), 4.22 (q, J=7.2 Hz, 2 H).

Example 59 ethyl 6-[9-(3-fluorobenzyl)-5,6,8,9-tetrahydro-7H-pyrido[4',3':4,5]pyrrolo[2,3-b]pyridin-7-yl]-6-oxo-2-hexynoic acid

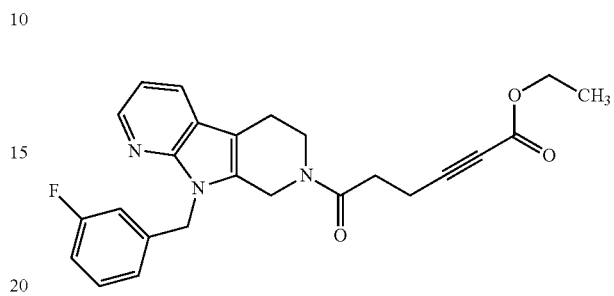

The compound (174 mg) produced in Example 58 and a tetrahydropyridopyrrolopyridine derivative (300 mg) produced by operation in accordance with Example 4→Example 5→Example 6→Example 7→Example 1 were dissolved in 4.3 mL of dimethylformamide, 1-(3-dimethylaminopropyl)-3-ethylcarbodiimide hydrochloride (245 mg), 1-hydroxybenzotriazole monohydrate (196 mg) and triethylamine (355 μL) were sequentially added while stirring at room temperature, and the mixture was stirred at that temperature overnight. After completion of the reaction, water was added, and extraction operation (hexane:ethyl acetate=2:1, three times) was performed. The resulting organic layer was dried with magnesium sulfate, and the solvent was distilled off under reduced pressure to obtain the crude product. The crude product was purified by silica gel column chromatography (ethyl acetate/hexane=33%→54%) to obtain the title compound (341 mg) having the following physical property values.

TLC: Rf 0.26 (hexane:ethyl acetate=2:1);
$^1$H-NMR (CDCl$_3$): δ 1.25-1.34 (m, 3 H), 2.43-2.91 (m, 6 H), 3.73-3.96 (m, 2 H), 4.16-4.25 (m, 2 H), 4.42-4.67 (m, 2 H), 5.43-5.52 (m, 2 H), 6.73-7.34 (m, 5 H), 7.77-7.86 (m, 1 H), 8.27-8.32 (m, 1 H).

Example 60

6-[9-(3-fluorobenzyl)-5,6,8,9-tetrahydro-7H-pyrido[4',3':4,5]pyrrolo[2,3-b]pyridin-7-yl]-6-oxo-2-hexynoic acid

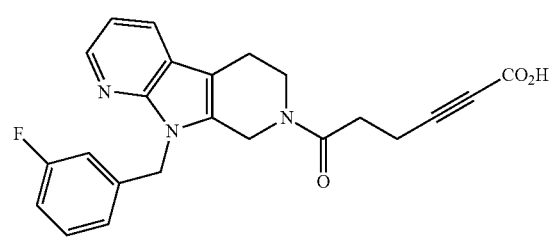 [SMILES: O=C(O)C#CCCC(=O)N1CCc2c(n(Cc3cccc(F)c3)c3ncccc23)C1]

The compound produced in Example 59 was subjected to operation in accordance with Example 3 to obtain the title compound having the following physical property values.

TLC: Rf 0.32 (chloroform:methanol:water=50:10:1);
MS (FAB, Pos.): m/z=406 (M+H)$^+$.

Example 61 ethyl 6-[9-(3-fluorobenzyl)-5,6,8,9-tetrahydro-7H-pyrido[4',3':4,5]pyrrolo[2,3-b]pyridin-7-yl]-6-oxo-2-hexanoate

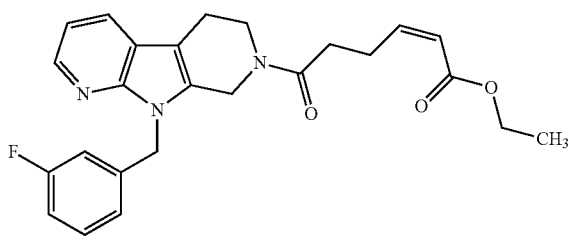 [SMILES: CCOC(=O)/C=C\CCC(=O)N1CCc2c(n(Cc3cccc(F)c3)c3ncccc23)C1]

The compound (109 mg) produced in Example 59 was dissolved in 1.5 mL of ethyl acetate and 1.5 mL of hexane, a Lindlar catalyst (20 mg) was added while stirring at room temperature, and the mixture was stirred at room temperature for 4.5 hours under the hydrogen atmosphere. After the reaction solution was filtered with Celite (registered trademark), the solvent was distilled off, and the residue was purified by silica gel column chromatography (ethyl acetate/hexane=35%→56%) to obtain the title compound (101 mg) having the following physical property values.

TLC: Rf 0.44 (hexane:ethyl acetate=1:1);

$^1$H-NMR (CDCl$_3$): δ1.25-1.34 (m, 3 H), 2.39-2.67 (m, 2 H), 2.78-3.06 (m, 4 H), 3.66-3.95 (m, 2 H), 4.16-4.23 (m, 2 H), 4.56-4.67 (m, 2 H), 5.43-5.56 (m, 2 H), 5.77-5.84 (m, 1 H), 6.28-6.40 (m, 1 H), 6.73-7.31 (m, 5 H), 7.77-7.85 (m, 1 H), 8.29-8.32 (m, 1 H).

Example 62

(2Z)-6-[9-(3-fluorobenzyl)-5,6,8,9-tetrahydro-7H-pyrido[4',3':4,5]pyrrolo[2,3-b]pyridin-7-yl]-6-oxo-2-hexenoic acid

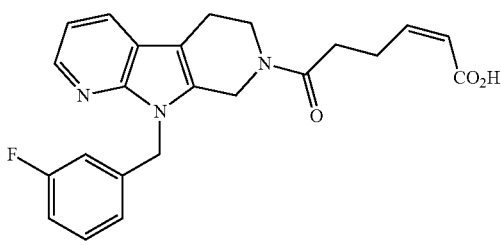 [SMILES: O=C(O)/C=C\CCC(=O)N1CCc2c(n(Cc3cccc(F)c3)c3ncccc23)C1]

The compound produced in Example 61 was subjected to operation in accordance with Example 3 to obtain the title compound having the following physical property values.

TLC: Rf 0.52 (chloroform:methanol=10:1);

$^1$H-NMR (CDCl$_3$): δ 2.38-2.95 (m, 6 H), 3.76-3.97 (m, 2 H), 4.47-4.50 (m, 2 H), 5.46-5.51 (m, 2 H), 5.88-6.15 (m, 2 H), 6.71-7.31 (m, 5 H), 7.77-7.87 (m, 1 H), 8.29-8.34 (m, 1 H).

Example 63 methyl 2-(benzyloxy)-4-{2-[9-(3-fluorobenzyl)-5,6,8,9-tetrahydro-7H-Pyrido[4',3':4,5]pyrrolo[2,3-b]pyridin-7-yl]-2-oxoethyl}benzoate

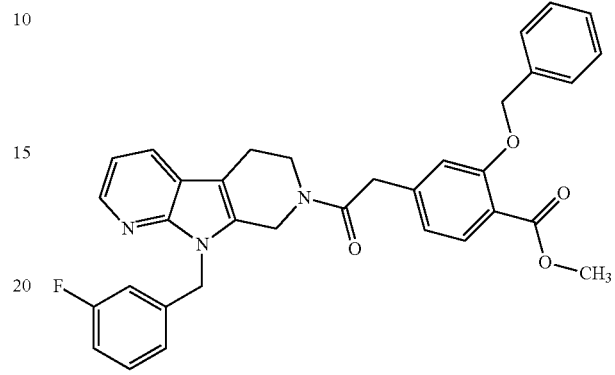

A compound produced by operation in accordance with Example 49 using methyl 2-(benzyloxy)-4-bromobenzoate in place of methyl 2-chloro-4-iodobenzoate was further subjected to operation in accordance with Example 50. The resulting compound and a tetrahydropyridopyrrolopyridine derivative produced by operation in accordance with Example 4→Example 5→Example 6→Example 7→Example 1 were used, which were subjected to operation in accordance with Example 11 to obtain the title compound.

Example 64 methyl 4-{2-[9-(3-fluorobenzyl)-5,6,8,9-tetrahydro-7H-pyrido[4',3':4,5]pyrrolo[2,3-b]pyridin-7-yl]-2-oxoethyl}-2-hydroxybenzoate

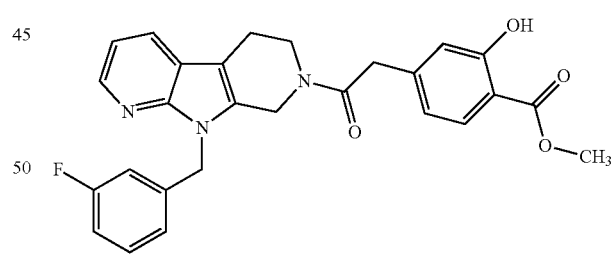

To 1.24 mL of a methanol/THF (1:1) solution of the compound (70 mg) produced in Example 63 was added 5% palladium carbon (7 mg, 10 wt %), and the mixture was stirred at room temperature for 3 hours under the hydrogen atmosphere. After the reaction solution was filtered with Celite, the solvent was concentrated under reduced pressure. The resulting residue was purified by silica gel column (hexane/ethyl acetate=70:30-40:60) to obtain the title compound (55.2 mg) having the following physical property values.

$^1$H-NMR (CDCl$_3$): δ 2.68, 2.83, 3.61, 3.72, 3.83, 3.94, 4.34, 4.69, 5.35, 5.36, 6.58-6.90, 6.90-7.00, 7.03-7.13, 7.20-7.29, 7.68-7.85, 8.28-8.31, 10.73, 10.77.

Example 65

4-{2-[9-(3-fluorobenzyl)-5,6,8,9-tetrahydro-7H-pyrido[4',3':4,5]pyrrolo[2,3-b]pyridin-7-yl]-2-oxoethyl}-2-hydroxybenzoic acid

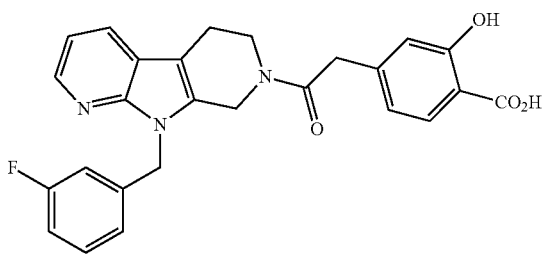 [SMILES: O=C(O)c1ccc(CC(=O)N2CCc3c(n(Cc4cccc(F)c4)c4ncccc34)C2)cc1O]

To 3.0 mL of a solution of the compound (53.8 mg) produced in Example 64 in dimethyl ether/methanol (1:1) was added a 1N aqueous sodium hydroxide solution (1.5 mL), the mixture was stirred at room temperature for 2.5 hours, and at 50° C. for 3 hours, and allowed to stand at room temperature overnight. On the next day, the resultant was stirred again at 50° C. for 5 hours, and water was added to the reaction solution. After washed with tert-butyl methyl ether, 1N hydrochloric acid was added to the aqueous layer to make the solution acidic (pH 3), and the resultant was extracted two times using ethyl acetate. The extracted organic layer was washed with an aqueous saturated sodium chloride solution, and dried with anhydrous magnesium sulfate, and the solution obtained by filter filtration was concentrated under reduced pressure to obtain the title compound (46.6 mg) having the following physical property values.

TLC: Rf 0.16 (methylene chloride:methanol:water=90:10:1);

MS (FAB, Pos.): m/z=460 (M+H)$^+$.

Example 65(1)

[3-(benzyloxy)-4-(methoxycarbonyl)phenyl]acetic acid produced in Example 63 and a tetrahydropyridopyrrolopyridine derivative produced by operation in accordance with Example 4→Example 5→Example 6→Example 7→Example 1 were used, which were subjected to operation in accordance with Example 11→Example 3 to obtain the following compound.

Example 65(1)

4-{2-[9-(2,4-difluorobenzyl)-5,6,8,9-tetrahydro-7H-pyrido[4',3':4,5]pyrrolo[2,3-b]pyridin-7-yl]-2-oxoethyl}-2-hydroxybenzoic acid TLC: Rf 0.16 (methylene chloride:methanol:water=90:10:1);

MS (FAB, Pos.): m/z=478 (M+H)$^+$.

Reference Example 2

9-(3-fluorobenzyl)-5,6,8,9-tetrahydro-7H-pyrido[4',3':4,5]pyrrolo[2,3-b]pyridin-7-carboxamide

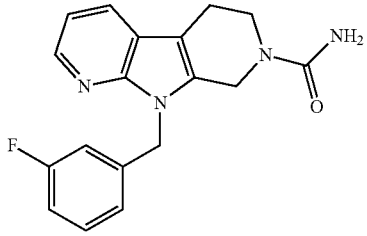 [SMILES: NC(=O)N1CCc2c(n(Cc3cccc(F)c3)c3ncccc23)C1]

9-(3-Fluorobenzyl)-6,7,8,9-tetrahydro-5H-pyrido[4',3':4,5]pyrrolo[2,3-b]pyridine (100 mg) produced by operation in accordance with Example 1, and triethylamine (263 μL) were dissolved in 3 mL of methylene chloride, trimethylsilyl isocyanate (311 mg) was added while stirring at room temperature, and the mixture was stirred at room temperature for 10 minutes. To this solution was added an aqueous saturated sodium bicarbonate solution, and extraction operation (methylene chloride, once) was performed. The resulting organic layer was dried with magnesium sulfate, and the solvent was distilled off under reduced pressure to obtain the crude product. The crude product was perspired with ethyl acetate and washed, and dried under reduced pressure to obtain the title compound (72 mg) having the following physical property values.

TLC: Rf 0.28 (chloroform:methanol=10:1);

$^1$H-NMR (DMSO-$d_6$): δ 2.67-2.73 (m, 2 H), 3.58-3.67 (m, 2 H), 4.50 (s, 2 H), 5.43 (s, 2 H), 6.17 (s, 2 H), 6.90-7.37 (m, 5 H), 7.84-7.91 (m, 1 H), 8.17-8.21 (m, 1 H).

Reference Example 2(1)-Reference Example 2(2)

A tetrahydropyridopyrrolopyridine derivative corresponding to 9-(3-fluorobenzyl)-6,7,8,9-tetrahydro-5H-pyrido[4',3':4,5]pyrrolo[2,3-b]pyridine was used, which was subjected to operation in accordance with Reference Example 2 to obtain the following compounds.

Reference Example 2(1)

9-{[2-(trifluoromethyl)-1,3-thiazol-5-yl]methyl}-5,6,8,9-tetrahydro-7H-pyrido[4',3':4,5]pyrrolo[2,3-b]pyridin-7-carboxamide TLC: Rf 0.36 (chloroform:methanol:water=100:10:1);
MS (ESI, Pos. 20 V): m/z=382 (M+H)$^+$.

Reference Example 2(2)

9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-carboxamide TLC: Rf 0.37 (chloroform:methanol:water=100:10:1);
MS (ESI, Pos. 20 V): m/z=396 (M+H)$^+$.

Example 66

Measurement of Human ENPP2 Inhibitory Activity

10 μL of a test compound solution (10% dimethyl sulfoxide) at each concentration and 40 μL of a 5 μg/mL human ENPP2 solution (buffer A: 100 mmol/L Tris-HCl (pH 9.0), 500 mmol/L NaCl, 5 mmol/L MgCl$_2$, 0.05% Triton X-100) were mixed, 50 μL of a 2 mmol/L 16:0-lysophosphatidylcholine (LPC) solution (buffer A) was further added to react at 37° C. for 24 hours. Subsequently, to 10 μL of the reaction solution was added 90 μL of a measurement buffer (0.5 mmol/L aminoantipyrine, 0.3 mmol/L N-ethyl-N-(2-hydroxy-3-sulfopropyl)-3-methylaniline, 1 U/mL peroxidase, 3 U/mL choline oxidase, 100 mmol/L Tris-HCl (pH 8.5), 5 mmol/L CaCl$_2$) to react at 37° C. for 20 minutes, and spectrophotometric determination was performed at 555 nm.

Using a standard curve, a choline production amount (enzyme activity) in each test compound was calculated, and the inhibitory activity rate of each test compound was calculated, wherein the enzyme activity in a positive control to which a test compound is not added, was a 0% inhibition rate, and the enzyme activity in a negative control to which a test compound and human ENPP2 are not added, were 100% inhibition. Further, concerning the present compounds shown in Table 3, an IC$_{50}$ value was calculated from inhibitory activity rate at each concentration.

[Results]

From Table 2, it was confirmed that the present compound has a high ENPP2 inhibition rate even at 1 μM and, from an IC$_{50}$ value of Table 3, the present compound has the significant ENPP2 inhibitory activity.

TABLE 2

| Example No. | ENPP2 inhibition rate(%) (1 μM) |
|---|---|
| 2 | 67.70 |
| 3(19) | 95.09 |
| 9(26) | 59.32 |
| 9(28) | 76.57 |
| 9(31) | 82.37 |
| 9(33) | 64.87 |
| 9(59) | 69.26 |
| 12(27) | 91.89 |
| 15 | 84.11 |
| 18(1) | 89.63 |
| 23 | 96.25 |
| 31(45) | 99.21 |
| 31(32) | 98.15 |
| 31(34) | 98.61 |
| 31(58) | 99.05 |
| 31(170) | 97.95 |
| 31(188) | 98.85 |
| 31(189) | 99.35 |
| 31(128) | 99.05 |
| 31(129) | 99.75 |
| 31(142) | 98.62 |
| 31(152) | 99.09 |
| 31(160) | 99.47 |
| 31(162) | 99.54 |
| 31(181) | 98.69 |
| 31(182) | 98.90 |
| 35(96) | 99.49 |
| 48(18) | 97.36 |
| 51(23) | 96.19 |
| 51(24) | 97.46 |

TABLE 3

| Example No. | ENPP2 inhibitory activity IC$_{50}$(μM) |
|---|---|
| 3 | 0.034 |
| 9 | 0.091 |
| 9(2) | 0.016 |
| 12(42) | 0.0096 |
| 12(97) | 0.0067 |
| 20 | 0.083 |
| 31(24) | 0.005 |
| 31(127) | 0.011 |
| 31(140) | 0.011 |
| 31(169) | 0.013 |
| 35(2) | 0.11 |
| 35(122) | 0.035 |
| 48(8) | 0.026 |
| 48(9) | 0.025 |
| 51(48) | 0.0078 |

Example 67

Measurement of Urethra Internal Pressure in Rat Under Anesthesia

A SD male rat (Crl: CD(SD), Charles River Laboratories Japan, Inc., 7-10 weeks old) was anesthetized by subcutaneous administration of 1.5 g/kg urethane at a back of a neck. After neck median incision, a jugular vein catheter for intravenous administration was inserted. A lower abdominal part was median incised, and a urethra was ligated at around pubis. A urethral catheter for measuring a urethra internal pressure, equipped with a collar at a tip and filled with a physiological saline was inserted into a urethra through an incised bladder top, and ligation-fixed at a bladder neck part. The urethral catheter was connected to a pressure transducer (manufactured by Nihon Kohden Corporation), and a urethra internal pressure was measured. Concerning a urethra internal pressure, first, a physiological saline was injected into a urethra to adjust at about 20 mmHg, thereafter, it was confirmed that a urethra internal pressure was reduced and stabilized (reduction in a pressure for 10 minutes is within 0.75 mmHg), and individuals having an internal pressure at stabilization of 10 mmHg or higher were used in an experiment. Each of the compound described in Example 3 (dose: 0.1, 0.3, 1.0 mg/kg) and the compound described in Example 31(24) (dose: 0.03, 0.1, 0.3 mg/kg) was administered intravenously and, after about 30 minutes, 1 mL of somnopentyl was administered intravenously. A urethra internal pressure reduction rate (%) was calculated based on a urethra internal pressure after compound administration, wherein a value obtained by subtracting a postmortem baseline value (minimum value of urethra internal pressure for 10 minutes after administration of somnopentyl) from a urethra internal pressure value before compound administration (0 minute) was 100%.

[Results]

Figure 2:
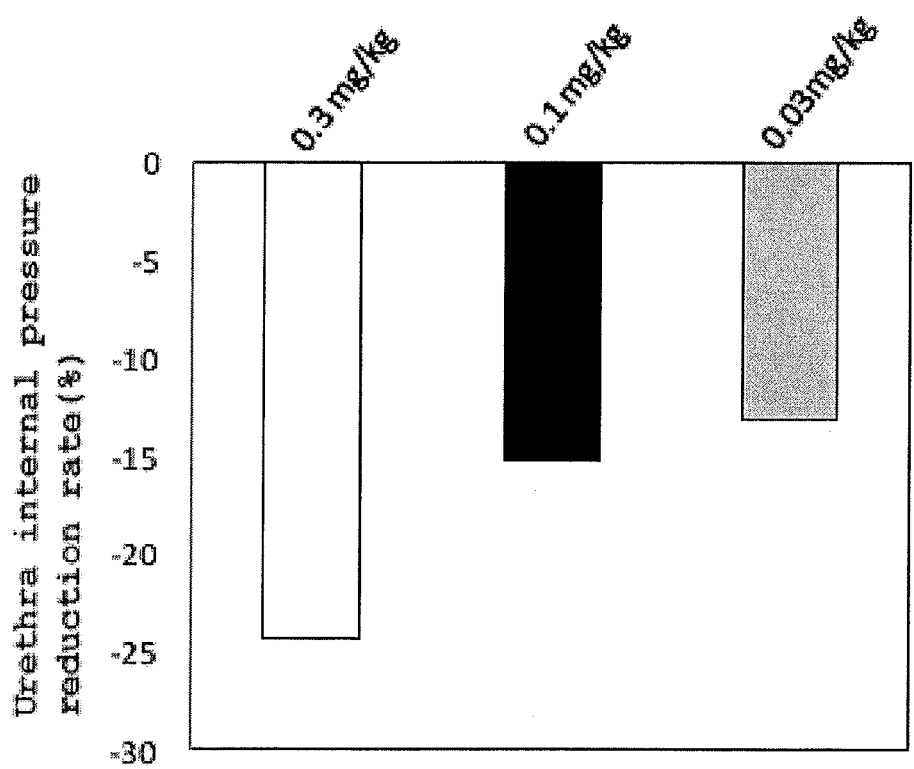
FIG. 2 shows the action of the present compound (compound described in Example 31 (24)) on a urethra internal pressure of a rat under urethane anesthesia.

The compound described in Example 3 (FIG. 1) and the compound described in Example 31 (24) (FIG. 2) significantly reduced a urethra internal pressure.

Preparation Example 1

The following respective ingredients were mixed and compressed by the conventional method to obtain 10000 tablets, one tablet containing 5 mg of an active ingredient.
  6-oxo-6-[9-(3-phenylpropyl)-1,3,4,9-tetrahydro-2H-β-carbolin-2-yl]hexanoic acid 50 g
  Carboxymethylcellulose calcium (disintegrating agent) 20 g
  Magnesium stearate (lubricant) 10 g
  Microcrystalline cellulose 920 g Preparation Example 2

The following respective ingredients were mixed according to the conventional method, the solution was sterilized by the conventional method, and each 5 mL was filled into an ampoule, and lyophilized by the conventional method to obtain 10000 ampoules, one ampoule containing 20 mg of an active ingredient.

6-oxo-6-[9-(3-phenylpropyl)-1,3,4,9-tetrahydro-2H-β-carbolin-2-yl]hexanoic acid 200 g
Mannitol 20 g
Distilled water 50 L

[Industrial Applicability]

The present compound has the ENPP2 inhibitory activity, and is useful as an agent for preventing or treating urinary excretion disorder and/or improving symptoms thereof.

The invention claimed is:

1. A compound represented by the general formula (I):

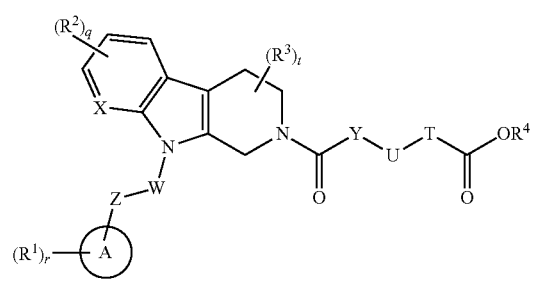

(I)

wherein $R^1$ represents a halogen atom, a C1-4 alkyl group, a C1-4 alkoxy group, a C1-4 haloalkyl group, a C1-4 haloalkoxy group, a carboxyl group, a cyano group, a C1-3 alkylsulfonyl group, a carbamoyl group or

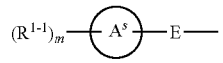

wherein the ring $A^S$ represents a 5- to 7-membered monocycle, E represents a bond, a methylene group or an oxygen atom, $R^{1-1}$ represents a halogen atom, a C1-4 alkyl group, a C1-4 alkoxy group, a C1-4 haloalkyl group or a C1-4 haloalkoxy group, and m represents an integer of 0 to 3, provided that groups represented by a plurality of $R^{1-1}$s may be the same or different, respectively, $R^2$ represents a hydrogen atom, a halogen atom, a C1-4 alkyl group, a C1-4 alkoxy group or a C1-4 haloalkyl group, $R^3$ represents a C1-4 alkyl group, $R^4$ represents a hydrogen atom or a C1-4 alkyl group, the ring A represents (i) a C3-7 monocyclic carbon ring, (ii) a C8-10 bicyclic carbon ring, (iii) a 4- to 7-membered monocyclic heterocyclic ring containing one to four heteroatoms selected from an oxygen atom, a nitrogen atom and a sulfur atom or (iv) a 8- to 10-membered bicyclic heterocyclic ring containing one to four heteroatoms selected from an oxygen atom, a nitrogen atom and a sulfur atom, X represents a nitrogen atom or a carbon atom, T represents a bond, or a straight C1-4 alkylene group, a C2-4 alkenylene group or a C2-4 alkynylene group, optionally substituted with one or two $R^5$s wherein $R^5$ represents a C1-4 alkyl group, a hydroxy group or an amino group, U represents (i) a methylene group, (ii) an oxygen atom, (iii) —$NR^6$— wherein $R^6$ represents a hydrogen atom or a methyl group or (iv) a 3- to 7-membered monocycle, a C5-10 bridged carbon ring or a 5- to 10-membered bridged heterocyclic ring, optionally substituted with one to five $R^7$s wherein $R^7$ represents a halogen atom, a C1-4 alkyl group, a hydroxy group, an oxo group, a C1-4 alkoxy group, a C1-4 haloalkoxy group, a cyano group or a benzyloxy group, Y represents (i) a bond or (ii) a straight C1-3 alkylene group or a C2-3 alkenylene group, optionally substituted with one or two $R^8$s wherein $R^8$ represents a methyl group, W represents a bond or a straight C1-3 alkylene group, Z represents a methylene group, an oxygen atom or an optionally oxidized sulfur atom, q represents an integer of 1 to 4, r represents an integer of 0 to 5, and t represents an integer of 0 to 2, provided that groups represented by a plurality of $R^1$s, $R^2$s, $R^3$s, $R^5$s, $R^7$s and $R^8$s may be the same or different, respectively, and two $R^3$s and $R^5$s bound to the same carbon atom may be taken together with the bound carbon atom to form C3-5 cycloalkyl, respectively;

a salt thereof or a solvate thereof.

2. The compound according to claim 1, which is represented by the general formula (II):

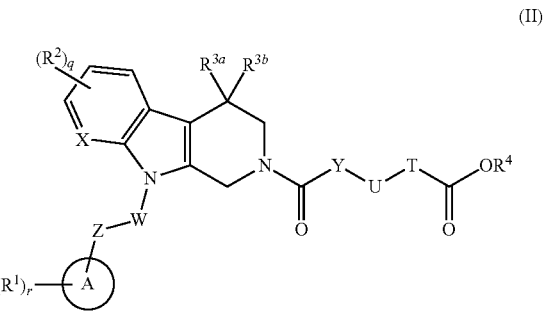

(II)

wherein $R^{3a}$ and $R^{3b}$ each represent independently a hydrogen atom or a methyl group, and other symbols are as defined in claim 1, provided that $R^{3a}$ and $R^{3b}$ are taken together with a carbon atom to which they are bound, to form a cyclopropyl.

3. The compound according to claim 2, wherein Y is a straight C1-3 alkylene group optionally substituted with one or two $R^8$s wherein $R^8$ is as defined in claim 1.

4. The compound according to claim 3, wherein X is a nitrogen atom.

5. The compound according to claim 3, wherein X is a carbon atom.

6. The compound according to claim 4, wherein $R^4$ is a hydrogen atom.

7. The compound according to claim 6, which is represented by the general formula (IV-2):

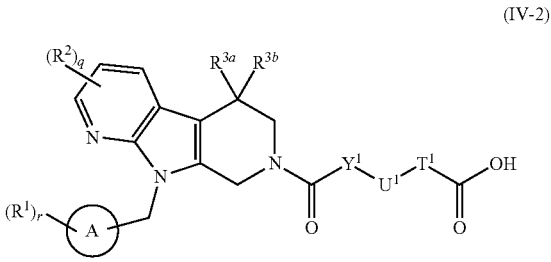

(IV-2)

wherein U¹ represents a 5- to 7-membered monocycle or a C5-10 bridged carbon ring, optionally substituted with one to five R⁷s wherein, R⁷ is as defined in claim 1, Y¹ represents a methylene group or an ethylene group, optionally substituted with one or two R⁸s, T¹ represents a bond, or a methylene group or an ethylene group, optionally substituted with one or two R⁵s, R³ᵃ and R³ᵇ each represent independently a hydrogen atom or a methyl group, or R³ᵃ and R³ᵇ are taken together with a carbon atom to which they are bound, to form a cyclopropyl and other symbols are as defined in claim 1.

8. The compound according to claim 7, wherein Y¹ is an unsubstituted methylene group, and T¹ is a bond or an unsubstituted methylene group.

9. The compound according to claim 7, wherein the C5-10 bridged carbon ring in the C5-10 bridged carbon ring optionally substituted with one to five R⁷s is bicyclo[2.2.1]heptane or bicyclo[2.2.2]octane.

10. The compound according to claim 7, wherein the 5- to 7-membered monocycle in the 5- to 7-membered monocycle optionally substituted with one to five R⁷s is (i) a C5-7 monocyclic carbon ring or (ii) a 5- to 7-membered monocyclic heterocyclic ring containing one to four heteroatoms selected from an oxygen atom, a nitrogen atom and a sulfur atom.

11. The compound according to claim 10, wherein the C5-7 monocyclic carbon ring is benzene, cyclopentane or cyclohexane.

12. The compound according to claim 6, which is represented by the general formula (IV-3):

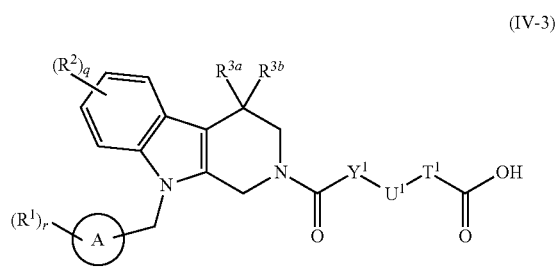

(IV-3)

wherein all symbols are as defined in claim 7.

13. The compound according to claim 6, which is represented by the general formula (V):

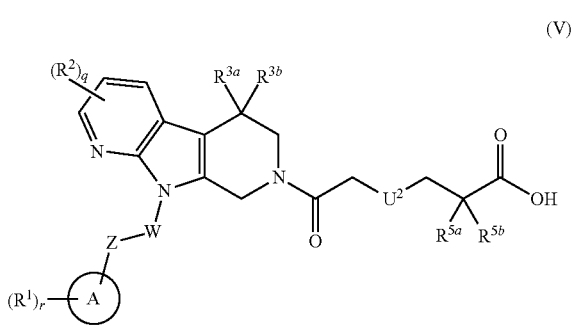

(V)

wherein U² represents a methylene group, an oxygen atom or —NR⁶—, R⁵ᵃ and R⁵ᵇ each represent independently a hydrogen atom or a methyl group, other symbols are as defined in claim 1, provided that R⁵ᵃ and R⁵ᵇ are taken together with a carbon atom to which they are bound, to form cyclopropyl.

14. The compound according to claim 7, wherein the ring A is a C5-6 monocyclic carbon ring or a C9-10 bicyclic carbon ring.

15. The compound according to claim 7, wherein the ring A is (i) a 5- to 6-membered monocyclic heterocyclic ring containing one to four heteroatoms selected from an oxygen atom, a nitrogen atom and a sulfur atom or (ii) a 9- to 10-membered bicyclic heterocyclic ring containing one to four heteroatoms selected from an oxygen atom, a nitrogen atom and a sulfur atom.

16. The compound according to claim 14, wherein the C5-6 monocyclic carbon ring is cyclopentane, cyclohexane, cyclohexene or benzene, and the C9-10 bicyclic carbon ring is naphthalene.

17. The compound according to claim 15, wherein the 5- to 6-membered monocyclic heterocyclic ring containing one to four heteroatoms selected from an oxygen atom, a nitrogen atom and a sulfur atom is thiophene, furan, pyrazole, isooxazole, thiazole or pyridine, and the 9- to 10-membered bicyclic heterocyclic ring containing one to four heteroatoms selected from an oxygen atom, a nitrogen atom and a sulfur atom is benzothiophene, indole or imidazopyridine.

18. The compound according to claim 16, wherein the compound represented by the general formula (IV-2) is:

(1) cis-4-{2-[9-(3-fluorobenzyl)-5,6,8,9-tetrahydro-7H-pyrido[4',3':4,5]pyrrolo[2,3-b]pyridin-7-yl]-2-oxoethyl}cyclohexanecarboxylic acid, (2) trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid, (3) trans-4-{2-[9-(4-chlorobenzyl)-5,6,8,9-tetrahydro-7H-pyrido[4',3':4,5]pyrrolo[2,3-b]pyridin-7-yl]-2-oxoethyl}cyclohexanecarboxylic acid, (4) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (5) 4-{2-[9-(3,5-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (6) 4-{2-oxo-2-[9-(2,4,5-trifluorobenzyl)-5,6,8,9-tetrahydro-7H -pyrido[4',3':4,5]pyrrolo[2,3-b]pyridin-7-yl]ethyl}bicyclo[2.2.2]octane-1-carboxylic acid, (7) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (8) 4-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid, (9) (1R,3R)-3-{2-[9-(4-chloro-2-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,

(10) (1R,3R)-3-{2-[9-(4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,

(11) (1R,3R)-3-{2-[9-(3-chloro-4-fluorobenzyl)-5,6,8,9-tetrahydro-7H-pyrido[4',3':4,5]pyrrolo[2,3-b]pyridin-7-yl]-2-oxoethyl}-1,2,2-trimethylcyclopentanecarboxylic acid,

(12) 4-{2-[9-(3-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(13) 4-{2-[9-(2,4-difluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(14) trans-4-{2-[9-(4-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid,

(15) trans-4-{2-[9-(4-chlorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid,

(16) 2-methoxy-4-{2-oxo-2-[9-(2,4,5-trifluorobenzyl)-5,6,8,9-tetrahydro-7H-pyrido[4',3':4,5]pyrrolo[2,3-b]pyridin-7-yl]ethyl}benzoic acid,

(17) 4-{2-[9-(3,4-difluorobenzyl)-5,6,8,9-tetrahydro-7H-pyrido[4',3':4,5]pyrrolo[2,3-b]pyridin-7-yl]-2-oxoethyl}bicyclo[2.2.2]octane-1-carboxylic acid,

(18) 4-{2-[9-(4-fluorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(19) 4-{2-[9-(4-chlorobenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, or

(20) 4-{2-[9-(3,5-difluorobenzyl)-5,6,8,9-tetrahydro-7H-pyrido[4',3':4,5]pyrrolo[2,3-b]pyridin-7-yl]-2-oxoethyl}-2-methoxybenzoic acid.

19. The compound according to claim 16, wherein the compound represented by the general formula (V) is 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoic acid.

20. The compound according to claim 17, wherein the compound represented by the general formula (IV-2) is 4-(2-{9-[(5-chloro-3-thienyl)methyl]-5,6,8,9-tetrahydro-7H-pyrido[4',3':4,5]pyrrolo[2,3-b]pyridin-7-yl}-2-oxoethyl)-2-methylbenzoic acid.

21. The compound according to claim 12, wherein the compound represented by the general formula (IV-3) is:
 (1) cis-4-(2-{9-[(2,5-dimethyl-1,3-thiazol-4-yl)methyl]-1,3,4,9-tetrahydro-2H-β-carbolin-2-yl}-2-oxoethyl)cyclohexanecarboxylic acid or
 (2) rel-[(2R,6S)-4-(2-{9-[(5-chloro-2-thienyl)methyl]-1,3,4,9-tetrahydro-2H-β-carbolin-2-yl}-2-oxoethyl)-2,6-dimethyl-1-piperazinyl]acetic acid.

22. A pharmaceutical composition containing the compound represented by the general formula (I) as defined in claim 1, or a salt thereof or a solvate thereof as an active ingredient.

* * * * *